US012472061B2

(12) United States Patent
Patel et al.

(10) Patent No.: US 12,472,061 B2
(45) Date of Patent: Nov. 18, 2025

(54) SYSTEMS, DEVICES, AND METHODS FOR TREATING HEART VALVES

(71) Applicant: Edwards Lifesciences Corporation, Irvine, CA (US)

(72) Inventors: Darshin S. Patel, San Juan Capistrano, CA (US); Hannah Reed Bettencourt, Huntington Beach, CA (US); Evan T. Schwartz, Huntington Beach, CA (US); Sean Chow, Tustin, CA (US); Jocelyn Chau, Buena Park, CA (US); Tri D. Tran, Fountain Valley, CA (US); Alyssa Joy Gross, Huntington Beach, CA (US); Yuanlong Du, Irvine, CA (US); Jason Seng-Che Lam, Lake Forest, CA (US); Alexander H. Cooper, Costa Mesa, CA (US); Tram Ngoc Nguyen, Santa Ana, CA (US); Ngoc Huong Thi Nguyen, Costa Mesa, CA (US); Kurt Kelly Reed, Huntington Beach, CA (US); Corey Maurice Marshall, Newport Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 925 days.

(21) Appl. No.: 17/456,532

(22) Filed: Nov. 24, 2021

(65) Prior Publication Data

US 2022/0079749 A1 Mar. 17, 2022

Related U.S. Application Data

(63) Continuation of application No. PCT/US2020/036577, filed on Jun. 8, 2020.

(Continued)

(51) Int. Cl.

*A61F 2/24* (2006.01)

(52) U.S. Cl.

CPC .......... *A61F 2/2436* (2013.01); *A61F 2/2409* (2013.01); *A61F 2/2466* (2013.01); *A61F 2230/0091* (2013.01)

(58) Field of Classification Search

CPC .... A61F 2/2427; A61F 2/2466; A61F 2/2457; A61F 2/9517; A61F 2/963;

(Continued)

(56) References Cited

U.S. PATENT DOCUMENTS

| | | |
|---|---|---|
| 519,297 A | 5/1894 | Bauer |
| 3,564,617 A | 2/1971 | Sauvage et al. |

(Continued)

FOREIGN PATENT DOCUMENTS

| | | |
|---|---|---|
| CN | 1684644 A | 10/2005 |
| CN | 216060881 U | 3/2022 |

(Continued)

OTHER PUBLICATIONS

Walther, et al., "Trans-catheter valve-in-valve implantation: in vitro hydrodynamic performance of the SAPIEN + cloth trans-catheter heart valve in the Carpentier-Edwards Perimount valves," European Journal of Cardio-thoracic Surgery, 40 (2011) 1120-1126, Sep. 23, 2010.

(Continued)

*Primary Examiner* — Sarah W Aleman

(74) *Attorney, Agent, or Firm* — Klarquist Sparkman LLP

(57) ABSTRACT

Systems, assemblies, and methods for treating valve regurgitation and other valve problems are described. Prosthetic valves can have integrated coverings or flanges. Prosthetic valves can have a flange attached to the inflow end of the annular frame and designed to extend outwardly therefrom. Docking devices can be used to repair or reshape native heart valves and to secure prosthetic heart valves at a specific location and position relative to a native heart valve.

(Continued)

Delivery systems can be used to deploy a docking device into the heart, including a lubricous sleeve in the delivery system. Packaging and storage systems suitable for the delivery systems are described.

16 Claims, 58 Drawing Sheets

Related U.S. Application Data

(60) Provisional application No. 62/908,402, filed on Sep. 30, 2019, provisional application No. 62/858,875, filed on Jun. 7, 2019.

(58) Field of Classification Search
CPC ....... A61F 2002/9534; A61M 25/0015; A61M 25/0097; A61M 2025/018
See application file for complete search history.

(56) References Cited

U.S. PATENT DOCUMENTS

| | | | |
|---|---|---|---|
| 4,035,849 | A | 7/1977 | Angell et al. |
| 4,490,859 | A | 1/1985 | Black et al. |
| 4,512,338 | A | 4/1985 | Balko et al. |
| 4,592,340 | A | 6/1986 | Boyles |
| 4,790,843 | A | 12/1988 | Carpentier et al. |
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,266,073 | A | 11/1993 | Wall |
| 5,325,845 | A | 7/1994 | Adair |
| 5,358,496 | A | 10/1994 | Ortiz et al. |
| 5,403,305 | A | 4/1995 | Sauter et al. |
| 5,411,552 | A | 5/1995 | Andersen et al. |
| 5,443,500 | A | 8/1995 | Sigwart |
| 5,554,185 | A | 9/1996 | Block et al. |
| 5,591,195 | A | 1/1997 | Taheri et al. |
| 5,599,305 | A | 2/1997 | Hermann et al. |
| 5,632,760 | A | 5/1997 | Sheiban et al. |
| 5,639,274 | A | 6/1997 | Fischell et al. |
| 5,728,068 | A | 3/1998 | Leone et al. |
| 5,749,890 | A | 5/1998 | Shaknovich |
| 5,782,809 | A | 7/1998 | Umeno et al. |
| 5,824,044 | A | 10/1998 | Quiachon et al. |
| 5,840,081 | A | 11/1998 | Andersen et al. |
| 5,908,405 | A | 6/1999 | Imran et al. |
| 5,916,147 | A | 6/1999 | Boury |
| 5,944,690 | A | 8/1999 | Falwell et al. |
| 5,957,949 | A | 9/1999 | Leonhardt et al. |
| 5,961,536 | A | 10/1999 | Mickley et al. |
| 5,968,068 | A | 10/1999 | Dehdashtian et al. |
| 6,019,777 | A | 2/2000 | Mackenzie |
| 6,027,510 | A | 2/2000 | Alt |
| 6,033,381 | A | 3/2000 | Kontos |
| 6,120,534 | A | 9/2000 | Ruiz |
| 6,143,016 | A | 11/2000 | Bleam et al. |
| 6,162,208 | A | 12/2000 | Hipps |
| 6,168,614 | B1 | 1/2001 | Andersen et al. |
| 6,174,327 | B1 | 1/2001 | Mertens et al. |
| 6,217,585 | B1 | 4/2001 | Houser et al. |
| 6,235,042 | B1 | 5/2001 | Katzman |
| 6,235,050 | B1 | 5/2001 | Quiachon et al. |
| 6,251,092 | B1 | 6/2001 | Qin et al. |
| 6,306,141 | B1 | 10/2001 | Jervis |
| 6,379,372 | B1 | 4/2002 | Dehdashtian et al. |
| 6,383,171 | B1 | 5/2002 | Gifford et al. |
| 6,406,492 | B1 | 6/2002 | Lytle |
| 6,409,758 | B2 | 6/2002 | Stobie et al. |
| 6,419,696 | B1 | 7/2002 | Ortiz et al. |
| 6,425,916 | B1 | 7/2002 | Garrison et al. |
| 6,432,134 | B1 | 8/2002 | Anson et al. |
| 6,454,799 | B1 | 9/2002 | Schreck |
| 6,458,153 | B1 | 10/2002 | Bailey et al. |
| 6,461,382 | B1 | 10/2002 | Cao |
| 6,471,672 | B1 | 10/2002 | Brown et al. |
| 6,500,147 | B2 | 12/2002 | Omaleki et al. |
| 6,514,228 | B1 | 2/2003 | Hamilton et al. |
| 6,527,979 | B2 | 3/2003 | Constantz et al. |
| 6,579,305 | B1 | 6/2003 | Lashinski |
| 6,582,462 | B1 | 6/2003 | Andersen et al. |
| 6,625,578 | B2 | 9/2003 | Spaur et al. |
| 6,652,578 | B2 | 11/2003 | Bailey et al. |
| 6,730,118 | B2 | 5/2004 | Spenser et al. |
| 6,730,121 | B2 | 5/2004 | Ortiz et al. |
| 6,733,525 | B2 | 5/2004 | Yang et al. |
| 6,764,504 | B2 | 7/2004 | Wang et al. |
| 6,767,362 | B2 | 7/2004 | Schreck |
| 6,797,002 | B2 | 9/2004 | Spence et al. |
| 6,830,584 | B1 | 12/2004 | Seguin |
| 6,893,460 | B2 | 5/2005 | Spenser et al. |
| 6,908,481 | B2 | 6/2005 | Cribier |
| 6,971,998 | B2 | 12/2005 | Rosenman et al. |
| 7,011,094 | B2 | 3/2006 | Rapacki et al. |
| 7,018,406 | B2 | 3/2006 | Seguin et al. |
| 7,018,408 | B2 | 3/2006 | Bailey et al. |
| 7,037,334 | B1 | 5/2006 | Hlavka et al. |
| 7,077,861 | B2 | 7/2006 | Spence |
| 7,101,395 | B2 | 9/2006 | Tremulis et al. |
| 7,125,421 | B2 | 10/2006 | Tremulis et al. |
| 7,137,993 | B2 | 11/2006 | Acosta et al. |
| 7,166,126 | B2 | 1/2007 | Spence |
| 7,166,127 | B2 | 1/2007 | Spence et al. |
| 7,276,084 | B2 | 10/2007 | Yang et al. |
| 7,318,278 | B2 | 1/2008 | Zhang et al. |
| 7,320,702 | B2 | 1/2008 | Hammersmark et al. |
| 7,320,704 | B2 | 1/2008 | Lashinski et al. |
| 7,374,571 | B2 | 5/2008 | Pease et al. |
| 7,393,360 | B2 | 7/2008 | Spenser et al. |
| 7,404,824 | B1 | 7/2008 | Webler et al. |
| 7,431,726 | B2 | 10/2008 | Spence et al. |
| 7,435,257 | B2 | 10/2008 | Lashinski et al. |
| 7,445,632 | B2 | 11/2008 | McGuckin, Jr. et al. |
| 7,510,575 | B2 | 3/2009 | Spenser et al. |
| 7,527,646 | B2 | 5/2009 | Rahdert et al. |
| 7,585,321 | B2 | 9/2009 | Cribier |
| 7,594,926 | B2 | 9/2009 | Linder et al. |
| 7,597,709 | B2 | 10/2009 | Goodin |
| 7,618,446 | B2 | 11/2009 | Andersen et al. |
| 7,637,946 | B2 | 12/2009 | Solem et al. |
| 7,708,775 | B2 | 5/2010 | Rowe et al. |
| 7,737,060 | B2 | 6/2010 | Strickler et al. |
| 7,758,639 | B2 | 7/2010 | Mathis |
| 7,780,723 | B2 | 8/2010 | Taylor |
| 7,780,726 | B2 | 8/2010 | Seguin |
| 7,785,366 | B2 | 8/2010 | Maurer et al. |
| 7,942,927 | B2 | 5/2011 | Kaye et al. |
| 7,951,195 | B2 | 5/2011 | Antonsson et al. |
| 7,959,661 | B2 | 6/2011 | Hijlkema et al. |
| 8,016,882 | B2 | 9/2011 | Macoviak et al. |
| 8,029,556 | B2 | 10/2011 | Rowe |
| 8,052,750 | B2 | 11/2011 | Tuval et al. |
| 8,092,520 | B2 | 1/2012 | Quadri |
| 8,128,691 | B2 | 3/2012 | Keranen |
| 8,142,492 | B2 | 3/2012 | Forster et al. |
| 8,167,932 | B2 | 5/2012 | Bourang et al. |
| 8,236,049 | B2 | 8/2012 | Rowe et al. |
| RE43,882 | E | 12/2012 | Hopkins et al. |
| 8,323,335 | B2 | 12/2012 | Rowe et al. |
| 8,377,115 | B2 | 2/2013 | Thompson |
| 8,398,708 | B2 | 3/2013 | Meiri et al. |
| 8,449,599 | B2 | 5/2013 | Chau et al. |
| 8,449,605 | B2 | 5/2013 | Lichtenstein et al. |
| 8,449,606 | B2 | 5/2013 | Eliasen et al. |
| 8,475,523 | B2 | 7/2013 | Duffy |
| 8,568,472 | B2 | 10/2013 | Marchand et al. |
| 8,657,872 | B2 | 2/2014 | Seguin |
| 8,663,322 | B2 | 3/2014 | Keranen |
| 8,672,998 | B2 | 3/2014 | Lichtenstein et al. |
| 8,685,086 | B2 | 4/2014 | Navia et al. |
| 8,734,507 | B2 | 5/2014 | Keranen |

(56) References Cited

U.S. PATENT DOCUMENTS

| | | | |
|---|---|---|---|
| 8,795,352 | B2 | 8/2014 | O'Beirne et al. |
| 8,801,776 | B2 | 8/2014 | House et al. |
| 8,840,664 | B2 | 9/2014 | Karapetian et al. |
| 9,061,119 | B2 | 6/2015 | Le et al. |
| 9,078,747 | B2 | 7/2015 | Conklin |
| 9,095,434 | B2 | 8/2015 | Rowe |
| 9,119,716 | B2 | 9/2015 | Lee et al. |
| 9,119,718 | B2 | 9/2015 | Keranen |
| 9,192,471 | B2 | 11/2015 | Bolling |
| 9,237,886 | B2 | 1/2016 | Seguin et al. |
| 9,314,335 | B2 | 4/2016 | Konno |
| 9,326,853 | B2 | 5/2016 | Olson et al. |
| 9,364,326 | B2 | 6/2016 | Yaron |
| 9,463,268 | B2 | 10/2016 | Spence |
| 9,474,599 | B2 | 10/2016 | Keranen |
| 9,526,572 | B2 | 12/2016 | Kunis |
| 9,597,205 | B2 | 3/2017 | Tuval |
| 9,622,863 | B2 | 4/2017 | Karapetian et al. |
| 9,795,477 | B2 | 10/2017 | Tran et al. |
| 9,867,702 | B2 | 1/2018 | Keränen et al. |
| 10,016,272 | B2 | 7/2018 | Spence et al. |
| 10,016,276 | B2 | 7/2018 | Brunnett et al. |
| 10,034,749 | B2 | 7/2018 | Spence et al. |
| 10,039,637 | B2 | 8/2018 | Maimon et al. |
| 10,052,198 | B2 | 8/2018 | Chau et al. |
| 10,195,028 | B2 | 2/2019 | Hosmer et al. |
| 10,195,033 | B2 | 2/2019 | Tuval et al. |
| 10,226,339 | B2 | 3/2019 | Spence et al. |
| 10,357,361 | B2 | 7/2019 | Rafi et al. |
| 10,463,479 | B2 | 11/2019 | Manash et al. |
| 10,828,150 | B2 | 11/2020 | Tamir |
| 11,020,225 | B2 | 6/2021 | Keränen et al. |
| 11,020,257 | B2 * | 6/2021 | Roeder .................. A61F 2/954 |
| 11,039,924 | B2 | 6/2021 | Yaron |
| 11,065,111 | B2 | 7/2021 | Manash et al. |
| 11,141,273 | B2 | 10/2021 | Dakin et al. |
| 11,185,406 | B2 | 11/2021 | Haivatov et al. |
| 11,273,038 | B2 | 3/2022 | Tang et al. |
| 11,364,114 | B2 | 6/2022 | Gorman, III et al. |
| 11,382,748 | B2 | 7/2022 | Keränen et al. |
| 11,471,282 | B2 | 10/2022 | Argento et al. |
| 11,547,563 | B2 | 1/2023 | Keränen et al. |
| 11,654,025 | B2 | 5/2023 | O'Carroll et al. |
| 11,666,441 | B2 | 6/2023 | McDaniel et al. |
| 2001/0002445 | A1 | 5/2001 | Vesely |
| 2001/0007082 | A1 | 7/2001 | Dusbabek et al. |
| 2002/0032481 | A1 | 3/2002 | Gabbay |
| 2002/0045936 | A1 | 4/2002 | Moe |
| 2002/0058995 | A1 | 5/2002 | Stevens |
| 2002/0107535 | A1 | 8/2002 | Wei et al. |
| 2002/0151970 | A1 | 10/2002 | Garrison et al. |
| 2002/0165461 | A1 | 11/2002 | Hayzelden et al. |
| 2002/0173841 | A1 | 11/2002 | Ortiz et al. |
| 2003/0040792 | A1 | 2/2003 | Gabbay |
| 2003/0050694 | A1 | 3/2003 | Yang et al. |
| 2003/0120341 | A1 | 6/2003 | Shennib et al. |
| 2003/0167089 | A1 | 9/2003 | Lane |
| 2003/0225420 | A1 | 12/2003 | Wardle |
| 2004/0093061 | A1 | 5/2004 | Acosta et al. |
| 2004/0111006 | A1 | 6/2004 | Alferness et al. |
| 2004/0133263 | A1 | 7/2004 | Dusbabek et al. |
| 2004/0143197 | A1 | 7/2004 | Soukup et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0080474 | A1 | 4/2005 | Andreas et al. |
| 2005/0096736 | A1 | 5/2005 | Osse et al. |
| 2005/0119682 | A1 | 6/2005 | Nguyen et al. |
| 2005/0119735 | A1 | 6/2005 | Spence et al. |
| 2005/0137689 | A1 | 6/2005 | Salahieh et al. |
| 2005/0137691 | A1 | 6/2005 | Salahieh et al. |
| 2005/0149160 | A1 | 7/2005 | McFerran |
| 2005/0182486 | A1 | 8/2005 | Gabbay |
| 2005/0203614 | A1 | 9/2005 | Forster et al. |
| 2005/0203617 | A1 | 9/2005 | Forster et al. |
| 2005/0245894 | A1 | 11/2005 | Zadno-Azizi |
| 2006/0025857 | A1 | 2/2006 | Bergheim et al. |
| 2006/0195134 | A1 | 8/2006 | Crittenden |
| 2006/0265056 | A1 | 11/2006 | Nguyen et al. |
| 2006/0271172 | A1 | 11/2006 | Tehrani |
| 2006/0282150 | A1 | 12/2006 | Olson et al. |
| 2007/0005131 | A1 | 1/2007 | Taylor |
| 2007/0073389 | A1 | 3/2007 | Bolduc et al. |
| 2007/0088431 | A1 | 4/2007 | Bourang et al. |
| 2007/0100356 | A1 | 5/2007 | Lucatero et al. |
| 2007/0112422 | A1 | 5/2007 | Dehdashtian |
| 2007/0185572 | A1 | 8/2007 | Solem et al. |
| 2007/0203575 | A1 | 8/2007 | Forster et al. |
| 2007/0213813 | A1 | 9/2007 | Von Segesser et al. |
| 2007/0219612 | A1 | 9/2007 | Andreas et al. |
| 2007/0232898 | A1 | 10/2007 | Huynh et al. |
| 2007/0239254 | A1 | 10/2007 | Chia et al. |
| 2007/0244546 | A1 | 10/2007 | Francis |
| 2007/0244553 | A1 | 10/2007 | Rafiee et al. |
| 2007/0250150 | A1 | 10/2007 | Pal et al. |
| 2007/0265700 | A1 | 11/2007 | Eliasen et al. |
| 2007/0293808 | A1 | 12/2007 | Williams et al. |
| 2008/0004697 | A1 | 1/2008 | Lichtenstein et al. |
| 2008/0033542 | A1 | 2/2008 | Antonsson et al. |
| 2008/0065011 | A1 | 3/2008 | Marchand et al. |
| 2008/0077235 | A1 | 3/2008 | Kirson |
| 2008/0103520 | A1 | 5/2008 | Selkee |
| 2008/0125853 | A1 | 5/2008 | Bailey et al. |
| 2008/0140190 | A1 | 6/2008 | Macoviak et al. |
| 2008/0208327 | A1 | 8/2008 | Rowe |
| 2008/0208330 | A1 | 8/2008 | Keranen |
| 2008/0228265 | A1 | 9/2008 | Spence et al. |
| 2008/0243245 | A1 | 10/2008 | Thambar et al. |
| 2008/0275503 | A1 | 11/2008 | Spence et al. |
| 2008/0294230 | A1 | 11/2008 | Parker |
| 2009/0024428 | A1 | 1/2009 | Hudock, Jr. |
| 2009/0043153 | A1 | 2/2009 | Zollinger et al. |
| 2009/0069889 | A1 | 3/2009 | Suri et al. |
| 2009/0138079 | A1 | 5/2009 | Tuval et al. |
| 2009/0157175 | A1 | 6/2009 | Benichou |
| 2009/0177278 | A1 | 7/2009 | Spence |
| 2009/0192585 | A1 | 7/2009 | Bloom et al. |
| 2009/0192601 | A1 | 7/2009 | Rafiee et al. |
| 2009/0228093 | A1 | 9/2009 | Taylor et al. |
| 2009/0234318 | A1 | 9/2009 | Loulmet et al. |
| 2009/0259307 | A1 | 10/2009 | Gross et al. |
| 2009/0276038 | A1 | 11/2009 | Tremulis et al. |
| 2009/0276040 | A1 | 11/2009 | Rowe et al. |
| 2009/0281619 | A1 | 11/2009 | Le et al. |
| 2009/0299456 | A1 | 12/2009 | Melsheimer |
| 2009/0299471 | A1 | 12/2009 | Keraenen |
| 2009/0319037 | A1 | 12/2009 | Rowe et al. |
| 2010/0030318 | A1 | 2/2010 | Berra |
| 2010/0036472 | A1 | 2/2010 | Papp |
| 2010/0036473 | A1 | 2/2010 | Roth |
| 2010/0036484 | A1 | 2/2010 | Hariton et al. |
| 2010/0049313 | A1 | 2/2010 | Alon et al. |
| 2010/0076402 | A1 | 3/2010 | Mazzone et al. |
| 2010/0076541 | A1 | 3/2010 | Kumoyama |
| 2010/0076549 | A1 | 3/2010 | Keidar et al. |
| 2010/0082089 | A1 | 4/2010 | Quadri et al. |
| 2010/0094394 | A1 | 4/2010 | Beach et al. |
| 2010/0121425 | A1 | 5/2010 | Shimada |
| 2010/0145431 | A1 | 6/2010 | Wu et al. |
| 2010/0145440 | A1 | 6/2010 | Keranen |
| 2010/0152839 | A1 | 6/2010 | Shandas et al. |
| 2010/0161036 | A1 | 6/2010 | Pintor et al. |
| 2010/0161047 | A1 | 6/2010 | Cabiri |
| 2010/0174363 | A1 | 7/2010 | Castro |
| 2010/0198347 | A1 | 8/2010 | Zakay et al. |
| 2010/0217382 | A1 | 8/2010 | Chau et al. |
| 2010/0256751 | A1 | 10/2010 | Rowe et al. |
| 2010/0274344 | A1 | 10/2010 | Dusbabek et al. |
| 2010/0312333 | A1 | 12/2010 | Navia et al. |
| 2010/0318183 | A1 | 12/2010 | Keraenen |
| 2010/0318184 | A1 | 12/2010 | Spence |
| 2010/0331971 | A1 | 12/2010 | Keraenen et al. |
| 2011/0015729 | A1 | 1/2011 | Jimenez et al. |
| 2011/0054596 | A1 | 3/2011 | Taylor |

(56) References Cited

U.S. PATENT DOCUMENTS

| | | | |
|---|---|---|---|
| 2011/0098802 | A1 | 4/2011 | Braido et al. |
| 2011/0106247 | A1 | 5/2011 | Miller et al. |
| 2011/0137331 | A1 | 6/2011 | Walsh et al. |
| 2011/0137397 | A1 | 6/2011 | Chau et al. |
| 2011/0160846 | A1 | 6/2011 | Bishop et al. |
| 2011/0178597 | A9 | 7/2011 | Navia et al. |
| 2011/0208298 | A1 | 8/2011 | Tuval et al. |
| 2011/0218621 | A1 | 9/2011 | Antonsson et al. |
| 2011/0224785 | A1 | 9/2011 | Hacohen |
| 2011/0245911 | A1 | 10/2011 | Quill et al. |
| 2011/0295361 | A1 | 12/2011 | Claiborne, III et al. |
| 2011/0319989 | A1 | 12/2011 | Lane et al. |
| 2012/0016464 | A1 | 1/2012 | Seguin |
| 2012/0053680 | A1 | 3/2012 | Bolling et al. |
| 2012/0059458 | A1 | 3/2012 | Buchbinder et al. |
| 2012/0123529 | A1 | 5/2012 | Levi et al. |
| 2012/0150287 | A1 | 6/2012 | Forster et al. |
| 2012/0239142 | A1 | 9/2012 | Liu et al. |
| 2012/0283820 | A1 | 11/2012 | Tseng et al. |
| 2012/0310328 | A1 | 12/2012 | Olson et al. |
| 2012/0316643 | A1 | 12/2012 | Keraenen |
| 2013/0006352 | A1 | 1/2013 | Yaron |
| 2013/0030519 | A1 | 1/2013 | Tran et al. |
| 2013/0190865 | A1 | 7/2013 | Anderson |
| 2013/0204311 | A1 | 8/2013 | Kunis |
| 2013/0310917 | A1 | 11/2013 | Richter et al. |
| 2013/0310928 | A1 | 11/2013 | Morriss et al. |
| 2013/0317598 | A1 | 11/2013 | Rowe et al. |
| 2014/0074299 | A1 | 3/2014 | Endou et al. |
| 2014/0081394 | A1 | 3/2014 | Keranen et al. |
| 2014/0163669 | A1 | 6/2014 | Ben-Zvi et al. |
| 2014/0172070 | A1 | 6/2014 | Seguin |
| 2014/0236287 | A1 | 8/2014 | Clague et al. |
| 2014/0296962 | A1 | 10/2014 | Cartledge et al. |
| 2014/0358222 | A1 | 12/2014 | Gorman, III et al. |
| 2014/0379074 | A1 | 12/2014 | Spence et al. |
| 2015/0025623 | A1 | 1/2015 | Granada et al. |
| 2015/0190227 | A1 | 7/2015 | Johnson et al. |
| 2015/0230921 | A1 | 8/2015 | Chau et al. |
| 2015/0245910 | A1 | 9/2015 | Righini et al. |
| 2015/0282931 | A1 | 10/2015 | Brunnett et al. |
| 2015/0335428 | A1 | 11/2015 | Keranen |
| 2015/0335430 | A1 | 11/2015 | Loulmet et al. |
| 2015/0374493 | A1 | 12/2015 | Yaron et al. |
| 2016/0015514 | A1 | 1/2016 | Lashinski et al. |
| 2016/0074165 | A1 | 3/2016 | Spence et al. |
| 2016/0095705 | A1 | 4/2016 | Keranen et al. |
| 2016/0143732 | A1 | 5/2016 | Glimsdale |
| 2016/0184095 | A1 | 6/2016 | Spence et al. |
| 2016/0199177 | A1 | 7/2016 | Spence et al. |
| 2016/0256276 | A1 | 9/2016 | Yaron |
| 2016/0346080 | A1 | 12/2016 | Righini et al. |
| 2017/0007399 | A1 | 1/2017 | Keranen |
| 2017/0007402 | A1 | 1/2017 | Zerkowski et al. |
| 2017/0065415 | A1 | 3/2017 | Rupp et al. |
| 2017/0217385 | A1 | 8/2017 | Rinkleff et al. |
| 2017/0266005 | A1 | 9/2017 | McGuckin, Jr. |
| 2017/0273788 | A1 | 9/2017 | O'Carroll et al. |
| 2017/0273789 | A1 | 9/2017 | Yaron et al. |
| 2017/0281337 | A1 | 10/2017 | Campbell |
| 2017/0360426 | A1 | 12/2017 | Hacohen et al. |
| 2018/0000580 | A1 | 1/2018 | Wallace et al. |
| 2018/0085217 | A1 | 3/2018 | Lashinski et al. |
| 2018/0153689 | A1 | 6/2018 | Maimon et al. |
| 2018/0206074 | A1 | 7/2018 | Tanasa et al. |
| 2018/0263764 | A1 | 9/2018 | Manash et al. |
| 2018/0289481 | A1 | 10/2018 | Dolan |
| 2018/0303606 | A1 | 10/2018 | Rothstein et al. |
| 2018/0318073 | A1 | 11/2018 | Tseng et al. |
| 2018/0318079 | A1 | 11/2018 | Patel et al. |
| 2018/0318080 | A1 | 11/2018 | Quill et al. |
| 2018/0344456 | A1 | 12/2018 | Barash et al. |
| 2020/0054453 | A1 | 2/2020 | Zerkowski et al. |
| 2020/0360143 | A1 | 11/2020 | O'Carroll et al. |
| 2021/0212826 | A1 | 7/2021 | Zerkowski et al. |
| 2021/0361426 | A1 | 11/2021 | Hacohen |
| 2023/0086853 | A1 | 3/2023 | Zerkowski et al. |

FOREIGN PATENT DOCUMENTS

| | | | |
|---|---|---|---|
| DE | 19532846 | A1 | 3/1997 |
| DE | 19907646 | A1 | 8/2000 |
| EP | 0592410 | B1 | 10/1995 |
| EP | 0850607 | A1 | 7/1998 |
| EP | 1432369 | A1 | 6/2004 |
| EP | 1521550 | A2 | 4/2005 |
| EP | 1296618 | B1 | 1/2008 |
| EP | 1827314 | B1 | 12/2010 |
| EP | 2620125 | A1 | 7/2013 |
| EP | 2726018 | A2 | 5/2014 |
| EP | 2806829 | A2 | 12/2014 |
| EP | 3395296 | B1 | 12/2019 |
| EP | 2747708 | B1 | 1/2022 |
| FR | 2815844 | A1 | 5/2002 |
| JP | 2015509023 | A | 3/2015 |
| JP | 2016165493 | A | 9/2016 |
| JP | 2016195827 | A | 11/2016 |
| JP | 2017524486 | A | 8/2017 |
| JP | 2018171463 | A | 11/2018 |
| WO | 9117720 | A1 | 11/1991 |
| WO | 9829057 | A1 | 7/1998 |
| WO | 9912483 | A1 | 3/1999 |
| WO | 0149213 | A2 | 7/2001 |
| WO | 0154625 | A1 | 8/2001 |
| WO | 0176510 | A2 | 10/2001 |
| WO | 0222054 | | 3/2002 |
| WO | 0236048 | A1 | 5/2002 |
| WO | 0247575 | A2 | 6/2002 |
| WO | 02060352 | | 8/2002 |
| WO | 03028558 | A2 | 4/2003 |
| WO | 03030776 | A2 | 4/2003 |
| WO | 03047468 | | 6/2003 |
| WO | 2004019825 | A1 | 3/2004 |
| WO | 2005084595 | A1 | 9/2005 |
| WO | 2005102015 | A2 | 11/2005 |
| WO | 2006011127 | A2 | 2/2006 |
| WO | 2006032051 | A2 | 3/2006 |
| WO | 2006111391 | A1 | 10/2006 |
| WO | 2006138173 | A2 | 12/2006 |
| WO | 2005102015 | A3 | 4/2007 |
| WO | 2007047488 | A2 | 4/2007 |
| WO | 2007067942 | A1 | 6/2007 |
| WO | WO-2009134701 | A2 | 11/2009 |
| WO | 2009155561 | A2 | 12/2009 |
| WO | WO-2010057262 | A1 | 5/2010 |
| WO | 2010121076 | A2 | 10/2010 |
| WO | 2012063228 | A1 | 5/2012 |
| WO | 2013110722 | A2 | 8/2013 |
| WO | 2013114214 | A2 | 8/2013 |
| WO | 2015023579 | A1 | 2/2015 |
| WO | 2015023862 | A2 | 2/2015 |
| WO | 2015127264 | A1 | 8/2015 |
| WO | 2015198125 | A1 | 12/2015 |
| WO | 2016038017 | A1 | 3/2016 |
| WO | 2016040881 | A1 | 3/2016 |
| WO | 2016130820 | A1 | 8/2016 |
| WO | 2017103833 | A1 | 6/2017 |

OTHER PUBLICATIONS

Bonhoeffer P., et al., "Percutaneous Replacement of Pulmonary valve in a Right-Ventricle to Pulmonary-Artery Prosthetic Conduit with Valve Dysfunction," Early Report, The Lancet, Oct. 21, 2000, vol. 356, pp. 1403-1405.

Casselman F., et al., "Reducing Operative Mortality in Valvular Reoperations: The "Valve in Ring" Procedure," Brief Technique Reports, The Journal of Thoracic and Cardiovascular Surgery, May 2011, vol. 141, No. 5, pp. 1317-1318.

Cheung A., et al., "Live Case Transmissions," Structural, Case Summary, Nyha III Chf, St. Paul's Hospital/University of British Columbia, Sep. 23, 2010, 6 Pages.

(56) References Cited

OTHER PUBLICATIONS

Cheung A., et al., "Transapical Transcatheter Mitral Valve-in-Valve Implantation in a Human," The Annals of Thoracic Surgery: The Society of Thoracic Surgeons, 2009, vol. 87, pp. e18-e20.
De Weger A., et al., "First-in-Man Implantation of a Trans-Catheter Aortic Valve in a Mitral Annuloplasty Ring: Novel Treatment Modality for Failed Mitral Valve Repair," European Journal of Cardio-Thoracic Surgery, 2011, vol. 39, pp. 1054-1056.
Descoutures F., et al., "Transcatheter Valve-in-Ring Implantation After Failure of Surgical Mitral Repair," European Journal of Cardio-Thoracic Surgery, 2013, vol. 44, pp. e8-e15.
Himbert D., et al., "Transseptal Implantation of a Transcatheter Heart Valve in a Mitral Annuloplasty Ring to Treat Mitral Repair Failure," Circulation Cardiovascular Interventions, American Heart Association, Aug. 2011, pp. 396-398 (5 Pages).
Himbert D., et al., "Transvenous Mitral Valve Repair Replacement After Failure of Surgical Ring Annuloplasty," Research Correspondence, Journal of the American College of Cardiology, Sep. 25, 2012, vol. 60, No. 13, pp. 1205-1206.
Kempfert J., et al., "Minimally Invasive Off-Pump Valve-in-a-Ring implantation: The Atria! Transcatheter Approach for Re-Operative Mitral Valve Replacement After Failed Repair," European Journal of Cardio-Thoracic Surgery, 2009, vol. 35, pp. 965-969.
Ma L., et al., "Double-crowned Valved Stents for Off-pump Mitral Valve Replacement," European Journal of Cardio-thoracic Surgery, 2005, vol. 28, No. 2, pp. 194-199, Discussion 198-9, (Aug. 2008).
Shuto T., et al., "Percutaneous Transvenous Melody Valve-in-Ring Procedure for Mitral Valve Replacement," Journal of the American College of Cardiology, Dec. 6, 2011, vol. 58, No. 24, pp. 2475-2480.
Walther T., et al., "Human Minimally Invasive Off-Pump Valve-in-a-Valve Implantation," Case Reports, The Society of Thoracic Surgeons, The Annals of Thoracic Surgery, 2008, vol. 85, pp. 1072-1073.
Walther T., et al., "Valve-in-a-Valve Concept for Transcatheter Minimally Invasive Repeat Xenograph Implantation," Preclinical Studies, Journal of the American College of Cardiology, Jul. 3, 2007, vol. 50, No. 1, pp. 56-60.
Webb J., et al., "Mitral Valve in Valve," TCT Sep. 2009, Live Case: 30 Minutes, St. Paul's Hospital/University of British Columbia, Sep. 23, 2009, 14 Pages.
Webb J.G., et al., "Transcatheter Valve-in-Valve Implantation for Failed Bioprosthetic Heart Valves," Journal of the American Heart Association, Apr. 27, 2010, vol. 121, pp. 1848-1857 (11 Pages).
Wenaweser P., et al., "Percutaneous Aortic Valve Replacement for Severe Aortic Regurgitation in Degenerated Bioprosthesis: The First Valve Procedure Using Corevalve Revalving System," Catheterization and Cardiovascular Interventions, 2007, vol. 70, pp. 760-764.

* cited by examiner

SYSTEMS, DEVICES, AND METHODS FOR TREATING HEART VALVES

CROSS REFERENCE TO RELATED APPLICATIONS

This application is a continuation of PCT Patent Application No. PCT/US2020/036577, filed Jun. 8, 2020, which claims the benefit of U.S. Provisional Application No. 62/908,402, filed Sep. 30, 2019 and U.S. Provisional Application No. 62/858,875, filed Jun. 7, 2019; all of which applications are incorporated herein by reference.

FIELD OF THE DISCLOSURE

The present disclosure relates to systems and methods for treating valvular regurgitation and/or other valve issues.

BACKGROUND OF THE DISCLOSURE

Prosthetic heart valves can be used to treat cardiac valvular disorders. The native heart valves (the aortic, pulmonary, tricuspid and mitral valves) serve critical functions in assuring the forward flow of an adequate supply of blood through the cardiovascular system. These heart valves can be rendered less effective by congenital, inflammatory, infectious, and other conditions. Such conditions can eventually lead to serious cardiovascular compromise or death.

A transcatheter technique can be used for introducing and implanting a prosthetic heart valve using a flexible catheter in a manner that is less invasive than open heart surgery. In this technique, a prosthetic valve can be mounted in a crimped state on the end portion of a flexible catheter and advanced through a blood vessel of the patient until the valve reaches the implantation site. The valve at the distal end of the catheter can then be expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter. Optionally, the valve can have a mechanically expandable frame, or the valve can have a combination of expansion mechanism, such as balloon expandable, self-expandable, and/or mechanically expandable portions.

Transcatheter heart valves (THVs) could theoretically be appropriately sized, or shaped to be placed inside native mitral and tricuspid valves. However, mitral and tricuspid valve anatomy can vary significantly from person to person and it can be difficult to appropriately size and shape a valve for many patients. Further, when treating valve insufficiency, the surrounding tissue may not be strong enough to hold certain types of valves in position as desired. It would be beneficial to have a docking system and/or apparatus to secure prosthetic valves in the proper position and appropriate delivery systems to ensure safe and effective delivery. Additionally, the shape of the native valve may allow for paravalvular leakage around the prosthetic valve (i.e., blood flow bypassing the prosthetic valve). As such, solutions to increase efficiency of prosthetic valve placement and to reduce paravalvular leakage would be beneficial.

SUMMARY OF THE DISCLOSURE

This summary is meant to provide examples and is not intended to be limiting of the scope of the invention in any way. For example, any feature included in an example of this summary is not required by the claims, unless the claims explicitly recite the feature. The description discloses exemplary embodiments of prosthetic valves, docking stations for prosthetic valves, delivery devices for docking stations, and packaging for delivery devices. The docking stations, catheters, and handles can be constructed in a variety of ways. Also, the features described can be combined in a variety of ways. Various features and steps as described elsewhere in this disclosure can be included in the examples summarized here.

In some embodiments, systems and/or apparatuses herein include a docking device (e.g., anchor, etc.), a delivery system, a prosthetic or implantable heart valve, a pusher device, other components, or combinations of one or more of these. The docking device, delivery system, prosthetic valve, etc. can be the same as or similar to those described below or elsewhere herein.

In one representative embodiment, a suture lock assembly for a delivery system for an implantable medical device can include: a spool configured to receive a suture and including a gear; a rotatable handle coupled to the spool and configured to rotate the spool and gear; a pawl configured to engage with teeth of the gear and allow rotation of the gear, spool, and handle in only one direction; and a directional selector coupled to the pawl and movable between two positions, each of the two positions corresponding to a different direction of rotation of the gear, the directional selector configured to pivot the pawl to adjust an orientation of the pawl relative to the gear and adjust a direction of rotation of the gear. In some embodiments, the pawl is pivotable between a first orientation which allows rotation of the gear in only a first direction and a second orientation which allows rotation of the gear in only an opposite, second direction. In some embodiments, the first direction is counterclockwise and the second direction is clockwise.

In some embodiments, the pawl is held in the first orientation and the second orientation by a spring plunger engaged with the pawl at a back side of the pawl and where, in the first orientation, the pawl is arranged on a first side of the spring plunger and, in the second orientation, the pawl is arranged on a second side of the spring plunger.

In some embodiments, the pawl includes two teeth spaced apart from one another and arranged on a front side of the pawl and the two teeth of the pawl are configured to engage with teeth of the gear.

In some embodiments, the suture lock assembly further includes hard stops arranged within a housing of the suture lock assembly, the gear and pawl arranged within the housing, and the pawl is configured to interface with one of the hard stops when the gear is rotated in a direction that is opposite a selected direction of rotation set by the directional selector.

In some embodiments, the suture lock assembly further includes a housing including a top housing and a bottom housing coupled to one another, the gear and pawl arranged within a space arranged between the top housing and bottom housing. The rotatable handle and the directional selector can extend outward from the top housing. The top housing can include a first icon indicating a slack position of the directional selector and a second icon indicating a tension position of the directional selector, and where the directional selector is movable between a first of the two position that points toward the first icon and a second of the two positions that points toward the second icon.

In some embodiments, a suture lock assembly further includes a release bar including a suture cutting location arranged at a distal end of the release bar, the release bar configured to receive a suture through an interior of the release bar and across the suture cutting location, the suture extending from the spool.

In some embodiments, the release bar includes one or more supporting ribs arranged on a center portion of the release bar, the center portion arranged between the distal end and proximal end of the release bar.

In some embodiments, the distal end of the release bar is shaped to form a first keyed connection with an adaptor of the delivery system and a proximal end of the release bar is shaped to form a second keyed connection with a bottom housing of the suture lock assembly, where the spool is arranged within an interior of the bottom housing.

In some embodiments, the suture lock assembly further includes a flushing port coupled to the bottom housing and extending outward from the bottom housing in an opposite direction from a direction which the release bar extends from the bottom housing.

In some embodiments, the suture lock assembly further includes a plurality of annular sealing elements, including a first annular sealing element arranged around a distal end portion of the release bar, proximate to the suture cutting location, and a second annular sealing element arranged around a proximal end portion of the release bar, the second annular sealing element arranged between, in a radial direction, the release bar and a bottom housing of the suture lock assembly, where the spool is arranged within the bottom housing. In some embodiments, the plurality of annular sealing elements further includes a third annular sealing element arranged around a portion of the spool and arranged between the portion of the spool and the bottom housing.

In some embodiments, a proximal end of the release bar is bonded to a bottom housing of the suture lock assembly.

In some embodiments, the release bar includes a divider arranged within the suture cutting location, where the divider is configured to separate two lines of a suture extending longitudinally through the release bar and expose only one line of the two lines of the suture to an exterior of the suture lock assembly at the suture cutting location.

In some embodiments, the spool includes a gap in a flange arranged around a bottom of the spool and the rotatable handle includes an indicator on its outer surface configured to track a number of turns applied to the spool and locate the gap.

In some embodiments, the gap is arranged adjacent to one or more apertures arranged within the spool, the one or more apertures configured to route the suture from inside the spool to an exterior surface of the spool that is configured to receive the suture thereon.

In some embodiments the rotatable handle is coupled to the spool via a central screw extending longitudinally through the rotatable handle and the spool and the suture lock assembly can further include one or more friction pads arranged around the central screw, adjacent to the central portion of the spool, and a friction nut coupled to the central screw, below a lower friction pad of the one or more friction pads. The one or more friction pads can be configured to increase friction on the central screw to stop rotation of the central screw and the rotatable handle when a tension in the suture increases above a predetermined threshold.

In some embodiments, a suture lock assembly further includes a pin-based clutch system including a spring plunger extending longitudinally through and coupled to a portion of the rotatable handle, the spring plunger including an end extending into the gear and configured to extend into and mate with a plurality of detents arranged in an outer-facing surface of the gear to allow rotation of the gear by the rotatable handle. The spring plunger can be configured to slip out of the detents in response to a tension in the suture above a predetermined threshold.

In another representative embodiment, a delivery system for delivering a docking device to a native valve annulus of a patient's heart can include: an outer shaft and a sleeve shaft at least partially arranged within the outer shaft. The sleeve shaft can include: a distal section configured to cover the docking device, the distal section including a flexible material with a lubricous outer surface; and a proximal section including a rigid material and including a tubular portion and a cut portion, the cut portion having an open, u-shaped cross-section. The delivery system can further include a pusher shaft at least partially arranged within the outer shaft, the pusher shaft including: a main tube arranged interior to, in a radial direction that is relative to a central longitudinal axis of the delivery system, the sleeve shaft; an annular shell surrounding a proximal end portion of the main tube and spaced away from, in the radial direction, an outer surface of the main tube; and a proximal extension connected to and extending proximally from a proximal end of the main tube, proximal to the shell, the proximal extension including a flexible material and extending along a portion of an inner surface of the cut portion of the proximal section of the sleeve shaft.

In some embodiments the pusher shaft further comprises an annular plug arranged within the annular shell, at a proximal end of the shell, and surrounding the main shaft, where the plug includes a crescent-shaped portion extending across and filling a first portion of an annular space arranged between the main tube and the shell.

In some embodiments, the annular space includes a second portion that is open and not filled by the plug, where the proximal section of the sleeve shaft is configured to slide within the annular space, and where the cut portion of the proximal section is configured to slide through the second portion of the annular space.

In some embodiments, the tubular portion of the proximal section has an end surface at an interface between the tubular portion and the cut portion, the end surface arranged normal to the central longitudinal axis, and the plug is configured to interface with the end surface of the proximal section and stop the sleeve shaft from traveling further in the proximal, axial direction.

In some embodiments, the sleeve shaft further includes a middle section arranged between the distal section and the proximal section of the sleeve shaft, the middle section forming a transition between the flexible material of the distal section and the rigid material of the proximal section.

In some embodiments, the sleeve shaft further includes a flexible polymer jacket forming an outer surface of the distal section and the middle section, the flexible polymer jacket including the flexible material, an inner liner forming an inner surface of each of the distal section and the middle section, and a rigid tube including a first section forming an entirety of the proximal section and a second section forming a proximal portion of the middle section.

In some embodiments, the rigid tube is a metal tube, where the second section includes a plurality of apertures arranged around a circumference of the rigid tube, along the second section, and where the rigid tube is coupled to the inner liner and the flexible polymer jacket via a bonding connection between the inner liner and the flexible polymer jacket, through the plurality of apertures.

In some embodiments, the delivery system further includes a handle assembly include a handle portion and a hub assembly extending proximally from a proximal end of the handle portion, where the outer shaft extends distally from a distal end of the handle portion, and where the hub assembly includes an adaptor with a straight section coupled to a suture lock assembly and a branch section coupled to sleeve actuating handle.

In some embodiments, the proximal extension of the pusher shaft extends into and through a portion of the branch section of the adaptor.

In some embodiments, the delivery system further includes a first flushing port coupled to the branch section of the adaptor and fluidly coupled with an inner lumen of the proximal extension of the pusher shaft. In some embodiments, the delivery system further includes a second flushing port coupled to the branch section, distal to the first flushing port, and fluidly coupled with a lumen formed between an outer surface of the proximal extension and an inner surface of the branch section.

In some embodiments, the delivery system further includes a first flushing port coupled to a proximal end of the suture lock assembly and fluidly coupled with an inner lumen of the proximal extension of the pusher shaft and a second flushing port coupled to the branch section, distal to the first flushing port, and fluidly coupled with a lumen formed between an outer surface of the proximal extension and an inner surface of the branch section.

In some embodiments, the cut portion of the sleeve shaft extends into the straight section of the adapted and is coupled to the sleeve actuating handle.

In some embodiments, the pusher shaft and the sleeve shaft are coaxial with one another, along the central longitudinal axis of the delivery system, and each of the sleeve shaft and the pusher shaft are configured to slide axially along the central longitudinal axis, relative to the outer shaft.

In some embodiments, a distal section of the main tube of the pusher shaft includes a plurality of cuts therein, spaced apart from one another along a length of the distal section, where the plurality of cuts is configured to increase a flexibility of the distal section of the main tube. In some embodiments, spacing between adjacent cuts of the plurality of cuts varies along the length of the distal section and where the spacing between adjacent cuts increases from a distal end to a proximal end of the distal section.

In another representative embodiment, a delivery system for delivering a docking device to a native valve annulus of a patient's heart includes: a handle portion; an outer shaft extending distally from a distal end of the handle portion; a sleeve shaft extending through an interior of the outer shaft and configured to cover the docking device; a pusher shaft including a main tube extending through an interior of the sleeve shaft; and a hub assembly extending proximally from a proximal end of the handle portion. The hub assembly can include: an adaptor coupled to the handle portion and including a first section and a second section that branches off from the first section, where a portion of the pusher shaft extends into the second section and a proximal section of the sleeve shaft extends through the first section; a suture lock assembly coupled to a proximal end of the second section and configured to adjust tension in a suture extending from the suture lock assembly, through the pusher shaft, to the docking device; a first flushing port coupled to the second section and fluidly coupled to a first fluid flow lumen arranged within an interior of the pusher shaft and to a second fluid flow lumen arranged between the sleeve shaft and the docking device; and a second flushing port coupled to the second section and fluidly coupled to a third fluid flow lumen arranged between the outer shaft and the sleeve shaft.

In some embodiments, the delivery system further includes a sleeve actuating handle arranged at a proximal end of the first section and coupled to an end of the proximal section of the sleeve shaft, the sleeve actuating handle configured to adjust an axial position of the sleeve shaft relative to the outer shaft.

In some embodiments, the first fluid flow lumen extends through an interior of a proximal extension of the pusher shaft and an interior of the main tube of the pusher shaft, the main tube coupled to the proximal extension and extending through an interior of the outer shaft and the proximal extension extending through a portion of the outer shaft and into the second section.

In some embodiments, the first fluid flow lumen extends to a distal end of the pusher shaft, the distal end arranged adjacent to but spaced away from a proximal end of the docking device when the docking device is arranged within the outer shaft.

In some embodiments, the second flushing port is fluidly coupled to the third fluid flow lumen via an annular cavity arranged between a shell of the pusher shaft and the main tube of the pusher shaft, and a fourth fluid flow lumen formed between an outer surface of the proximal extension and an inner surface of the second section, the fourth fluid flow lumen fluidly coupled to the annular cavity. In some embodiments, the third fluid flow lumen is arranged between an inner surface of the outer shaft and a distal portion of the sleeve shaft, the distal portion configured to cover the docking device while the docking device is arranged inside the outer shaft and being implanted at the native valve annulus.

In some embodiments, the delivery system further includes a third flushing port coupled to the handle portion and fluidly coupled to the annular cavity.

In some embodiments, the delivery system further includes a gasket arranged within and across a diameter of the second section, between where the first flushing port is coupled to the second section and where the second flushing port is coupled to the second section. The gasket is configured to fluidly separate the first fluid flow lumen and the third fluid flow lumen from one another.

In some embodiments, the first flushing port and the second flushing port are connected to a single fluid source. In some embodiments, the single fluid source is an infusion pump and where the infusion pump is coupled to the first flushing port and the second flushing port via a y-connector.

In some embodiments, the first flushing port and the second flushing port are connected to different fluid sources.

In some embodiments, the first flushing port is directly coupled to the second section of the adaptor, distal to the suture lock assembly and proximal to the second flushing port.

In some embodiments, the first flushing port is part of the suture lock assembly and arranged at a proximal end of the suture lock assembly.

In some embodiments, the delivery system further includes a hemostatic seal arranged within the first section of the adaptor, proximate to the sleeve actuating handle, where the hemostatic seal includes an opening surrounding a cut portion of the sleeve shaft that extends through the first section, to the sleeve actuating handle, the hemostatic seal configured to seal around the cut portion of the sleeve shaft. In some embodiments, the delivery system further includes a locking cap assembly arranged on the first section, around the hemostatic seal, the locking cap assembly configured to apply inward pressure on the hemostatic seal and lock axial translation of the sleeve shaft relative to a remainder of the hub assembly.

In some embodiments, the pusher shaft is configured to deploy the docking device from inside a distal end portion of the outer shaft upon reaching the native valve annulus and a distal end of the sleeve shaft is spaced away from a distal end of the outer shaft, within the outer shaft, while the docking device is arranged within the outer shaft during navigating the delivery system to the native valve annulus.

In some embodiments, the docking device is configured to receive and secure a prosthetic heart valve at the native valve annulus.

In one representative embodiment, a method of delivering a docking device to a native valve of a heart can include: deploying the docking device from a distal end of a delivery system, the docking device covered by a distal section of a sleeve shaft of the delivery system, the docking device including a coil extending along a central axis and including a central region including a plurality of turns, a leading turn extending from a first end of the central region, and a stabilization turn extending from an opposite, second end of the central region, where a covering extends around and along a top turn of the central region, the top turn arranged at the second end of the central region; positioning the covered docking device at the native valve, such that the covering of the top turn of the central region crosses and plugs a medial commis sure of the native valve, at least a portion of the leading turn is positioned in a ventricle of the heart, and at least a portion of the stabilization turn is positioned in an atrium of the heart; and after positioning the covered docking device, retracting the sleeve shaft, in a proximal direction, to uncover the docking device.

In some embodiments, deploying the docking device from the distal end of the delivery system includes pushing the covered docking device outside of the outer shaft of the delivery system with the pusher shaft of the delivery system.

In some embodiments, retracting the sleeve shaft to uncover the docking device includes moving the sleeve actuating handle in the proximal direction.

In some embodiments, the method can further include maintaining a position of the pusher shaft while retracting the sleeve shaft to uncover the docking device and, after uncovering the docking device, retracting the pusher shaft back into the outer shaft of the delivery system.

In some embodiments, the method can further include, during deploying the covered docking device and positioning the covered docking device at the native valve, flushing a plurality of lumens of the delivery system including a first lumen arranged between the distal section of the sleeve shaft and the docking device and a second lumen arranged between an outer shaft of the delivery system and the sleeve shaft.

In some embodiments flushing the first lumen includes providing flush fluid to a pusher shaft lumen extending through the pusher shaft from a proximal end of the pusher shaft arranged within a branch section of a hub assembly, where a suture lock is coupled to the branch section, to a distal end of the pusher shaft, the distal end arranged proximate to, but spaced away from, a proximal end of the docking device and flowing the flush fluid through the pusher shaft lumen and into and through the first lumen.

In some embodiments, the flush fluid is provided to the pusher shaft lumen via a flush port coupled to the branch section, distal to the suture lock.

In some embodiments, the flush fluid is provided to the pusher shaft lumen via a flush port that is part of the suture lock and arranged at a proximal end of the suture lock.

In some embodiments, flushing the second lumen includes providing flush fluid to a first cavity formed between an outer surface of the pusher shaft and an inner surface of a conduit of the branch section, flowing the flush fluid from the first cavity into a second cavity formed between a shell of the pusher shaft and a main tube of the pusher shaft, and flowing the flush fluid from the second cavity to the second lumen.

In some embodiments, the method can further include, during the deploying and positioning of the covered docking device, arranging a distal tip of the distal section of the sleeve shaft to extend a distance past, in the distal direction, a distal end of the docking device.

In some embodiments, the method can further include deploying a prosthetic heart valve within the central region of the docking device.

In another representative embodiment, a method for providing flush fluid to a delivery system configured to deliver a docking device to a native valve of a heart can include: flowing flush fluid through an inner, pusher shaft lumen extending through an interior of a pusher shaft of the delivery system to a distal end of the pusher shaft, where the pusher shaft is arranged coaxial with and at least partially within a sleeve shaft of the delivery system, the sleeve shaft and pusher shaft arranged within an outer shaft of the delivery system that extends distally from a handle assembly of the delivery system, the sleeve shaft include a distal section that surrounds and covers the docking device within the outer shaft; flowing flush fluid from the pusher shaft lumen into a sleeve shaft lumen formed between an outer surface of the docking device and an inner surface of the distal section of the sleeve shaft; and flowing flush fluid through a delivery shaft lumen formed between an outer surface of the sleeve shaft and an inner surface of the outer shaft.

In some embodiments, flowing flush fluid through the pusher shaft lumen and into the sleeve shaft lumen and flowing fluid through the delivery shaft lumen includes flowing flush fluid continuously, from a common fluid source to the pusher shaft lumen, the sleeve shaft lumen, and the delivery shaft lumen.

In some embodiments, flowing flush fluid through the pusher shaft lumen and into the sleeve shaft lumen and flowing fluid through the delivery shaft lumen includes flowing flush fluid continuously from a first fluid source to the pusher shaft lumen and the sleeve shaft lumen and flowing flush fluid continuously from a separate, second fluid source to the delivery shaft lumen.

In some embodiments, flowing flush fluid through the pusher shaft lumen and into the sleeve shaft lumen and flowing fluid through the delivery shaft lumen occurs during advancing a distal end portion of the delivery system, including the docking device arranged therein, to the native valve and positioning the docking device, while covered by the sleeve shaft, at the native valve.

In some embodiments, flowing flush fluid through the pusher shaft lumen and into the sleeve shaft lumen and flowing fluid through the delivery shaft lumen occurs during preparing the delivery device for an implantation procedure, prior to inserting the delivery device into a patient.

In some embodiments, flowing the flush fluid through the delivery shaft lumen includes flowing flush fluid from a first flushing port coupled to a conduit of a hub assembly of the delivery system to a first cavity formed between an outer surface of the pusher shaft and an inner surface of the conduit, flowing flush fluid from the first cavity into a second cavity arranged between an inner surface of a shell of the pusher shaft and an outer surface of a main tube of the pusher shaft, and flowing flush fluid from the second cavity to the delivery shaft lumen.

In some embodiments, flowing the flush fluid through the delivery shaft lumen includes flowing flush fluid from a first flushing port coupled to the conduit and in direct fluid communication with the first cavity, into the first cavity.

In some embodiments, flowing the flush fluid through the pusher shaft lumen and into the sleeve shaft lumen includes flowing the flush fluid from a second flushing port coupled to the conduit, proximal to where the first flushing port is coupled to the conduit, and in direct fluid communication with the pusher shaft lumen, into the pusher shaft lumen.

In some embodiments, the method can further include maintaining the flush fluid flow from the first flushing port into the first cavity separate from the flush fluid flow from the second flushing port into the pusher shaft lumen.

In some embodiments, a docking device for docking a prosthetic valve at a native heart valve includes a coil extending along a central axis, including a leading coil, a central region, and a stabilization coil, where the central region possesses a plurality of turns having substantially equal inner diameters, the leading turn extends from one end of the central region and has a diameter greater than the diameter of the central region, and the stabilization turn has a diameter greater diameter than the diameter of the central region and extends from the opposing end of the central region from the leading turn.

In some embodiments of a docking device, the stabilization turn is designed to create three points of contact in a native anatomy.

In some embodiments of a docking device, the stabilization turn is designed to sit lower in free space than the central region thus lifting the central region.

In some embodiments of a docking device, the stabilization turn has a diameter larger than an opening of a native mitral valve but smaller enough to rest on the mitral plane.

In some embodiments of a docking device, the stabilization turn is configured to create a ring around a deployed prosthetic valve.

In some embodiments of a docking device, the central region possesses at least three full turns.

In some embodiments of a docking device, the stabilization turn possesses a covering to form a seal against a prosthetic valve.

In some embodiments of a docking device, the covering is and/or comprises a foam.

In some embodiments of a docking device, the covering is and/or comprises a braided structure, such as a nitinol braided structure and/or a covered nitinol braided structure (e.g., covered in cloth, fabric, polymer, foam, etc.).

In some embodiments of a docking device, the covering possesses pores sized to be atraumatic to native tissues and allow tissue ingrowth into the covering.

In some embodiments of a docking device, the docking device further includes a soft covering over the entire length of the coil to reduce friction and maintain retention forces for a prosthetic valve.

In some embodiments of a docking device, the soft covering comprises a plurality of layers of ePTFE bonded together.

In some embodiments of a docking device, the bonding is intermittent to increase gumminess of the soft covering.

In some embodiments of a docking device, the central region forms comprises at least 3 turns, including a proximal turn, a distal turn, and at least 1 intermediate turn, where the proximal turn is the turn nearest the stabilization turn and the distal turn is the turn nearest the leading turn, and where the central region forms a generally hourglass structure, where the distal turn and the proximal turn have a greater diameter than the at least 1 intermediate turn.

In some embodiments of a docking device, the central region forms comprises at least 3 turns, including a proximal turn, a distal turn, and at least 1 intermediate turn, where the proximal turn is the turn nearest the stabilization turn and the distal turn is the turn nearest the leading turn, and where the central region forms a generally barrel structure, where the at least 1 intermediate turn has a greater diameter than the distal turn and the proximal turn.

In a some embodiments of a docking device, the docking device includes a flange created by linking the stabilization turn to the next adjacent turn in the central region using cloth.

In some embodiments of a docking device, the coil incorporates a radiopaque marker.

In some embodiments of a docking device, the radiopaque marker is located at one-quarter turn around the leading turn.

In some embodiments, an implantable prosthetic heart valve includes an annular frame having an inflow end and an outflow end and being radially collapsible and expandable between a radially collapsed configuration and a radially expanded configuration, the frame defining an axial direction extending from the inflow end to the outflow end, a leaflet structure positioned within the frame and secured thereto, and a flange attached to the inflow end of the annular frame and designed to extend outwardly therefrom.

In some embodiments, an implantable prosthetic heart valve has a flange constructed of and/or comprising a memory material (e.g., a shape memory alloy, a shape memory metal, nitinol, etc.).

In one embodiment of an implantable prosthetic heart valve, the flange is made of and/or comprises nitinol.

In some embodiments of an implantable prosthetic heart valve, the flange is attached to the annular frame with a cloth intermediary.

In some embodiments of an implantable prosthetic heart valve, the implantable prosthetic heart valve further includes a skirt attached to an outer surface of the annular frame.

In some embodiments of an implantable prosthetic heart valve, the skirt is constructed of and/or comprises at least one of foam and cloth.

In some embodiments of an implantable prosthetic heart valve, the foam is selected from at least one of the group consisting of polyurethane and polyurethane-polycarbonate matrix.

In some embodiments of an implantable prosthetic heart valve, the skirt is expandable.

In some embodiments of an implantable prosthetic heart valve, the skirt comprises both cloth and foam.

In some embodiments of an implantable prosthetic heart valve, the annular frame includes a memory material incorporated with or located under the skirt to aid in expansion of the skirt is manufactured using cloth and foam.

In some embodiments of an implantable prosthetic heart valve, the skirt possesses a larger diameter near the inflow end of the prosthetic valve than near the outflow end of the prosthetic valve.

In some embodiments of an implantable prosthetic heart valve, the skirt possesses a pocket for the placement of an embolic material.

some embodiments of an implantable prosthetic heart valve, the pocket possesses a pore to allow for insertion of the embolic material.

some embodiments of an implantable prosthetic heart valve, the pocket possesses a permeable or semipermeable covering to allow for the exchange of fluids between the embolic material and native blood.

some embodiments of an implantable prosthetic heart valve, the embolic material is selected from a hydrogel, an ethylene vinyl alcohol dissolved in dimethyl sulfoxide, and an n-butyl cyanoacrylate.

In some embodiments, a system for implanting a docking device at a native valve includes a delivery catheter, an elongated coiled docking device having an end portion, a pusher shaft disposed in the delivery catheter and coupled to the end portion of the coiled docking device, and a sleeve shaft coaxially located with the pusher shaft and disposed between the delivery catheter and the pusher shaft, where the system is configured such that the pusher shaft and sleeve shaft to operate in parallel.

In some embodiments of a system for implanting a docking device at a native valve, the sleeve shaft comprises a distal section, a middle section, and a proximal section, where the distal section forms a lubricous sleeve covering the docking device, and the proximal section is used to actuate the position of the lubricous sleeve.

In some embodiments of a system for implanting a docking device at a native valve, the lubricous sleeve is and/or comprises a low friction material.

In some embodiments of a system for implanting a docking device at a native valve, the lubricous sleeve possesses a hydrophilic coating.

In some embodiments of a system for implanting a docking device at a native valve, the lubricous sleeve possesses a hydrogel coating.

In some embodiments of a system for implanting a docking device at a native valve, the proximal section is rigid and possesses a cut portion to allow access to the pusher shaft.

In some embodiments of a system for implanting a docking device at a native valve, the distal section and the middle section are flexible and are each constructed of a polymer and braid structure.

In some embodiments of a system for implanting a docking device at a native valve, the polymer is and/or comprises a polyether-amide block copolymer or blend of two or more polyether-amide block copolymers.

In some embodiments of a system for implanting a docking device at a native valve, the braid is and/or comprises stainless steel.

In some embodiments of a system for implanting a docking device at a native valve, the distal section possesses a high density braid.

In some embodiments of a system for implanting a docking device at a native valve, the middle section possesses a lower density braid than the distal section.

In some embodiments of a system for implanting a docking device at a native valve, the pusher shaft includes a main hypo tube having a distal end affixed to the docking device and a proximal end opposite the distal end, a shell, a plug, and a proximal extension, where the shell runs coaxially to the main hypo tube and sleeve shaft, is welded to the proximal end of the main hypo tube using the plug, and is disposed between the catheter and the sleeve shaft, and where the proximal extension extends from the proximal end of the main hypo tube.

In some embodiments of a system for implanting a docking device at a native valve, the proximal extension is constructed of a flexible material.

In some embodiments of a system for implanting a docking device at a native valve, the shell and the plug are welded to the main hypo tube to allow the cut portion of the sleeve shaft to slide between the main hypo tube and the shell.

In some embodiments of a system for implanting a docking device at a native valve, the system for implanting a docking device at a native valve further includes a handle assembly.

In some embodiments of a system for implanting a docking device at a native valve, the handle assembly includes a general Y-shape connector.

In some embodiments of a system for implanting a docking device at a native valve, the Y-shaped connector possesses a straight section and a branch, where the sleeve shaft extends to the end of the straight section, and the proximal extension extends to the end of the branch.

In some embodiments of a system for implanting a docking device at a native valve, the handle assembly further includes a flushing port.

In some embodiments of a system for implanting a docking device at a native valve, the flushing port is configured such that a plurality of lumens formed between the catheter, the sleeve shaft, and the pusher shaft are simultaneously flushable from a single port.

In some embodiments of a system for implanting a docking device at a native valve, the handle assembly includes a hemostatic seal located in the straight section formed and possessing a first end located proximal to an opening in the shape of the sleeve shaft.

In some embodiments of a system for implanting a docking device at a native valve, the sleeve shaft possesses a laser cut portion forming a general U-shape structure, and the opening possesses a U-shape.

In some embodiments of a system for implanting a docking device at a native valve, the handle assembly further includes a first rigid washer located on one end of the hemostatic seal and a second rigid washer on the second end of the hemostatic seal.

In some embodiments of a system for implanting a docking device at a native valve, the first and second rigid washers place inward pressure on the hemostatic seal to form a seal between the hemostatic seal and the sleeve shaft.

In some embodiments of a system for implanting a docking device at a native valve, the handle assembly further includes a locking cap assembly.

In some embodiments of a system for implanting a docking device at a native valve, the locking cap assembly allows adjustment of inward pressure between the first and second rigid washers and the hemostatic seal to immobilize the sleeve shaft.

The present disclosure provides for methods of delivering implants to native valves of a heart. The methods can be used to deliver any of the implants described herein, including the docking devices described herein. In some embodiments the methods can comprise positioning the selected docking device at the native valve of the heart, such that at least a portion of the leading turn of the docking device is positioned in a ventricle of the heart and around one or more valve leaflets of the native valve. In certain embodiments, the implantation of the docking device can act to reshape one or more tissues in the heart to repair the function of the native valve. In some embodiments, the methods can comprise delivering the docking device to a native mitral valve to repair the left ventricle and associated heart function. In some embodiments, the methods can reduce the annulus diameter and place tension on the chordae. In some embodiments, the methods can further include performing an edge to edge repair on the native leaflets of the native mitral valve, such as by attaching a clip to attach a free edge of the anterior mitral valve leaflet to a free edge of the posterior mitral valve leaflet.

In some embodiments, the methods can comprise delivering an implantable prosthetic heart valve within the docking device after the docking device is positioned at the native valve of the heart in the desired position. The methods can be used to deliver any of the implantable prosthetic heart valves described herein. In some embodiments, suitable implantable prosthetic heart valves that can be used in the methods can have an annular frame with an inflow end and an outflow end that is radially collapsible and expandable between a radially collapsed configuration and a radially expanded configuration, with the frame defining an axial direction extending from the inflow end to the outflow end; a leaflet structure positioned within the frame and secured thereto; and a flange attached to the inflow end of the annular frame and designed to extend outwardly therefrom. In certain embodiments, the methods can further comprise positioning the implantable prosthetic heart valve in a radially collapsed configuration within the docking device and expanding the implantable prosthetic heart valve from the radially collapsed configuration to a radially expanded configuration, such that a radially outward pressure is applied by the frame of the implantable prosthetic heart valve on at least a portion of a central region of the docking device.

In some aspects, the present disclosure further provides for methods of delivering implants using the delivery systems described elsewhere herein. In certain embodiments, the delivery systems suitable for use in the methods can include a delivery catheter, the docking device with an end portion at the end of the stabilization turn located opposite the central region, a pusher shaft disposed in the delivery catheter and coupled to the end portion of the docking device, and a sleeve shaft coaxially located with the pusher shaft and disposed between the delivery catheter and the pusher shaft. In some embodiments, the delivery system can be configured such that the pusher shaft and sleeve shaft to operate in parallel. In certain embodiments, the positioning step of the methods can comprise pushing the docking device out of the catheter with the pusher shaft.

In various embodiments, the methods can be performed on a living animal or on a non-living cadaver, cadaver heart, simulator (e.g. with the body parts, tissue, etc. being simulated), anthropomorphic ghost, etc.

The foregoing and other objects, features, and advantages of the disclosed technology will become more apparent from the following detailed description, which proceeds with reference to the accompanying figures.

DETAILED DESCRIPTION OF THE DISCLOSURE

Disclosed herein are various systems, apparatuses, methods, etc., including anchoring or docking devices, which can be used in conjunction with expandable prosthetic valves (e.g., transcatheter heart valves (THV)) at a native valve annulus (e.g., mitral or tricuspid valve annulus), in order to more securely implant and hold the prosthetic valve at the implant site. Anchoring/docking devices according to embodiments of the invention provide or form a more circular and/or stable anchoring site, landing zone, or implantation zone at the implant site, in which prosthetic valves can be expanded or otherwise implanted. Many of these docking devices and prosthetic valves have circular or cylindrically-shaped valve frames or stents that can be expanded or otherwise implanted into locations with naturally circular cross sections. However, further embodiments of docking devices and prosthetic valves have other geometries (e.g., oblong, ovular, longitudinally curved, etc.) which are more appropriate for non-circular and/or non-cylindrical anatomies. In addition to providing an anchoring site for the prosthetic valve, the anchoring/docking devices can be sized and shaped to cinch or draw the native valve (e.g., mitral, tricuspid, etc.) anatomy radially inwards. In this manner, one of the main causes of valve regurgitation (e.g., functional mitral regurgitation), specifically enlargement of the heart (e.g., enlargement of the left ventricle, etc.) and/or valve annulus, and consequent stretching out of the native valve (e.g., mitral, etc.) annulus, can be at least partially offset or counteracted. Some embodiments of the anchoring or docking devices further include features which, for example, are shaped and/or modified to better hold a position or shape of the docking device during and/or after expansion of a prosthetic valve therein. By providing such anchoring or docking devices, replacement valves can be more securely implanted and held at various valve annuluses, including at the mitral annulus which does not have a naturally circular cross-section.

Figure 1:
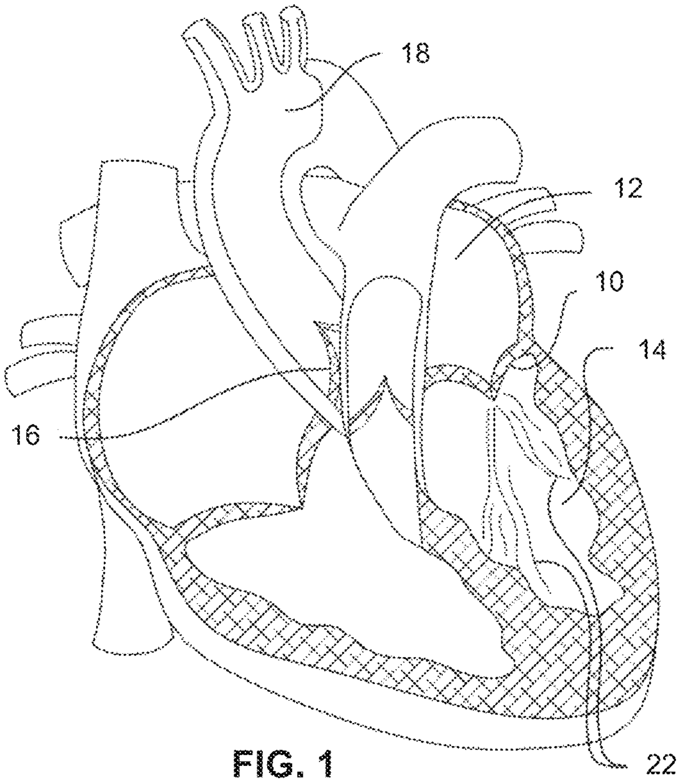
FIG. 1 shows a schematic cross-sectional view of a human heart in accordance with various embodiments.
Figure 2:
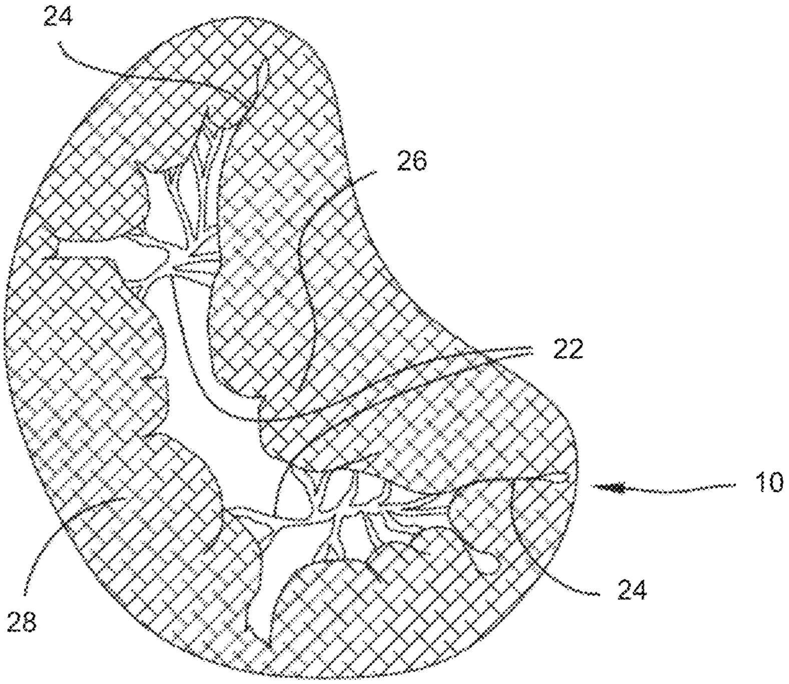
FIG. 2 shows a schematic top view of a mitral valve annulus of a heart in accordance with various embodiments.

Referring first to FIGS. 1 and 2, the mitral valve 10 controls the flow of blood between the left atrium 12 and the left ventricle 14 of the human heart. After the left atrium 12 receives oxygenated blood from the lungs via the pulmonary veins, the mitral valve 10 permits the flow of the oxygenated blood from the left atrium 12 into the left ventricle 14. When the left ventricle 14 contracts, the oxygenated blood that was held in the left ventricle 14 is delivered through the aortic valve 16 and the aorta 18 to the rest of the body. Meanwhile, the mitral valve should close during ventricular contraction to prevent any blood from flowing back into the left atrium. When the left ventricle contracts, the blood pressure in the left ventricle increases substantially, which serves to urge the mitral valve closed. Due to the large pressure differential between the left ventricle and the left atrium during this time, a large amount of pressure is placed on the mitral valve, leading to a possibility of prolapse, or eversion of the leaflets of the mitral valve back into the atrium. A series of chordae tendineae 22 therefore connect the leaflets of the mitral valve to papillary muscles located on the walls of the left ventricle, where both the chordae tendineae and the papillary muscles are tensioned during ventricular contraction to hold the leaflets in the closed position and to prevent them from extending back towards the left atrium. This helps prevent backflow of oxygenated blood back into the left atrium. The chordae tendineae 22 are schematically illustrated in both the heart cross-section of FIG. 1 and the top view of the mitral valve of FIG. 2.

A general shape of the mitral valve and its leaflets as viewed from the left atrium is shown in FIG. 2. Commissures 24 are located at the ends of the mitral valve 10 where the anterior leaflet 26 and the posterior leaflet 28 come together. Various complications of the mitral valve can potentially cause fatal heart failure. One form of valvular heart disease is mitral valve leak or mitral regurgitation, characterized by abnormal leaking of blood from the left ventricle through the mitral valve back into the left atrium. This can be caused, for example, by dilation of the left ventricle causing the native mitral leaflets to not coapt completely, resulting in a leak, by damage to the native leaflets, or weakening of (or damage to) the chordae tendineae and/or papillary muscles. In these circumstances, it may be desirable to repair the mitral valve or to replace the functionality of the mitral valve with that of a prosthetic heart valve.

The field of transcatheter aortic valve replacement has developed much more and has gained widespread success than transcatheter mitral valve replacement. This discrepancy stems, in part, from replacement of a mitral valve being more difficult than aortic valve replacement in many respects, such as, for example, due to the non-circular physical structure of the mitral valve, its sub-annular anatomy, and more difficult access to the valve. Additionally, the mitral valve often lacks calcification limiting the ability of prosthetic valves to anchor within the mitral valve.

One of the most prominent obstacles for mitral valve replacement is effective anchoring or retention of the valve at the mitral position, due to the valve being subject to a large cyclic load. As noted above, another issue with mitral valve replacement is the size and shape of the native mitral annulus, as can be seen in FIG. 2. Aortic valves are more circular or cylindrical in shape than mitral valves. Also, the mitral and tricuspid valves are both larger than the aortic valve, and more elongate in shape, making them more difficult and unconventional sites for implanting a replacement valve with a generally circular or cylindrical valve frame. A circular prosthetic valve that is too small can result in leaking around the implant (i.e., paravalvular leakage) if a good seal is not established around the valve, while a circular prosthetic valve that is too large can stretch out and damage the narrower parts of the native mitral annulus. Further, in many cases, the need for aortic valve replacement arises due, for example, to aortic valve stenosis, where the aortic valve narrows due to calcification or other hardening of the native leaflets. Therefore, the aortic annulus generally forms a more compact, rigid, and stable anchoring site for a prosthetic valve than the mitral annulus, which is both larger than the aortic annulus and non-circular. Instances of mitral valve regurgitation are unlikely to provide such a good anchoring site. Also, the presence of the chordae tendineae and other anatomy at the mitral position can form obstructions that make it much more challenging to adequately anchor a device at the mitral position.

Other obstacles to effective mitral valve replacement can stem from the large cyclic loads the mitral valve undergoes and the need to establish a sufficiently strong and stable anchoring and retention. Also, even a slight shift in the alignment of the valve can still lead to blood flow through the valve or other parts of the heart being obstructed or otherwise negatively impacted.

Embodiments of a Prosthetic Valve

Prosthetic valves according to exemplary embodiments are shown in FIGS. 3A to 6B. While specific examples of prosthetic heart valves are discussed herein, general structure, method of manufacture, and methods of use of various prosthetic valves, which can be adapted for use with the anchoring/docking devices herein, are described in at least U.S. Pat. No. 10,195,025 entitled "Prosthetic Heart Valve;" U.S. Pat. Pub. No. US 2018/0206982 entitled "Covered Prosthetic Heart Valve," and U.S. patent application Ser. No. 16/252,890 entitled "Covered Prosthetic Heart Valve," the disclosure of each of which is incorporated herein by reference in its entirety.

Figure 3A:
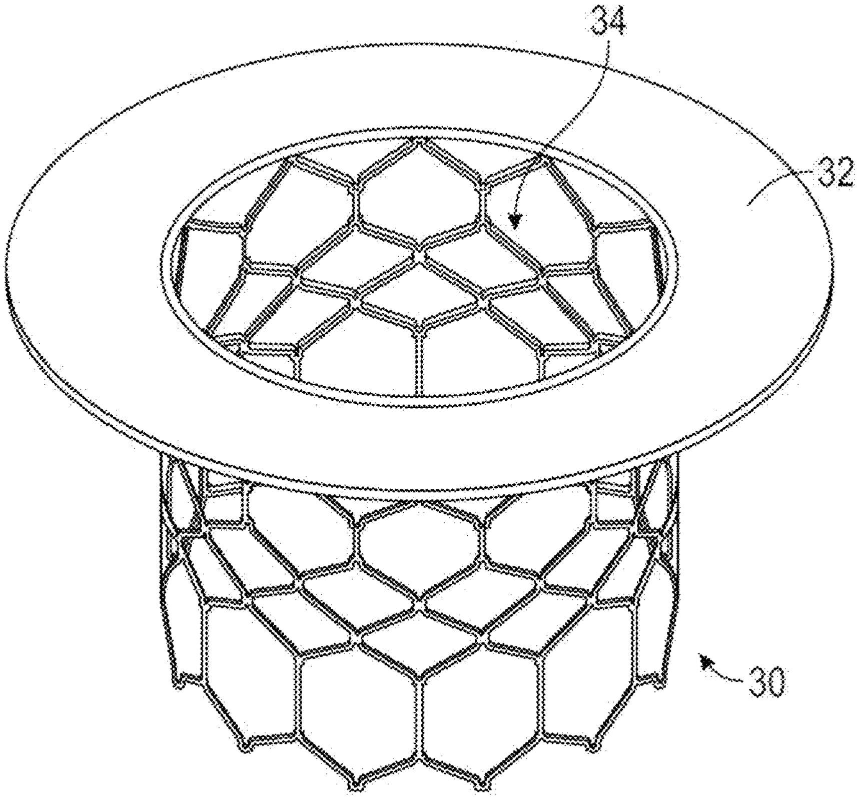
FIG. 3A illustrates a perspective view of an embodiment of a prosthetic heart valve possessing a flange in accordance with various embodiments.
Figure 3B:
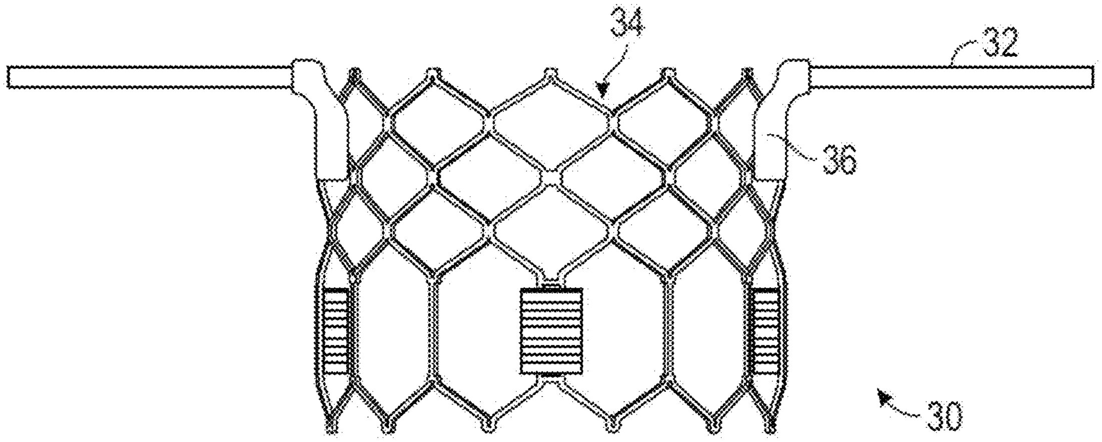
FIG. 3B illustrates a side view of an embodiment of a prosthetic heart valve possessing a flange in accordance with various embodiments.
Figure 3C:
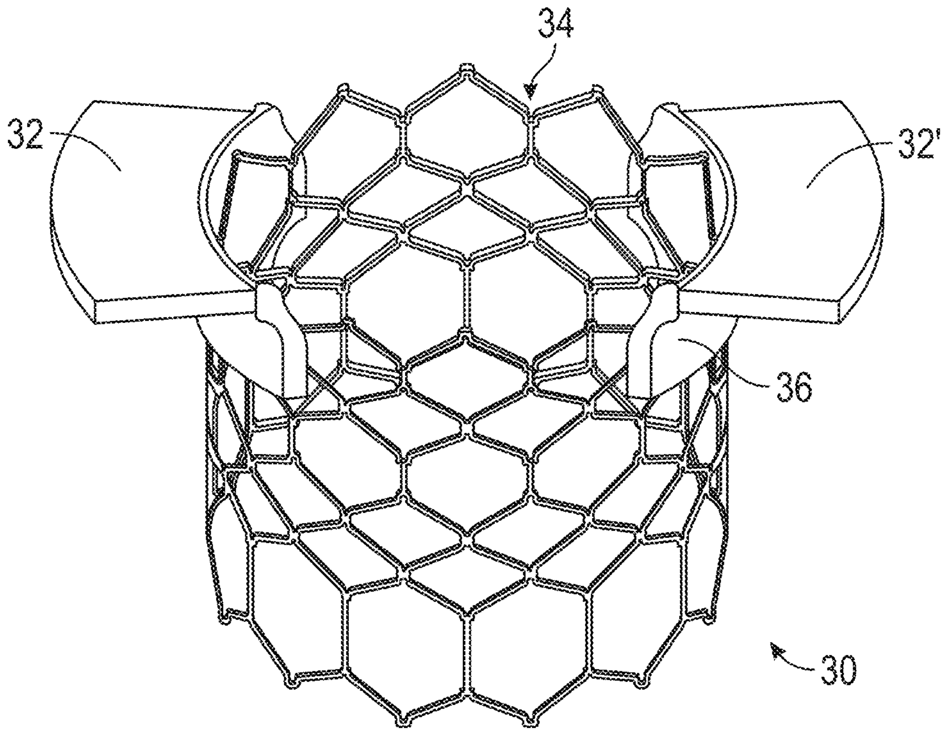
FIG. 3C illustrates a perspective view of an example embodiment of a prosthetic heart valve possessing commissure flanges in accordance with various embodiments.

FIGS. 3A and 3B illustrate an example prosthetic valve 30 with a flange 32 attached to the atrial (inflow end) 34 of the prosthetic valve 30 and extending radially outward in 360° in accordance with various embodiments. In many of these embodiments, the flange 32 is designed to rest on a plane of the native valve, such as on a plane of the native mitral valve, tricuspid valve, etc. The flange 32 of some embodiments is designed to encourage flow through the prosthetic valve 30 to prevent and/or reduce paravalvular leakage. FIG. 3C illustrates a prosthetic valve 30 which includes flanges 32 and 32' that are designed to only cover the mitral commissures rather than the entire mitral plane. Flanges 32 and 32' that only cover the commissures could beneficially reduce the crimped or compressed size of the valve for narrower profile during delivery, but may require the repositioning or adjusting of the prosthetic valve 30 during deployment. In various embodiments, the flange 32 (or flanges 32 and 32') is made of a resilient material that is capable of being compacted on a catheter for delivery. In certain embodiments, the flange 32 (or flanges 32 and 32') is made of and/or comprises a memory material that can be compressed or manipulated and returns to a specific shape once a force is removed. An example of a memory material is nitinol (or NiTi), but other shape memory alloys or shape memory metals can be used. The memory material can be formed into a weave or a frame that is compressible and returns to its formed shape (e.g., a flange) once released from a catheter. In some embodiments, the flange 32 is attached to the frame of the prosthetic valve via a cloth intermediary 36.

Figure 4A:
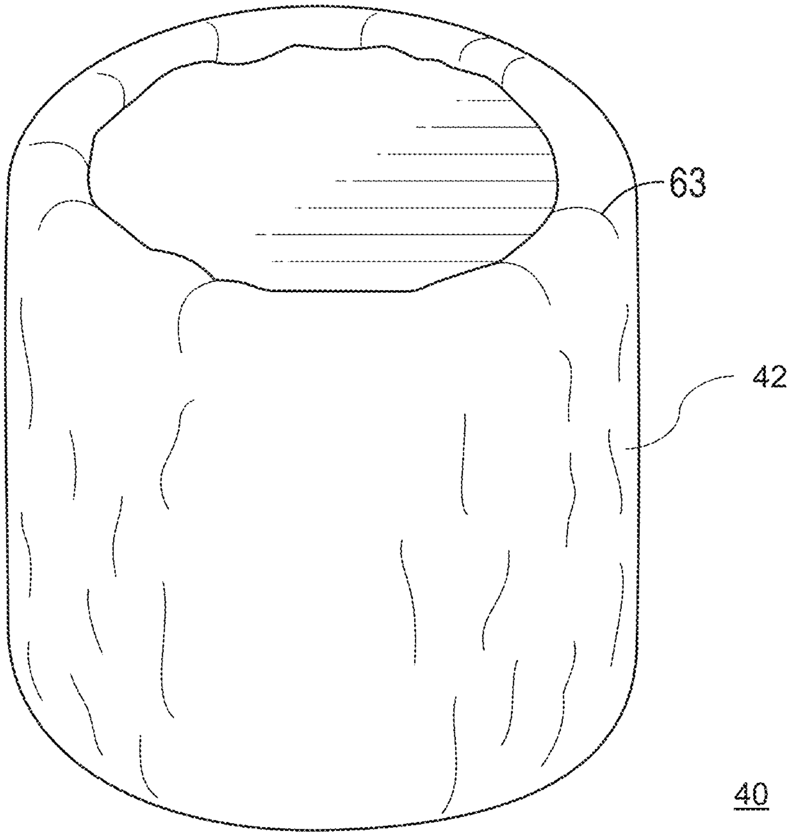
FIGS. 4A-C illustrates views of example embodiments of a prosthetic heart valve possessing a covering in accordance with various embodiments.
Figure 4B:
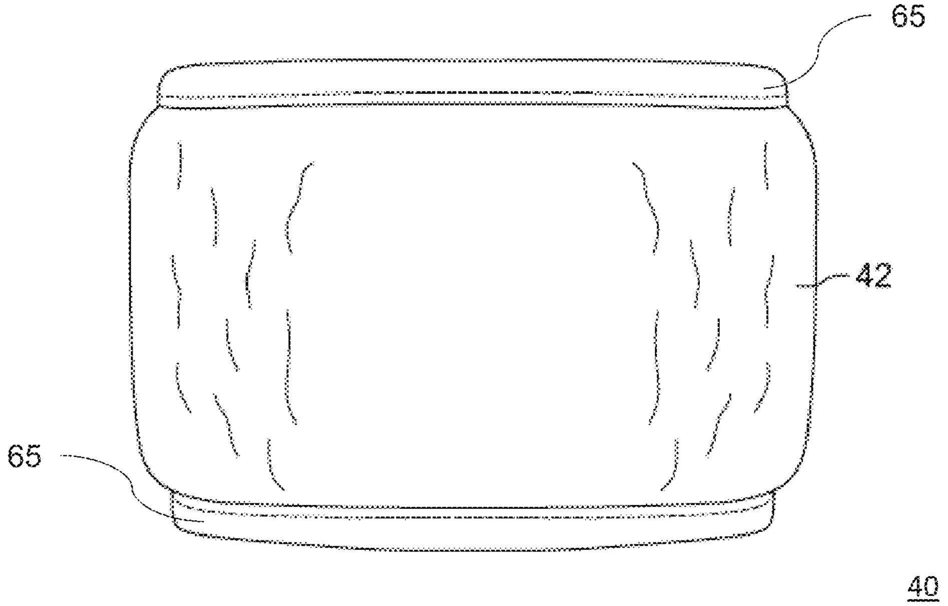

Turning to FIGS. 4A to 4B, exemplary embodiments of prosthetic valves 40 comprising a covering 42, such as a skirt, on the outer surface of the prosthetic valve 40 are illustrated. In covered embodiments, the covering can be designed and/or configured to prevent paravalvular leakage between the prosthetic valve 40 and the native valve, to protect the native anatomy, to promote tissue ingrowth, and/or designed/configured for other purposes. Due to the general D-shape of the mitral valve (see FIG. 2) and relatively large annulus compared to the aortic valve, the covering 42 acts as a seal around the prosthetic valve 40 (e.g., when the valve is sized smaller than the annulus) and allows for smooth coaptation of the native leaflets against the prosthetic valve 40. In various embodiments, the covering 42 is comprised of a material that can be crimped for transcatheter delivery of the prosthetic valve and is expandable to prevent paravalvular leakage around the prosthetic valve. Examples of possible materials include foam, cloth, fabric, one or more polymers, and/or an encapsulated material, such as an encapsulated hydrogel. In certain embodiments, the covering is attached via loop-over stitching 63, as illustrated in FIG. 4A, while additional embodiments will utilize an edge covering strip 65 with radial, horizontal stitching, as illustrated in FIG. 4B. The edge covering strip 65 of many embodiments is constructed of any suitable material that is biocompatible and atraumatic to native tissue, including ePTFE, bovine pericardium, porcine pericardium, equine pericardium, woven PTFE, knitted PTFE, braided PTFE, polyurethane, electrospun ePTFE, dipped thermoplastic, sprayed thermoplastic, other organic tissues, other non-organic tissues, and combinations thereof.

Figure 4C:
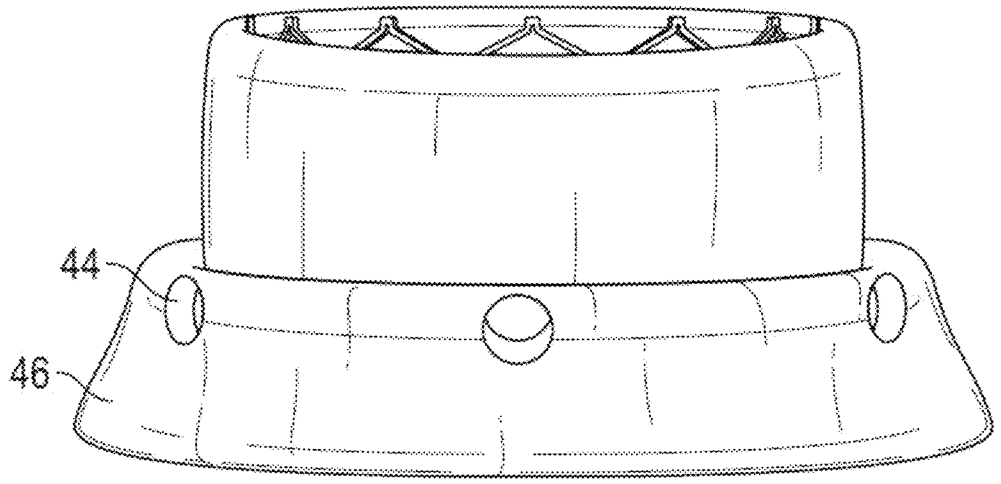

Turning to FIG. 4C, covering (e.g., in cloth, fabric, etc.) solutions of some embodiments will form a pocket 46, such as a cup or purse shape, to allow for insertion, injection, or encapsulation of an embolic material after placement of a valve and allow free exchange of fluid with native blood. Certain embodiments including a pocket include one or more pores 44 in a layer of the covering to allow an outer layer to inflate during systole. In some embodiments, an encapsulated material may provide an appealing mechanism of expansion. Certain embodiments inflate by receiving blood from the atrial side of the prosthetic valve. In additional embodiments, a pore 44 or port allows for insertion of the embolic material with limited exposure to native blood, while further embodiments encapsulate the embolic material completely or nearly completely. In some encapsulated embodiments, the skirt can possess a permeable or semipermeable covering to allow for the exchange of fluids between the encapsulated material and blood. In some embodiments, the embolic material is injected through a catheter or syringe. Further embodiments expand the pocket using monofilament warping and/or buckling. An example of monofilament warping is discussed further herein in reference to FIG. 8.

In a number of embodiments, the embolic material will be a hydrogel. Some hydrogels expand at body temperature; thus, selecting a body-temperature-expandable hydrogel allows the natural heat of a patient to provide the expansion of the hydrogel around a prosthetic valve to prevent paravalvular leakage. Further embodiments will possess a hydrogel that expands by absorbing a fluid, e.g., blood. In such embodiments, the hydrogel can be inserted into the skirt prior to valve deployment, and the presence of blood after deployment will allow the hydrogel to expand. Additional embodiments will utilize a precipitating composition, such as ethylene vinyl alcohol (EVOH) dissolved in dimethyl sulfoxide (DMSO). Certain EVOH-DMSO compositions are known in the art, including ONYX® LIQUID EMBOLIC SYSTEM™ (Micro Therapeutics, Inc., Irvine, California, U.S.A.) formulations ONYX® 18 (6% EVOH), ONYX® 34 (8% EVOH), ONYX® HD-500 (20% EVOH), or blends thereof. In such embodiments, the EVOH-DMSO composition will be inserted into the skirt after or during valve deployment. The DMSO in these compositions will be carried away by the blood, leaving EVOH behind, thus forming an embolic to prevent paravalvular leakage.

In certain embodiments, the embolic material can be an n-butyl cyanoacrylate. Some suitable embolic materials can be liquid alkyl-2-cyanoacrylate monomers that, on contact with ionic mediums (e.g., water, blood), form flexible polymers that can form adhesive bonds to soft tissues. These liquid monomers in isolation are nonviscous, radiolucent, and can rapidly polymerize. In certain embodiments, the embolic material can be a multi-component formulation including the cyanoacrylate and a radiopaque material, ethiodized oil, or both. In some embodiments, the additional components can prolong polymerization time, opacify the liquid agent, and allow for visualization under fluoroscopy. Certain n-butyl cyanoacrylates are known in the art, including TRUFILL® n-butyl-2-cyanoacrylate (n-BCA) liquid embolic system (DePuy Synthes Companies, Raynham, Massachusetts, U.S.A.).

In further embodiments, the embolic material can include one or more radiopaque materials that provide for visualization under fluoroscopy. In certain embodiments, the radiopaque materials can comprise one or more salts, compounds, or nanoparticles containing iodine, barium, tantalum, bismuth, or gold. In some embodiments, the radiopaque material can be a tantalum powder.

Embodiments incorporating foam solutions provide a covering that is attached to the exterior of the valve frame in order to provide a substantial paravalvular leakage solution, while maintaining a low crimp profile enabling the device to be delivered via a catheter. In certain embodiments, one or more foam materials can be used to achieve a low device profile while crimped, and provide for expansion in the mitral position and a soft, smooth surface to interact with the native mitral valve. Possible foam materials include polyethylene terephthalate, polyurethane, and polyurethane-polycarbonate matrix intended for long-term implantation. Foam may be advantageous over a cloth covering, because foam typically is able to compress to a smaller crimp profile, and the amount of swelling in the mitral valve is substantially more effective in reducing the amount of paravalvular leakage based on the increased volume of the foam. Additionally, foam can be extremely compliant and atraumatic against the coaptation of the mitral anatomy. Further advantages of foam include tissue ingrowth and echogenicity. The tissue ingrowth advantages arise because foam is typically more porous than other materials, and the porosity can allow better or improved tissue ingrowth. The improved echogenicity is advantageous because it allows a user, such as a physician, cardiologist, surgeon, or other medical professional to view the placement of the prosthetic valve based on where the foam has expanded.

Figure 5A:
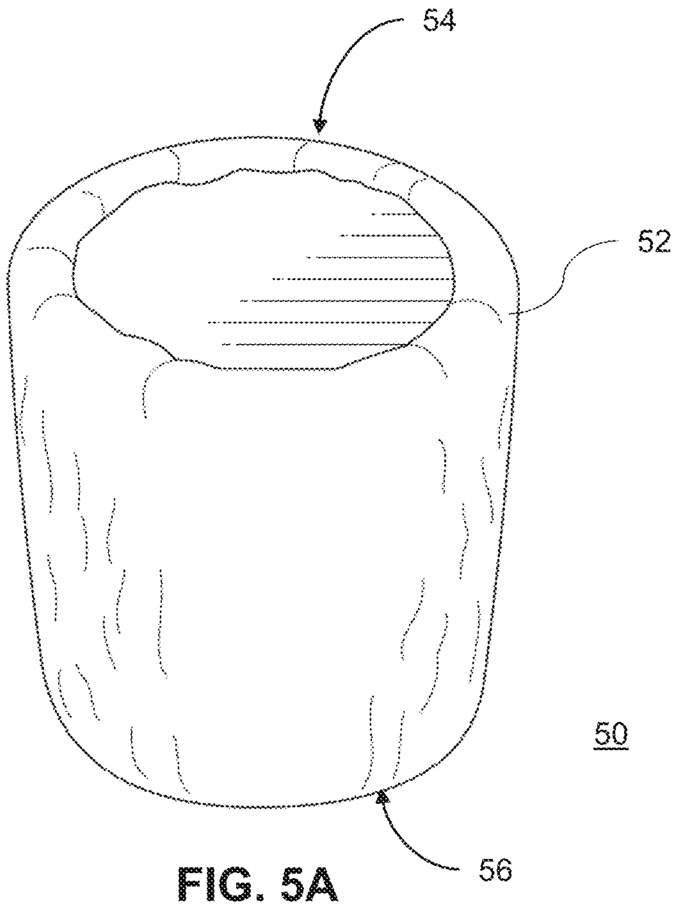
FIGS. 5A-5F illustrate views of example embodiments possessing sculpted coverings in accordance with various embodiments.
Figure 5B:
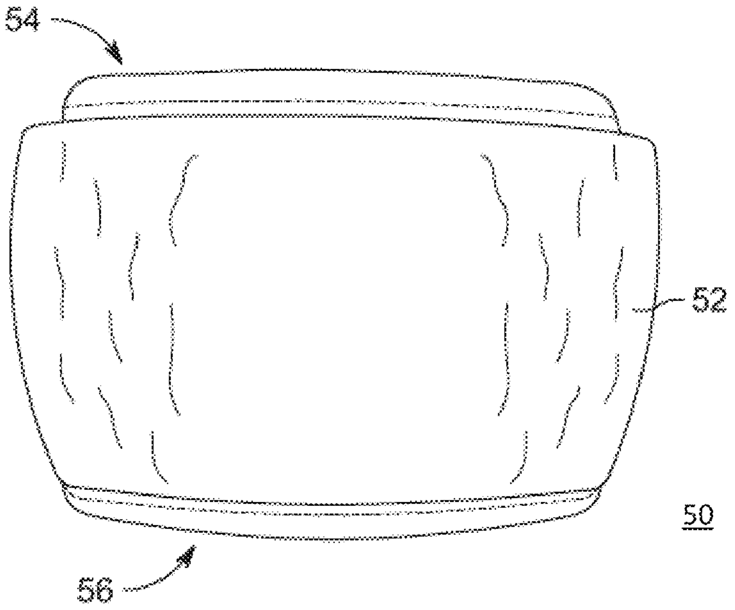

A covering for the prosthetic valve can further be altered to allow for alterations in the inflow and outflow portions of a prosthetic valve (e.g., the shapes need not always be perfectly cylindrical, as shown previously), as seen in FIGS. 5A-5F. In these figures, frame 50 possesses a covering 52 that is machined, thermally molded, or otherwise manufactured into a shape to allow for a larger outer diameter at the inflow portion 54. Various embodiments will possess certain shapes, as illustrated in FIGS. 5A-5F. Some embodiments will possess a generally conical shape, as illustrated in FIG. 5A, having a larger outer diameter at the inflow portion 54 that gradually tapers to a smaller outer diameter at the outflow portion 56. Another set of embodiments will possess a curved and tapered covering 52, such as in FIG. 5B, where the covering 52 is wider near the inflow portion 54 and has a generally curved taper toward the outflow portion 56.

Figure 5C:
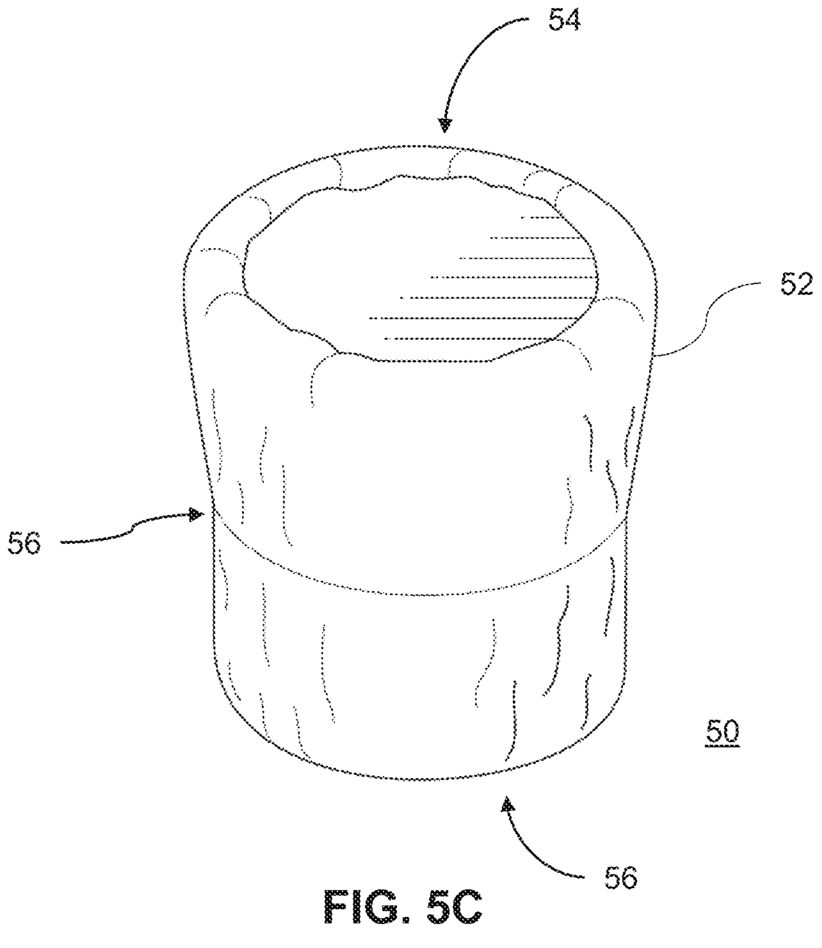
Figure 5D:
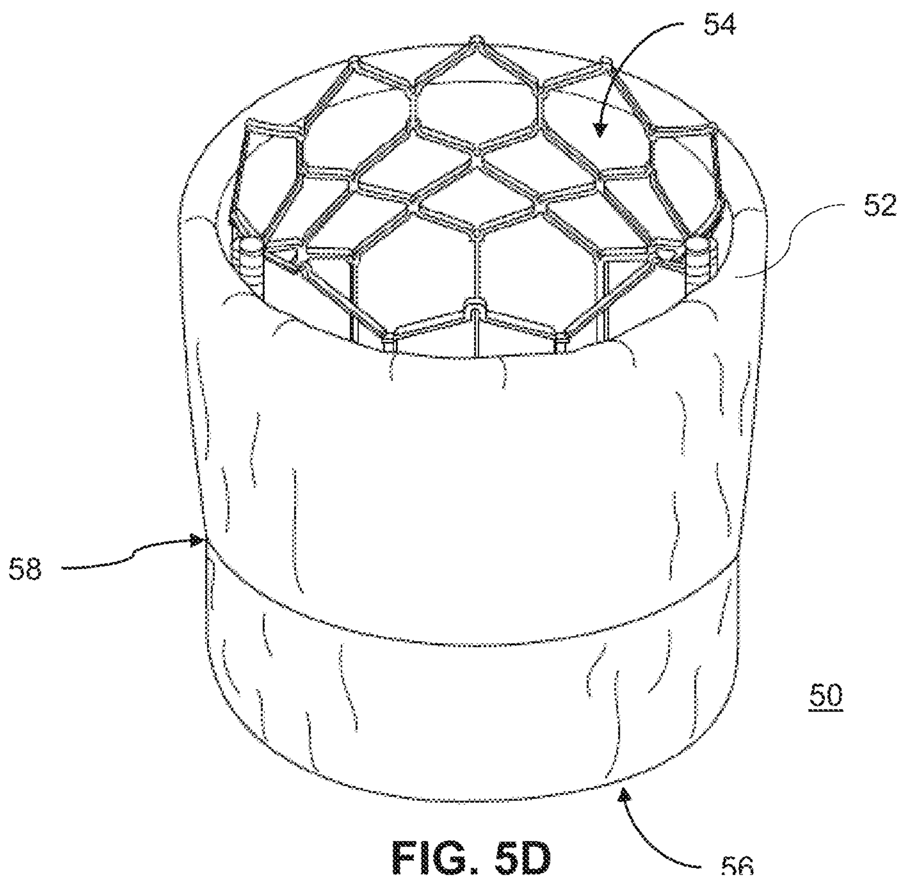
Figure 5E:
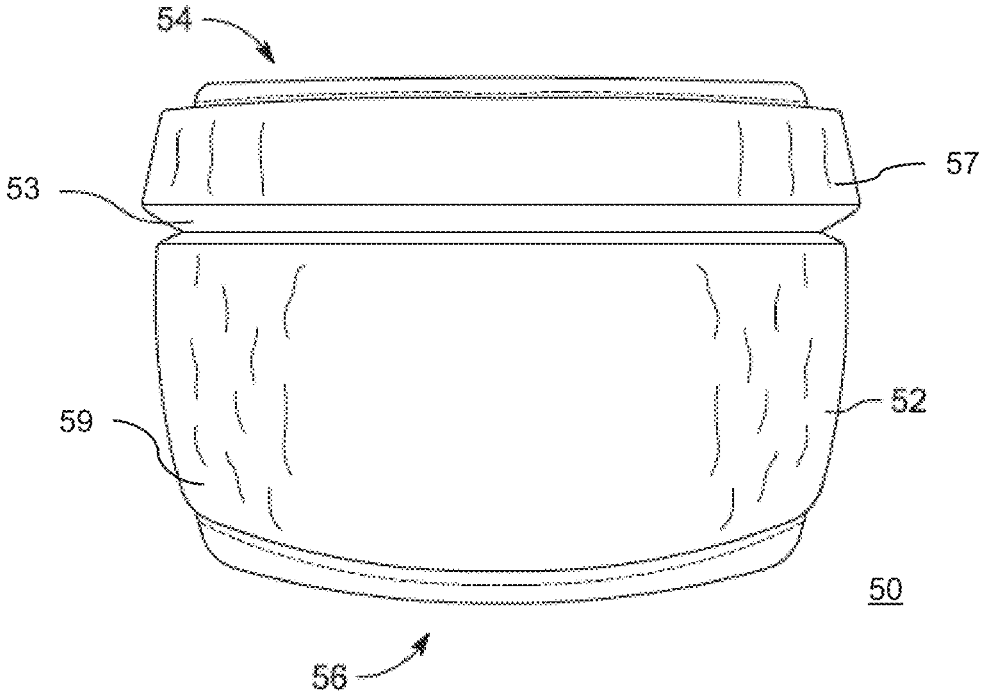

Additional embodiments will possess generally hourglass shapes, such as those illustrated in FIGS. 5C to 5E. As illustrated in FIG. 5C, some embodiments will have larger outer diameters at the inflow portion 54 and at the outflow portion 56, while possessing a narrower outer diameter at the middle portion 58 of the prosthetic valve 50. Another shape of coverings 52 used in some embodiments is illustrated in FIG. 5D, where the covering 52 is retracted slightly from the inflow portion 54 of the prosthetic valve 50 and possesses a larger outer diameter toward the inflow portion 54; additionally, the covering 52 possesses a larger outer diameter at the outflow portion 56 and has a smaller outer diameter at a position 58 proximal to the outflow portion 56. FIG. 5E illustrates embodiments where the covering 52 possesses a constriction 53 designed to prevent compression of the foam from influencing the volume and/or shape of a first portion 57. Because the constriction 53 is designed to prevent compression of first portion 57, the constriction 58 can be located at any position along the body to effectuate this goal. For example, constriction 53 can be proximal to inflow portion (as illustrated), or it can be located proximal to the outflow portion 56 or in a middle position between outflow 56 and inflow 54 portions. In many of these embodiments, constriction 53 is a machined slit. In many embodiments with constrictions 53, the overall shape of covering 52 is cylindrical (e.g., similar to FIG. 4A), while many embodiments will add contours or other shapes to covering 52. For example, first portion 57 has a gradual increase in thickness from the inflow portion 54, and the second portion 59 has a generally curved taper toward the outflow portion 56, as illustrated in FIG. 5E.

Figure 5F:
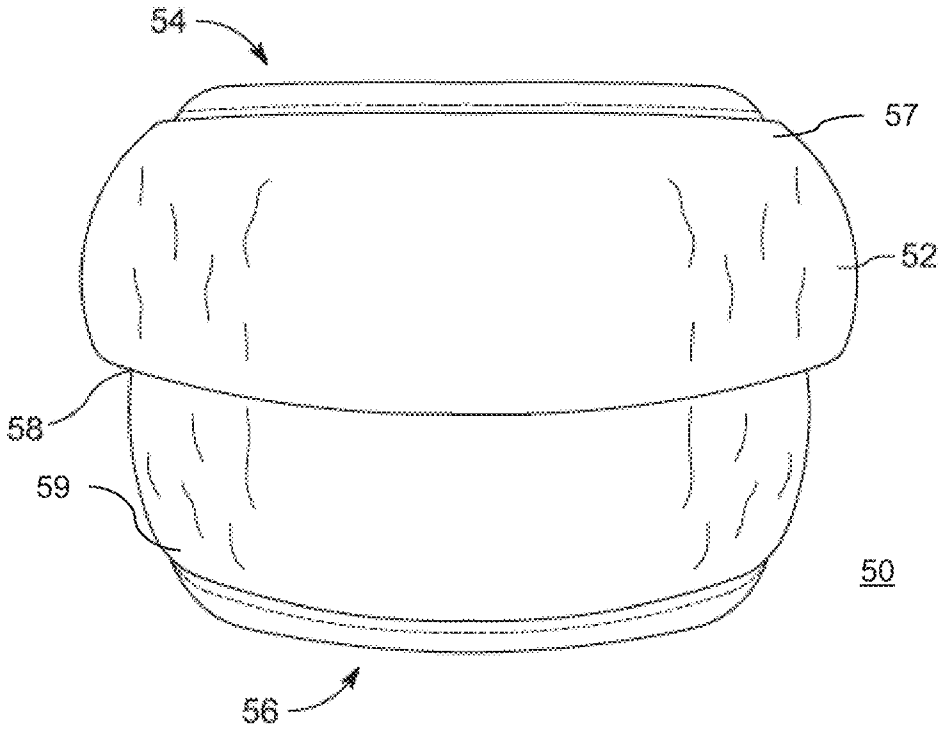

Turning to FIG. 5F, further embodiments of prosthetic valve 50 will possess a covering 52 with a general mushroom shape, where covering 52 possesses a first portion 57 with a curved increase in thickness from inflow portion 54 toward a position 58. The covering 52 will also possess a second portion 59 extending toward the outflow portion 56 from position 58, which has a generally cylindrical shape.

It should be noted that while some of the embodiments illustrated in FIGS. 5A to 5F are illustrated with loop-over stitching and other embodiments are illustrated with an edge strip and radial, horizontal stitching, these illustrations are not meant to be limiting the stitching type on any specific embodiment, and many embodiments will possess loop-over stitching or an edge strip independent of the shape of the covering 52 on the prosthetic valve 50.

Figure 6A:
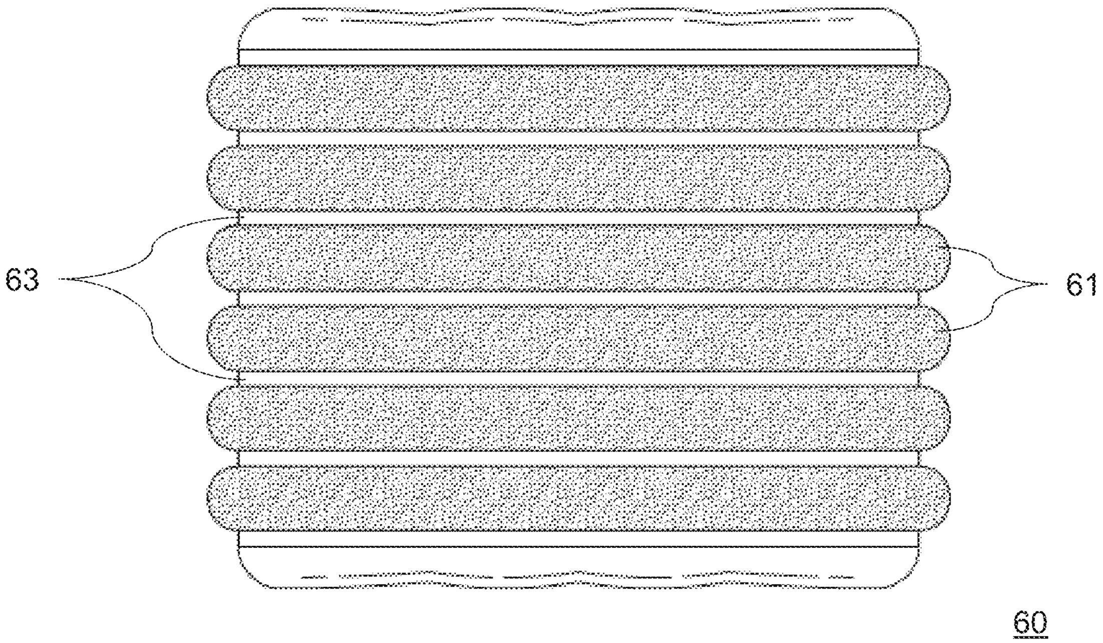
FIG. 6A illustrates a side view of an embodiment of a prosthetic heart valve possessing a woven cloth covering in accordance with various embodiments

Turning to FIG. 6A, numerous embodiments of a covered valve 60 possess a covering made of a woven cloth or fabric possessing a plurality of floated yarn sections 61 (e.g., protruding or puffing sections). Details of exemplary covered valves with a plurality of floated yarn sections 61 are further described in U.S. Patent Pre-Grant Publication Nos. US2019/0374337 A1, US2019/0192296 A1, and US2019/0046314 A1, the disclosures of which are incorporated herein in their entireties for all purposes. In certain embodiments, the float sections are separated by one or more horizontal bands 63. In many embodiments, horizontal bands 63 are constructed via a leno weave, which improve the strength of the woven structure. In some embodiments of woven cloth, vertical fibers (e.g., running along the longitudinal axis of the valve 60) comprise a yarn or other fiber possessing a high level of expansion, such as a texturized weft yarn, while horizontal (e.g., running circumferentially around valve 60) fibers in a leno weave comprise a low expansion yarn or fiber.

Floated yarn sections 61 can be heat set to obtain a desired size and texture, e.g., to make them softer and more texturized. Texturizing can be achieved by having the constituent fibers of the strands/yarns used in section 61 twisted, heat set, and untwisted such that the fibers retain their deformed, twisted shape and create a voluminous fabric. In some embodiments, floated yarn section 61 can be formed from textured PET yarns without any weave structure. In certain embodiments, the covering of covered valve 60 can be heat shrunk to achieve a stretchability between 80-160%.

In a variety of embodiments, a woven cloth resembles a greige fabric when assembled and under tension (e.g., when stretched longitudinally on a compressed valve 60 prior to delivery of a valve 60). When a valve 60 is deployed and expanded, tension on floats 61 is relaxed allowing expansion of the floats 61. In many embodiments, the number and sizes of floats 61 is optimized to provide a level of expansion to prevent paravalvular leakage across the mitral plane (e.g., to have a higher level of expansion thickness) and/or a lower crimp profile (e.g., for delivery of the valve), as further described in U.S. Patent Pre-Grant Publication Nos. US2019/0374337 A1, US2019/0192296 A1, and US2019/0046314 A1. Additionally, bands 63 can be optimized to allow for attachment of the covering to the valve based on the specific size or position of struts or other structural elements on the valve.

Figure 6B:
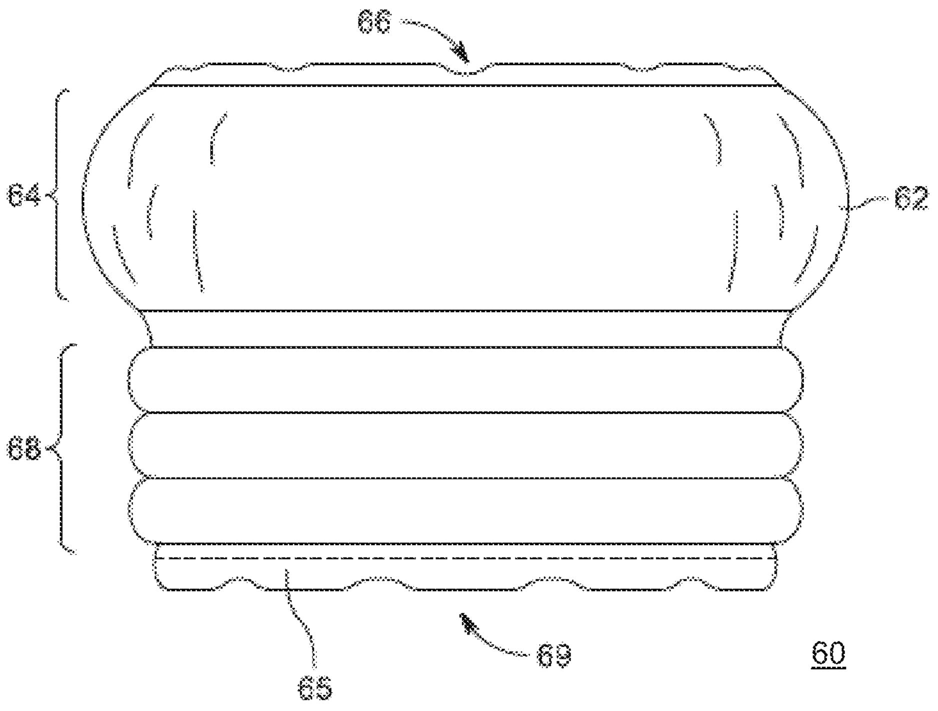
FIG. 6B illustrates a side view of an embodiment of a prosthetic heart valve possessing a hybrid covering in accordance with various embodiments.

In some embodiments, a covered valve 60 (e.g., as shown in FIG. 6B) possesses a hybrid covering 62, which can comprise a plurality of different types of coverings working together. In the example shown in FIG. 6B, a first portion 64 of the hybrid covering 62 near the inflow portion 66 of the valve 60 comprises foam or other expandable material, while a second portion 68 of the hybrid covering 62 near the outflow portion 69 of the valve 60 comprises woven cloth or fabric, which can have one or more expandable portions 61. Further, in FIG. 6B, the foam or other expandable material has a larger expanded profile at the inflow portion to increase the ability to form a seal and prevent paravalvular leakage around the mitral plane. Due to the compressibility of the foam/expandable material coupled with the low-profile ability of the woven cloth, this foam-cloth hybrid skirt beneficially achieves a low profile when the valve is crimped. The expanded valve expands radially outwardly at the inflow end to allow for good paravalvular sealing.

Figure 6C:
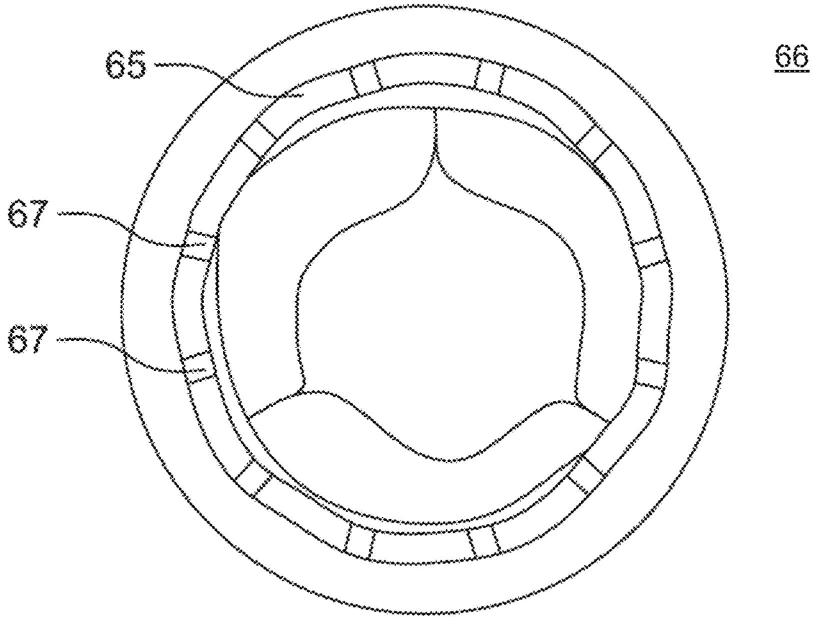
FIGS. 6C-6E illustrate views of an embodiment of a prosthetic heart valve possessing an edge covering in accordance with various embodiments.
Figure 6D:
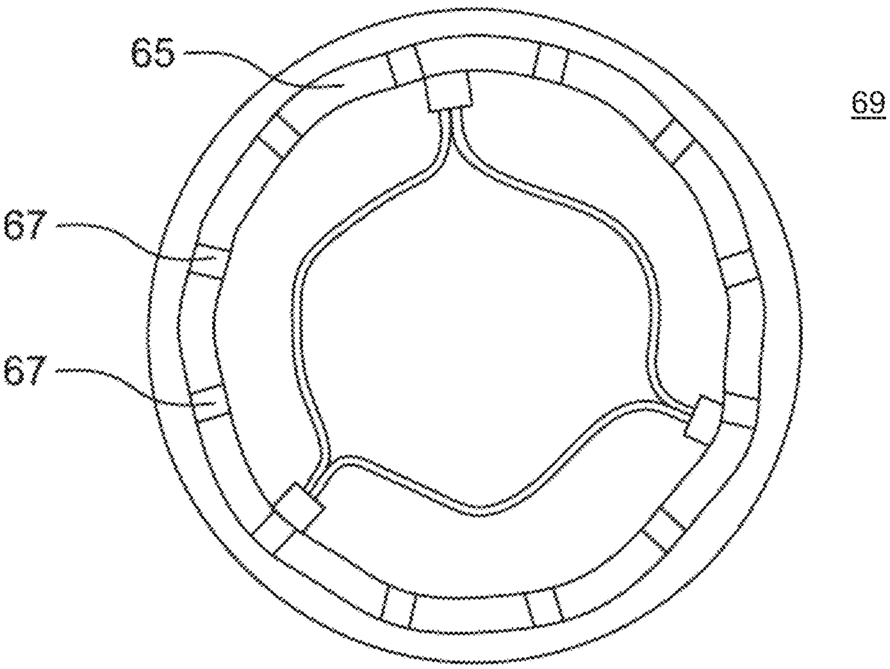
Figure 6E:
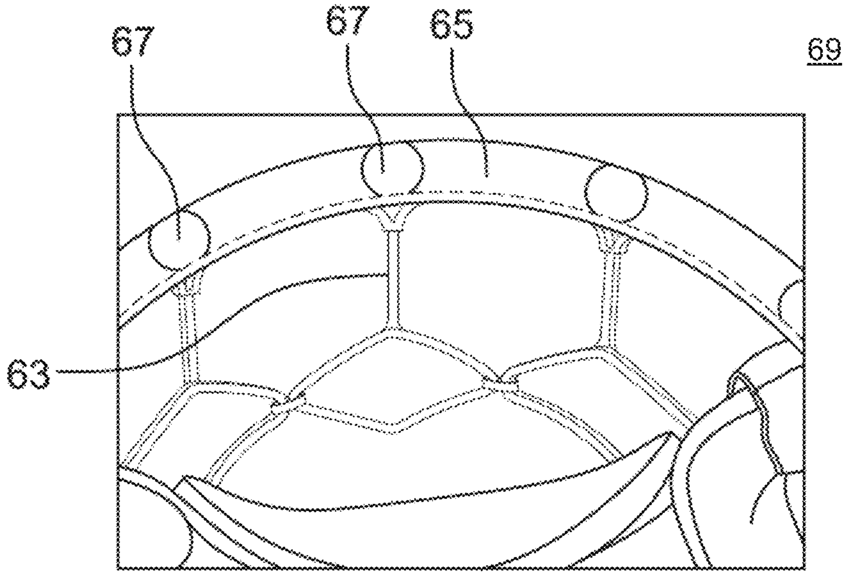

Additionally, FIG. 6B illustrates a variation on edge covering 65. In particular, edge covering 65 in many embodiments will possess a series of openings 67 placed in edge covering 65 (FIGS. 6C-6E). In certain embodiments, the openings are created via die cutting, laser cutting, punching, or any other method of creating an opening in the material of the edge covering 65. Turning to FIGS. 6C and 6D, perspective views of the inflow portion 66 (FIG. 6C) and outflow portion 69 (FIG. 6D) are illustrated. As seen in these figures, the edge covering 65 will possess openings 67 on both ends of a prosthetic valve of many embodiments. Further, FIG. 6E illustrates a perspective view from within the outflow portion 69, illustrating edge covering 65 with a series of openings 67. As illustrated in FIG. 6E, the frame 63 of a prosthetic valve of many embodiments possesses angled struts, which allow compressibility around a catheter or other delivery device. The openings 67 are cut, such that they align between apices in frame 63. By placing openings between apices, the edge covering 65 will not bulge, thus minimize the outer diameter of a crimped valve, when the prosthetic valves of certain embodiments are crimped around a catheter or other delivery device.

The various embodiments illustrated in FIGS. 3A-6E are described as being of foam and/or woven cloth, additional embodiments are constructed of materials capable of providing the same effect, including woven PET, knitted PET, braided PET, woven PTFE, knitted PTFE, braided PTFE, ePTFE membrane, electrospun ePTFE, thermoplastic membrane, dipped thermoplastic, sprayed thermoplastic, foam, and combinations thereof.

Figure 7A:
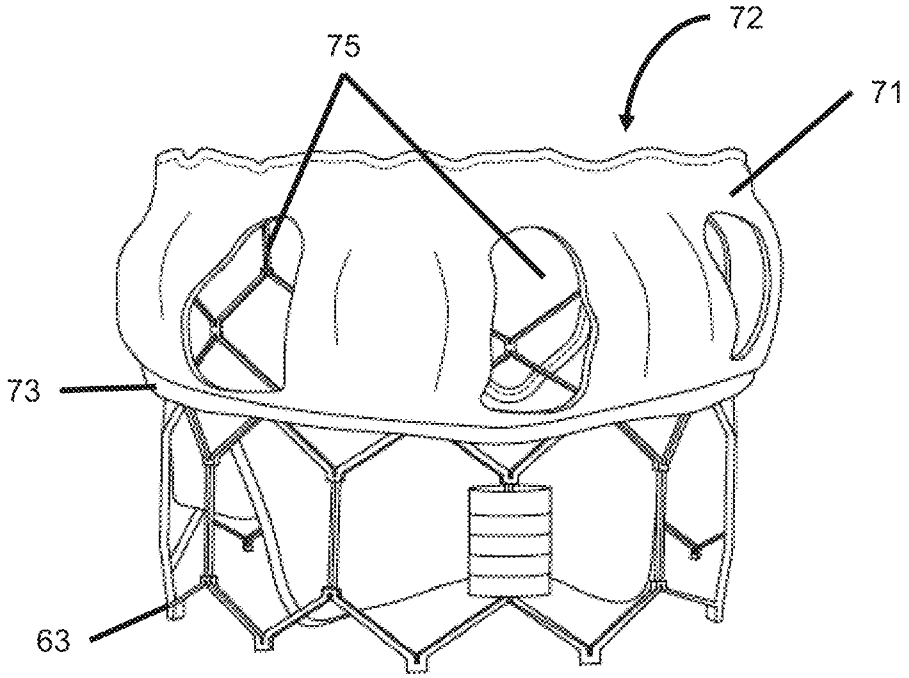
FIGS. 7A-7C illustrate views of a prosthetic heart valve possessing a flexible flange support in accordance with various embodiments.
Figure 7B:
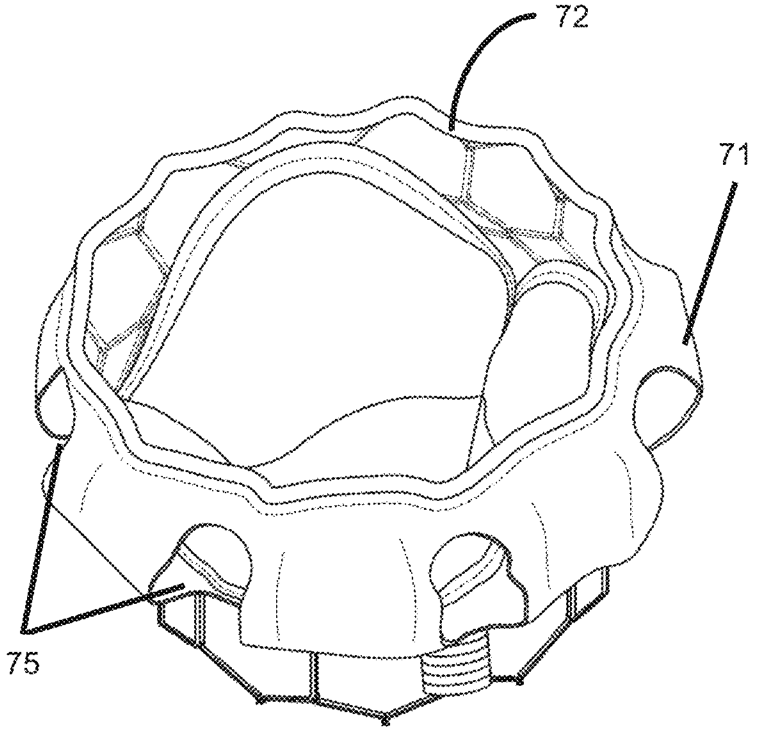
Figure 7C:
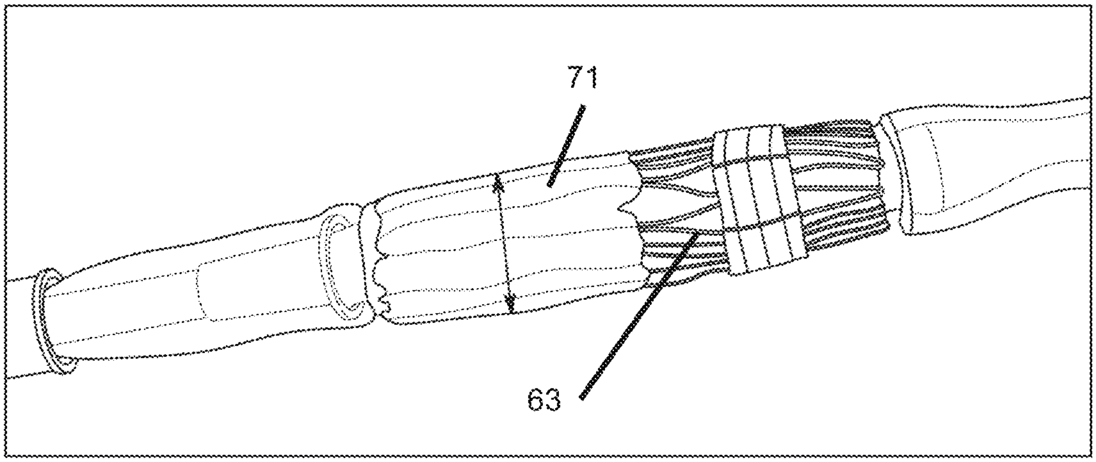

In some embodiments, prosthetic valves with coverings will utilize a material that is placed under and/or incorporated with the covering that can be compressed or manipulated and returns to a specific shape once a force is removed. FIGS. 7A to 7B illustrate a flange support structure 71 to allow a covering to expand into its full position. Specifically, FIGS. 7A to 7B illustrate a flange support structure 71 secured to a frame 63 of many embodiments. In a number of embodiments, the flange support structure 71 is secured near the inflow portion 72 and at a middle position 73 of frame 63. In some embodiments, the securing is accomplished via stitching, welding, or any other suitable method for securing a flange support structure 71 to the frame 63. In a number of embodiments, the flange support structure 71 possess a series of windows 75, which allow the flange support structure 71 to bulge radially outward from the frame 63 and allow the covering to expand to its full position. FIG. 7C illustrates an embodiment of prosthetic valve with a flange support structure 71 crimped onto a delivery device, such as a catheter. In FIG. 7C, the compressed frame 63 and flange support structure 71 do not drastically increase the outer diameter (double arrow) of the crimped frame 63. The flange support structure 71 can be constructed of any suitable material, such as biocompatible and/or atraumatic to native tissue. In certain embodiments, the flange support structure 71 is constructed from ePTFE. Additionally, the number of windows 75 placed in flange support structure 71 can be any number that is capable of allowing the flange support structure 71 to bulge outwardly from frame 63. In some embodiments, 8 windows will be cut, but additional embodiments will possess 10, 12, 16, 24, or more windows.

Figure 8:
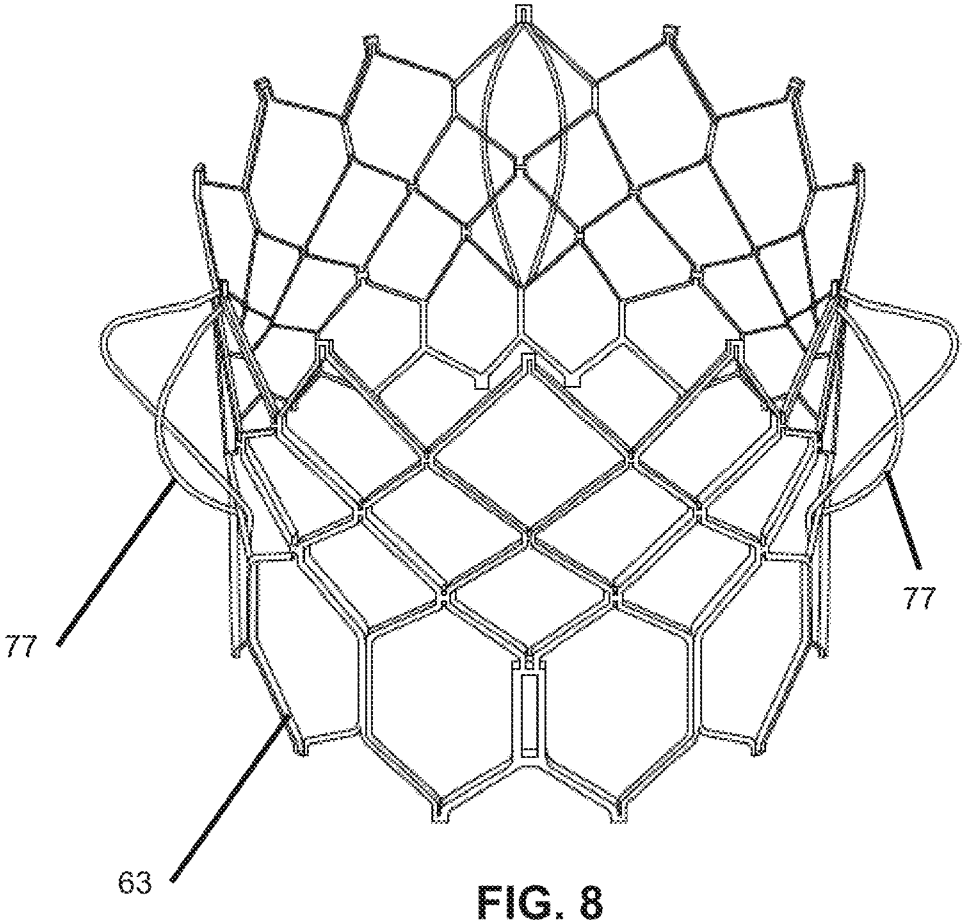
FIG. 8 illustrates a prosthetic heart valve possessing outward struts in accordance with various embodiments.

Additional embodiments, such as illustrated in FIG. 8, outward struts 77 will be placed on the frame 63 of many embodiments that expand via monofilament warping and/or buckling. In many of these embodiments, the outward struts 77 are constructed of a memory material, such as nitinol, and placed under or incorporated within a foam or cloth/fabric covering, the memory material can aid in the resilient expansion of the covering. Any number of outward struts 77 of many embodiments can be placed at positions to allow for the expansion of the covering. Some embodiments will place outward struts 77 at 3 positions around the frame 63, while additional embodiments will place outward struts 77 at 4, 6, or 8 locations around the frame 63. In some embodiments, two outward struts 77 are joined to frame 63 at approximately the same position and expand in a general V-shape outwardly from the frame 63, while other embodiments will possess a single outward strut 77 at a specific location expanding outwardly from the frame 63. While FIG. 8 is illustrated for expansion at or near the atrial or inflow side of frame 63, a similar mechanism is used to expand pocket coverings (e.g., FIG. 4C) in the ventricular or outflow side of frame 63 to assist in expansion of a pocket for encapsulating blood or embolic material.

It should be noted that the embodiments illustrated in FIGS. 3A to 8 are illustrative and not meant to be exclusive to or limiting on any other embodiment, unless the features illustrated are not combinable. For example, several embodiments will combine flange support structures, such as illustrated in FIGS. 7A to 7C along with a foam covering, such as illustrated in any of FIGS. 4A to 6A and/or with a flange as illustrated in any of FIGS. 3A to 3C.

Docking Devices

Anchors/docking devices (e.g., docks) according to example embodiments of the invention are shown in FIGS. 9A to 16, and these can comprise a coiled shape. It is possible that certain docking devices in an atrio-ventricular position may migrate further or deeper into the ventricle post-deployment of the docking device than desired. It may be beneficial to avoid too much "dock drop" to help avoid paravalvular leakage, e.g., sealing the docking device and prosthetic valve seal together higher on the native leaflets may help prevent paravalvular leaks that might occur if done lower on the chordae tendineae. Additionally, higher placement (e.g., by avoiding dock drop) may help long term stability of the valve, because the leaflets are thicker and more robust near the annulus rather than near their distal end, thus anchoring at or near the annulus is expected to be stronger and provide longer term stability. Also, higher placement of the prosthetic valve may help avoid abrasion of the valve against the native tissue (e.g., against the native leaflets and/or chordae tendineae), by making the artificial valve less likely to rub against the leaflets and/or chordae tendineae.

Figure 9A:
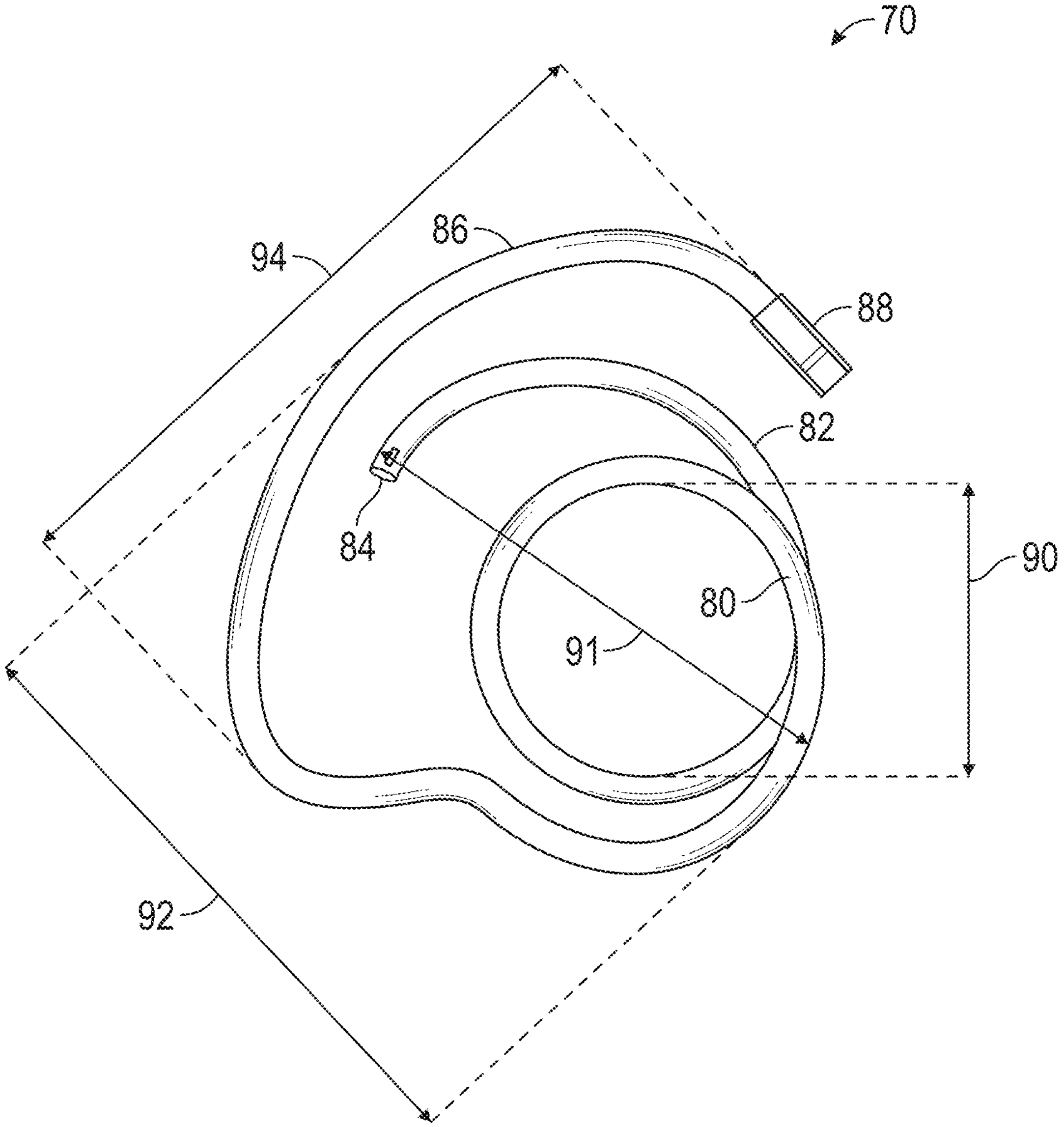
FIG. 9A illustrates a top view of an example embodiment of a docking device or a core of a docking device with three points of contact in the left atrium in accordance with various embodiments.
Figure 9B:
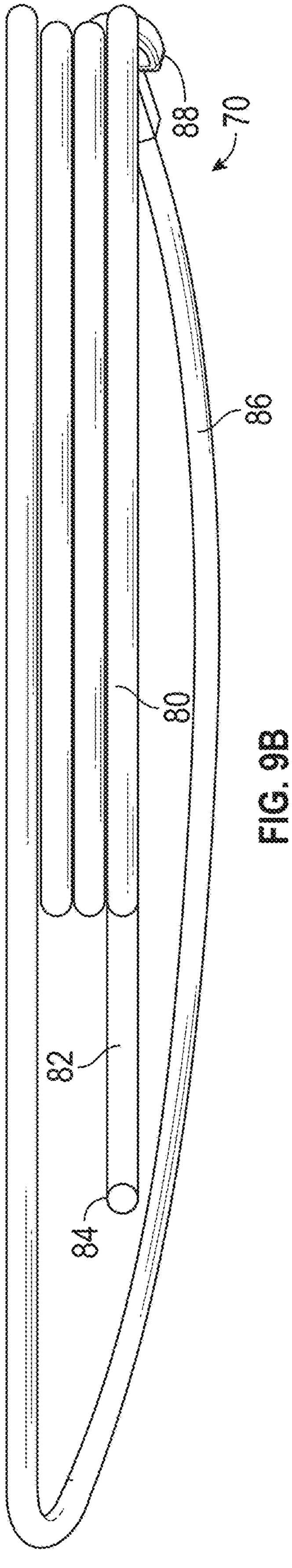
FIGS. 9B and 9C illustrate side views of an example embodiment of a docking device or a core of a docking device with three points of contact in the left atrium in accordance with various embodiments.
Figure 9C:
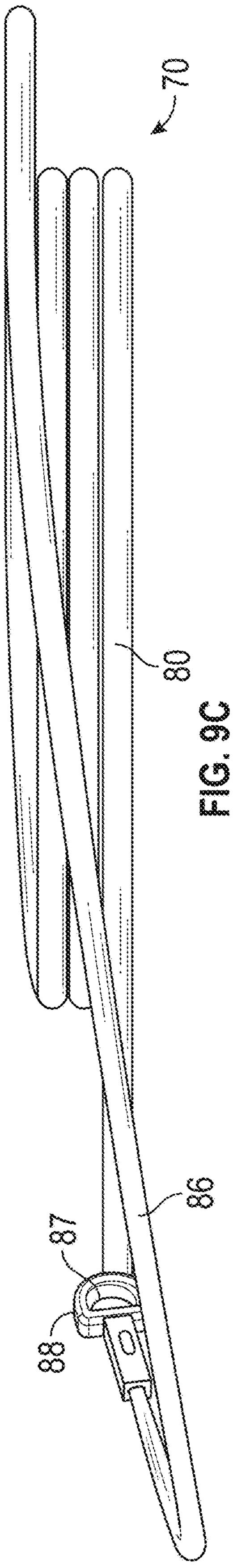
Figure 10A:
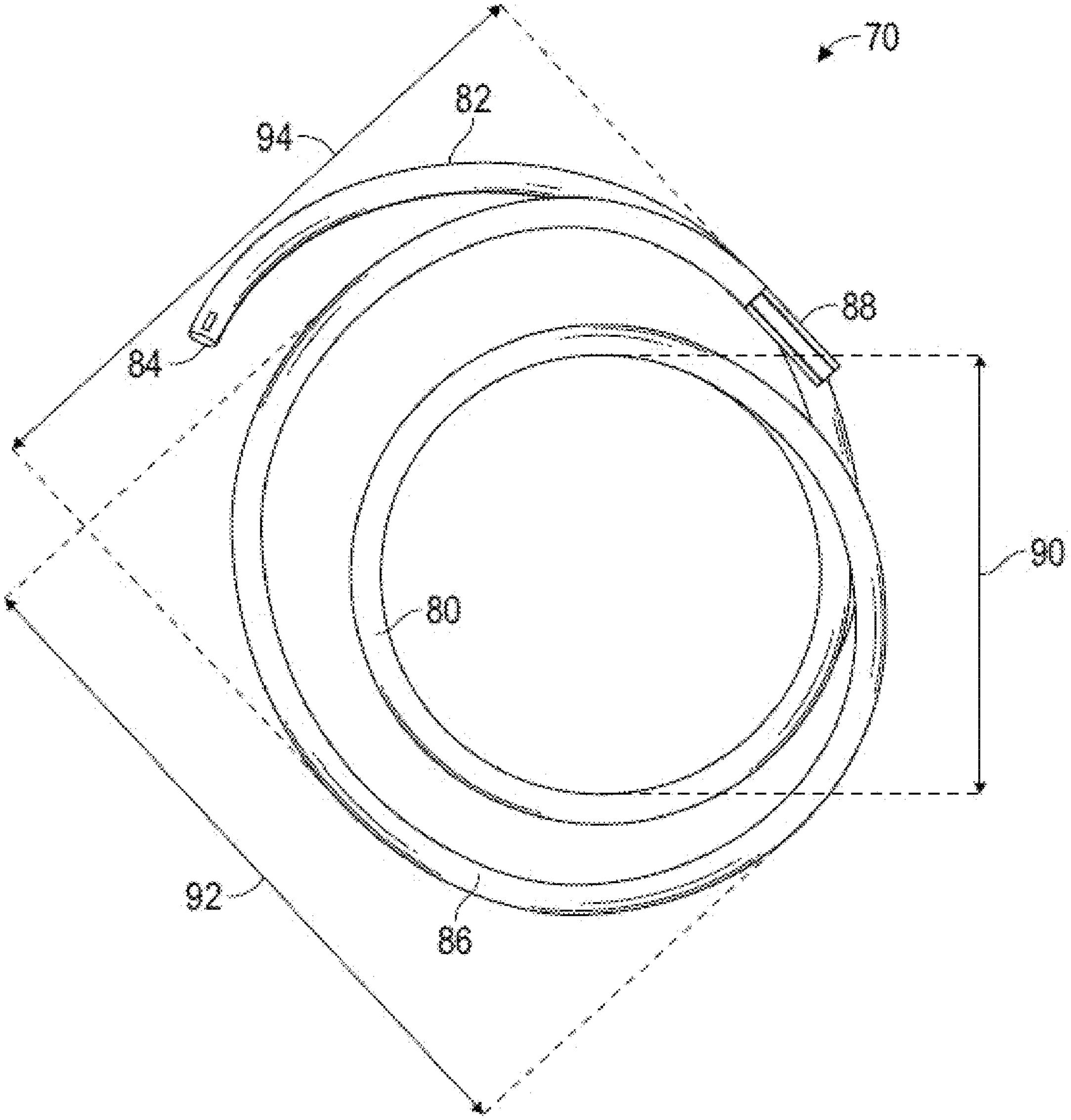
FIGS. 10A and 10B illustrate top views of example embodiments of docking devices with a flat stabilization or atrial turn in accordance with various embodiments.
Figure 10B:
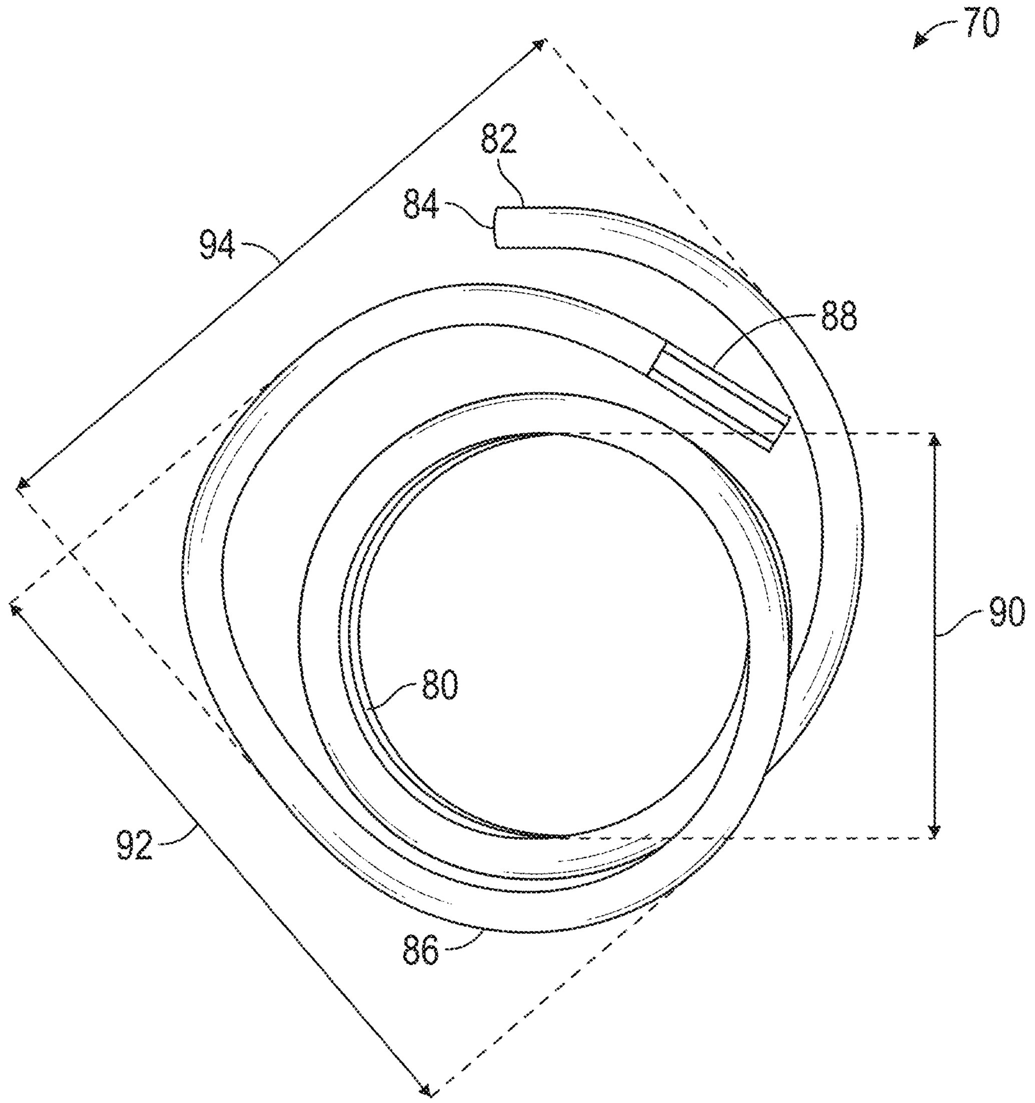
Figure 10C:
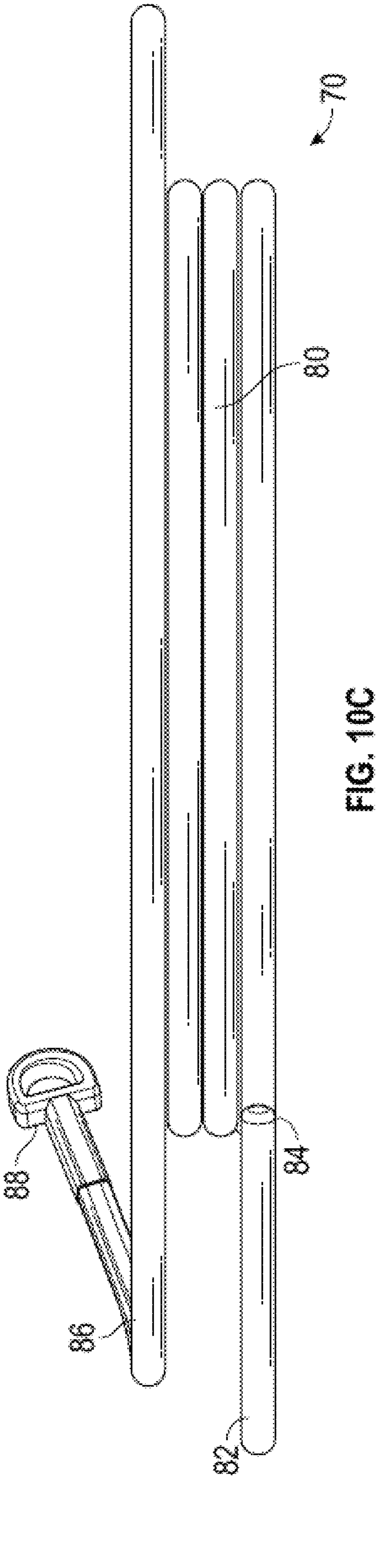
FIGS. 10C and 10D illustrate side views of an example embodiment of a docking device or a core of a docking device with a flat stabilization or atrial turn in accordance with various embodiments.
Figure 10D:
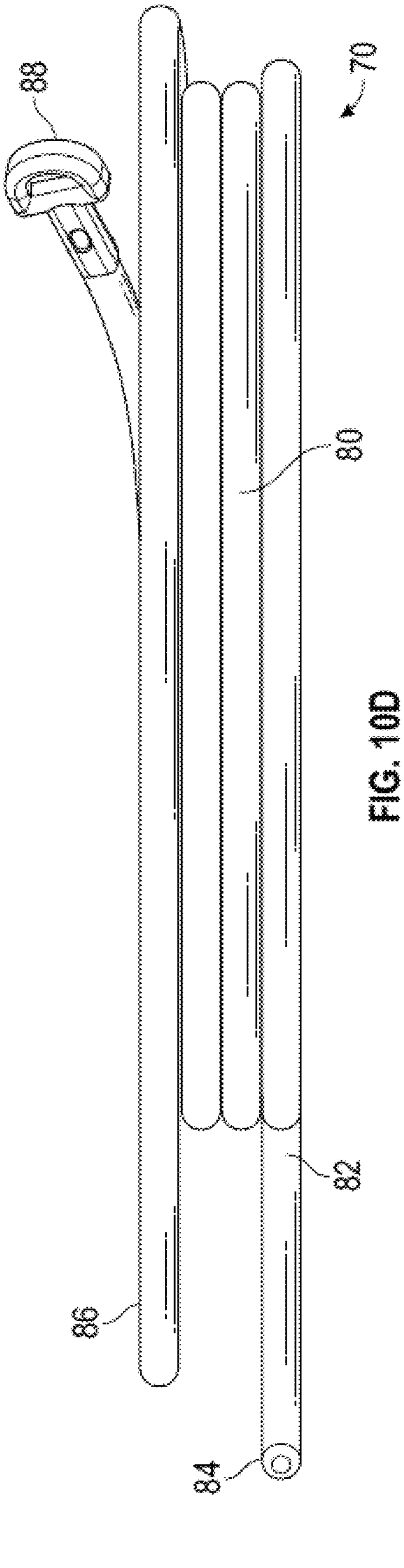
Figure 11A:
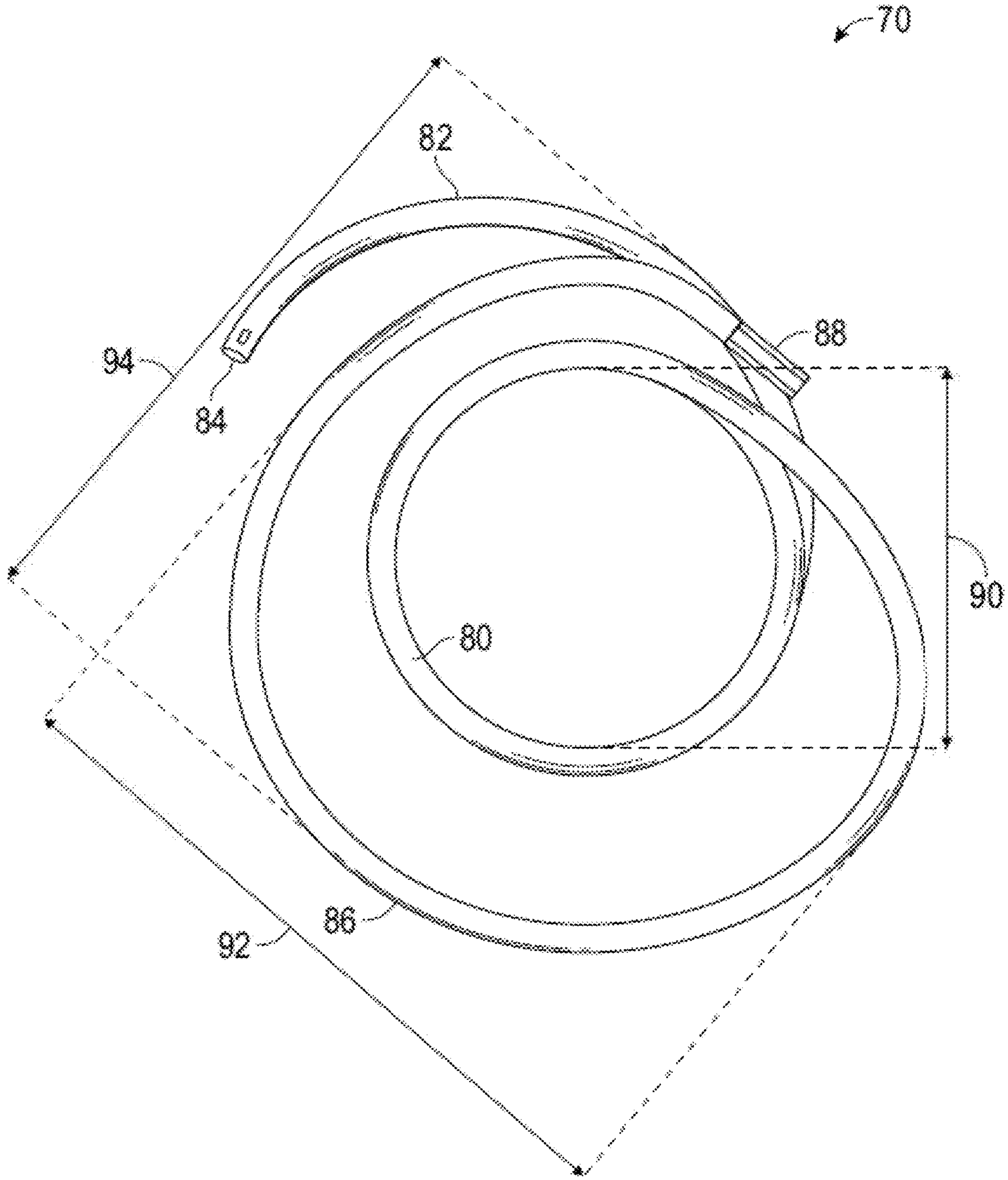
FIG. 11A illustrates a top view of an example embodiment of a hybrid docking device or a core of a hybrid docking device in accordance with various embodiments.
Figure 11B:
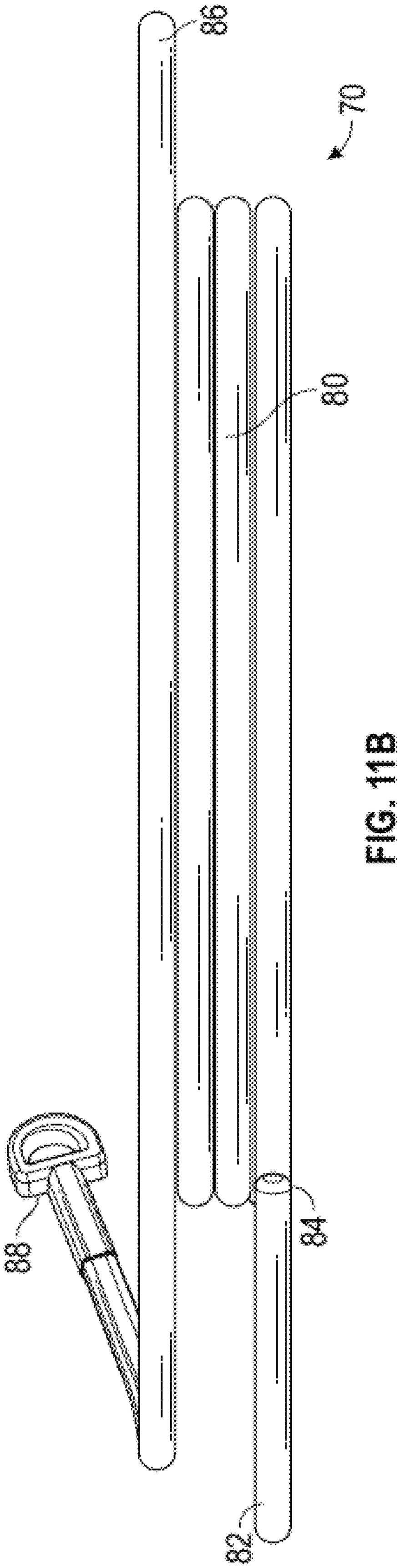
FIGS. 11B and 11C illustrate side views of an example embodiment of a hybrid docking device or a core of a hybrid docking device in accordance with various embodiments.
Figure 11C:
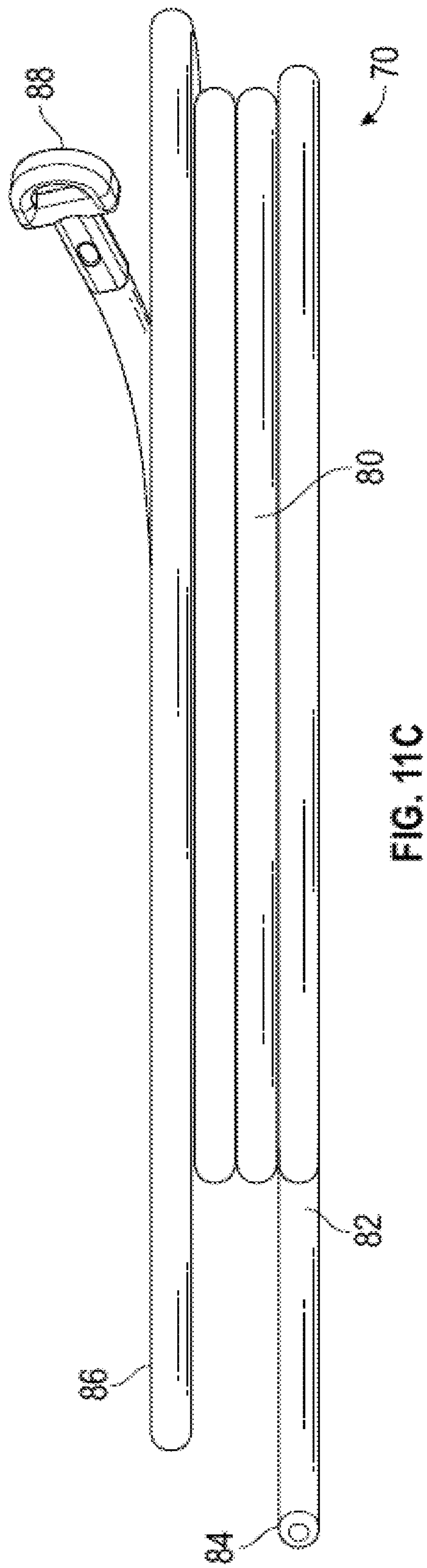

Paravalvular leakage can occur due to a number of causes, including where the native annulus is too large in comparison the prosthetic valve; the commissural leaflets are too short and/or are damaged; the implantation of a docking device did not completely capture the native leaflets; the crossing of a docking device from one side of the valve to the other causes a small gap (e.g., in the commissure); the placement of a prosthetic valve is too biased toward the lateral, anterior, posterior, and/or medial sides of a native valve; and/or anatomical abnormalities in certain patients (e.g., clefts, those associated with degenerative mitral regurgitation, etc.). Various embodiments of this disclosure are designed to compensate for, avoid, reduce, and/or obviate many of these issues, including by holding the dock up on both sides of the native mitral valve (thus reducing and/or inhibiting dock drop by maintaining the dock and prosthetic valve close to the native annulus plane), by creating a better seal around a prosthetic valve, by creating a better seal above the native annulus, etc. For example, FIGS. 9A-9C illustrate a version of the dock or a core of the dock configured to provide one or more points or regions of contact between the dock and the left atrial wall, such as at least three points of contact in the left atrium or complete contact on the left atrial wall, while FIGS. 10A-10C illustrate a flat dock or core of a flat dock, where the atrial portion lies on the mitral plane, and FIGS. 11A-11C illustrate a hybrid dock or core of the hybrid dock where the stabilization or atrial turn creates a ring around a deployed prosthetic valve to seal the valve and reduce paravalvular leakage. In the examples of FIGS. 9A to 11C, the docking device 70 includes a coil or coiled portion with a plurality of turns extending along a central axis of the docking device 70. The coil or coiled portion can be continuous and can extend generally helically, with various differently sized and shaped sections, as described in greater detail below. The docking devices 70 shown in FIGS. 9A to 11C can be configured to fit at the mitral position but can be shaped and/or adapted similarly or differently in other embodiments for better accommodation at other native valve positions as well, such as at the tricuspid valve. Advantageously, the docking device geometries of the present disclosure provide for engagement with the native anatomy that can provide for increased stability and reduction of relative motion between the docking device, the prosthetic valve docked therein, and the native anatomy. Reduction of such relative motion can prevent material degradation of components of the docking device and/or the prosthetic valve docked therein and can prevent damage/trauma to the native tissues.

The docking device 70 of many embodiments includes a central region 80 with a coil, coiled portion, or multiple coils (e.g., 2 coils, 3 coils, 4 coils, between 2-5 coils, or more). The coiled portion or coils of the central region 80 can be similarly sized and shaped or vary in size and/or shape. In some implementations, the central region 80 comprises three or approximately three full coil turns having substantially equal inner diameters. The central region 80 of the docking device 70 serves as the main landing region or holding region for holding the expandable prosthetic valve when the docking device 70 and the valve prosthesis are implanted into a patient's body. In some embodiments, the docking device 70 has a central region 80 with more or less than three coil turns, depending for example, on the patient's anatomy, the amount of vertical contact desired between the docking device 70 and the valve prosthesis (e.g., transcatheter heart valve or THV), and/or other factors. The coiled portion or coil(s) of the central region 80 can also be referred to as the "functional coils" or "functional turns" since the properties of these coils contribute the most to the amount of retention force generated between the valve prosthesis, the docking device 70, and the native mitral leaflets and/or other anatomical structures.

Various factors can contribute to the total retention force between the docking device 70 and the prosthetic valve held therein. A main factor is the number of turns included in the functional coils, while other factors include, for example, an inner diameter of the functional coils, friction force (e.g., between the coils and the prosthetic valve), and the strength of the prosthetic valve and the radial force the valve applies on the coil. A docking device can have a variety of numbers of coils and/or turns. The number of functional turns can be in ranges from just over a half turn to 5 turns, or one full turn to 5 turns, or more. In one embodiment with three full turns, an additional one-half turn is included in the ventricular portion of the docking device. In another embodiment, there can be three full turns total in the docking device. In one embodiment, in the atrial portion of the docking device, there can be one-half to three-fourths turn or one-half to three-fourths of a circle. While a range of turns is provided, as the number of turns in a docking device is decreased, the dimensions and/or materials of the coil and/or the wire that the coil is made from can also change to maintain a proper retention force. For example, the diameter of the wire can be larger and/or the diameter of the function coil turn(s) in a docking device with fewer coils. There can be a plurality of coils in the atrium and in the ventricle.

A size of the functional coils or coils of the central region 80 is generally selected based on the size of the desired THV to be implanted into the patient. Generally, the inner diameter 90 of the functional coils/turns (e.g., of the coils/turns of the central region 80 of the docking device 70) will be smaller than the outer diameter of the expandable heart valve, so that when the prosthetic valve is expanded in the docking device, additional radial tension or retention force will act between the docking device and the prosthetic valve to hold the prosthetic valve in place. The retention force needed for adequate implantation of a prosthetic valve varies based on the size of the prosthetic valve and on the ability of the assembly to handle mitral pressures of approximately 180 mm Hg. For example, based on hemodynamic data using a prosthetic valve with a 29 mm expanded outer diameter, a retention force of at least 15.8 N can be needed between the docking device and the prosthetic valve in order to securely hold the prosthetic valve in the docking device and to resist or prevent valve regurgitation or leakage. However, under this example, to meet this 15.8 N retention force requirement with statistical reliability, a target average retention force should be substantially greater, for example, approximately 30 N.

In many embodiments, the retention force between the docking device and the valve prosthesis reduces dramatically when a difference between the outer diameter of the prosthetic valve in its expanded state and the inner diameter of the functional coils is less than about 5 mm, since the reduced size differential can be too small to create sufficient retention force between the components. For example, when, in one embodiment, a prosthetic valve with a 29 mm expanded outer diameter was expanded in a set of coils with a 24 mm inner diameter, the retention force observed was about 30 N, but when the same prosthetic valve was expanded in a set of coils with a 25 mm inner diameter (e.g., only 1 mm larger), the retention force observed dropped significantly to only 20 N. Therefore, in some embodiments, in order to create a sufficient retention force between the docking device and a 29 mm prosthetic valve, the inner diameter of the functional coils (e.g., the coils of the central region 10 of docking device 1) should be 24 mm or less. Often, the inner diameter of the functional coils (e.g., central region 80 of the docking device 70) should be selected to be at least about 5 mm less than the prosthetic valve that is selected for implantation, though other features and/or characteristics (e.g., friction enhancing features, material characteristics, etc.) can be used to provide better retention if other sizes or size ranges are used, as various factors can affect retention force.

However, diameter of the functional coils should be selected based on consideration and balancing of several factors to obtain optimal results. For example, the native anatomy between the mitral annulus at the mitral plane and the papillary muscle heads forms a generally trapezoidal shape, and the tissue of the mitral leaflets is thicker near the mitral plane and thins the further below the mitral plane. Smaller diameters of the central region 80 may encourage the docking device 70 to install further below the mitral plane than desirable (a similar effect can be observed at the tricuspid valve as well). When docking occurs at a location where the mitral leaflets are thinner, this may result in a suboptimal anchoring position for the prosthetic valve. Accordingly, size, diameters, and other features that help hold the prosthetic valve higher on the leaflets can be beneficial. In addition, a size of the inner diameter of the functional coils or central region 80 can also be selected to draw the native anatomy closer together, in order to at least partially offset or counteract valve regurgitation that is caused by stretching out of the native valve annulus as a result of, for example, left ventricular enlargement.

It is noted that the desired retention forces discussed above are applicable to embodiments for mitral valve replacements. Therefore, other embodiments of the docking device that are used for replacement of other valves can have different size relationships based on the desired retention forces for valve replacement at those respective positions. In addition, the size differentials can also vary, for example, based on the materials used for the valve and/or the docking device, whether there are any other features to prevent expansion of the functional coils or to enhance friction/locking, and/or based on various other factors.

In embodiments where the docking device 70 is used at the mitral position, the docking device can first be advanced and delivered to the native mitral valve annulus, and then set at a desired position, prior to implantation of the prosthetic heart valve. In some embodiments, the docking device 70 is flexible and/or made of a shape memory material, so that the coils of the docking device 70 can be straightened for delivery via a transcatheter approach as well. In some embodiments, the coil is made of another biocompatible material, such as stainless steel. Some of the same catheters and other delivery tools can be used for both delivery of the docking device 70 and the prosthetic valve, without having to perform separate preparatory steps, simplifying the implantation procedure for the end user.

Since the functional coils/turns or coils/turns of the central region 80 of the docking device 70 are kept relatively small in diameter (e.g., the central region 80 in one embodiment can have an inner diameter of between approximately 21-24 mm (e.g., ±2 mm) or another diameter smaller than the prosthetic valve and/or the native annulus) in order to increase retention force with the prosthetic valve, it might be difficult to advance the docking device 70 around the existing leaflets and/or chordae tendineae to a desired position relative to the native mitral annulus. This is especially true, if the entire docking device 70 is made to have the same small diameter as the central region 80. Therefore, the docking device 70 can have a distal or lower region 82 that comprises and/or consists of a leading coil/turn (sometimes referred to as an encircling turn or a leading ventricular coil/turn) of the docking device 70, which has a lower diameter that is greater than the diameter of the functional coils/turns or of the coils/turns of central region 80.

Features of the native anatomy, especially in the right and left ventricles, have variable dimensions. For example, native mitral anatomy can have an approximately 35 mm to 45 mm greatest width on a long axis. The diameter or width of the encircling turn or leading coil/turn (e.g., ventricular coil/turn) of the lower region 82 can be selected to be larger to more easily navigate a distal or leading tip 84 of the docking device 70 around and encircle the features of the native anatomy (e.g., leaflets and/or chordae tendineae).

Various sizes and shapes are possible, for example, in one embodiment, the diameter could be any size from 25 mm to 75 mm. The term "diameter" as used in this disclosure does not require that a coil/turn be a complete or perfectly-shaped circle but is generally used to refer to a greatest width across opposing points of the coil/turn. For example, with respect to the leading coil/turn, diameter can be measured from the distal tip 84 to the opposite side, as if the lower region or leading coil/turn 82 formed a complete rotation, as shown as diameter 91 in FIG. 9A. Alternatively, the diameter can be considered double a radius of curvature of the leading coil/turn. In various embodiments, the diameter 91 of the lower region 82 is enough to encircle anatomical features within the ventricle, including mitral leaflets and chordae, such that the inner diameter of the lower region 82 is equal to or greater than the inner diameter of the central region 80 (e.g., diameter 90 shown in FIG. 10A). Further embodiments are designed to be atraumatic to other ventricular anatomy, including walls or septa within the ventricle. As such, the diameter 91 of the lower region 82 is small enough to not contact walls or septa. In certain embodiments, the diameter 91 of the lower region 82 ranges from approximately 33-37 mm (e.g., ±2 mm). In one embodiment, the lower region 82 of the docking device 70 (e.g., the leading coil/turn) has a diameter 91 of 43 mm or approximately 43 mm (e.g., ±2 mm), in other words the radius of curvature at the leading coil/turn can be 21.5 mm or approximately 21.5 mm (e.g., 2 mm). In other embodiments, the diameter 91 of the lower region 82 of the docking device 70 is in a range of 28-38 mm, 30-36 mm, 31-35 mm, 32-34 mm, or 32.5-33.5 mm (e.g., radius of curvature in a range of 16.25-16.75 mm).

Having a leading coil/turn with a larger size than the functional coils can help more easily guide the coils around and/or through the chordae tendineae geometry, and most importantly, adequately around both native leaflets of the native valve (e.g., the native mitral valve, tricuspid valve, etc.). Once the distal tip 84 is navigated around the desired native anatomy, the remaining coils of the docking device 70 can also be guided around the same features. In some embodiments, the size of the other coils can be reduced sufficiently to cause the corralled anatomical features to be pulled radially inwardly or slightly radially inwardly. Meanwhile, the length of the enlarged lower region 82 or the leading coil/turn can be kept relatively short, to prevent or avoid obstruction or interference of the flow of blood along the ventricular outflow tract by the lower region 82 or the leading coil/turn. For example, in one embodiment, the enlarged lower region 82 or the leading coil/turn extends for only about half a loop or rotation. With a lower region 82 or the leading coil/turn having this relatively short length, when a prosthetic valve is expanded into the docking device 70 and the coils of the docking device 70 start to unwind slightly due to the size differential between the docking device and the prosthetic valve, the lower region 82 or the leading coil/turn may also be drawn in and shift slightly. Under this example, after expansion of the prosthetic valve, the lower region 82 or the leading coil/turn can be similar in size and be aligned substantially with the functional coils of the docking device 70, rather than continuing to project away from the functional coils, thereby reducing any potential flow disturbances. Other docking device embodiments can have lower regions that are longer or shorter, depending on the particular application.

In various embodiments, the docking device 70 illustrated in FIGS. 9A to 11 also includes an enlarged proximal or upper region 86 that comprises and/or consists of a stabilizing coil/turn (e.g., which can be an atrial coil/turn) of the docking device 70. During a transient or intermediate stage of the implantation procedure, that is, during the time between the deployment and release of the docking device 70 and final delivery of the prosthetic valve, there is a possibility that the coil could be shifted and/or dislodged from its desired position or orientation, for example, by regular heart function. Shifting of the docking device 70 could potentially lead to a less secure implantation, misalignment, and/or other positioning issues for the prosthetic valve. A stabilization feature or coil can be used to help stabilize the docking device in the desired position. For example, the docking device 70 can include the upper region 86 with an enlarged stabilization coil/turn (e.g., an enlarged atrial coil/turn having a greater diameter 92 and/or 94 than the functional coils) intended to be positioned in the circulatory system (e.g. in the left atrium) such that it can stabilize the docking device. For example, the upper region 86 or stabilization coil/turn can be configured to abut or push against the walls of the circulatory system (e.g., against the walls of the left atrium), in order to improve the ability of the docking device 70 to stay in its desired position prior to the implantation of the prosthetic valve.

The stabilization coil/turn (e.g., atrial coil/turn) at the upper region 86 of the docking device 70 in the embodiments shown can extend up to about one full turn or rotation, and terminates at a proximal tip 88. In other embodiments, the stabilization coil/turn (e.g., atrial coil) can extend for more or less than one turn or rotation, depending for example on the amount of contact desired between the docking device and the circulatory system (e.g., with the walls of the left atrium) in each particular application. The radial size of the stabilization coil/turn (e.g., atrial coil) at the upper region 86 can also be significantly larger than the size of the functional coils in the central region 80, so that the stabilization coil/turn (e.g., atrial coil or atrial turn) flares or extends sufficiently outwardly in order to contact the walls of the circulatory system (e.g., the walls of the left atrium). Additionally, the stabilization coil/turn of various embodiments will be configured to be less abrasive to the native tissue and/or anatomy. For example, the surface texture can be made smoother and/or softer, such that movement of the docking device against the native anatomy will not damage the native tissue.

The proximal tip 88 as shown in these figures also includes an eyelet or eyehole. The eyelet at the proximal tip will be used to secure the docking device 70 to a delivery system (as described below) through various means, including a suture. As such, various embodiments comprising an eyelet at the proximal tip 88 will utilize different shapes and sizes of eyelets. As such, some embodiments will utilize larger eyelets, while other embodiments will use smaller eyelets. Additionally, the shape will vary in certain embodiments, such that some embodiments will possess round eyelets, while others will utilize D-shaped eyelets. Further, various embodiments will not possess eyelets such as those illustrated, but will possess holes drilled into the docking device itself, such as laser-drilled holes.

Turning to FIGS. 9A to 9C, these figures are representative of a docking device, but are also representative of a core that can be covered and/or added to in order to form a docking device. The stabilization coil 86 is designed to create a plane formed by at least three points of contact in the atrium. These three anchoring points or points of contact are the posterior shelf of the native valve (e.g., of the mitral valve, etc.), the anterior wall of the atrium, and either an atrial appendage of the atrium or the lateral shelf of the native valve. This plane formed by three points of contact will be parallel to a plane of the native valve, which will maintain the dock position parallel to the native valve plane. In some embodiments, the diameter of stabilization coil is desirably larger than the annulus, native valve plane, and atrium for better stabilization, but the stabilization coil is flexible with a thin and weak cross section to prevent damage to the atrium of a patient over a long-term placement of the docking device 70.

Suitable materials for the docking device include a nitinol core with a core size range from approximately 0.3 mm to approximately 1 mm. The flexible core will allow the stabilization coil to conform to varying atrium shapes and sizes. Additionally, in some embodiments with a three-point contact design as illustrated in FIGS. 9B and 9C, the stabilization coil is designed, when unconstrained (e.g., when not installed into a patient's native valve), to sit lower in free space than the functional coils or cross downwardly across the functional coils. This can beneficially lift the functional coils (central region 80) relative to the native anatomy, a plane of the native valve, and the leaflets when implanted. For example, a stabilization coil that crosses from a proximal side of the central region or functional coils to or toward a distal side of the central region/functional coils, when deployed in an atrium, push down on the atrium and/or native valve plane to cause the central region/functional coils to move up or be biased up higher on the ventricular side of the valve and higher under the leaflets. With respect to FIGS. 10A to 10D, these figures are representative of a docking device, but are also representative of a core that can be covered and/or added to in order to form a docking device. In FIGS. 10A-10D, the docking device 70 is designed to have a flat stabilization coil 86 that sits on a plane of the native valve (e.g., on a native mitral plane or a native tricuspid plane). In these embodiments, the stabilization coil 86 is designed to be larger than the opening of the native valve (e.g., of the mitral valve or tricuspid valve), yet not so large that the stabilization coil 86 does not sit on a plane of the native valve. The stabilization coil 86 can form a continuous curve, such as illustrated in FIG. 10A or can be flared out or biased toward the posterior wall of the atrium, as seen in FIG. 10B, thus taking advantage of the posterior shelf, to prevent the docking device 70 from falling into the ventricle prior to deployment of an artificial or prosthetic valve therein. Additionally, in certain flat embodiments, the stabilization coil will have a smooth cover to prevent trauma to native anatomy in regions that exhibit relative motion (e.g., where the docking device 70 crosses from the atrium to the ventricle through the mitral valve).

Turning to FIGS. 11A to 11C, these figures are representative of a docking device, but are also representative of a core that can be covered and/or added to in order to form a docking device. In FIGS. 11A to 11C, a hybrid dock design is illustrated that is configured to improve prevention and/or inhibition of paravalvular leakage. In embodiments of this hybrid docking device 70, the stabilization coil 86 is designed to create a closer ring around a deployed prosthetic valve, thus helping to seal the valve and preventing paravalvular leakage. In some embodiments, this sealing effect is maximized by offsetting radially outwardly the dock core from the maximum valve outer diameter plus half the cross section of the docking device. In some embodiments, the stabilization coil 86 allows for the largest outer diameter (e.g., optimal contact with the atrium) to help also with dock drop prior to prosthetic valve deployment. Additionally, in some embodiments, the docking device is configured such that, after prosthetic valve deployment, the stabilization coil will be flush with the outer diameter of the implanted and expanded prosthetic valve. This hybrid design can be manufactured to rely on different prosthetic valve outer diameters to prevent paravalvular leakage close around the prosthetic valve. For example, the docking device can be designed to accommodate a valve with an outer diameter of approximately 30 mm or approximately 34 mm or any diameter therebetween. Additionally, the dimensions of the docking device 70 can be adjusted to handle prosthetic valves with outer diameters ranging from approximately 20 mm to approximately 50 mm.

In some embodiments, the various docking devices herein are configured to have a small enough cross section during delivery to fit inside a catheter/sleeve/sheath of a delivery device (discussed in greater detail below), but expand post-deployment to maximize OD and create an improved seal around a prosthetic valve after implantation. Additionally, some embodiments comprise and/or utilize a material configured to optimize tissue ingrowth (e.g., with pores and/or other openings sized to provide more available surface area to assist in encouraging such ingrowth). In some embodiments, the pore and/or opening sizes are approximately 30 μm-1000 μm, which can encourage optimal tissue ingrowth. The tissue ingrowth can allow for improved sealing and better integration with the native valve anatomy to stabilize the docking device and prosthetic valve and prevent abrasions and/or damage over time. In certain embodiments, the docking devices can comprise a material having openings (e.g., pores) with sizes in a range of about 400-800 μm, 500-750 μm, 500-660 μm, 600-650 μm, or 625-650 μm.

The various docking devices herein can also incorporate additional modifications to the functional coils (e.g., central region 80 in FIGS. 9A to 11C) and/or the stabilization coil (e.g., item 86 in FIGS. 9A to 11C) to improve the functionality of the docking devices. Examples of some such additional modifications are illustrated in FIGS. 12A to 16.

FIGS. 12A to 12G illustrate examples of possible coverings 100 that can be placed on all or only a portion of a docking device (e.g., docking device 70 as illustrated in FIGS. 9A to 11C or elsewhere herein) to form a seal against the prosthetic valve and reduce paravalvular leakage. In many embodiments, covering 100 covers predominately or only the stabilization turn/coil (e.g., atrial turn/coil) or a portion thereof. In some embodiments, the covering 100 is attached on the atrial turn and extends toward the functional turns in the central region and/or onto a portion of the functional turns. In some embodiments, the covering 100 is attached on the functional turn and extends towards the atrial turn. Certain embodiments possess the covering 100 on only the functional turns. In some embodiments, covering 100 extends over the entirety of the docking device 70. When on the stabilization coil/turn or atrial coil/turn, covering 100 can help cover an atrial side of an atrioventricular valve to prevent and/or inhibit blood from leaking through the native leaflets, commissures, and/or around an outside of the prosthetic valve by blocking blood in the atrium from flowing in an atrial to ventricular direction other than through the prosthetic valve. In some embodiments, the covering 100 is configured to have a compressed configuration for delivery through vasculature to the heart valve with a narrow profile and an expanded configuration in which the covering 100 is expanded to a larger outer diameter (which can beneficially help prevent and/or inhibit paravalvular leakage).

In some embodiments, the covering 100 can expand to a diameter of approximately 5 mm (e.g., ±4 mm) to prevent and/or inhibit paravalvular leakage. In some embodiments, the covering 100 is configured to expand such that an improved seal is formed closer to and/or against a prosthetic valve deployed therein (such as describe above in regard to FIGS. 11A to 11C). In some embodiments, covering 100 is configured to prevent and/or inhibit leakage at the location where the docking device 70 crosses between leaflets of the native valve (e.g., without covering 100, the docking device may push the leaflets apart at the point of crossing the leaflets and allow for leakage at that point (e.g., along the docking device or to its sides), but covering 100 can be configured to expand to cover and/or fill any opening at that point and inhibit leakage along the docking device).

Figure 12A:
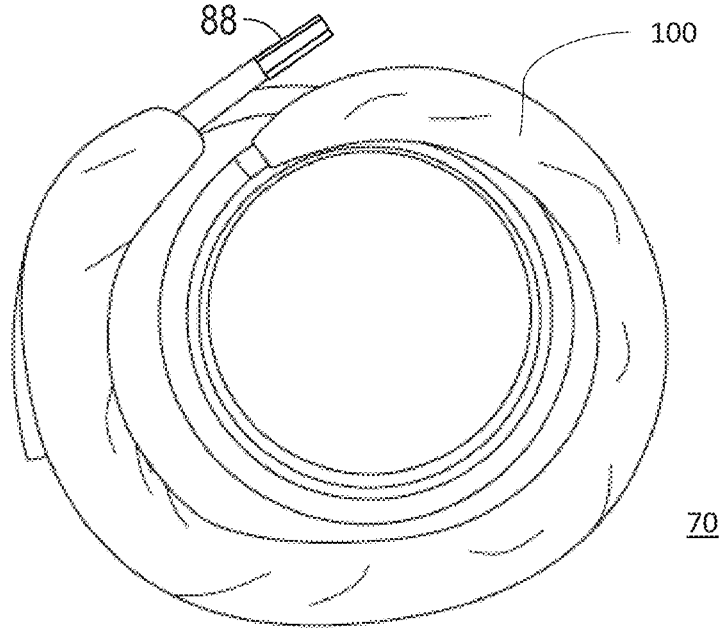
FIGS. 12A-12D illustrate top views of example embodiments of a docking device possessing a covering on the stabilization or atrial turn in accordance with various embodiments.

In some embodiments, e.g., as illustrated in FIG. 12A, covering 100 can comprise and/or consist of an expandable foam. In some embodiments, the covering comprises and/or consists of an expandable foam that is a memory foam, such that it will expand to a specific shape or specific pre-set shape upon removal of a crimping pressure prior to delivery of the docking device 70. Examples of such foams are polyethylene terephthalate (PET), polyurethane, and polyurethane-polycarbonate matrix. In some embodiments, the foam is configured to expand the cross-sectional diameter of the docking device 70, such that the cross-sectional diameter in the region of the covering is 2 mm to 7 mm. Additionally, in some embodiments utilizing foam, the foam comprises large enough pores to be atraumatic to the native anatomy and allow tissue ingrowth.

Figure 12B:
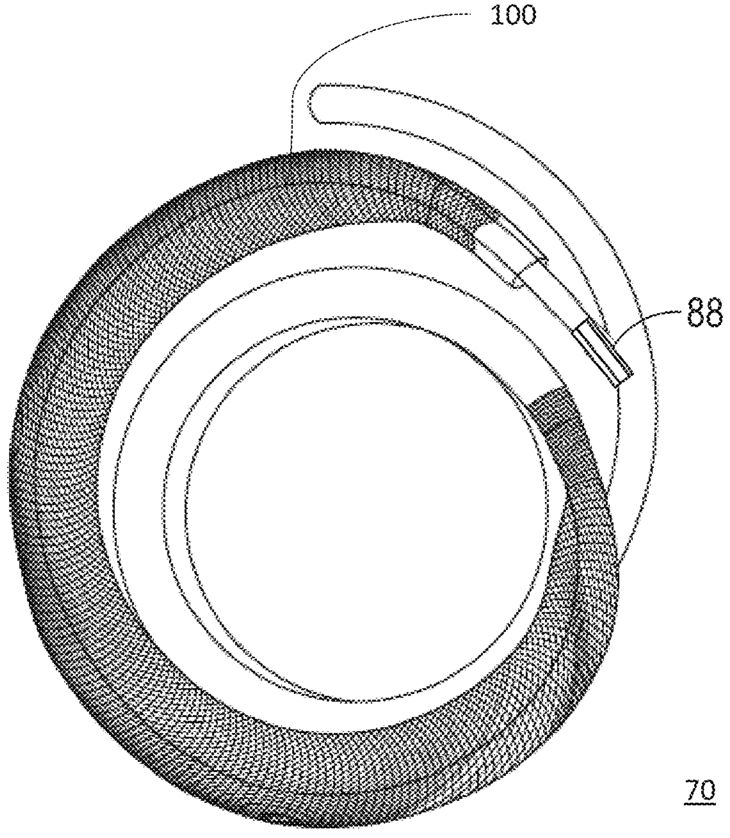

In some embodiments covering 100 comprises an expandable, non-foam structure over the docking device 70. For example, as illustrated in FIG. 12B, covering 100 can comprise a braided structure over the docking device 70. A braided structure can be stretched inside of a sleeve or covering prior to deployment of the docking device 70, but after the deployment, the braided structure can be allowed to expand to its largest possible diameter to create a seal. In some embodiments, the braided structure is a braided shape memory material (e.g., shape memory alloy, shape memory metal, nitinol, etc.) that is shape set and/or pre-configured to expand to a particular shape and/or size when unconstrained and when deployed at a native valve.

Figure 12C:
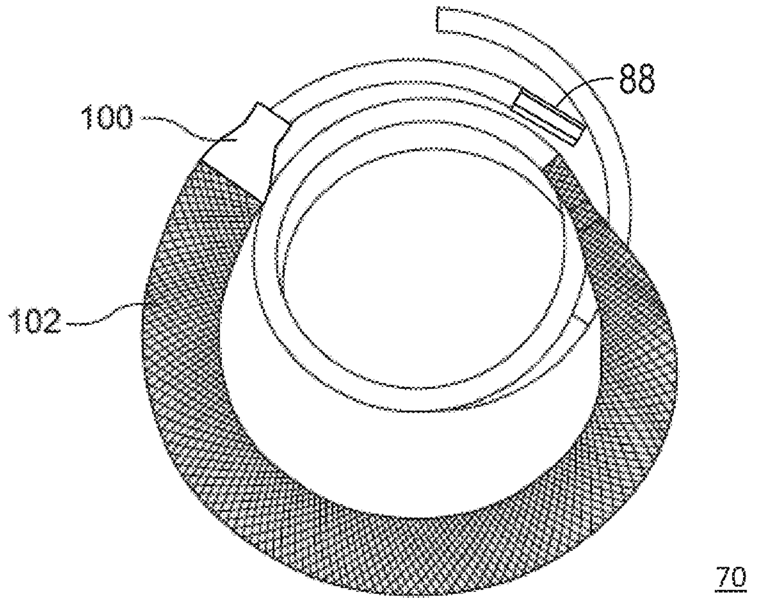

In FIG. 12C, some embodiments the covering 100 comprises multiple layers of the same and/or different materials. In these embodiments, the covering (such as a braided structure, foam, or expandable non-foam structure) can be covered with a second covering 102. In these embodiments, the second covering 102 is designed to be atraumatic to native tissue and/or promote tissue ingrowth into the second covering 102 and possibly the first covering 100. The second covering can be constructed of any suitable material, including foam, cloth, fabric, and/or polymer, which is flexible to allow for compression and expansion of the first 100 and second 102 coverings.

Figure 12D:
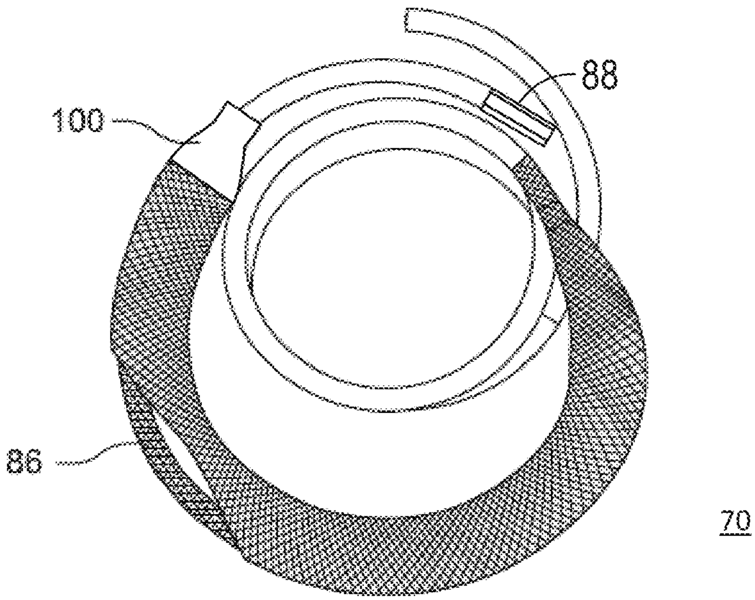

Motion between a docking device 70 and a covering 100 can cause trauma to native tissue, as such, several embodiments of docking devices 70 will incorporate means to limit motion, thus reducing the risk of trauma to native tissue. Turning to FIG. 12D, an embodiment of a covered docking device with a braided stabilization coil 86 is illustrated. In embodiments such as illustrated in FIG. 12D, a braided texture on the stabilization coil 86 of the dock can interact with the covering 100 surrounding the stabilization coil 86. By forming an interaction between the stabilization coil 86 and the covering 100, motion of the docking device 70 can be reduced, thus limiting trauma to the native tissue.

Figure 12E:
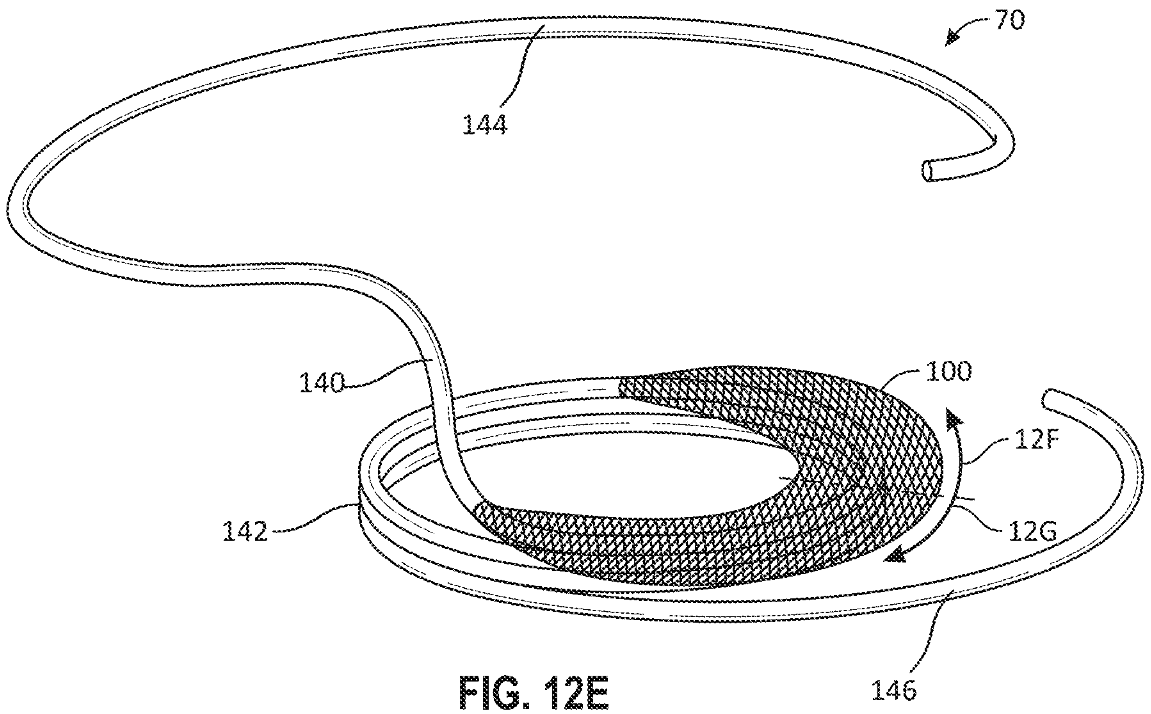
FIG. 12E illustrates a perspective view of an example embodiment of a docking device possessing a covering on a functional turn in accordance with various embodiments.

In FIG. 12E, an embodiment of a docking device 70 is illustrated with a covering 100 on a functional coil in the central region of the docking device. Like the example illustrated in FIG. 12B, covering 100 can comprise a braided structure over the docking device 70. A braided structure can be stretched inside of a sleeve or covering prior to deployment of the docking device 70, but after the deployment, the braided structure can be allowed to expand to its largest possible diameter to create a seal. In some embodiments, the braided structure is a braided shape memory material (e.g., shape memory alloy, shape memory metal, nitinol, etc.) that is shape set and/or pre-configured to expand to a particular shape and/or size when unconstrained and when deployed at a native valve. As shown in FIG. 12E, the docking device 70 can have an extension 140 substantially positioned between the central region 142 having the functional turns and the upper region 144 having the atrial turn. As described elsewhere herein, the docking device 70 can have a lower region 146 having an encircling turn with a larger diameter relative to the functional turns in the central region 142. In FIG. 12E, the extension 140 is made up of or includes a vertical part of the coil that extends substantially parallel to a central axis of the docking device 70. In some embodiments, the extension 140 can be angled relative to the central axis of the docking device 70, but will generally serve as a vertical or axial spacer that spaces apart the adjacent connected portions of the docking device 70 in a vertical or axial direction, so that a vertical or axial gap is formed between the coil portions on either side of the extension 140 (e.g., a gap can be formed between an upper or atrial side and a lower or ventricular side of the docking device 70). In certain embodiments, the extension 140 is intended to be positioned at or near the anterolateral commissure AC when the docking device 70 is implanted, with covering 100 crossing the mitral annulus plane and positioned such that a portion of covering 100 is positioned in the posteromedial commissure PC. Additional details of exemplary shapes for the docking device 70 having an extension 140 can be seen in U.S. Pre-Grant Publication No. US2018/0055628A1, the entirety of which is incorporated herein for all purposes.

Turning to FIG. 12E, an embodiment of a docking device 70 is illustrated with covering 100 extending on the top functional turn of the central region. In such embodiments, covering 100 can help cover the ventricular side of an atrioventricular valve to prevent and/or inhibit blood from leaking through the native leaflets, commissures, and/or around an outside of the prosthetic valve by blocking blood in the atrium from flowing in an atrial to ventricular direction other than through the prosthetic valve. Like the example illustrated in FIG. 12B, covering 100 can comprise a braided structure over the docking device 70. A braided structure can be stretched inside of a sleeve or covering prior to deployment of the docking device 70, but after the deployment, the braided structure can be allowed to expand to its largest possible diameter to create a seal. In some embodiments, the braided structure is a braided shape memory material (e.g., shape memory alloy, shape memory metal, nitinol, etc.) that is shape set and/or pre-configured to expand to a particular shape and/or size when unconstrained and when deployed at a native valve. In some embodiments, the covering 100 is attached on the atrial turn and extends toward the functional turns in the central region and/or onto a portion of the functional turns. In some embodiments, the covering 100 is attached on the functional turn and extends towards the atrial turn. In further embodiments, the covering 100 can be attached to the docking device core at both ends of the covering 100 and have a free-floating portion therebetween. Additionally, covering 100 can comprise and/or consist of an expandable foam. In some embodiments, the covering comprises and/or consists of an expandable foam that is a memory foam, such that it will expand to a specific shape or specific pre-set shape upon removal of a crimping pressure prior to delivery of the docking device 70, like the example in FIG. 12A.

Figure 12F:
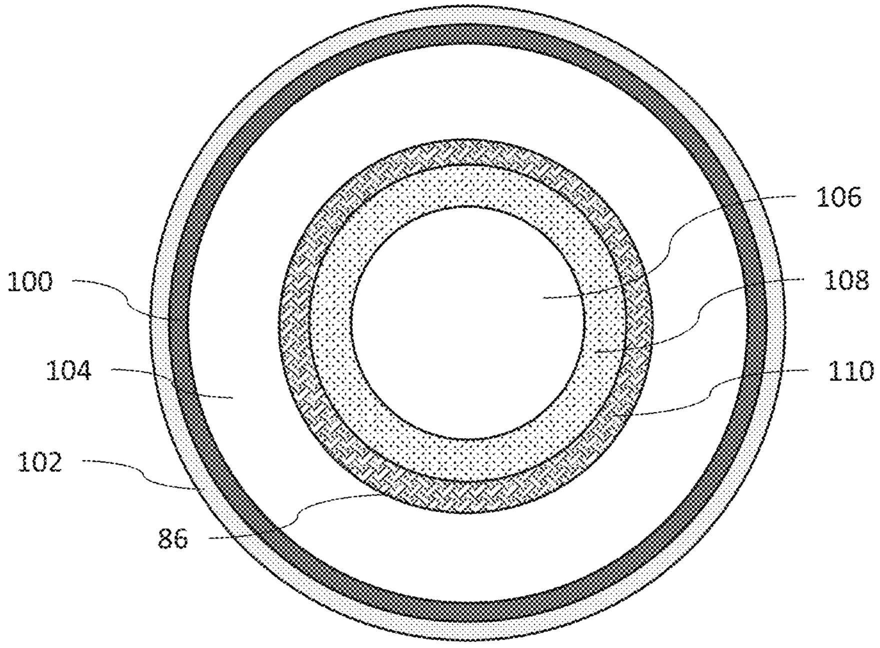
FIG. 12F illustrates a cross-sectional view of a first portion of the covering of the docking device of FIG. 12E in accordance with various embodiments.
Figure 12G:
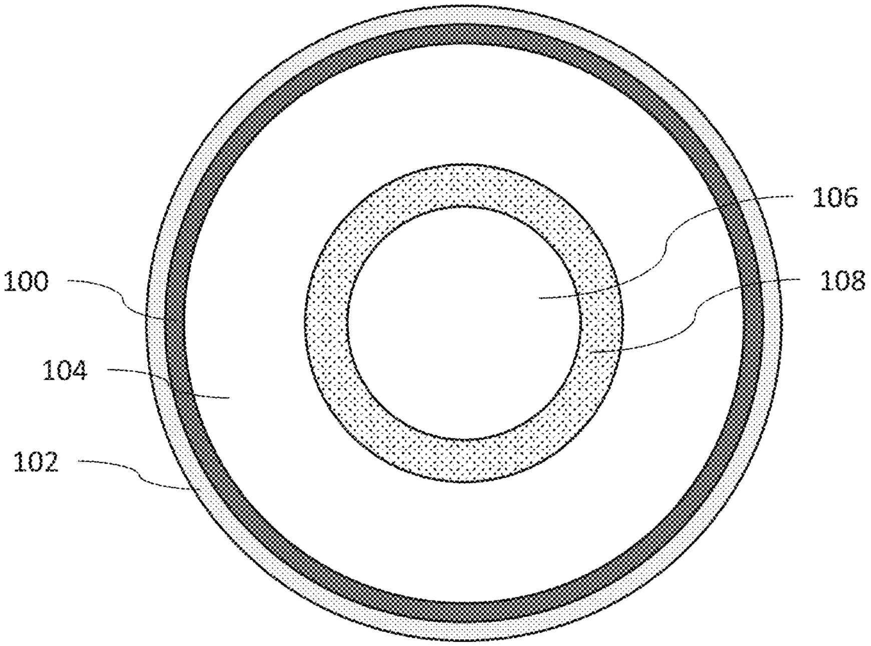
FIG. 12G illustrates a cross-sectional view of a second portion of the covering of the docking device of FIG. 12E in accordance with various embodiments.

FIGS. 12F and 12G illustrate different arrangements of the various components that can be integrated on or around the stabilization coil 86 of many embodiments. In particular, FIG. 12F illustrates a cross section of the stabilization coil 86 along with covering 100 and second covering 102. As illustrated, as the covering 100 and second covering 102 expand, a cavity 104 is formed between stabilization coil 86 and the coverings 100, 102. Also illustrated are the construction of the atrial turn including a core 106, which can be for example, a NiTi core, or a core that is made of or includes one or more of various other biocompatible materials. FIG. 12F also illustrates tubular layer 108 to provide a cushioned, padded-type layer for the atrial turn to be atraumatic against native tissue. In certain embodiments, tubular layer 108 is constructed of ePTFE. FIG. 12F further illustrates braided layer 110 placed over the tubular layer 108. As noted above, the braided layer 110 is designed to interact with covering 100 to limit motion and/or limit trauma to native tissue. It should be noted that FIG. 12F illustrates a variety of options that can be utilized in construction of docking devices of various embodiments, and the particular arrangement is only illustrative of some embodiments. As such, a number of embodiments will not possess all of the components illustrated in FIG. 12F in constructing a docking device.

In some embodiments, the cross-section of FIG. 12F can be implemented in the coils shown FIGS. 12B-12D. Further, in some embodiments, the stabilization coil 86 can have two portions, a first portion having the cross-section shown in FIG. 12F and an adjacent, second portion having a cross-section shown in FIG. 12G. The cross-section shown in FIG. 12G may be the same as the cross-section shown in 12F, except it does not include the braided layer 110. In some embodiments, as shown in FIG. 12E, the area of covering 100 can be split into two portions (as denoted by the dashed line), including a first portion extending in the direction of arrow 12F and a second portion extending in the opposite direction, as shown by arrow 12G. The first portion can have the cross-section shown in FIG. 12F while the second portion can have the cross-section shown in FIG. 12G. In certain embodiments, the first portion having the cross-section shown in 12F can have a smaller total cross-sectional diameter than the total cross-sectional diameter of the second portion having the cross-section shown in FIG. 12G. One potential advantage of these embodiments is a reduced potential for LVOT obstruction due to the reduced cross-sectional diameter of a portion of the coverings 100, 102 that are present in the left ventricle under the anterior leaflet.

Figure 12H:
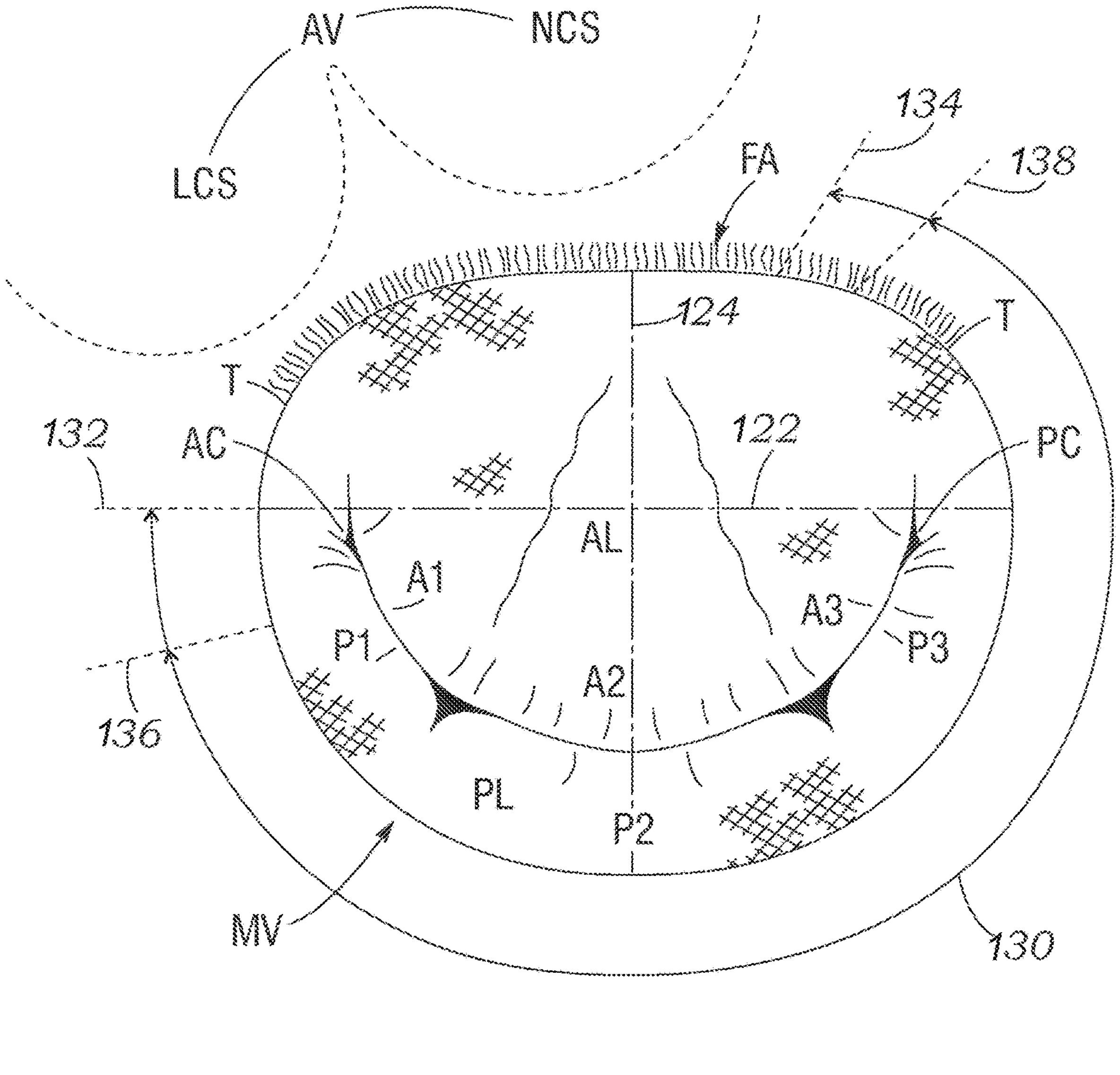
FIG. 12H illustrates a superior or plan view of a mitral valve, with the leaflets closed and coapting and indicating primary anatomical landmarks as well as diagram lines indicating features of the docking device of FIG. 12E in accordance with various embodiments.

FIG. 12H illustrates a circumferential span 130 around the mitral annulus generally illustrating exemplary ranges of covering 100 that can be included in certain embodiments of the docking device 70. FIG. 12H is a plan view of the mitral valve with posterior being down and anterior being up. In a healthy heart, the annulus of the mitral valve MV creates an anatomic shape and tension such that a posterior leaflet PL and an anterior leaflet AL coapt in the flow orifice, forming a tight junction, at peak contraction or systolic pressures, as seen in FIG. 12H. The mitral valve MV annulus has a posterior aspect to which the posterior leaflet PL attaches and an anterior aspect to which the anterior leaflet AL attaches. Where the leaflets meet at the opposing medial and lateral sides of the annulus are called the leaflet commissures: the anteriorolateral commissure AC, and the posteromedial commissure PC. The posterior leaflet is divided into three scallops or cusps, sometimes identified as P1, P2, and P3, starting from the anterior commissure and continuing in a counterclockwise direction to the posterior commissure. The posterior scallops P1, P2, and P3 circumscribe particular arcs around the periphery of the posterior aspect of the annulus, which may vary depending on a variety of factors, including actual measurement of the mitral valve posterior leaflet scallops, and surgeon preference. As a rule, however, a major axis 122 of the mitral annulus intersects both the first and third posterior scallops P1 and P3, approximately at the commissures AC, PC, and a minor axis 124 intersects and generally bisects the middle posterior scallop P2. The anterior leaflet also features scallops or regions labeled A1, A2, and A3 as indicated in FIG. 12H. The mitral anterior leaflet AL attaches to the fibrous portion FA of the mitral annulus, which makes up about one-third of the total mitral annulus circumference. The muscular portion of the mitral annulus constitutes the remainder of the mitral annulus, and the posterior leaflet PL attaches thereto. The anterior fibrous annulus FA, the two ends of which are called the fibrous trigones T, forms part of the central fibrous body of the heart. The anterior commissure AC and the posterior commissure PC are located just posterior to each fibrous trigone. The fibrous mitral valve annulus FA is intimate with or adjacent to the aortic valve AV, in particular the left coronary sinus LCS and non-coronary sinus NCS. The central fibrous body is fairly resistant to elongation, and thus the great majority of mitral annulus dilation occurs in the posterior two-thirds of the annulus, or around the muscular mitral annulus. The covering 100, with or without additional covering 102, can be provided on the docking device 70 with a desired length upon implantation that has a circumferential span 130. In some embodiments, the covering 100 can extend from a first radial angular location 134 in the left ventricle, through the PC and into the left atrium, and to a second radial angular location 136 in the left atrium. In FIG. 12H, the first angular location 134 is shown at a point between the PC and the AC, but in other implementations, the circumferential span 130 can extend further around the annulus towards or past the AC, or can extend less of a radial angle around the annulus as shown as exemplary angular location 138 in FIG. 12H.

The first radial angular location can be at one of various locations relative to the anatomy of the mitral annulus in various embodiments upon implantation. In some embodiments, the first radial angular location 134 can be at a radial angular location that corresponds to a point in A1, a point in A2, or a point in A3. In certain embodiments, upon implantation the first radial angular location 134 is underneath the A2 region of the AL, which can provide an advantage of reducing the risk of LVOT obstruction. In some embodiments, the first angular location 134 is selected to avoid overlapping with the adjacent aortic valve structures of the left coronary sinus LCS and non-coronary sinus NCS. In other embodiments, the first radial angular location 134 can be at a point representing a percentage of the circumferential distance from the PC to the AC (in the counter-clockwise direction in FIG. 12H), of about 10%, about 20%, about 30%, about 40%, about 50% (at about the middle of A2 at about the point intersected by minor axis 124), about 60%, about 70%, about 80%, about 90%, or about 100% (at about the AC).

The second radial angular location 136 can be at one of various locations relative to the anatomy of the mitral annulus in various embodiments upon implantation. In some embodiments, the second radial angular location 136 can be at radial angular location 132 at or near the AC. In other embodiments, the second radial angular location 136 can be at a point in P1, at a point in P2, or at a point in P3. In yet other embodiments, the second radial angular location 136 can be at a point representing a percentage of the circumferential distance from the PC to the AC (in the clockwise direction as shown in FIG. 12H), of about 10%, about 20%, about 30%, about 40%, about 50% (at about the middle of P2 at about the point intersected by minor axis 124), about 60%, about 70%, about 80%, about 90%, or about 100% (at about the AC). In further embodiments, the covering 100 can extend all the way to the radial angular location 132 of the AC and upwards onto a portion of the extension 140 of the docking device 70 that extends into the left atrium.

In certain embodiments, the first radial angular location 134 and the second radial angular location 136 can be selected such that the covering 100 forms a complete circumferential span around the MV. In some embodiments, both radial angular locations 134, 136 can be at or near the AC. In certain embodiments, the first radial location 134 can be selected such that the portion of covering 100 in the left ventricle extends counter-clockwise, as seen in FIG. 12H, beyond the second radial angular location 136 such that the covering 100 is implanted with a total radial angular length more than one complete circumference of the MV.

In some embodiments, a sleeve or sheath to prevent the covering 100 from expanding until the docking device 70 is deployed is provided. This additional sleeve or sheath can be integrated into a delivery system and/or delivery device (e.g., such as will be described below with reference to FIGS. 17A-20D, 22A-22C, 24A-24B, and 33-34). In some embodiments, the sleeve or sheath can be a biodegradable or bioabsorbable material, such that the sleeve or sheath will degrade over a period of time after deployment without additional requirements on the manufacture of a delivery device or on the user withdrawing the sleeve or sheath. In these cases, the sleeve or sheath can be more of a coating on the covering. In embodiments using a bioabsorbable sleeve, the material can be designed to biodegrade over a period of time sufficient to allow deployment and/or redeployment of the docking device 70 and/or a prosthetic valve without obstructing the work of a doctor, surgeon, or other medical professional deploying the docking device 70 or a prosthetic valve.

In some embodiments of docking devices with coverings 100, such as illustrated in FIGS. 12A to 12G, the covering is made of braided NiTi, braided NiTi covered with braided PET, braided NiTi covered with woven PET, braided NiTi covered with knitted PET, braided NiTi covered with ePTFE membrane, braided NiTi covered with electrospun ePTFE, braided NiTi dipped in an elastomer, braided NiTi sprayed with an elastomer, braided NiTi between thermally compressed layers of thermoplastic membranes, foam, PET braid, PET woven cloth, PET knitted cloth, composite braided materials having yarns of NiTi and PET, composite braided materials having yarns of NiTi and PET covered with one or more of braided PET, woven PET, knitted PET, ePTFE membrane, electrospun ePTFE, composite braided materials having yarns of NiTi and PET dipped in or sprayed with an elastomer, composite braided materials having yarns of NiTi and PET between thermally compressed layers of thermoplastic membranes, or combinations thereof. In certain embodiments the composite braided materials can comprise a braided composite having 48 yarn ends, with 30 of the yarn ends comprising PET and 18 of the yarn ends comprising NiTi. In further embodiments, the covering 100 can be impregnated with growth factors to stimulate or promote tissue ingrowth, such as transforming growth factor alpha (TGF-alpha), transforming growth factor beta (TGF-beta), basic fibroblast growth factor (bFGF), vascular epithelial growth factor (VEGF), and combinations thereof.

The various docking devices herein can comprise weaved or braided textures or coverings on various surfaces of the docking device. For example, docking devices with a weaved or braided texture or coverings on the central region or on the functional coils can beneficially help raise friction between the docking device, the native anatomy, and/or the prosthetic heart valve when the prosthetic heart valve is deployed in the docking device, which can help improve the retention forces. This can also provide more surface area for tissue ingrowth. While these textures provide benefits such as better retention force for prosthetic valves, the texture may also cause unwanted friction on the native anatomy while the docking device is being positioned at the native valve, which can slow down deployment of a docking device and/or may cause damage to the native anatomy. In some embodiments, the weaved or braided textures or covering are part of and/or are tightly held against the outer wall of the docking device to maintain low profile and secure location. In some embodiments, the weaved or braided textures or covering comprises an ePTFE covering and/or a PET covering.

Figure 13A:
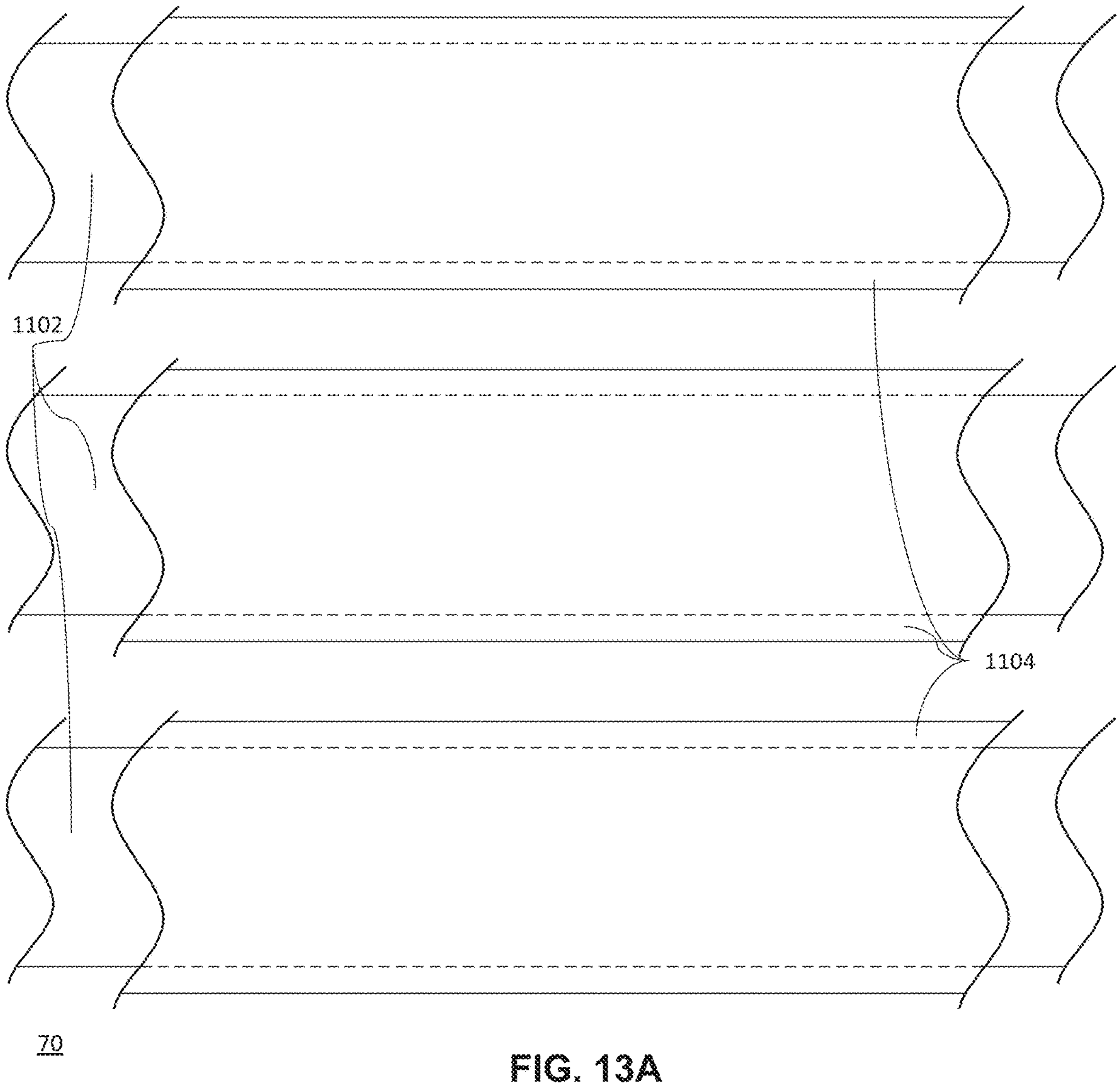
FIG. 13A illustrates a schematic view of example embodiments of a docking device possessing a covering in accordance with various embodiments.
Figure 13B:
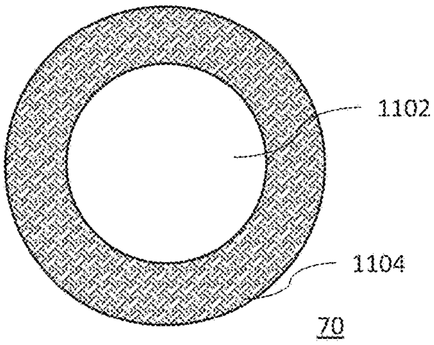
FIGS. 13B-13C illustrate cross sectional views of example embodiments of a docking device possessing a covering in accordance with various embodiments.
Figure 13C:
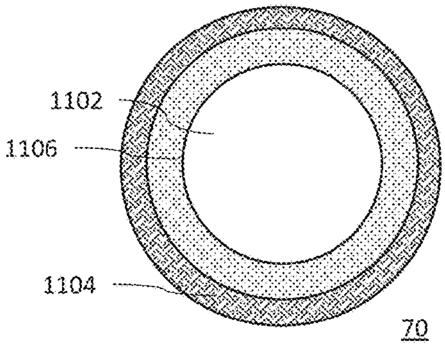

FIGS. 13A to 13C show schematic and cross-sectional views of a portion of an example docking device configured for improving retention forces between the docking device and a replacement valve. FIG. 13A illustrates portions of three turns of a docking device 70 (such as the central region 80) are illustrated, while FIG. 13B illustrates a cross-sectional view of a docking device 70. The docking device 70 includes a main coil or core 1102, which can be for example, a NiTi coil/core, or a coil/core that is made of or includes one or more of various other biocompatible materials. The docking device 70 further includes a covering 1104 that covers the coil/core 1102. The covering 1104 can be made of or include a high friction material, so that when the expandable valve is expanded in the docking device 70, an increased amount of friction is generated between the valve and the covering 1104 to hold a shape of the docking device 400 and prevent or inhibit/resist the docking device 70 from unwinding. In some embodiments, the covering also or alternatively increases the amount of friction between the docking device and native leaflets and/or the prosthetic valve to help retain the relative positions of the docking device, leaflets, and/or prosthetic valve. In some embodiments, the covering 1104 is made from one or more high friction materials that is placed over the coil wire/core 1102. In some embodiments, the covering 1104 is made of or includes a PET braid.

In additional embodiments, the covering 1104 is made of or includes a PET braid over an ePTFE tube (e.g., 1106, FIG. 13C), the latter of which serves as a core for the covering 1104. The ePTFE tube is porous, providing a cushioned, padded-type layer for struts or other portions of a frame of the expandable valve to dig into, improving engagement between the valve and the docking device 70. Meanwhile, the PET layer provides additional friction against the native valve leaflets when the prosthetic valve is expanded, and the struts or other portions of the valve frame apply outward pressure on the docking device 70. These features can work together to increase radial forces between the docking device 70 and the native leaflets and/or prosthetic valve, thereby also increasing retention forces and preventing the docking device 70 from unwinding.

In other embodiments, the covering 1104 can be made from one or more other high friction materials that covers the coil 1102 in a similar manner. The material or materials selected for making the covering 1104 can also promote rapid tissue ingrowth. In addition, in some embodiments, an outer surface of a frame of the replacement valve can also be covered in a cloth material or other high friction material to further increase the friction force between the docking device and the valve, thereby further reducing or preventing the docking device from unwinding. The friction provided by the covering can provide a coefficient of friction greater than 1. The covering can be made of ePTFE and can be a tube that covers the coil and can be smooth or can have pores (or be braided or have other structural features that provide a larger accessible surface area like pores do) to encourage tissue ingrowth. The covering can also have a PET braid over the ePTFE tube when the ePTFE tube is smooth. The outermost surface of the covering or braid over the covering can be any biocompatible material that provides friction, such as a biocompatible metal, silicone tubing, or PET. Pore size in the covering can range from 30 to 100 microns. In embodiments where there is a PET covering on top of the ePTFE, the PET layer can be only attached to the ePTFE covering, and not directly to the coil of the docking device. The ePTFE tube covering can be attached to the docking device coil at the coverings proximal and distal ends. The ePTFE tube covering can also be laser welded on to the coil, or swaged to hold them in place to the coil, including using radiopaque markers placed on the outside of the ePTFE tube covering or PET braid as the swaging material The covering 1104 can be added to any of the docking devices described herein and can cover all or a portion of the docking device. For example, the covering can be configured to only cover the functional coils, the leading coil, the stabilization coil, or just a portion of one or more of these (e.g., just a portion of the functional coils).

Figure 14A:
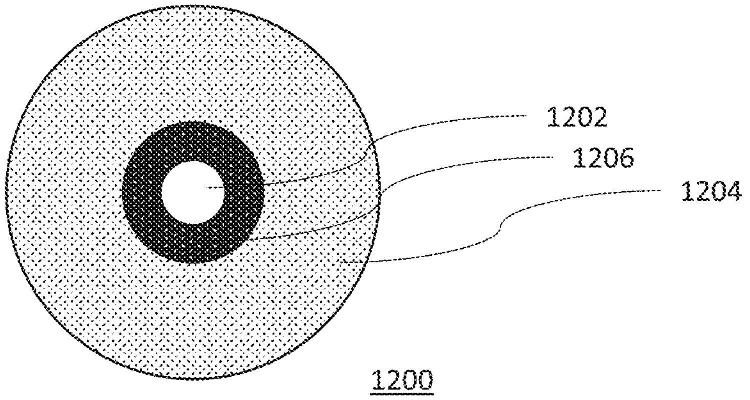
FIGS. 14A and 14B illustrate cross-sectional views of example embodiments of a docking device possessing soft coverings in accordance with various embodiments.
Figure 14B:
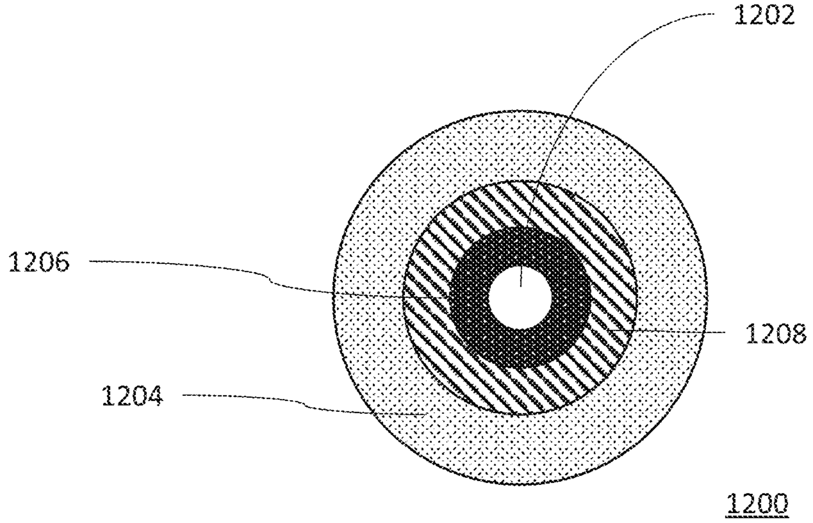
Figure 14C:
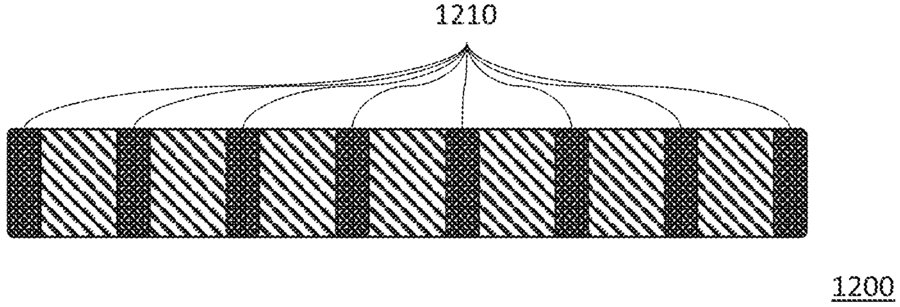
FIG. 14C illustrates an elongated linear view of a bonding schematic of a soft covering in accordance with various embodiments.

FIGS. 14A to 14C illustrate embodiments that utilize a smooth and/or soft covering 1200 over the core 1202 of a docking device to reduce friction while maintaining retention forces for a prosthetic valve. In certain embodiments, the soft cover 1200 is expanded polytetrafluoroethylene (ePTFE), but other materials are also possible. In FIG. 14A, the core 1202 is surrounded by two layers, which can be two layers of ePTFE. Outer layer 1204 can be a low density ePTFE that allows a prosthetic valve to embed itself into the ePTFE, thus providing a retention force for the prosthetic valve. Additionally, inner layer 1206 can be a higher density ePTFE that prevents ripping and bunching of the ePTFE at the distal and proximal ends of a docking device during deployment (e.g., items 21 and 31, FIGS. 9A to 11C). An exemplary lower density ePTFE can be an ePTFE with approximately 0.2 g/cm$^3$. An exemplary higher density ePTFE can be an ePTFE with approximately 1.3 g/cm$^3$, 1.4 g/cm$^3$, 1.5 g/cm$^3$, 1.6 g/cm$^3$, 1.7 g/cm$^3$, 1.8 g/cm$^3$, 1.85 g/cm$^3$, or 1.9 g/cm$^3$. In some embodiments using a 2-layer soft and/or smooth covering, the core diameter will be approximately 0.84 mm (e.g., ±0.5 mm), while some embodiments will possess a core diameter of at least 0.83 mm. Additionally, the outer diameter of inner layer 1206 of some embodiments will be approximately will be 1.34 mm (e.g., ±1 mm). Further, the outer diameter of outer layer 1104 will be 3.1 mm (e.g., ±1 mm). In certain embodiments, the outer diameter of outer layer 1204 will be no greater than 3.1 mm.

In some embodiments, a soft and/or smooth covering utilizes a 3-layer method, as illustrated in FIG. 14B. In the 3-layer example, an intermediate layer 1208 of ePTFE possessing an intermediate layer of ePTFE between the inner layer 1206 and outer layer 1204. In some embodiments, the intermediate layer 1208 will utilize an ePTFE with a higher density than the outer layer 1204 but lower density than the inner layer 1206. For example, a 3-layer embodiment as illustrated in FIG. 14B can have an outer layer 1204 of about 0.2 g/cm$^3$ ePTFE, an inner layer 1206 of ePTFE having a density of between about 1.3 g/cm$^3$ and about 1.9 g/cm$^3$, and an intermediate layer 1208 using ePTFE having a density of between about 0.2 g/cm$^3$ and about 1.9 g/cm$^3$. In some embodiments using a 2-layer soft and/or smooth covering, the core diameter will be approximately 0.84 mm (e.g., ±0.5 mm), while some embodiments will possess a core diameter of at least 0.83 mm. Additionally, the outer diameter of inner layer 1206 of some embodiments will be approximately will be 1.34 mm (e.g., ±1 mm). Also, the outer diameter of intermediate layer 1208 of some embodiments will be approximately 1.62 mm (e.g., ±1 mm), while the outer diameter of outer layer 1204 will be 3.1 mm (e.g., ±1 mm) in various embodiments. In some embodiments, the outer diameter of outer layer 1204 will be no greater than 3.1 mm.

Some embodiments comprising multiple layers of ePTFE to create a soft and/or smooth covering will have the layers bonded together for the entire length of the covering and/or docking device. However, additional embodiments will use an intermittent bonding pattern to increase gumminess of the covering, such as illustrated in FIG. 14C. In FIG. 14C, the length of the docking device with a smooth and/or soft covering is shown. Bonding 1210 is shown at various positions along the length of the soft covering 1200. The distance between bonding can be every 5 mm, 8 mm, or 12 mm in various embodiments. In some embodiments, the bonding can be at variable distances to adjust properties along the length of the docking device.

Figure 15A:
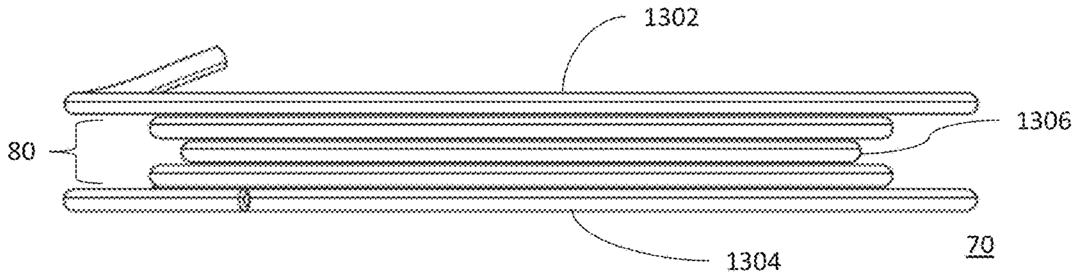
FIGS. 15A and 15B illustrate side views of example embodiments of docking devices possessing an hourglass shape in the central region in accordance with various embodiments.
Figure 15B:
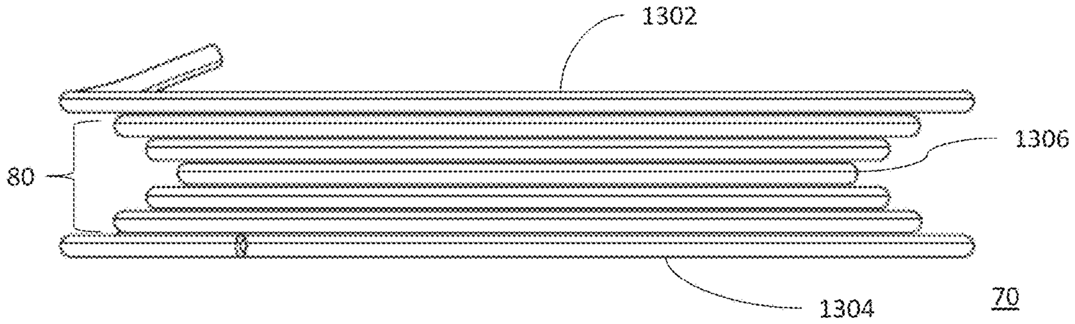
Figure 15C:
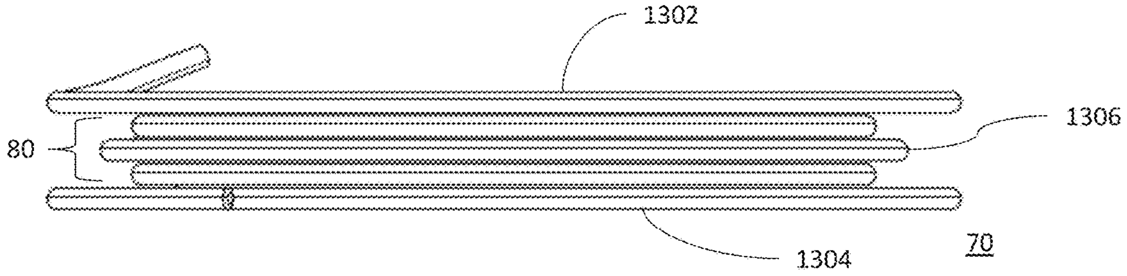
FIGS. 15C and 15D illustrate side views of example embodiments of docking devices possessing a barrel shape in the central region in accordance with various embodiments.
Figure 15D:
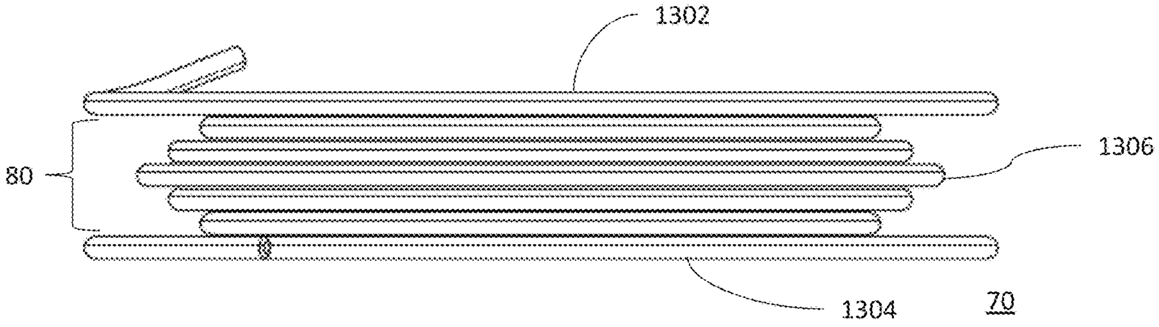

The functional coils of the docking devices herein can be similar or the same in size and shape or can vary in sized and/or shape. Turning to FIGS. 15A to 15D, variations to the functional coils of docking device 70 are illustrated. In FIGS. 15A and 15B, the central region 80 possesses a generally hourglass shape in the functional coils, such that functional coils possess a larger inner diameter at the inflow portion 1302 and outflow portion 1304 of the central region 80 with a smaller inner diameter at the medial position 1306. Conversely, FIGS. 15C and 15D illustrates a central region 80 possessing a generally barrel shape possessing a larger inner diameter at the medial position 1306 and smaller inner diameters at the inflow portion 1302 (e.g., atrial or proximal) and the outflow portion 1304 (e.g., ventricular or distal). The hourglass and/or barrel designs of FIGS. 15A to 15D, respectively, may allow better washout of leaflets of the prosthetic valve, which may help prevent thrombus from forming.

The hourglass and barrel shapes of FIGS. 15A to 15D can be formed a variety of ways, including by forming the docking device 70 with a uniform cross section from the proximal tip 88 to distal tip 84, but the shape of the central region 80 maintains the hourglass or barrel shape illustrated in FIGS. 15A to 15D, respectively. Another method to create these shapes is to vary the cross section from the proximal tip 88 to distal tip 84, such that the inner diameter in the central region 80 possesses either the hourglass or barrel shapes. Additionally, the number of functional coils can be increased to form the hourglass or barrel shapes of FIGS. 15A to 15D. For example, some embodiments of the hourglass shape will utilize a 3-coil central region 80 (as illustrated in FIG. 15A), where the most distal and proximal functional coils possess the larger inner diameter, while the intermediate coil possesses a relatively smaller inner diameter, while other embodiments may utilize a 5-coil central region 80 (as illustrated in FIG. 15B), while other embodiments will use 7- or more coils in the central region 80 with more gradual changes in inner diameter between the larger diameters of the most proximal and distal functional coils an the intermediate coil. Conversely, embodiments of the barrel shape will utilize similar numbers of coils as described for the hourglass shape, including a 3-coil form (FIG. 15C), a 5-coil form (FIG. 15D), or 7- or more coils; however, it should be noted that the barrel shape will increase the inner diameter for the intermediate coils relative the most distal and proximal functional coils. Further, these examples of 3-, 5-, and 7-coils are merely for illustration and should not be construed to limit the number of coils to odd numbers of coils nor limit them only to these examples.

Figure 16:
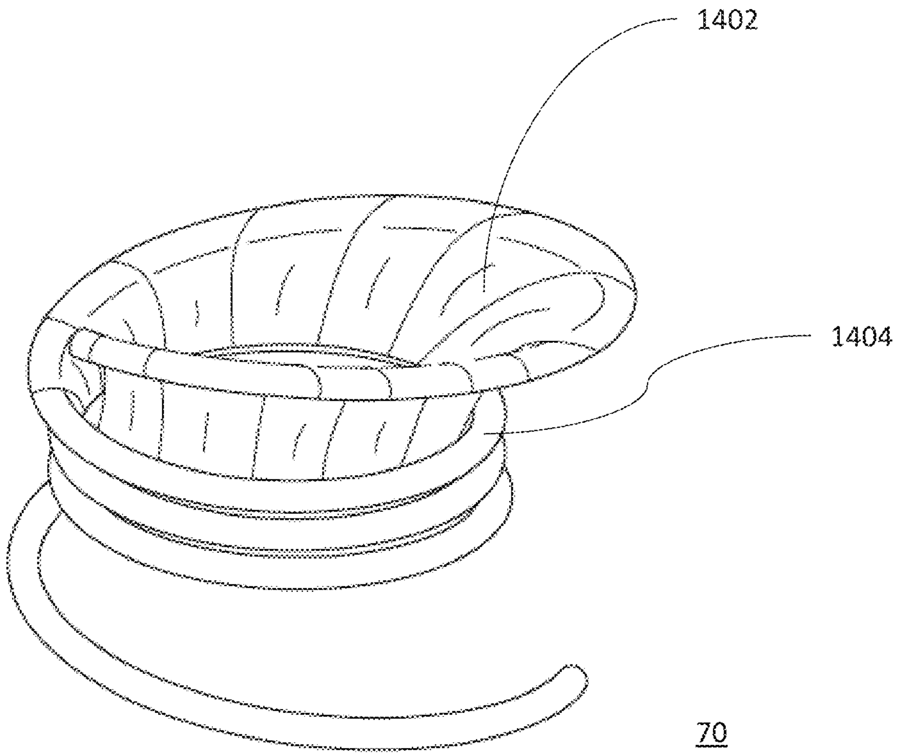
FIG. 16 illustrates a perspective view of an example embodiment of a docking device possessing a flange on the stabilization or atrial turn in accordance with various embodiments.

In some embodiments, the docking devices herein can further incorporate a flange 1402 on the stabilization coil of docking device 70, as shown for example in FIG. 16. In FIG. 16, the stabilization coil 86 possesses cloth or other fabric connected to the next adjacent turn 1404 in the central region 80. This cloth will act as a flange 1402 to reduce paravalvular leakage and/or increase the amount of blood flowing through a prosthetic valve.

In some embodiments, the various docking devices herein include one or more radiopaque markers along the length of the docking device. For example, a radiopaque marker can be placed at the distal tip of some embodiments, and some embodiments will include a radiopaque marker at a location approximately one-quarter turn through the coils of the docking device. Additional embodiments include a plurality of radiopaque markers located at positions throughout the docking device. For example, radiopaque markers could be placed every 25 mm, 29 mm, 30 mm, 34 mm, or more, which could be used by a medical professional to identify the amount of expansion in the diameter of the functional turns, such as when a prosthetic valve is subsequently deployed in the docking device. Radiopaque marker bands can be laser welded on to the coil, or radiopaque markers can be placed on the outside of the ePTFE tube covering or PET braid and swaged to the materials to hold them in place to the coil.

It should be noted that various embodiments will encompass multiple features, such as those described in reference to FIGS. 12A to 16 and all combinations of these features are contemplated herein, unless certain features are mutually exclusive and/or physically cannot be combined (e.g., a docking device possessing both the hourglass and barrel shapes of FIGS. 15A to 15D). Additionally, while the stabilization coil/turn and atrial coil/turn are used simultaneously or interchangeably herein, it should be noted that the docking device can also be used in other locations, where similar shapes would be beneficial, and the use of these terms is not meant to limit the use of embodiments described herein for atrial deployment.

Delivery System

Figure 24A:
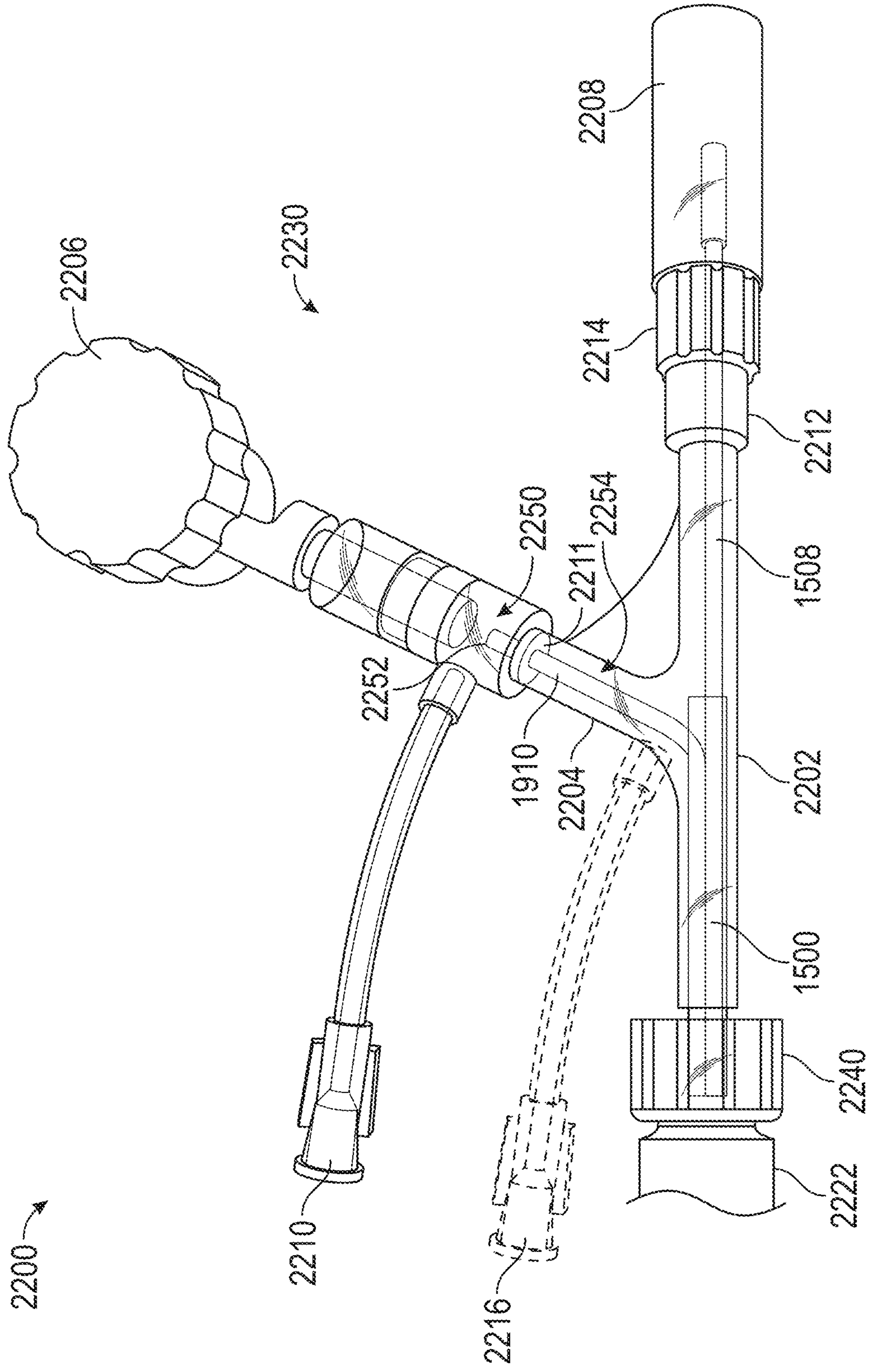
FIG. 24A illustrates an example embodiment of a portion of a handle assembly for a delivery system for a docking device in accordance with various embodiments.
Figure 24B:
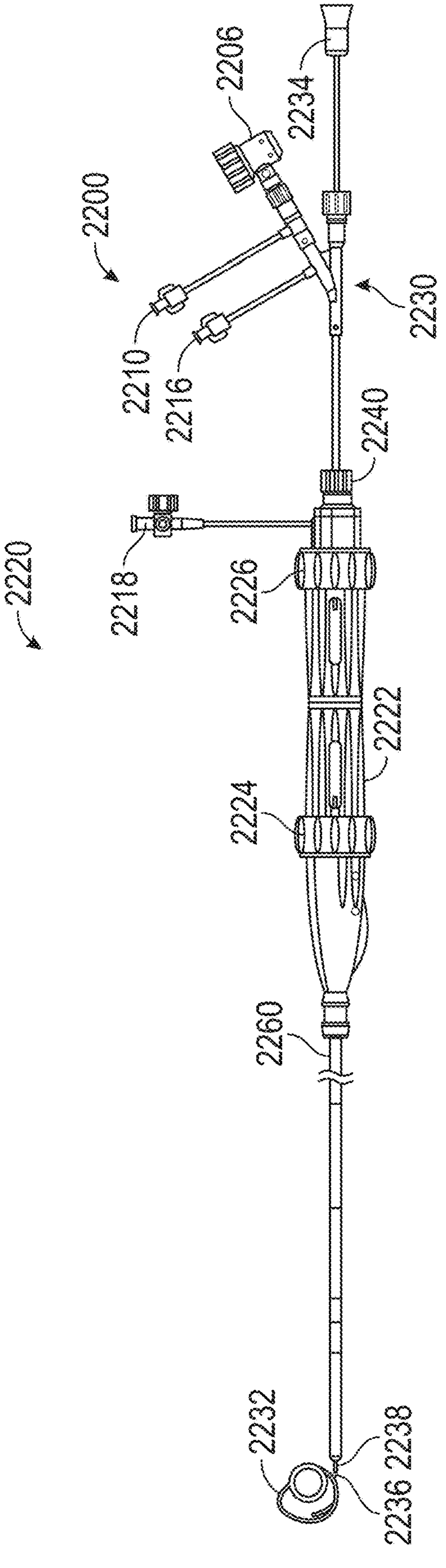
FIG. 24B illustrates an example embodiment of a delivery system for a docking device.

Certain embodiments are directed to delivery systems and/or devices to deliver anchors/docking devices (such as one of the docking devices described above with reference to FIGS. 9A-16) to a heart and/or native valve of an animal, human, cadaver, cadaver heart, anthropomorphic ghost, and/or simulation/simulator. Such devices include transcatheter devices that can be used to guide the delivery of a docking device through vasculature. An exemplary delivery system 2220 configured to deliver a docking device 2232 to a target implantation site is shown in FIG. 24B. In some embodiments, the docking device 2232 can be one of the docking devices described above with reference to FIGS. 9A-16. The delivery system can include a handle assembly 2200 and an outer shaft (e.g., delivery catheter) 2260 extending distally from the handle assembly 2200. The handle assembly 2200 can include a handle 2222 including one or more knobs, buttons, wheels, or the like. For example, in some embodiments, as shown in FIG. 24B, the handle 2222 can include knobs 2224 and 2226 which can be configured to control flexing of the delivery system (e.g., the outer shaft 2260). Further details on delivery systems, such as delivery system 2220, that are configured to deliver a docking device to a target implantation site can be found in U.S. Patent Publication Nos. US2018/0318079, US2018/0263764, and US2018/0177594, which are all incorporated by reference herein in their entireties.

During delivery of some docking devices at the target implantation site, the docking device risks catching, getting stuck on, and/or being obstructed by native portions of the anatomy, such as on the heart wall, trabeculae, native leaflets, chordae tendineae, etc. due to a number of factors such as friction forces relative to the native anatomy, getting a distal end or tip caught in trabeculae and/or chordae, size differentials between the inner diameter of functional turns of a docking device and the outer diameter of native leaflets, etc. Some docking devices have a woven or braided texture and/or covering on the surface of the docking device to increase friction. This friction can create difficulties in advancing a docking device around that native anatomy. Further, the native leaflets can have a diameter of up to about 55 mm, whereas functional turns of the docking device are generally designed to be considerably smaller (e.g., as little as approximately 22 mm). When the functional turns of a docking device are smaller, the native leaflets can push out on a docking device, increasing friction forces between the native leaflets and a docking device.

Once the docking device runs into an obstacle such as these, the doctor, surgeon, or other medical professional may need to retract the docking device into the delivery system (e.g., transcatheter device) and try again to deploy the docking device. This trial-and-error methodology can cause damage to the native tissue due to textures or braids existing on the docking device rubbing against and/or catching portions of tissue and dragging it back into a transcatheter delivery system, which can damage or clog the transcatheter delivery system. Further, this may extend the amount of time for the deployment procedure.

To overcome these challenges, it is desirable to provide a docking device having a lubricous outer surface (e.g., such as on the functional turns and/or other portions), but also having higher-friction functional coils/turns once properly positioned and during subsequent deployment of a prosthetic valve therein. In some embodiments, this is accomplished with a temporary lubricous sleeve or sheath that can be placed over the docking device during delivery, and which is retractable from off of the docking device after the docking device is in a desired position/location. In some embodiments, a lubricous or low-friction sleeve/sheath can be incorporated into a transvascular and transcatheter delivery system, such as the delivery system 2220 of FIG. 24B.

Embodiments of delivery systems including a lubricous sleeve, such as delivery system 2220, can comprise one, some, or all of the following characteristics: a durably lubricous, kink-resistant sleeve that is capable of sustaining numerous cycles of repositioning (e.g., more than 30 cycles); a sleeve able to advance into the anatomy simultaneously with the docking device but move independently of the docking device and the delivery system's pusher shaft; a sleeve that increases the ease of encircling the mitral leaflets and reduces risk of damage to the mitral anatomy; a sleeve that can be retracted prior to releasing the docking device without impacting the position of the docking device; a sleeve that will not significantly increase the length of the delivery system and/or the cross section of the docking device; a sleeve that does not increase the deployment or retrieval forces of the docking device; a sleeve that is ergonomic and does not significantly increase the number of procedural steps or include simultaneous steps; the delivery system allows a lumen inside and a lumen outside of the sleeve in order to have a continuous flush to avoid thrombosis; and a sleeve that has a radial strength to compress a paravalvular leakage solution (e.g., foam or braid as discussed above) on the dock prior to retracting the sleeve. To include a retractable sleeve to cover the docking device, certain embodiments include two main shafts for delivery of a docking device, which can be actuated independently of each other: a pusher shaft to push a docking device into place and a sleeve shaft which actuates a lubricous sleeve surrounding the docking device with a minimal increase in outer diameter of the delivery system. In many embodiments, the two shafts run coaxially inside of a delivery catheter.

For example, in some embodiments, the delivery system 2220 can include a pusher shaft 2238 and a sleeve shaft (not visible in FIG. 24B) which are coaxially located within the outer shaft 2260 and each have portions that extend into the handle assembly 2200. The pusher shaft 2238 can be configured to deploy the docking device 2232 from inside a distal end portion of the outer shaft 2260, upon reaching the target implantation site, and the sleeve shaft can be configured to cover the docking device while inside the delivery system 2220 and while being implanted at the target implantation site. Further, the delivery system 2220 can be configured to adjust an axial position of the sleeve shaft to remove a sleeve portion (e.g., distal section) of the sleeve shaft from the docking device 2232, after implantation at the target implantation site, as explained further below. As shown in FIG. 24B, during delivery, the docking device 2232 can be coupled to the delivery system via a release suture (or other retrieval line comprising a string, yarn, or other material that can be configured to be tied around the docking device and cut for removal) 2236 that extends through the pusher shaft 2238. As explained further below with reference to FIGS. 24A and 27A-30C, the release suture 2236 can extend through the delivery system 2220, through an inner lumen of the pusher shaft 2238, to a suture lock assembly 2206 of the delivery system 2220. Further details regarding the pusher shaft and sleeve shaft are discussed below with reference to FIGS. 24A, FIGS. 17A-23B, and FIGS. 33-34.

The handle assembly 2200 can further include a hub assembly 2230 with the suture lock assembly (e.g., suture lock) 2206 and a sleeve handle 2234 attached thereto. The hub assembly can be configured to control the pusher shaft and sleeve shaft of the delivery system 2220 while the sleeve handle 2234 can control a position of the sleeve shaft relative to the pusher shaft. In this way, operation of the various components of the handle assembly 2200 can actuate and control operation of the components arranged within the outer shaft 2260. In some embodiments, the hub assembly 2230 can be coupled to the handle 2222 via a connector 2240.

The handle assembly 2200 can further include one or more flushing ports to supply flush fluid to one or more lumens arranged within the delivery system 2220 (e.g., annular lumens arranged between coaxial components of the delivery system 2220) in order to reduce potential thrombus formation. One embodiment where the delivery system 2220 includes three flushing ports (e.g., flushing ports 2210, 2216, and 2218) is shown in FIG. 24B. Further details on these flushing ports and the components of the handle assembly 2200 are discussed below with reference to FIG. 24A.

Sleeve Shaft

Figures 17A, 17B, 17C:
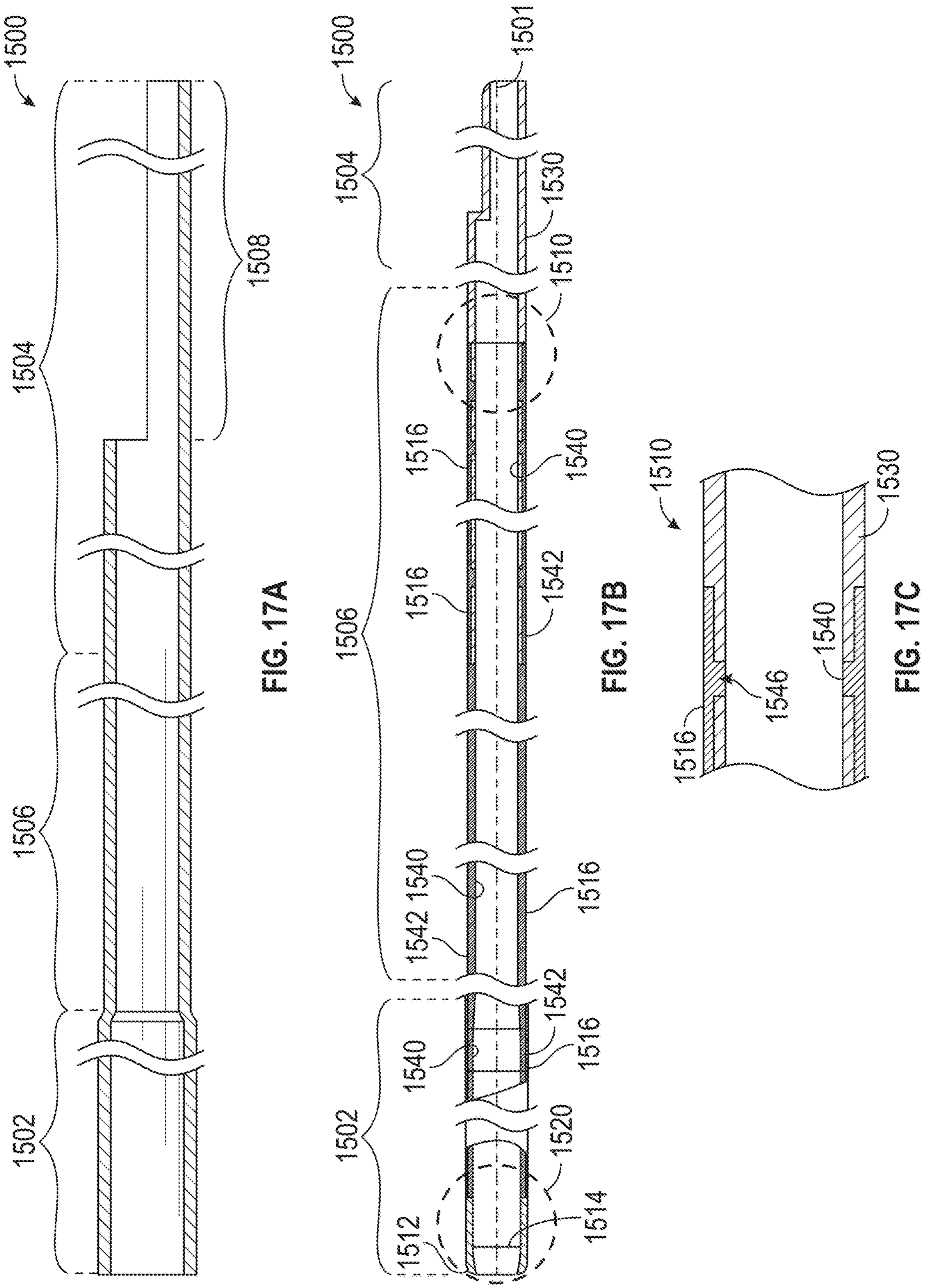
FIG. 17A illustrates an example embodiment of a sleeve shaft in accordance with various embodiments.
FIG. 17B illustrates a side cross-sectional view of the sleeve shaft of FIG. 17A.
FIG. 17C illustrates a detail view of a portion of the sleeve shaft of FIG. 17B, showing an interface between different materials of the sleeve shaft.

An example sleeve shaft 1500 in accordance with various embodiments, which can be implemented within a docking device delivery system, such as delivery system 2220 of FIG. 24B, is illustrated in FIGS. 17A-20D. Other variations of a sleeve shaft with only some of the illustrated features in these figures and/or with additional non-illustrated features are also possible. In some embodiments, as illustrated in FIG. 17A, the sleeve shaft 1500 comprises three sections: a distal or sleeve section 1502, which comprises the lubricous sleeve to cover the docking device during deployment, a proximal section 1504 used to manipulate or actuate the sleeve position, and a middle section 1506 to connect the distal 1502 and proximal 1504 sections. A portion of the proximal section 1504 can be arranged in the handle assembly (as discussed further below with reference to FIGS. 24A and 35-37). Further, the sections 1502, 1504, and 1506 of the sleeve shaft 1500 can be formed by a plurality of components and/or materials, including a flexible polymer jacket 1516 (FIG. 17D), a more rigid tube 1530 (FIG. 17E), an inner liner 1540 (FIGS. 17B, 17C, 19, and 20C), and a metal braid 1542 (which may be part of or imbedded within portions of the polymer jacket 1516). For example, as explained further below, the polymer jacket 1516 can be part of the distal section 1502 and middle section 1506, the inner liner 1540 can extend along and form an interior surface of the distal section 1502 and the middle section 1506, and the tube 1530 can form the proximal section 1504, with a portion that extends into a proximal portion of the middle section 1506. In this way, each of the distal section 1502, proximal section 1504, and middle section 1506 of the sleeve shaft 1500 can include different layers and compositions of materials, as explained further below. As the distal section 1502 is configured to cover the docking device, the distal section of various embodiments can be flexible, have a lower durometer (e.g., hardness), and have a hydrophilic coating. The hydrophilic coating of some embodiments acts as a lubricous surface to improve the ease of encircling the native anatomy, reduce risk of damage to the native anatomy, and reduce procedure time. The lubricious sleeve can cover higher-friction areas of the docking device during implantation. Additionally, the distal section 1502 can act as a cover for a foam or braided paravalvular leakage solution that may exist on the docking device, as discussed above. As the distal section 1502 acts as a sleeve or cover for a docking device, it can form a tubular structure in many embodiments (e.g., as shown in FIG. 17D, as discussed further below). This tubular structure comprises an inner diameter sufficient to surround a docking device and an outer diameter that is not too much larger than the diameter of the docking device. For example, in some embodiments, the inner diameter of the distal section 1502 of the sleeve shaft 1500 is approximately 2.4 mm (e.g., ±0.3 mm), while the outer diameter is approximately 3.4 mm (e.g., ±0.5 mm). In some embodiments, the inner diameter is 2.4 mm±0.1 mm and the outer diameter is 3.4 mm±0.2 mm. Further, in some embodiments, the length of the distal section 1502 is sufficient to cover the full length of the docking device from distal end to proximal end thereof. In some embodiments, the distal section 1502 will be longer than the docking device to allow some room to cover connecting regions of the docking device or to give extra space for added flexibility or any other reasonable purpose. For example, in some embodiments, during delivery, a distal tip (or end) 1512 of the distal section 1502 can extend past a distal end of the docking device (labeled as 1514 in FIG. 17B; however, in alternate embodiments, the location 1514 of the distal end of the docking device can be farther away from the distal tip 1512), thereby providing the distal section 1502 of the sleeve shaft 1500 with a more atraumatic tip that can bend, squeeze, deform, or the like, as it is navigated around the native architecture of the implantation site for the docking device. This is explained further below with reference to FIG. 33. In some embodiments, the distal section 1502 will be approximately 400 mm (e.g., ±10 mm) in length. In some embodiments, the length of the distal section 1502 can be in a range of 385 mm to 415 mm.

Figure 18:
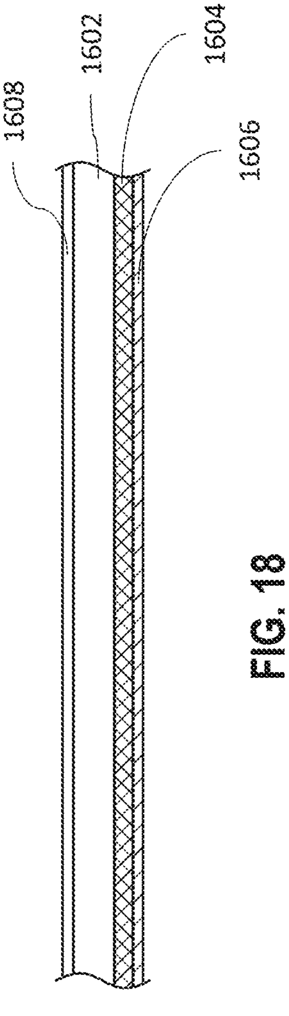
FIG. 18 illustrates an example embodiment of a layered construction of a lubricous sleeve in accordance with various embodiments.

As illustrated in FIG. 18, in some embodiments, the distal section 1502 comprises multiple different components. In some embodiments, the distal section 1502 is constructed of a flexible polymer 1602 over a supporting braid 1604. The flexible polymer 1602 (which may be part of the polymer jacket 1516) can be selected from a variety of elastomeric materials, while the braid needs to be supportive and flexible, including high density braids (as measured by picks per inch; e.g., 80 ppi, 90 ppi, or the like). In some embodiments, the braid 1604 can be constructed of metals, such as nitinol or stainless steel. In some embodiments, the braid 1604 can a stainless steel braid having a density of approximately 90 ppi. In certain embodiments, the flexible polymer can be a polyether-amide block copolymer or a blend of two or more polyether-amide block copolymers. The flexible polymer can have a Shore D hardness measured according to ISO 868:2003 of between about 20 and about 40, between about 20 and about 30, about 22, or about 25. In some embodiments, the flexible polymer can have a flexural modulus measured according to ISO 178:2010 of between about 10 MPa and about 80 MPa, between about 10 MPa and about 25 MPa, between about 10 MPa and about 20 MPa, between about 10 MPa and about 15 MPa, between about 10 MPa and about 12 MPa, about 10 MPa, about 11 MPa, about 12 MPa, about 13 MPa, about 14 MPa, or about 15 MPa. In certain embodiments, the flexible polymer can be one of or a blend of two or more of PEBAX® grades 2533, 3533, 4033, 4533, and 5513 (Arkema S.A., France) and VESTAMID® grade E40 (Evonik Industries AG, Germany). In some embodiments, the flexible polymer can be PEBAX® 2533.

Additional embodiments of the distal section 1502 can include an inner layer (e.g., inner liner) 1606 to provide an inner layer (which may be part of the inner liner 1540) against the docking device, which can be made of various polymeric materials, such as PTFE. Finally, in some embodiments, if the flexible polymer 1602 is not sufficiently lubricous, a hydrophilic coating 1608, such as a hydrogel, is applied on the outer side of the sleeve. The hydrophilic coating can serve various purposes, such as allowing a sleeved docking device to navigate more easily around the native valve anatomy without significant friction. Additionally, hydrophilic compounds increase echogenicity, thus allowing visualization of the sleeve using sonography. Further, the distal section 1502 of some embodiments can include a radiopaque material to increase the ability to visualize the sleeve during deployment of a docking device, as described further below with reference to FIG. 19.

While FIG. 18 illustrates one exemplary construction of the distal section 1502, other embodiments can utilize a cut (such as laser cut), higher durometer material. In such laser cut and higher durometer material embodiments, the cuts may allow the distal section 1502 to be more flexible and bend, while the higher durometer material can provide integrity to the distal section.

Figure 19:
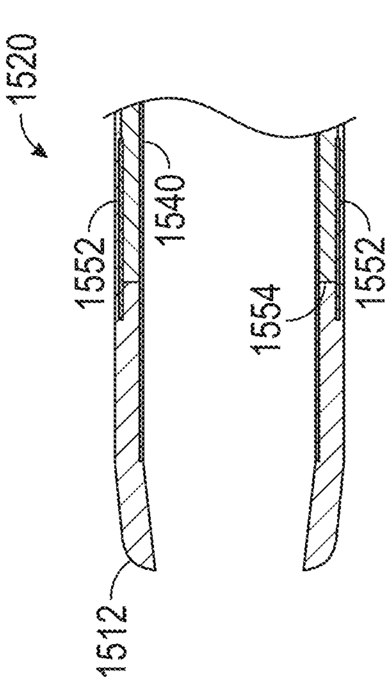
FIG. 19 illustrates a side cross-sectional view of an example embodiment of a flexible tip for the sleeve shaft of FIG. 17B.

Additionally, the distal section 1502 of the sleeve shaft 1500 of various embodiments includes a distal tip 1520, as illustrated in FIG. 17B and shown in more detail in FIG. 19. The distal tip 1520 can incorporate a thinner and/or softer material to help deflect the sleeve, if the distal tip contacts an obstruction. In some embodiments, the distal tip 1520 is also tapered such that it has a smaller diameter at its distal end 1512. As shown in FIG. 19, in some embodiments, the inner liner 1540 may not extend to the distal end 1512, thereby leaving the distal end portion of the distal tip 1520 to be comprised of only the flexible polymer (e.g., the flexible polymer material of the polymer jacket 1516). Further, several embodiments incorporate a radiopaque material in the distal tip 1520 to increase the visibility of the distal tip 1520 of the sleeve shaft 1500 during deployment from the delivery system (e.g., at the target implantation site). In some embodiments, as shown in FIG. 19, the radiopaque material can be in the form of one or more marker bands 1552, embedded within the polymer jacket 1516 and spaced away from the distal end 1512. In some embodiments, a metal braid or braided portion of the polymer jacket 1516 can terminate a distance before a distal end of the marker band 1552, such as at location 1554 shown in FIG. 19. In some embodiments, the radiopaque material of the marker band 1552 is a platinum-iridium marker, while other embodiments will utilize a section of flexible polymer loaded with bismuth or $BaSO_4$, 60% $BaSO_4$.

The middle section 1506 of the sleeve shaft 1500 of various embodiments serves to provide column strength to push the distal section with the dock and retract the distal section 1502 after the docking device encircles the native valvular anatomy as well as navigate the anatomy of a patient from the point of insertion of the delivery system to the heart. Therefore, the middle section 1506 of various embodiments can be both flexible and possess a braided polymer shaft. Additionally, in some embodiments, the middle section 1506 can comprise a flexible polymer of varying durometer along its length, as explained further below with reference to FIG. 17D. The middle section 1506 of many embodiments can be constructed of a flexible polymer over a supporting braid. In certain embodiments, the flexible polymer can be a polyether-amide block copolymer or a blend of two or more polyether-amide block copolymers. The flexible polymer can have a Shore D hardness measured according to ISO 868:2003 of between about 35 and about 70, between about 45 and about 65, between about 50 and about 60, or about 55. In some embodiments, the flexible polymer can have a flexural modulus measured according to ISO 178:2010 of between about 75 MPa and about 400 MPa, between about 100 MPa and about 250 MPa, between about 150 MPa and about 200 MPa, between about 160 MPa and about 180 MPa, between about 160 MPa and about 170 MPa, about 160 MPa, about 165 MPa, about 170 MPa, about 175 MPa, about 180 MPa, or about 185 MPa. In certain embodiments, the flexible polymer can be one of or a blend of two or more of PEBAX® grades 4033, 4533, 5533, 6333, and 7033 (Arkema S.A., France) and VESTAMID® grades E40, E47, E55, E58, and E62 (Evonik Industries AG, Germany). In some embodiments, the flexible polymer can be PEBAX® 5533. In other embodiments, the flexible polymer can be VESTAMID® E55. The braid can be the same density (e.g., 80 ppi, 90 ppi, or the like) or a lower density (e.g., 60 ppi) braid than the distal section 1502. Additionally, in some embodiments, the middle section 1506 is a tubular structure adapted and/or configured such that the sleeve shaft can operate over a pusher shaft. As a tubular structure, the inner diameter can be approximately 2.25 mm (e.g., ±0.3 mm), while the outer diameter is approximately 3.0 mm (e.g., ±0.5 mm). In some embodiments, the inner diameter is 2.21 mm and the outer diameter is 3.07 mm. In various embodiments the length of the middle section will be sufficient to navigate through a patient's anatomy. In many embodiments, the length of the middle section will be approximately 940 mm (e.g., ±50 mm).

Figure 17D:
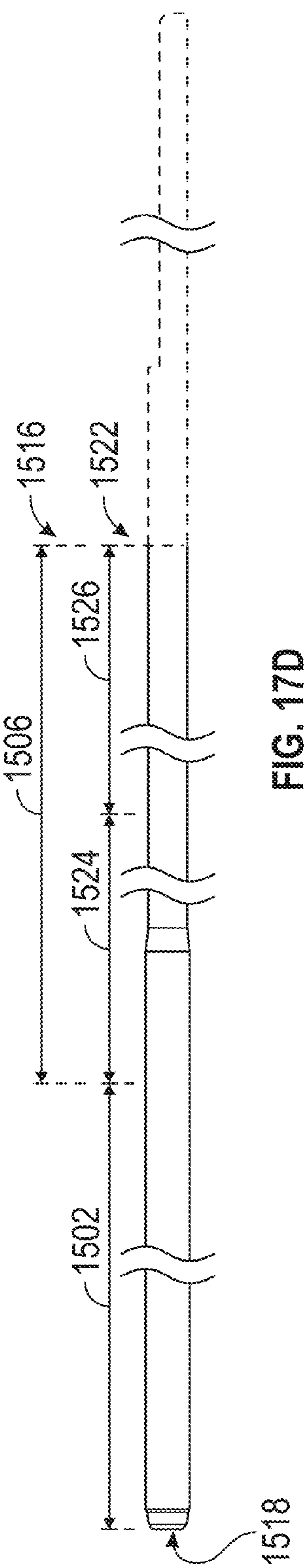
FIG. 17D illustrates a side view of an example embodiment of a flexible polymer jacket of the sleeve shaft of FIG. 17B.

In some embodiments, the distal section 1502 and the middle section 1506 are formed as a single, continuous unit with varying properties (e.g., dimensions, polymers, braids, etc.) along the length of the singular unit. For example, FIG. 17D shows an exemplary embodiment of a flexible polymer jacket (or covering) 1516 and its relative location on the above-described sections of the sleeve shaft 1500. The polymer jacket 1516 can be included on and/or at least partially forms the distal section 1502 and middle section 1506 of the sleeve shaft 1500. The dashed lines in FIG. 17D illustrate the proximal section 1504 of the sleeve shaft 1500, which does not include the flexible polymer jacket. In some embodiments, as explained above, the polymer jacket 1516 can comprise different grades or hardness of the same flexible polymer (e.g., PEBAX®), along its length. Said another way, the polymer jacket 1516 can have a varying (e.g., increasing) hardness (may also be referred to as durometer) along its length, from its distal end 1518 to its proximal end 1522.

As an example, the distal section 1502 can comprise a flexible polymer (e.g., PEBAX®) with a first hardness (e.g., shore D hardness). Possible grades and shore D hardness for the distal section 1502 are discussed above. The portion of the polymer jacket 1516 forming the middle section 1506 can comprise a first portion 1524 comprising the same flexible polymer with a second hardness, which is greater (e.g., less flexible) than the first hardness of the distal section 1502, and a second portion 1526 comprising the same flexible polymer with a third hardness, which is greater (e.g., less flexible) than the second hardness. Possible grades and shore D hardness for the middle section 1506 are discussed above. In some embodiments, the first hardness can be from about 20 to about 24, the second hardness can be from about 50 to about 60, and the third hardness can be from about 55 to about 65. As such, the polymer jacket 1516 can increase in hardness and decrease in flexibility toward its proximal end 1522. In alternate embodiments, the polymer jacket 1516 can comprise more sections than those shown in FIG. 17D with varying hardness. For example, in some embodiments, the portion of the polymer jacket 1516 forming the middle section 1506 can comprise more than two sections with different hardness (e.g., three sections, each having a different hardness).

In some embodiments, the inner liner 1540 can be arranged along an inner surface of the polymer jacket 1516, in the distal section 1502 and middle section 1506. As explained above, in some embodiments the inner liner 1540 can comprise a thin layer of polymer, such as PTFE. The polymeric materials of the inner layer 1540 and the polymer jacket 1516 can be configured to bond to one another.

Figure 17E:
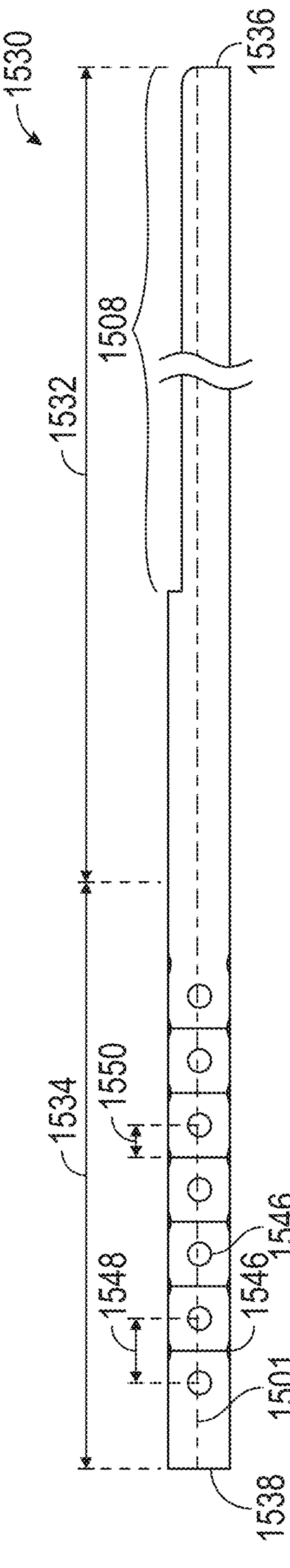
FIG. 17E illustrates a side view of an example embodiments of a more rigid tube portion of the sleeve shaft of FIG. 17B.

The proximal section 1504 of the sleeve shaft is designed to be more rigid and provide column strength to actuate the position of the lubricous sleeve by pushing the middle section 1506 and distal section 1502 with the docking device (e.g., docking device 70, as shown in FIGS. 9A to 11C) and retracting the distal section 1502 after the docking device encircles the native anatomy. As the sleeve shaft 1500 of various embodiments operates surrounding the pusher shaft (e.g., pusher shaft 1900 of FIGS. 21A-21G, as described further below), the structure can be shaped and configured to be generally tubular in structure and more rigid. For example, the proximal section 1504 can be formed by a relatively rigid tube 1530, as shown in FIG. 17E. In some embodiments, the tube 1530 can be constructed of a surgical grade metal, such as stainless steel. In some embodiments the tube 1530 can be a hypo tube.

Figure 20A:
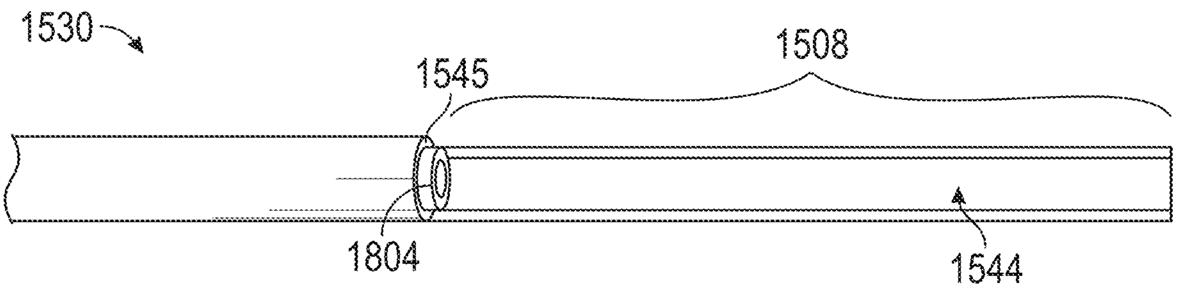
FIG. 20A illustrates a side view of an example embodiment of a proximal section of a sleeve shaft in accordance with various embodiments.
Figure 20B:
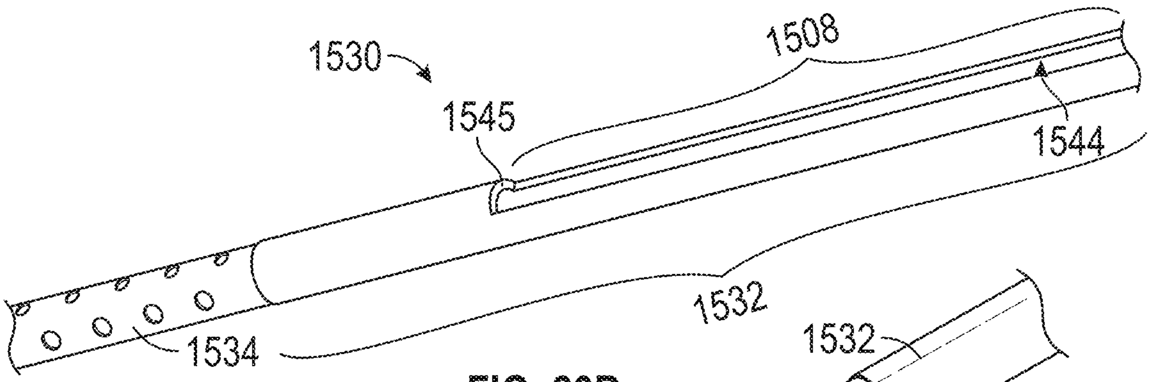
FIG. 20B illustrates a perspective view of an example embodiment of a more rigid tube portion of a proximal section of a sleeve shaft in accordance with various embodiments.

The tube 1530 can include a first section 1532 (which can form the entirety of the proximal section 1504) and a second section 1534 which extends into the middle section 1506 (see FIGS. 17E and 20B). As explained further below, the first section 1532 includes a cut portion 1508 which has a cross-section (in a plane normal to a central longitudinal axis 1501 of the sleeve shaft 1500) that is not a complete circle (e.g., is open and does not form a closed tube). A remainder of the tube 1530 can be tubular (e.g., a closed tube having a relatively circular cross-section). As also explained further below, the second section 1534 can be configured to facilitate boding between the inner liner 1540, arranged on an inner surface of the second section 1534, to the polymer jacket 1516, arranged on an outer surface of the second section 1534.

As a tubular structure, the tube 1530 of various embodiments can have an inner diameter of approximately 2.4 mm (e.g., ±0.3 mm), while the outer diameter can be approximately 3.0 mm (e.g., ±0.5 mm). In some embodiments, the inner and outer diameters of the tube 1530 can vary over a length of the tube 1530. For example, in some embodiments, the proximal end 1536 of the tube 1530 can have an inner diameter of 2.21 mm (±0.02 mm) and an outer diameter of 3.07 mm (+0.02 mm). In some embodiments, the distal end 1538 of the tube 1530 can have an inner diameter of 2.67 mm (+0.3 mm) and an outer diameter of 2.87 mm (+0.3 mm).

Figure 35:
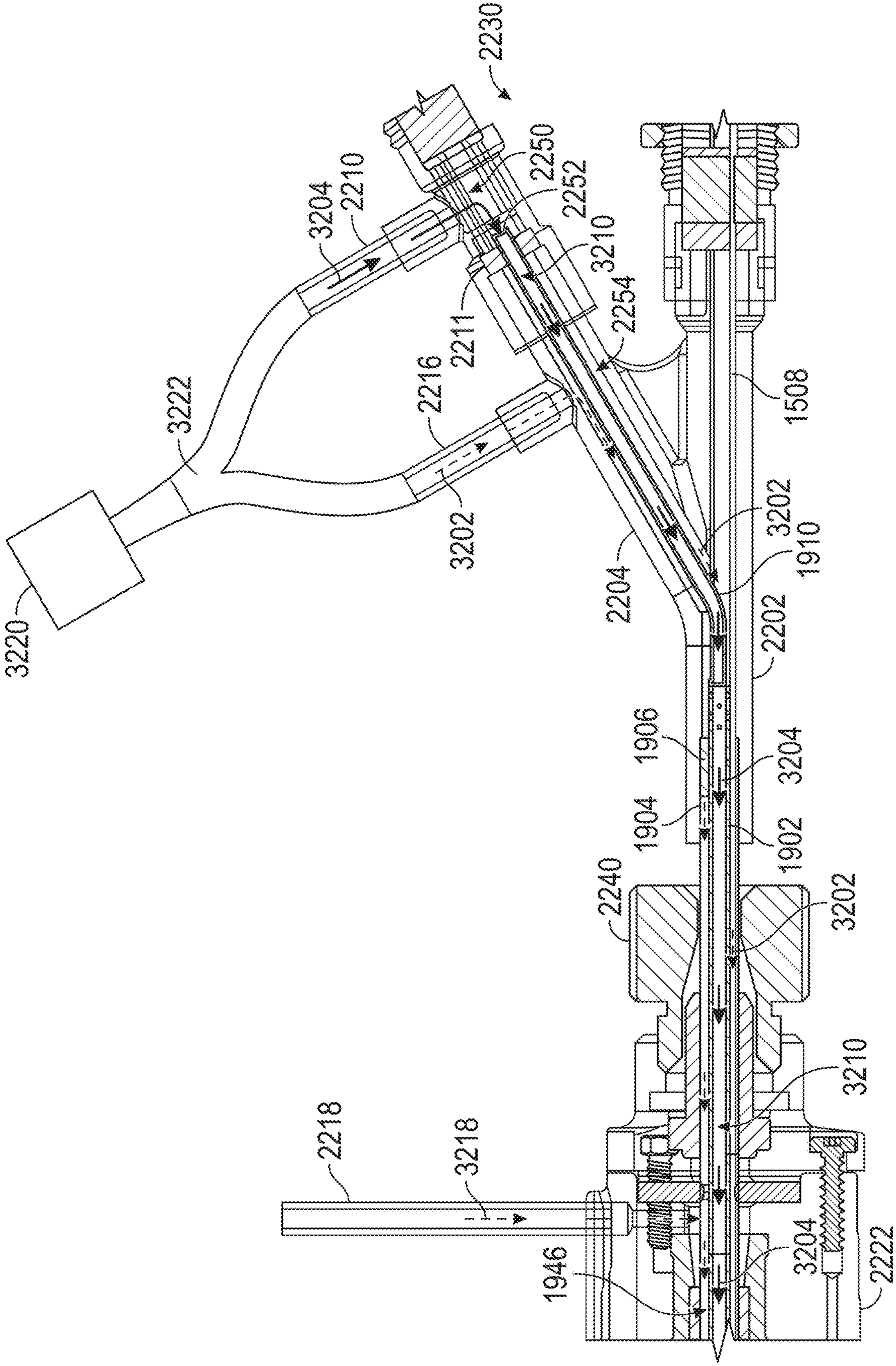
FIG. 35 illustrates a side cross-sectional view of a portion of a handle assembly and fluid flow through lumens of the handle assembly.
Figure 36:
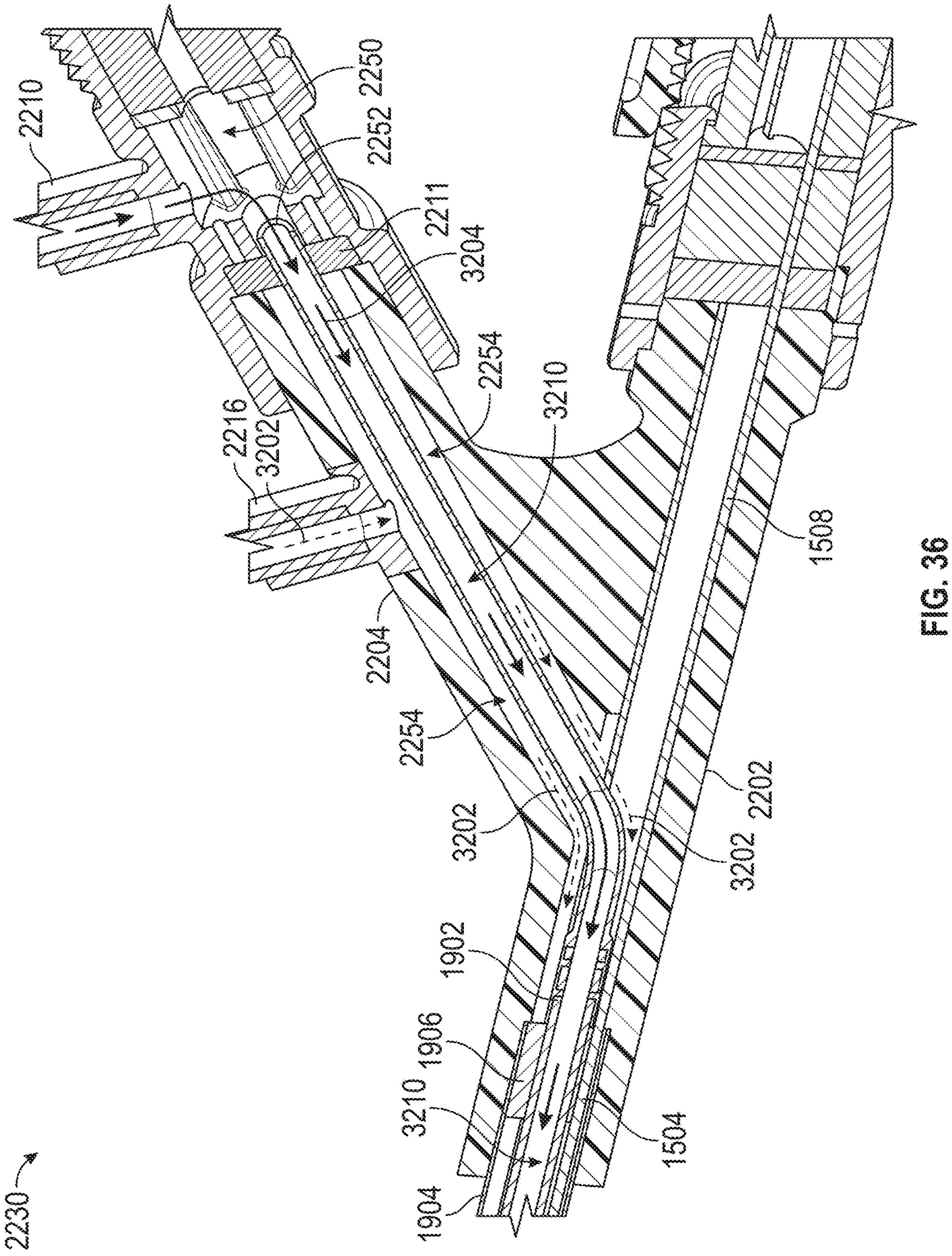
FIG. 36 illustrates a perspective cross-sectional view of a more detailed portion of the handle assembly of FIG. 35 and fluid flow through lumens of the handle assembly.

As introduced above, the first section 1532 of the tube 1530 can include the cut portion 1508, proximate to the proximal end 1536. As shown in FIGS. 24A, 35, and 36 (which are described in further detail below), the cut portion 1508 of the sleeve shaft 1500 extends into the hub assembly 2230 of the handle assembly 2200 and a portion (e.g., proximal extension 1910) of the pusher shaft 1900 extends along an inner surface of the cut portion 1508. The cut (e.g., open) profile of the cut portion 1508 can allow the proximal extension 1910 of the pusher shaft 1900 to extend out of a void space 1544 formed in the cut portion 1508 (FIGS. 20A and 20B) and branch off, at an angle relative to the cut portion 1508, into the branch 2204 of the hub assembly (e.g., a suture lock 2206 can be connected at an end of the branch 2204, as shown in FIG. 24A). As such, the pusher shaft 1900 and sleeve shaft 1500 can be operated in parallel with one another and an overall length of the delivery system in which the sleeve shaft 1500 and pusher shaft 1900 are incorporated can be maintained similar to or only minimally longer than previous delivery systems that do not incorporate sleeves.

Figure 22A:
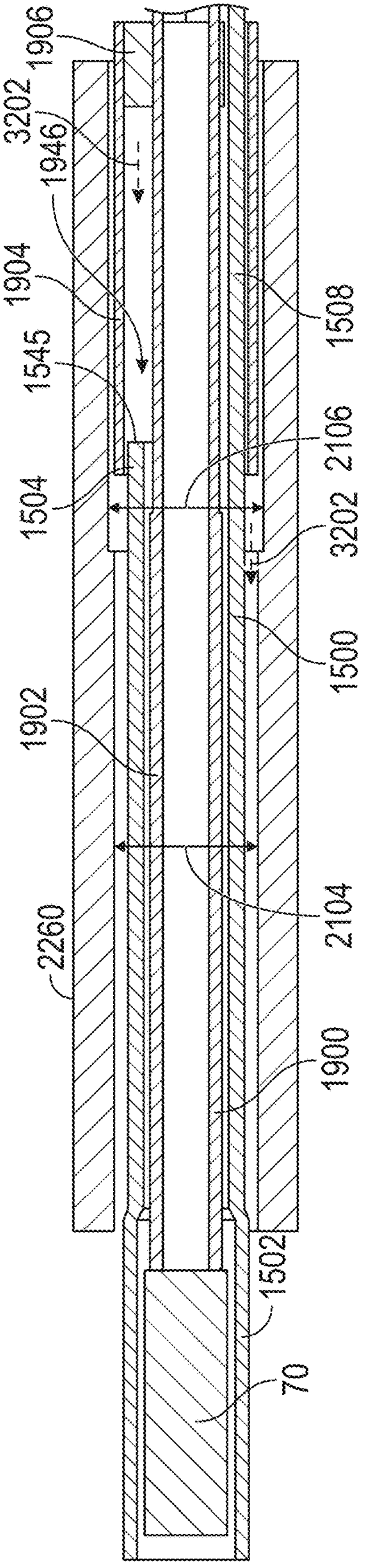
FIGS. 22A-22C illustrate an example embodiment of a sleeve shaft and a pusher shaft interoperating in accordance with various embodiments.
Figure 22B:
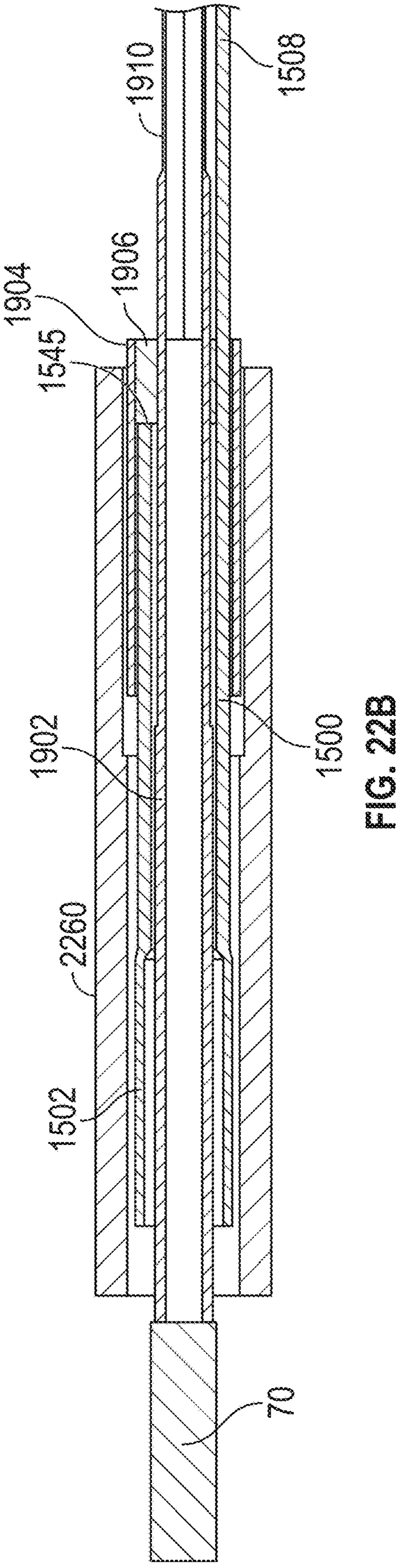

In some embodiments, the cut portion 1508 can have a generally U-shaped cross-section with a portion of the complete tubular structure removed. For example, the cut portion 1508 can form an open channel or conduit. In various embodiments, the cut portion 1508 can be cut using a laser, although any other means for removing part of the tubular structure can be used. Example embodiments of a shape of the cut portion 1508 can be seen in FIGS. 20A and 20B. However, in alternate embodiments, a different portion of the circumference of the tube 1530 can be removed/cut to form the cut portion 1508 than that shown in FIGS. 20A and 20B. An end surface 1545 (FIGS. 20A and 20B) is formed (e.g., exposed) on the full, tubular portion of the first section 1532, at an interface between the cut portion 1508 and the remainder of the first section 1532. This end surface 1545 can be arranged normal to the central longitudinal axis 1501 and can be configured to come into face-sharing contact with a stop element (e.g., plug 1906) of the pusher shaft (e.g., as shown in FIG. 22B, as explained further below)

Figure 20C:
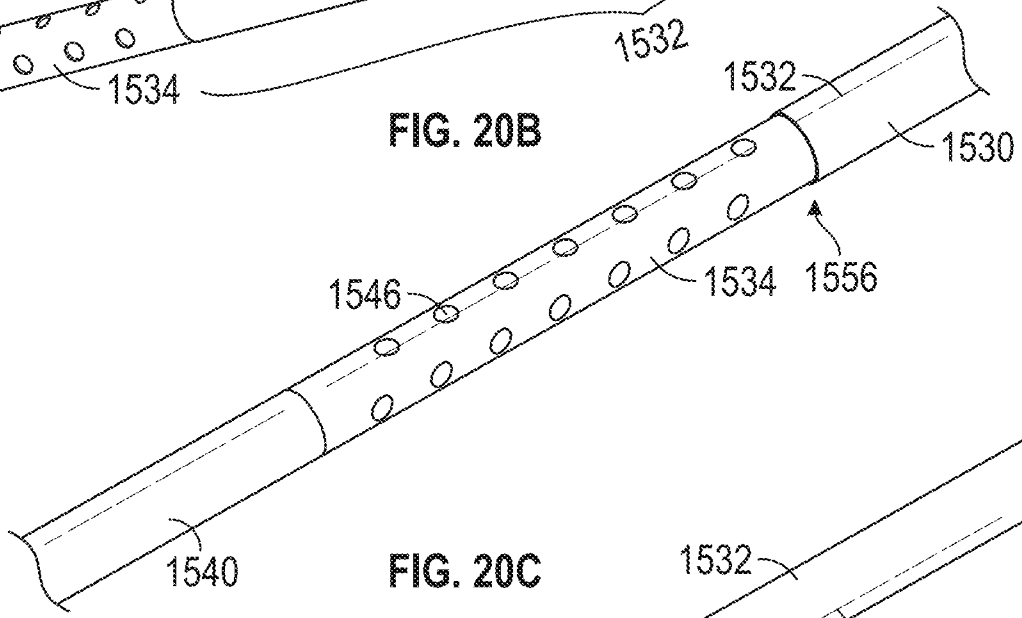
FIG. 20C illustrates a perspective view of an example embodiment of an interface between the tube portion of FIG. 20B and an inner liner at the proximal section of the sleeve shaft in accordance with various embodiments.
Figure 20D:
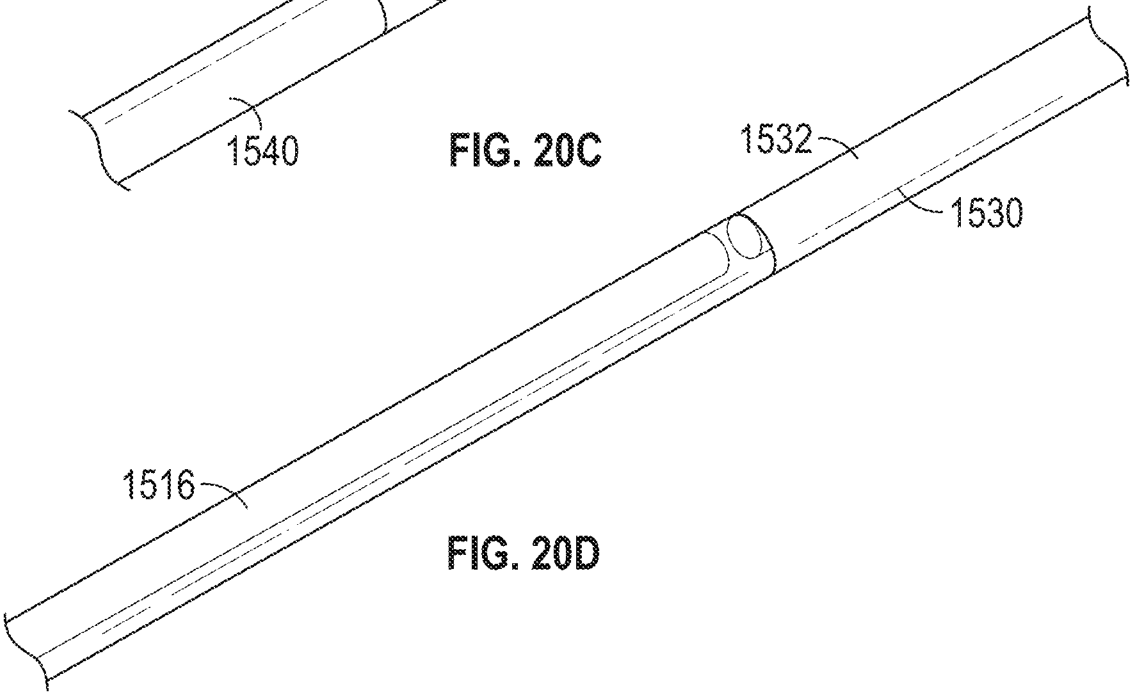
FIG. 20D illustrates a perspective view of an example embodiment of an outer flexible polymer layer arranged over the tube portion and inner liner of FIG. 20C at the proximal section of the sleeve shaft in accordance with various embodiments.

As shown in FIG. 17E, the second section 1534 of the tube 1530 can include a plurality of apertures 1546 that are configured to enable bonding of a proximal end of the second portion 1526 of the polymer jacket 1516, arranged on the outer surface of the second section 1534, to the inner liner 1540, arranged on the inner surface of the second section 1534. For example, as shown in FIG. 20C, the inner liner 1540 can extend along the inner surface of the second section 1534, to an edge 1556 of the second section 1534 which forms an interface between the first section 1532 and the second section 1534 of the tube 1530. However, in FIG. 20C the inner liner 1540 and the second section 1534 of the tube 1530 are not bonded together. As shown in FIG. 20D, the polymer jacket 1516 can be reflowed over the outer surface of the second section 1534 and bond, through the apertures 1546, to the inner liner 1540. Thus, in FIG. 20D the second section 1534 of the tube 1530 is sandwiched between the polymer jacket 1516 and the inner liner 1540.

For example, the polymers of the polymer jacket 1516 and the inner liner 1540 may not be able to bond (e.g., adhere) directly to the material (e.g., metal) of the tube 1530, but can bond to one another. Thus, the size and shape of each aperture 1546 and the relative arrangement of apertures 1546 on the second section 1534 can be selected to allow the outer polymer jacket 1516 to bond securely to the inner liner 1540, with the second section 1534 of the tube 1530 arranged therebetween. As such, the tube 1530 can be secured to the polymer jacket 1516 and the inner liner 1540.

In some embodiments, each of the plurality of apertures 1546 can extend through an entire thickness of the tube 1530. In some embodiments, the apertures 1546 can be formed as through-holes that are punched or cut through an entirety of the second section 1534 of the tube 1530 (e.g., through-and-through apertures). As such, in some embodiments, at each axial location of one visible aperture 1546 in FIG. 17E, another aperture 1546 can be located 180 degrees around a circumference of the tube 1530 from the visible aperture 1546. For example, as shown in FIG. 17E, the second section 1534 can include 28 apertures 1546, with adjacent sets of apertures 1546 offset from one another by 90 degrees. In some embodiments, along the length of the second section 1532, in the axial direction, the apertures can be spaced apart from one another at a first (center-to-center) distance 1548 and each set of apertures 1546 at the same axial position can be spaced apart from an adjacent set of apertures 1546 at a second distance 1550. In some embodiments, the first distance 1548 is approximately 3 mm and the second distance 1550 is 1.5 mm. In some embodiments, the first distance 1548 is in a range of 2.5 mm to 3.5 mm and the second distance 1550 is in a range of 1.0 mm to 2.0 mm. In some embodiments the second distance 1550 is half the first distance 1548. In alternate embodiments, a different number of apertures 1546 and/or relative spacing between and arrangement of the apertures 1546 than that shown in FIG. 17E and described is above is possible, while still providing adequate bonding between the inner liner 1540 and the polymer jacket 1516.

In some embodiments, the apertures 1546 can be circular with a diameter in a range of 0.5 to 1.5 mm, 0.8 mm to 1.2 mm, or 0.95 to 1.05 mm. In some embodiments, the diameter of the apertures 1546 can be approximately 1.0 mm. In some embodiments, the apertures 1546 can have another shape, such as oblong, square, rectangular, star-shaped, triangular, or the like. The diameter or width of each aperture 1546 can be selected so that a flexible polymer jacket 1516 can be reflowed over the outer surface of the tube 1530, flow into the apertures 1546, and securely bond to the inner liner 1540 arranged on the inner surface of the tube 1530, as shown in the detail view 1510 of FIG. 17C, at an interface between the middle section 1506 and proximal section 1504.

In some embodiments, as shown in FIG. 20A, a gasket 1804 can be located within the tubular portion of the distal portion 1504 of the sleeve shaft 1500, to form a seal between the sleeve shaft 1500 and a pusher shaft (e.g., pusher shaft 1900 shown in FIGS. 21A-21G, as explained further below) extending through sleeve shaft 1500. A seal formed by the gasket 1804, in accordance with some embodiments, is to prevent fluids being flushed through the delivery system to back flow or find a lower resistance path through another lumen than intended, as explained further below.

Pusher Shaft

Figure 21A:
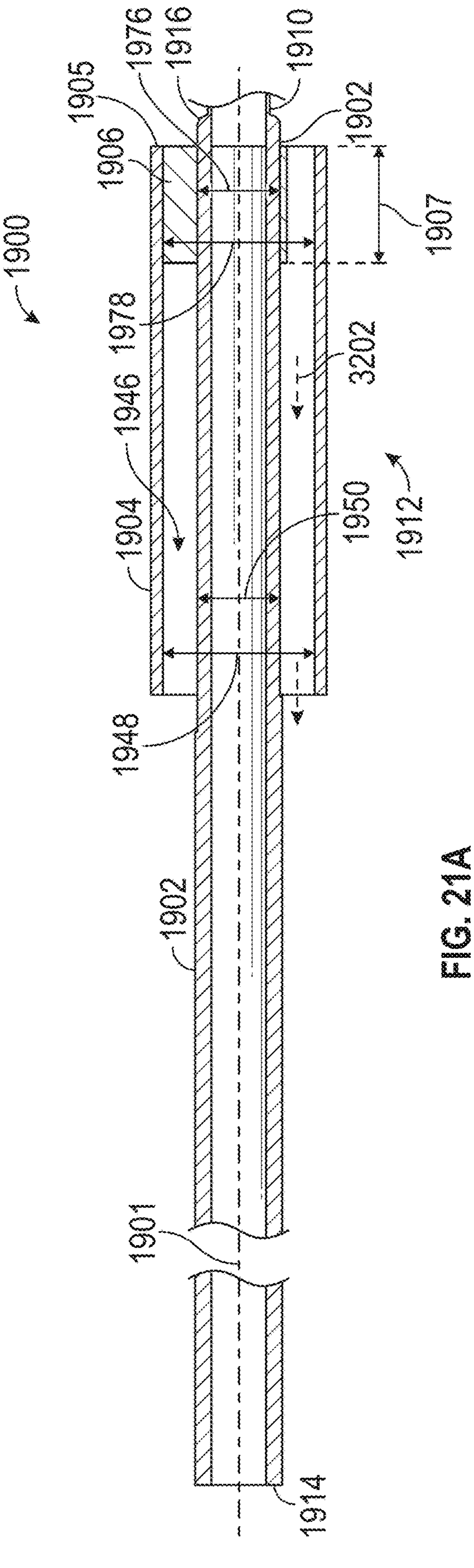
FIG. 21A illustrates a first side cross-sectional view of an example embodiment of a pusher shaft in accordance with various embodiments.
Figures 21B, 21C, 21D:
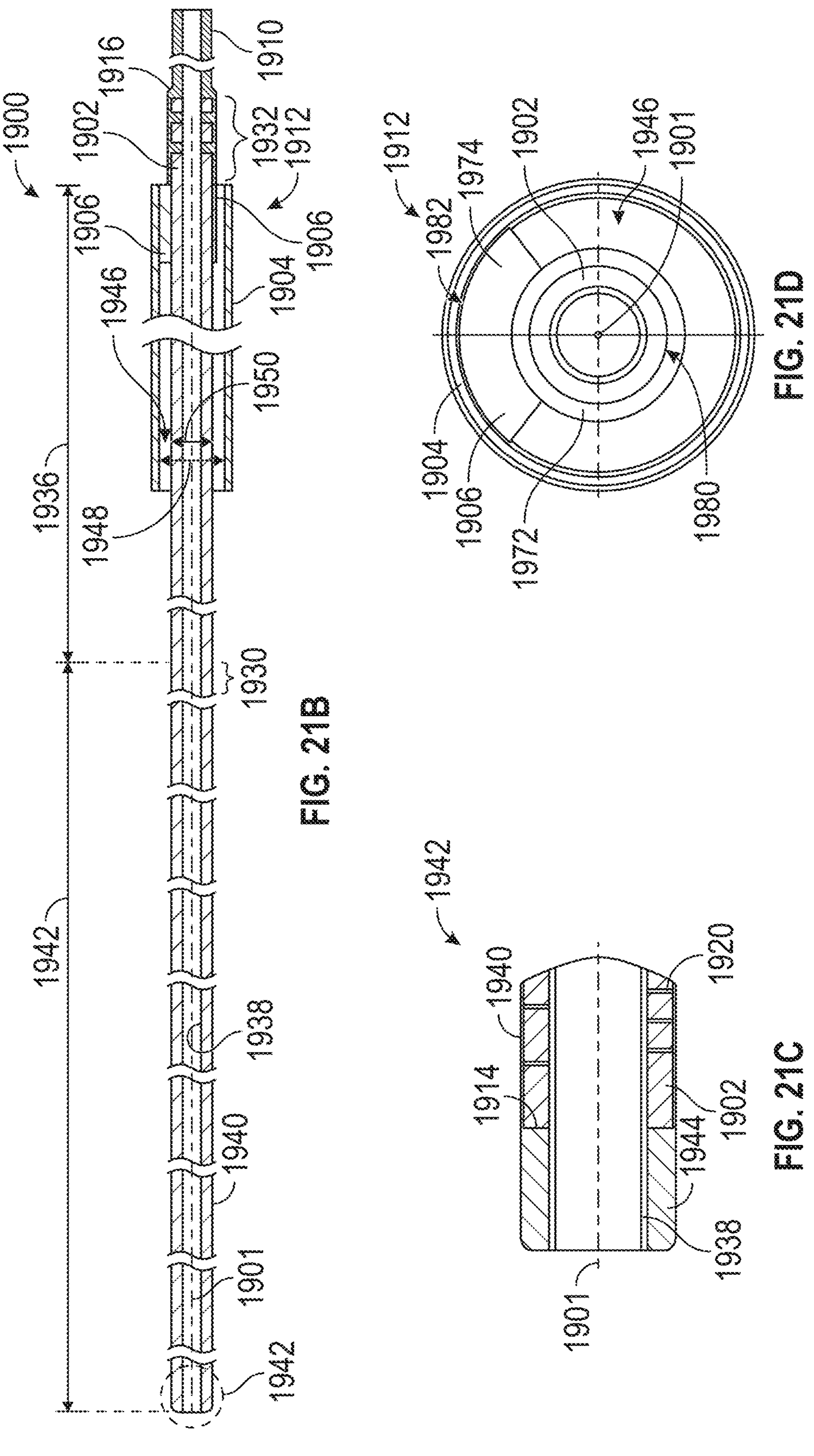
FIG. 21B illustrates a second side cross-sectional view of an example embodiment of a pusher shaft in accordance with various embodiments.
FIG. 21C illustrates a detail view of a distal end of the pusher shaft of FIG. 21B.
FIG. 21D illustrates a proximal end view of the pusher shaft of FIG. 21B.
Figure 21E:
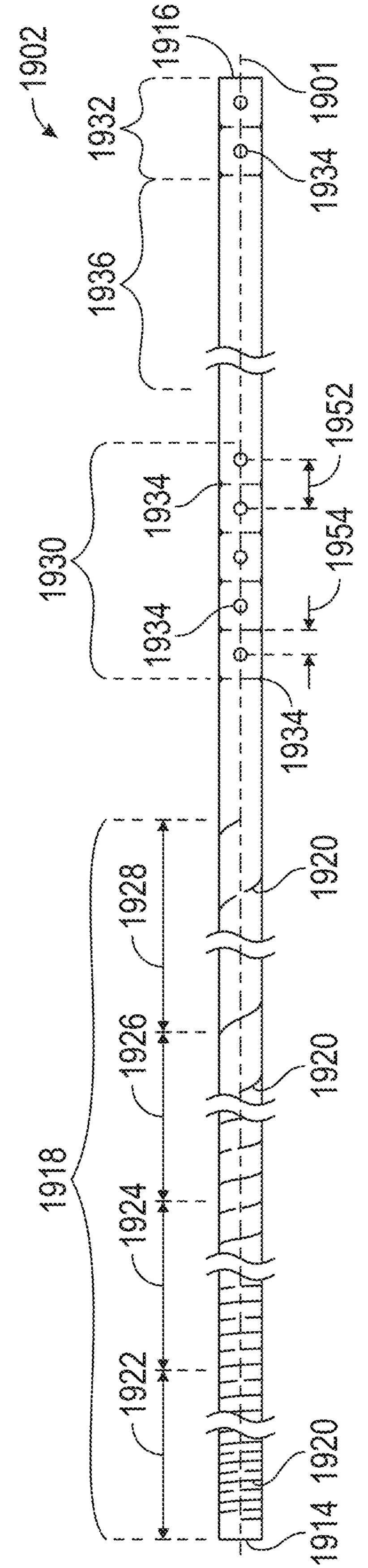
FIG. 21E illustrates a side view of a tube portion of the pusher shaft of FIG. 21B.
Figure 21F:
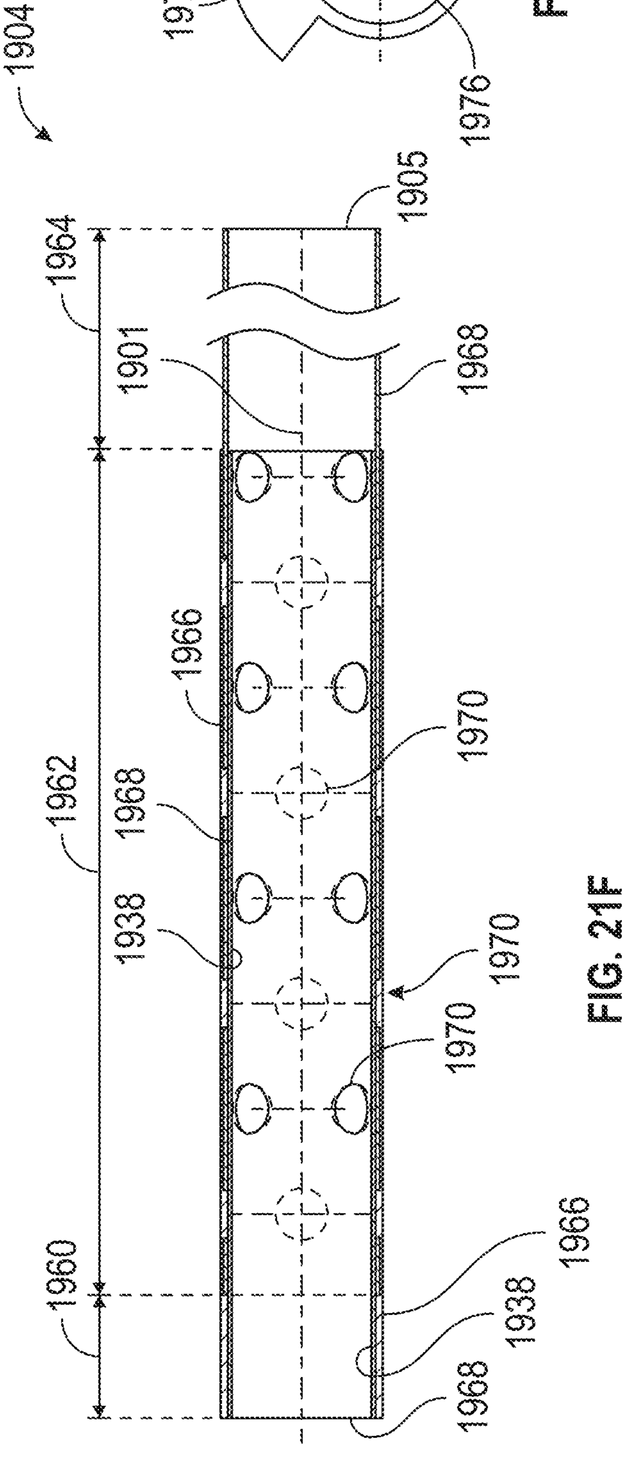
FIG. 21F illustrates a side view of a shell of the pusher shaft of FIG. 21B.
Figure 21G:
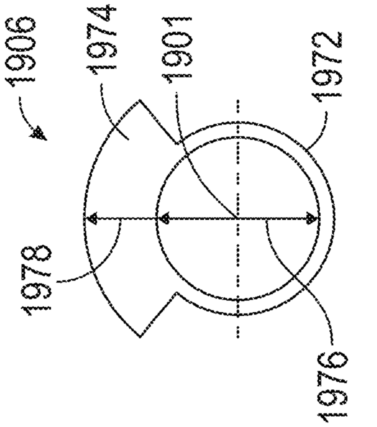
FIG. 21G illustrates an end view of a plug of the pusher shaft of FIG. 21B.
Figure 22C:
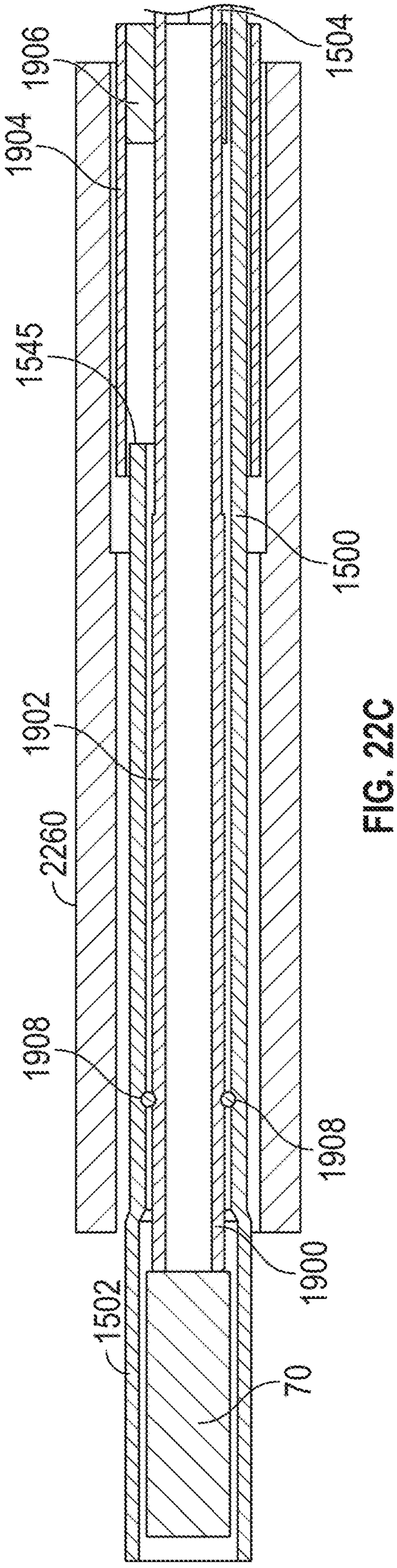
Figure 23A:
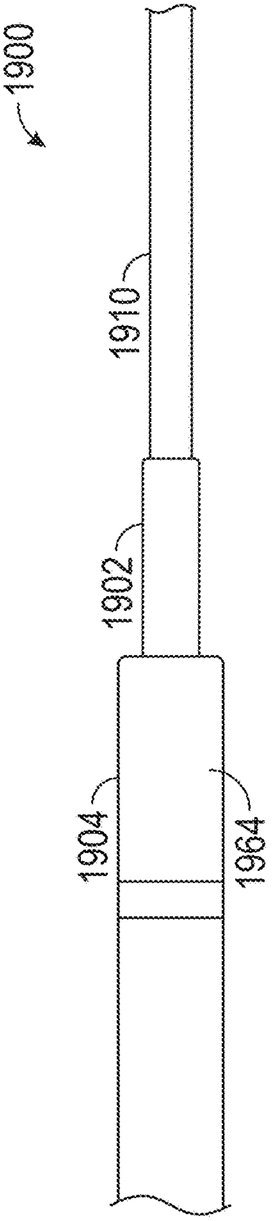
FIG. 23A illustrates a side view of an example embodiment of a proximal extension of a pusher shaft in accordance with various embodiments.
Figure 23B:
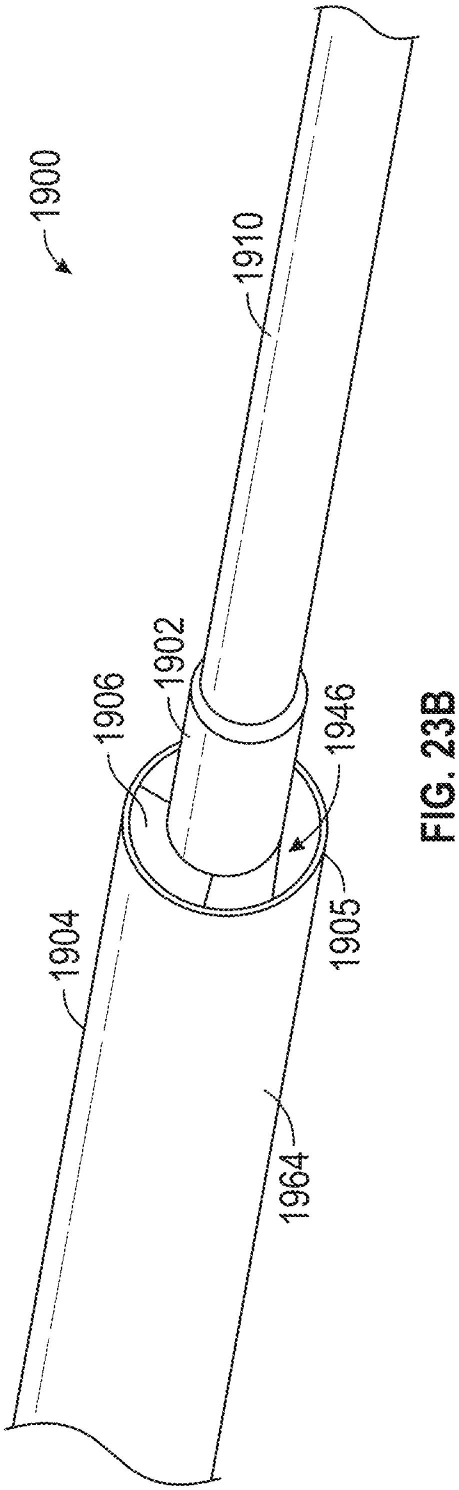
FIG. 23B illustrates a perspective view of the pusher shaft including the proximal extension of FIG. 23A.

An example pusher shaft 1900 that can be used in a delivery system for a docking device, such as delivery system 2220 of FIG. 24B, in accordance with various embodiments, is illustrated in FIGS. 21A-G and 23A-23B. FIG. 21A illustrates the four major components of the pusher shaft 1900, while FIG. 21B illustrates a more detailed embodiment of the pusher shaft 1900. A side view of an exemplary distal end of the pusher shaft 1900 is shown in FIG. 21C and a proximal end view of the pusher shaft 1900 is shown in FIG. 21D. FIGS. 21E-21G show some of the individual components of the pusher shaft 1900, including a main tube (which in some embodiments, can be a hypo tube) 1902 (FIG. 21E), a shell 1904 (FIG. 21F), and a plug 1906 (FIG. 21G). FIGS. 23A-23B show views of a portion of the pusher shaft 1900 where the shell 1904, main tube 1902, and a proximal extension 1910 of the pusher shaft 1900 interface with one another. These figures of the pusher shaft 1900 show a central longitudinal axis 1901 of the pusher shaft 1900, which can be coaxial with the central longitudinal axis 1501 of the sleeve shaft 1500 and outer shaft 2260 of the delivery system, as explained further below with reference to FIGS. 22A-22C.

As shown in FIGS. 21A-21G, the example pusher shaft 1900 can comprise four sections or components: the main tube (e.g., shaft) 1902 for advancing and retracting a docking device (such as one of the docking devices described herein) and housing the release suture that secures the docking device to the pusher shaft, the shell 1904 that surrounds the pusher shaft 1900 and allows for locking the shaft and provides a hemostatic seal on the pusher shaft without interfering with the movement of the sleeve shaft, the plug 1906 that connects the main tube 1902 to the shell 1904 and acts as a stop for the sleeve shaft, and the proximal extension 1910 (as best shown in FIGS. 23A-23B) that allows for the pusher shaft to route from the inside of the sleeve shaft to the outside of the sleeve shaft allowing the two shafts to be actuated in parallel and reducing an overall length of the delivery system.

The main tube 1902 can extend from a distal end of an outer shaft (e.g., outer shaft 2260 shown in FIG. 24B) of the delivery system into a handle assembly (e.g., handle assembly 2200 of FIGS. 24A and 24B) of the delivery system. For example, as shown in FIGS. 35 and 36, as described further below, a proximal end portion 1912 of the pusher shaft 1900, which includes the interface between the main tube 1902, shell 1904, plug 1906, and proximal extension 1910 (as shown in FIGS. 21A, 21B, and 21D), can be arranged within or proximate to the hub assembly (e.g., hub assembly 2230) of the handle assembly. Thus, the main tube 1902 can be an elongate tube that extends along a majority of the delivery system.

In some embodiments, the main tube 1902 can be a hypo tube. Hypo tubes are components that can be utilized for deploying docking devices and have been previously described in U.S. Pat. Pub. No. 2018/0318079 entitled “Deployment systems, tools, and methods for delivery an anchoring device for a prosthetic valve,” the disclosure of which is incorporated herein by reference in its entirety. In some embodiments, the main tube 1902 can comprise a biocompatible metal, such as stainless steel.

In various embodiments, the main tube 1902 (shown by itself, in greater detail in FIG. 21E) is a relatively rigid tube that provides column strength for actuating deployment of a docking device. The main tube 1902 can possess a distal end 1914 at the point of interfacing with a docking device and a proximal end 1916, where the proximal extension 1910 is attached (as discussed further below).

In some embodiments, as shown in FIG. 21E, the main tube 1902 can have a distal section 1918 including a plurality of cuts 1920 therein that provide the main tube 1902 with increased flexibility at its distal end. Thus, the distal section 1918 may be referred to as a flexible section or portion of the main tube 1902. In some embodiments, the cuts 1920 can be laser cuts formed by laser cutting into a surface (e.g., outer surface) of the main tube 1902. In alternate embodiments, the cuts 1920 can be another type of cut formed by another cutting process (e.g., via etching, scoring, through-cutting, etc., into the outer surface of the main tube 1902). A width and depth of the cuts 1920 can be configured to add flexibility to the main tube 1902. In some embodiments, each of the cuts 1920 can be through-and-through cuts that penetrate through an entirety of the main tube 1902 (e.g., from one side to the other, in a direction perpendicular to the central longitudinal axis 1901). In some embodiments, the width of each cut 1920 can be approximately 0.05 mm. In some embodiments, the width of each cut 1920 can be in a range of 0.03 mm to 0.08 mm.

In some embodiments, a spacing between adjacent cuts 1920 can vary along a length of the distal section 1918. For example, as shown in FIG. 21E, adjacent cuts 1920 can be arranged closest together at the distal end 1914 and then the spacing between adjacent cuts 1920 can increase from the distal end 1914 to the proximal end of the distal section 1918. In some embodiments, the cuts 1920 can be formed as helical threads cut into (and through) the outer surface of the distal section 1918 of the main tube 1902. Thus, in these embodiments, the spacing or distance between adjacent cuts 1920 can be defined as the pitch of the cuts. In an exemplary embodiment, as shown in FIG. 21E, a first portion 1922 of the distal section 1918 can have a pitch in a range of 0.4 mm to 0.64 mm, a second portion 1924 of the distal section 1918 can have a pitch in a range of 0.64 to 1.2 mm, a third portion 1926 of the distal section 1918 can have a pitch of 1.2 mm, and a fourth portion 1928 of the distal section 1918 can have a pitch in a range of 1.2 mm to 3.0 mm. In some embodiments, the pitch of the first portion 1922 can increase from 0.4 mm (at its distal end 1914) to 0.64 mm along its length, the pitch of the second portion 1924 can increase from 0.64 mm to 1.2 mm along its length, the pitch of the third portion 1926 can be approximately 1.2 mm along its length, and the pitch of the fourth portion 1928 can increase from 1.2 mm to 3.0 mm along its length. It should be noted that the above pitch values for the distal section 1918 are exemplary and other pitches may be possible, where the pitch values can be selected to provide the main tube 1902 with increased flexibility at its distal end 1914 and a decreasing amount of flexibility along the length of the distal section 1918. In this way, the distal section 1918 can be configured to flex and/or bend along with the outer shaft 2260 of the delivery system, as it is navigated through an inner lumen of a patient, to the target implantation site.

The main tube 1902, in some embodiments, can include one or more portions or sections that include a plurality of apertures 1934 that are configured to enable bonding of an outer, flexible polymer layer (e.g., covering or jacket), arranged along a portion of an outer surface of the main tube 1902, to an inner liner, the inner liner arranged along an inner surface of the main tube 1902 (e.g., similar to apertures 1546 of the sleeve shaft 1500). At the same time, the apertures 1934 can be configured to provide rigidity to the pusher shaft 1900.

The embodiment of the main tube 1902 shown in FIG. 21E includes a first section 1930 and a second section 1932, spaced apart from one another, each including one or more apertures 1934 extending through a thickness of the main tube 1902 (e.g., through-holes extending from and through an outer surface to an inner surface of the main tube 1902). The apertures 1934 can be spaced around a circumference of the main tube 1902. In some embodiments, as shown in FIG. 21E, each aperture 1934 can extend through an entirety of the main tube 1902, thereby creating two apertures 1934 arranged 180 degrees apart from one another around the circumference of the main tube 1902. Further, in some embodiments, adjacent sets of apertures 1934 can be offset from one another by 90 degrees (e.g., as shown in FIG. 21E, the first section 1930 may include 20 apertures).

The size and/or shape of each aperture 1934 and a number and spacing between the apertures 1934 of each of the first section 1930 and the second section 1932 can be selected to allow the outer, flexible polymer layer to bond (e.g., bind) to the inner liner, with the main tube 1902 arranged therebetween and still, providing rigidity to the pusher shaft 1900. For example, in some embodiments, the apertures 1934 can be circular with a diameter in a range of 0.4 to 0.6 mm. In some embodiments, the diameter of the apertures 1934 can be approximately 0.5 mm. In some embodiments, the apertures 1934 can have another shape, such as oblong, square, rectangular, star-shaped, triangular, or the like.

In some embodiments, along the length of the first section 1930 and the second section 1932, in the axial direction, the apertures can be spaced apart from one another at a first (center-to-center) distance 1952 and each set of apertures 1934 at the same axial position can be spaced apart from an adjacent set of apertures 1934 at a second distance 1954. In some embodiments, the first distance 1952 is approximately 2 mm and the second distance 1550 is approximately 1.0 mm. In some embodiments, the first distance 1952 is in a range of 1.5 mm to 2.5 mm and the second distance 1954 is in a range of 0.5 mm to 1.5 mm. In some embodiments the second distance 1954 is half the first distance 1952. In alternate embodiments, a different number of apertures 1934 and/or relative spacing between and arrangement of the apertures 1934 than that shown in FIG. 17E and described is above is possible, while still providing adequate bonding between the inner liner and the outer flexible polymer, while providing rigidity to the pusher shaft 1900.

As shown in FIG. 21E, the second section 1932 is arranged at the proximal end 1916 of the main tube 1902 and includes fewer apertures 1934 than the first section 1930. However, in alternate embodiments, the second section 1932 can include more apertures 1934 than shown in FIG. 21E. In some embodiments, the first section 1930 can include 20 apertures 1934 and the second section 1932 can include 8 apertures. In other embodiments, the first section 1930 can include more or less than 20 apertures 1934 and the second section 1932 can include more or less than 8 apertures 1934.

As shown in FIG. 21E, the main tube 1902 can include a third section 1936 arranged and extending between the first section 1930 and the second section 1932 which does not include any apertures 1934.

FIG. 21B illustrates an exemplary embodiment of the materials and components of the pusher shaft 1900. As shown in FIG. 21B, the pusher shaft 1900 can include an inner liner 1938 covering an inner surface of the main tube 1902 and forming an inner surface of the proximal extension 1910. In some embodiments, the inner liner 1938 can extend along an entire length of the pusher shaft 1900. The inner liner can be the same or similar to the inner layer 1606 (shown in FIG. 18). In some embodiments, the inner liner can comprise PTFE. Further, in some embodiments, a thickness of the inner liner 1938 can be in a range of 0.012 mm to 0.064 mm.

Additionally, in some embodiments, a portion of the pusher shaft 1900 can include a polymer layer (also referred to as an outer covering or jacket) 1940. The polymer layer can be a flexible polymer, as explained further below. In some embodiments, the outer polymer layer 1940 is arranged over and along a fourth section 1942 (the fourth section 1942 including the distal section 1918 and the first section 1930) of the main tube 1902, while the third section 1936 of the main tube 1902 does not include the outer polymer layer 1940 (FIGS. 21B and 21E). In some embodiments, the outer polymer layer 1940 is also included on the second section 1932 of the main tube 1902 and forms an outer layer of the proximal extension 1910. For example, the proximal extension 1910 can comprise the inner liner 1938 and the outer polymer layer 1940.

The outer polymer layer 1940 can be reflowed over the cuts 1920 and the apertures 1934. In certain embodiments, the outer polymer layer 1940 can comprise a polyether-amide block copolymer or a blend of two or more polyether-amide block copolymers. The polymer of the outer polymer layer 1940 can have a Shore D hardness measured according to ISO 868:2003 of between about 60 and about 75, between about 65 and about 75, between about 70 and about 75, or about 72. In some embodiments, the outer polymer layer 1940 can have a flexural modulus measured according to ISO 178:2010 of between about 350 MPa and about 550 MPa, between about 450 MPa and about 550 MPa, between about 500 MPa and about 550 MPa, between about 500 MPa and about 525 MPa, between about 510 MPa and about 520 MPa, about 500 MPa, about 505 MPa, about 510 MPa, about 515 MPa, about 520 MPa, or about 525 MPa. In certain embodiments, the outer polymer layer 1940 can be one of or a blend of two or more of PEBAX® grades 7033 and 7233 (Arkema S.A., France) and VESTAMID® grades E62, E72, and EX9200 (Evonik Industries AG, Germany). In some embodiments, the outer polymer layer 1940 can be PEBAX® 7233. In other embodiments, the outer polymer layer 1940 can be VESTAMID® EX9200.

In some embodiments, the main tube 1902 can possess a uniform inner diameter, from its distal end 1914 to its proximal end 1916, in a range of about 1.0 mm to about 1.34 mm, while the outer diameter can vary from approximately 1.8 to 2.0 mm (e.g., ±0.2 mm) in the proximal and distal sections.

An exemplary embodiment of the distal tip 1942 of the pusher shaft 1900 is shown in FIG. 21C. In some embodiments, the distal tip 1942 includes a more flexible, polymeric tip or distal end portion 1944 which comprises a flexible polymer. In some embodiments, the polymeric distal end portion 1944 can comprise the same flexible material as and/or be continuous with the outer polymer layer 1940. Thus, the polymeric distal end portion 1944 of the distal tip 1942 can be reflowed over the distal end 1942 of the main tube 1902 and bonded to the inner liner 1938.

As shown in FIGS. 21A, 21B, and 21D, an inner diameter 1948 of the shell 1904 is larger than an outer diameter 1950 of the main tube 1902, thereby forming an annular cavity 1946 between (in the radial direction) the main tube 1903 and the shell 1904. As such, the proximal portion 1504 of the sleeve shaft 1500 can slide within the annular cavity (e.g., space) 1946, as described further below with reference to FIGS. 22A-22C. Further, flush fluid provided to a lumen on an exterior of the proximal extension 1910, in the hub assembly, can flow through the annular cavity 1946 and exit the distal end of the shell, as shown by arrows 3202 to enter a lumen (delivery shaft lumen 3216 shown in FIG. 38) between the sleeve shaft 1500 and outer shaft 2260 of the delivery system, as discussed further below with reference to FIGS. 35-38.

A side view of an exemplary embodiment of the shell 1904 of the pusher shaft 1900 is shown in FIG. 21F. The shell 1904 can include a distal section 1960, a middle section 1962, and a proximal section 1964. The distal section 1960 can be formed by the inner liner 1938 and an outer polymer layer 1966. In some embodiments, the outer polymer layer 1966 can comprise one of the flexible polymers described herein, such as PEBAX®. In some embodiments, the outer polymer layer 1966 can be a same or different grade of PEBAX® than the outer polymer layer 1940 of the main shaft 1902 and/or have a same or different hardness than that of the outer polymer layer 1940. As shown in FIG. 21F, a distal end 1968 of the shell 1904 can have a rounded edge. Together, the rounded edge of the distal end 1968 and the more flexible nature of the distal section 1960 (due to being comprised of the inner liner 1938 and outer polymer layer 1966 and not a more rigid tube), may provide a more atraumatic distal tip to the shell 1904, thereby reducing or preventing abrasion to an inner surface of the outer shaft of the delivery system surrounding the shell 1904 (e.g., outer shaft 2260).

The middle section 1962 of the shell 1904 can comprise the inner liner 1938, the outer polymer layer 1966, and a more rigid tube 1968 arranged between the inner liner 1938 and the outer polymer layer 1966 (in the radial direction). In some embodiments, the tube 1968 can comprise metal, such as stainless steel. In some embodiments, the tube 1968 can be a hypo tube. The tube 1968 can comprise a plurality of apertures 1970 extending through an entire thickness of the tube 1968, similar to the apertures 1934 of the main tube 1902, as described above. As described above, a size, number, and arrangement of the apertures 1970 can be selected to provide rigidity to the second section 1962 while also allowing the outer polymer layer 1966 to flow through the apertures 1970 and form a secure bond to the inner liner 1938. In some embodiments, a diameter of the apertures 1970 can be in a range of 1.0 to 1.4 mm. In some embodiments, the dimeter of the apertures 1970 can be approximately 1.2 mm.

Figure 37:
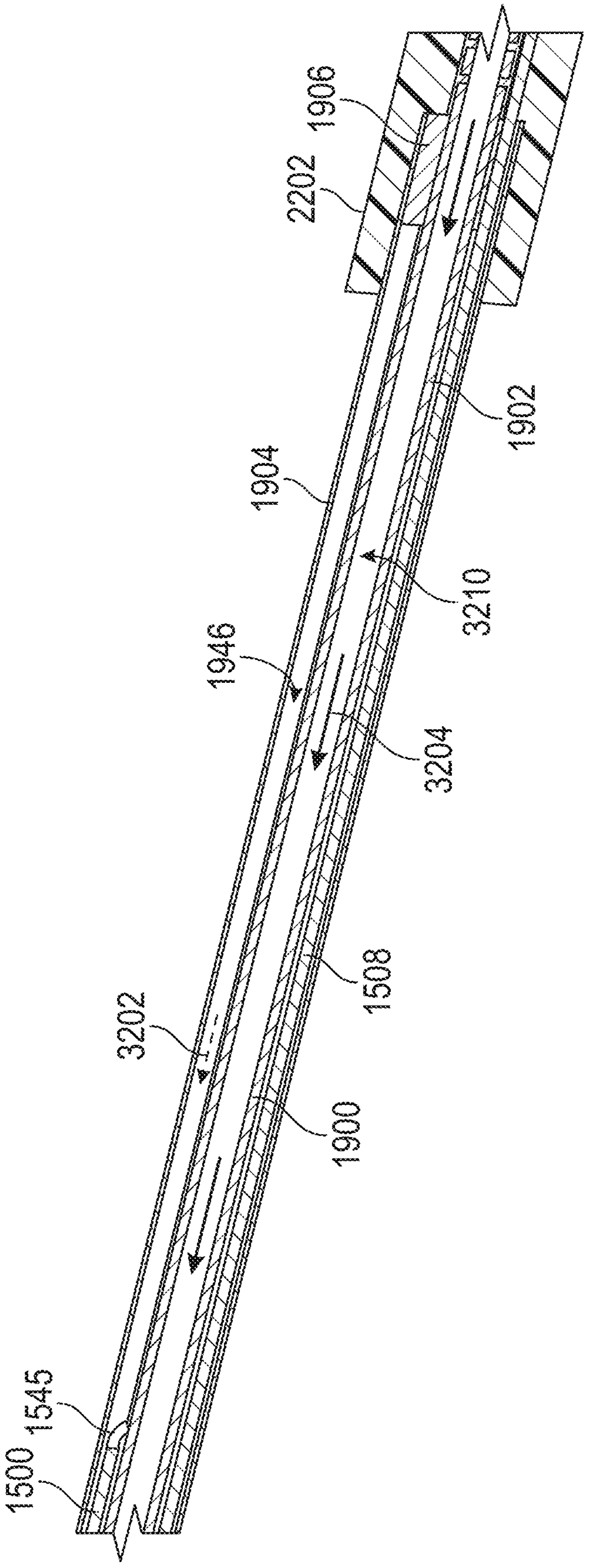
FIG. 37 illustrates a perspective cross-section view of a portion of a delivery system, including a pusher shaft and sleeve shaft, arranged coaxially with one another, and fluid flow through lumens arranged between the coaxial components.

The proximal section 1964 of the shell 1904 can comprise the tube 1968, without any apertures. Further, as shown in FIG. 21F, the proximal section 1964 does not include the outer polymer layer 1966 or the inner liner 1938. As shown in FIGS. 35-37, the proximal section 1964 of the shell 1904 can extend to and/or into the hub assembly 2230, proximate to where the proximal extension 1910 of the pusher shaft 1900 angles off and away from the cut portion 1508 of the sleeve shaft 1500. A proximal end 1905 of the proximal section 1964 of the shell 1904 can be configured to receive the plug 1906, as explained further below.

The plug 1906 can be configured to be arranged within the annular cavity 1946, at the proximal end 1905 of the shell 1904 (as shown in FIGS. 21A, 21B, 21D, and 23B). In some embodiments, the plug 1906 can have a length 1907, extending in a direction of the central longitudinal axis 1901 (as shown in FIG. 21A). In some embodiments, the length 1907 is in a range of 3.0 mm to 9.0 mm, of 4.0 mm to 8.0 mm, of 5.0 mm to 7.0 mm, or of 5.5 to 6.5 mm. In some embodiments, the length 1907 is approximately 6.0 mm.

The plug 1906 can be configured to “plug” or fill a portion of the annular cavity 1946, at the proximal end 1905, while leaving a remainder of the portion of the annular cavity open to receive the cut portion 1508 of the sleeve shaft 1500 therein. For example, as shown in the end view of FIG. 21G, in some embodiments, the plug 1906 of the pusher shaft 1900 can include an annular portion 1972 and a crescent-shaped portion 1974 extending radially outward from one side of the annular portion 1972. An inner diameter 1976 of the annular portion 1972 can be selected such that the annular portion 1972 encircles an outer surface of the main shaft 1902 and an outer diameter 1978 of the crescent-shaped portion 1974 can be selected such that the crescent-shaped portion 1974 fills the annular space 1946. For example, the inner diameter 1976 can be selected to be slightly larger than the outer diameter 1950 of the main shaft 1902 and the outer diameter 1978 can be selected to be slightly smaller than the inner diameter 1948 of the shell 1904 (as shown in FIG. 21A). In some embodiments, the inner diameter 1976 is approximately 1.81 mm and the outer diameter 1978 is approximately 3.42 mm. An arc length of the crescent-shaped portion 1974 can be in a range of 60 to 140 degrees, 80 to 120 degrees, 90 to 110 degrees, or 95 to 105 degrees.

The shell 1904 and the plug 1906 of various embodiments are welded to the main tube 1902 to allow the cut portion 1508 of the sleeve shaft (FIGS. 20A and 20B) to slide between the main tube 1902 and the shell 1904. For example, as shown in the FIG. 21D, a first weld 1980 can secure the annular portion 1972 of the plug 1906 to the main shaft 1902 and a second weld 1982 can secure the crescent-shaped portion 1972 of the plug 1906 to the shell 1904. In some embodiments, each of the welds 1980 and 1982 can be tack welds that do not extend along an entirety of the mating surfaces between the plug 1906 and main shaft 1902 and shell 1904.

The proximal extension 1910, of certain embodiments, is illustrated in FIGS. 23A and 23B. FIGS. 23A and 23B illustrate the proximal extension 1910 extending from the proximal end of the main tube 1902 and the shell 1904. As noted above, the proximal extension 1910 provides the pusher shaft 1900 with flexibility such that it may be routed from the inside of the sleeve shaft (e.g., the cut portion 1508) to the outside of the sleeve shaft, thereby allowing the two shafts to be actuated in parallel. In many embodiments, as discussed above, the proximal extension 1910 can be made of a flexible polymer. In certain embodiments, the flexible polymer is a polyether-amide block copolymer or a blend of two or more polyether-amide block copolymers, such as PEBAX® grades 2533, 3533, 4033, 4533, 5533, 6333, and 7033, and 7233 (Arkema S.A., France) and VESTAMID® grades E40, E47, E55, E62, E72, and EX9200 (Evonik Industries AG, Germany).

Pusher Shaft and Sleeve Shaft Assembly

Figure 33:
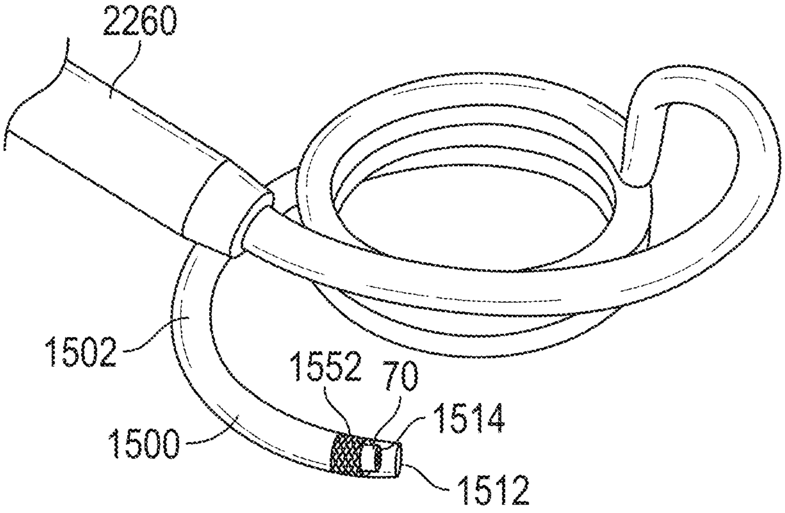
FIG. 33 illustrates a perspective view of an example embodiment of a sleeve shaft covering a docking device and extending outside of a delivery catheter of a delivery system.
Figure 34:
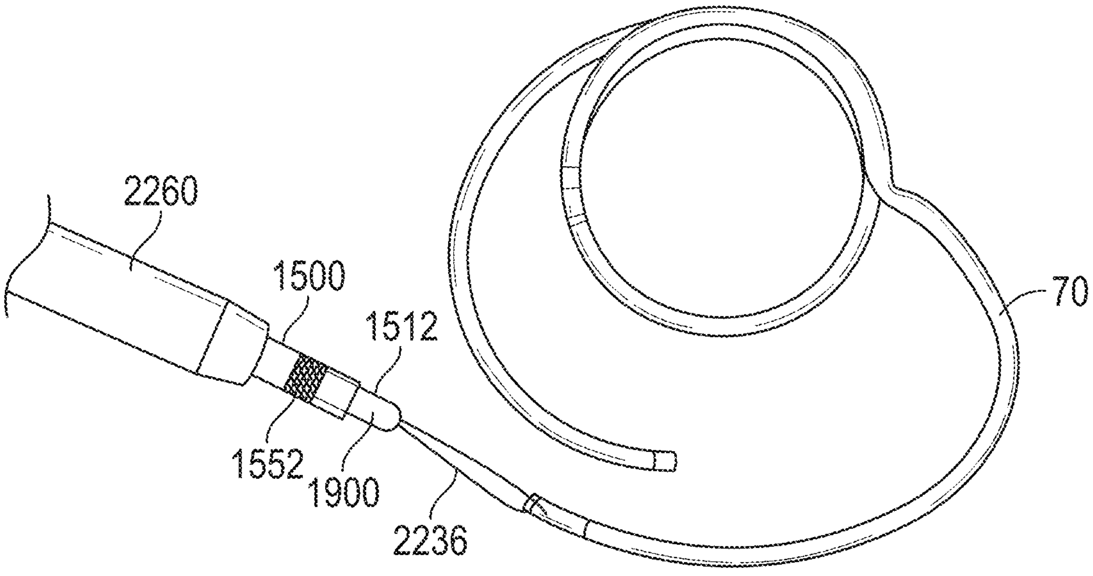
FIG. 34 illustrates the sleeve shaft surrounding a pusher shaft after deploying the docking device from the delivery system of FIG. 33 and removing the sleeve shaft from the docking device.

As introduced above, the pusher shaft 1900 and sleeve shaft 1500 can be coaxial with one another, at least within an outer shaft 2260 (e.g., catheter portion) of the delivery system (e.g., delivery system 2220 of FIG. 24B). FIGS. 22A-22C are assembly views illustrating an arrangement of the pusher shaft 1900 and sleeve shaft 1500 in the outer shaft 2260 of the delivery system. Additionally, FIGS. 33 and 34 are perspective views showing an exemplary docking device 70 deployed from the outer shaft 2260 of the delivery system, covered by a distal (or sleeve) portion 1502 of the sleeve shaft 1500 (FIG. 33), and the exemplary docking device 70 after the sleeve shaft 1500 has been retracted back into the outer shaft 2260 (FIG. 34).

As shown in FIGS. 22A-22C, 33, and 34, the sleeve shaft 1500 can be configured to cover (e.g., surround) the docking device 70 and, together, the pusher shaft 1900 and sleeve shaft 1500 can be configured to deploy the docking device 70 from the outer shaft 2260 of the delivery system, upon reaching the target implantation site. As described further below, FIGS. 22A-22C, 33, and 34 illustrate different stages of the implantation process.

FIGS. 22A and 22B illustrate how the proximal section 1504 of sleeve shaft 1500, including the cut portion 1508, passes through the proximal end portion 1912 of the pusher shaft 1900, between the main tube 1902 and the shell 1904, within the annular cavity 1946. Specifically, FIG. 22A illustrates an example of a first configuration of the pusher shaft 1900 and sleeve shaft assembly, pre-deployment or during deployment of the docking device 70, where the sleeve shaft 1500 is arranged over the docking device 70 and the end surface 1545 of the tube 1530 is positioned away from the plug 1906. During deploying the docking device 70 from the outer shaft 2260 of the delivery system, the pusher shaft 1900 and the sleeve shaft 1500 can move together, in the axial direction, with the docking device 70. For example, actuation of the pusher shaft 1900, to push against the docking device 70 and move it out of the outer shaft 2260 may also cause the sleeve shaft 1500 to move along with the pusher shaft 1900 and the docking device 70. As such, the docking device 70 may remained covered by the distal section 1502 of the sleeve shaft 1500 during pushing the docking device 70 into position at the target implantation site via the pusher shaft 1900, as also shown at FIG. 33.

In some embodiments, as shown in FIG. 22A, the outer shaft 2260 can have a first inner diameter 2104 at a distal end portion of the outer shaft 2260 and a second inner diameter 2106 at a more proximal end portion of the outer shaft 2260. The second inner diameter 2106 can be larger than the first inner diameter 2104 in order to accommodate the wider shell 1904 therein.

Additionally, as introduced above with reference to FIG. 17B and as shown in FIG. 33, during delivery and implantation of the covered docking device 70 at the target implantation site, the distal tip 1512 of the distal section 1502 of the sleeve shaft 1500 can extend distal to (e.g., past) a distal end 1514 of the docking device 70, thereby providing the distal section 1502 of the sleeve shaft 1500 with a more atraumatic tip. In some embodiments, the distance between the distal tip 1512 of the sleeve shaft 1500 and the distal end 1514 of the docking device 70, during implantation at the target implantation site and prior to retracting the sleeve shaft 1500 from the docking device 70, can be in a range of about 3 mm to about 1 mm, of about 2 mm to about 1.2 mm, or of about 1.7 mm to about 1.4 mm. As shown in FIG. 33, in some embodiments, the distal end 1514 of the docking device 70 can be arranged proximate to or just distal to a marker band 1552 of the sleeve shaft 1500.

FIG. 22B illustrates a second configuration of the pusher shaft 1900 and sleeve shaft 1500 assembly, after deploying the docking device 70 from the outer shaft 2260 at the target implantation site and retracing the sleeve shaft 1500 away from the implanted docking device 70. As shown in FIG. 22B, after implanting the docking device 70 at the target implantation site, in its desired position, the sleeve shaft 1500 can be pulled off the docking device 70 and retracted back into the outer shaft 2260. In some embodiments, as shown in FIG. 22B, the sleeve shaft 1500 can be stopped from further retraction into the delivery system upon the end surface 1545 coming into contact with the plug 1906.

FIG. 34 shows the sleeve shaft 1500 removed from the docking device, leaving the docking device 70 uncovered. As shown in FIG. 34, the distal tip 1512 of the sleeve shaft 1500 can be arranged proximal to (e.g., retracted past) the distal end of the pusher shaft 1900 which can still be connected to the end of the docking device 70 via a suture 2236. As explained further below, after implanting the docking device 70 at the target implantation site and removing the distal portion 1502 of the sleeve shaft 1500 from covering the docking device, the docking device 70 can be disconnected from the delivery system by cutting the suture 2236 via a suture lock assembly of the delivery system (e.g., suture lock assembly 2206 shown in FIG. 24A and/or suture lock 2700 shown in FIGS. 27A-29D).

Turning to FIG. 22C, certain embodiments include a sealing mechanism 1908 located on the main tube 1902 of the pusher shaft 1900 of some embodiments. A sealing mechanism 1908 in some embodiments forms a seal between the main tube 1902 of the pusher shaft 1900 and the sleeve shaft 1500 to prevent fluids being flushed through the system to back flow or find a lower resistance path through another lumen (as described further below with reference to FIGS. 35-38). Certain embodiments will use a gasket made of plastic, rubber, PTFE, PBAX, or another suitable material that is placed on the main tube 1902 of the pusher shaft 1900. In embodiments using a gasket, the gasket is bonded in place by fusing the gasket to the main tube 1902, while some embodiments will adhere the gasket using a glue or other adhesive. Additional embodiments will manufacture main tube 1902 to include a bump or protrusion on the main tube 1902 extending toward sleeve shaft 1500 as the sealing mechanism 1908, while certain embodiments will form a bump or protrusion on sleeve shaft 1500 extending toward the main tube 1902 as the sealing mechanism. Certain embodiments will include multiple sealing mechanisms 1908 to form a seal between the main tube 1902 of the pusher shaft 1900 and the sleeve shaft 1500 of any combination of bumps and/or gaskets. Additional embodiments will further include a gasket located toward the proximal end (e.g., gasket 1804 of FIG. 20A) of the sleeve shaft 1500 in addition to one or more sealing mechanisms 1908.

Handle System

As introduced above, the delivery system (e.g., delivery system 2220 of FIG. 24B) can include a handle assembly 2200 that is configured to control operation of the delivery system, including the pusher shaft and the sleeve shaft. The handle assembly can be configured in a variety of ways with one or more of a variety of components, handles, hubs, connectors, knobs, shafts, etc. An example embodiment of the complete handle assembly 2200 is shown in FIG. 24B, as described above. As illustrated in FIG. 24A and introduced above, the handle assembly 2200 of some embodiments comprises the hub assembly 2230, which in some embodiments can comprise a Y-shaped connector (e.g., adaptor) having a straight section (e.g., straight conduit) 2202 and at least one branch (e.g., branch conduit) 2204 (though, in some embodiments, it can include more than one branch).

In some embodiments, the suture lock assembly (e.g., suture lock) 2206 can be attached to the branch 2204 and a sleeve actuating handle 2208 (which may be similar to sleeve handle 2234 of FIG. 24B) can be arranged at a proximal end of the straight section 2202. The hub assembly 2230 can be adapted and configured to allow the proximal extension 1910 of the pusher shaft 1900 (or another, similar pusher shaft) to extend to the suture lock assembly 2206 arranged at the end of the branch 2204, while the cut portion 1508 of the sleeve shaft 1500 extends to the sleeve actuating handle 2208, arranged at the end of the straight section 2202. With this configuration, a medical professional can execute the deployment of the docking device (e.g., docking device 2232 of FIG. 24B and/or docking device 70 of FIGS. 9A-12G and 22A-22C) by manipulating the position of the handle assembly 2200 (e.g., moving it in the axial direction) and also execute retraction of the sleeve shaft (off of and away from the implanted docking device) by pulling back, in the axial direction, on the sleeve actuating handle 2208. Thus, such a handle configuration may only add one additional step in retracting the sleeve shaft, as compared to delivery systems that do not include a sleeve shaft or another removable cover for the docking device.

The sleeve shaft and pusher shaft assembly can be configured to work together such that they can be moved simultaneously together when deploying and positioning the docking device at the native valve (e.g., by moving the entire hub assembly 2230 forward and/or backward, in the axial direction), but can also to move independently so the pusher shaft 1900 can hold the docking device in position while the sleeve shaft 1500 is retracted off of the docking device (e.g., by holding the hub assembly 2230 in place relative to the outer shaft 2260 of the delivery system and/or other parts of the delivery system and/or docking device while pulling proximally on the sleeve actuating handle 2208 to withdraw the sleeve). As introduced above and shown in FIGS. 22A-22C, the sleeve shaft 1500 and pusher shaft 1900 can be coaxial along some, all, or a majority of the delivery system to facilitate this working together.

Figure 38:
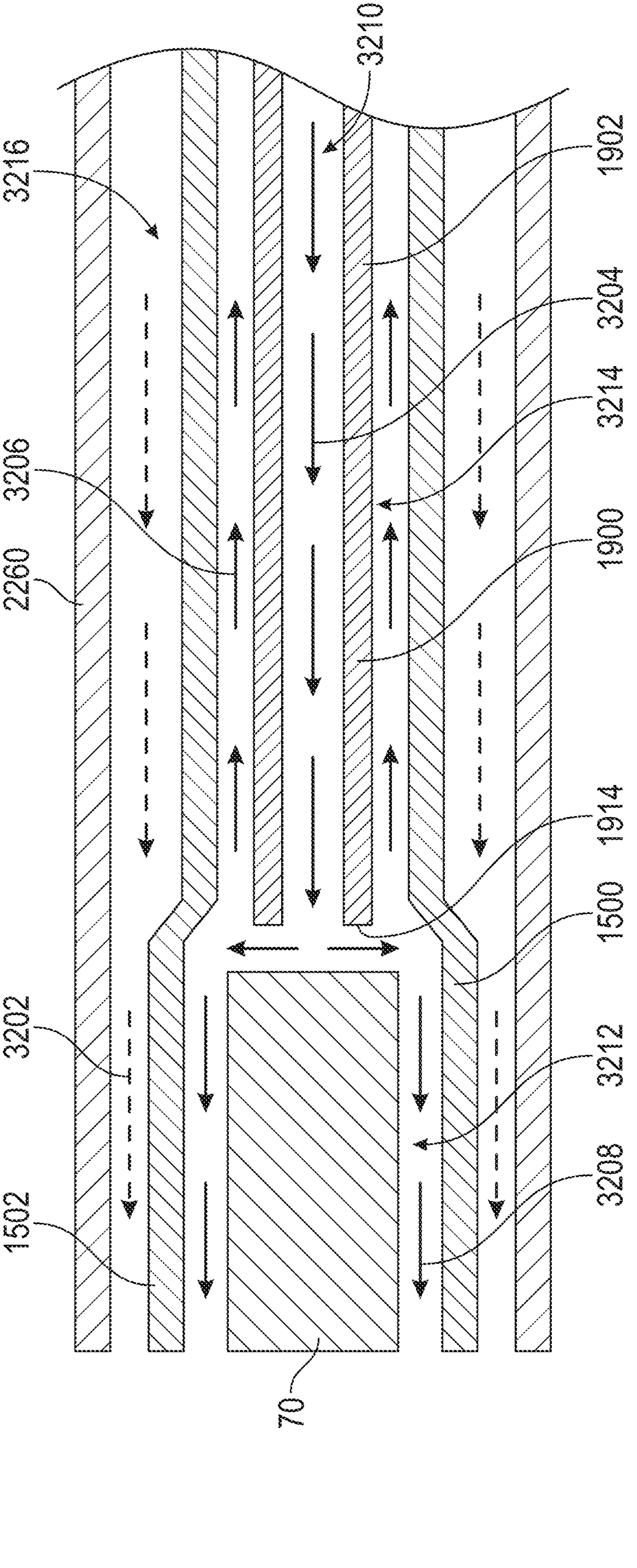
FIG. 38 illustrates a schematic of fluid flow through lumens of a distal end portion of a delivery system, the delivery system including a pusher shaft, sleeve shaft, and docking device arranged in an outer shaft of the delivery system.

The handle assembly 2200 can include one or more flushing ports that enable flushing of the various lumens (e.g., annular spaces arranged between components, such as coaxial shafts) arranged between the axially-extending components of the delivery system. For example, as shown in FIG. 38 which illustrates a distal end portion of a delivery system (e.g., delivery system 2220) including a pusher shaft (e.g., pusher shaft 1900) and sleeve shaft (e.g., sleeve shaft 1500) arranged within an outer shaft 2260 of the delivery system, various lumens configured to receive flush fluid during a delivery and implantation procedure are formed between the docking device 70, pusher shaft 1900, sleeve shaft 1500, and outer shaft 2260. A first, pusher shaft lumen 3210 can be formed within an interior of the pusher shaft (e.g., within an interior of the main tube 1902). The pusher shaft lumen 3210 can receive a flush fluid from a first fluid source, which may be fluidly coupled to a portion of the handle assembly (e.g., the branch 2204, as described further below). The flush fluid flow 3204 through the pusher shaft lumen 3210 can travel along a length of the main tube 1902 of the pusher shaft 1900, to the distal end 1914 of the pusher shaft 1900. Since, as shown in FIG. 38, the distal end 1914 of the pusher shaft 1900 can be spaced away from a proximal end of the docking device 70, at least a portion of the flush fluid flow 3204 can flow into a first portion of a second, sleeve shaft lumen 3212, which is arranged between an outer surface of the docking device 70 and an inner surface of the distal section 1502 of the sleeve shaft 1500, as flush fluid flow 3208. Further, in some embodiments, a portion of the flush fluid flow 3204 can also flow into a second portion of the sleeve shaft lumen 3214, which is arranged between an outer surface of the pusher shaft 1900 and an inner surface of the sleeve shaft 1500, as flush fluid flow 3206. In this way, the same, first fluid source may provide flush fluid to each of the pusher shaft lumen 3210, the first portion of the sleeve shaft lumen 3212, and the second portion of the sleeve shaft lumen 3214, via the pusher shaft lumen 3210.

As also shown in FIG. 38, a third, delivery shaft lumen 3216 can be formed in an annular spaced between an inner surface of the outer shaft 2260 and an outer surface of the sleeve shaft 1500. The delivery shaft lumen 3216 can receive a flush fluid from one or more second fluid sources, which may be fluidly coupled to a portion of the handle assembly (e.g., branch 2204 and/or handle 2222, as described further below), and which may result in flush fluid flow 3202 flowing through the delivery shaft lumen 3216, to a distal end of the outer shaft 2260.

Flushing the above-described lumens is important to prevent thrombosis on and around the docking device and other concentric parts of the delivery system during deployment of the docking device from the delivery system and implantation of the docking device at a target implantation site. To flush these lumens, various embodiments will possess one or more flushing (flush) ports arranged on and/or coupled to the handle assembly 2200 of the delivery system. FIGS. 24A, 24B, 28A, 35, and 36 show different embodiments of an arrangement of possible flushing ports configured to provide flush fluid to the lumens described above with reference to FIG. 38. Additionally, FIG. 37 illustrates a flow of the flush fluid through a portion of the delivery system arranged between the hub assembly 2230 (as shown in FIGS. 24A, 35, and 36) and the distal end portion of the delivery system (as shown in FIG. 38).

In a first embodiment of a flushing port arrangement, the handle assembly 2200 can include two flushing ports arranged on the branch 2204 (which may be referred to as a suture lock branch) of the hub assembly 2230, one of which provides the flush fluid flow 3204 to the pusher shaft lumen 3210 and another of which provides the flush fluid flow 3202 to the delivery shaft lumen 3216. For example, the two flushing ports on the branch 2204 can include a first flushing port 2210 and a second flushing port 2216, the first flushing port 2210 arranged proximal to the second flushing port 2216 on the branch 2204. In some embodiments, the location of the second flushing port 2216 on the branch 2204 can be closer to or farther away from the first flushing port 2210 than shown in FIGS. 24A, 35, and 36.

As shown in FIGS. 24A, 35, and 36, the first flushing port 2210 has an inner flow lumen that is fluidly connected to an internal cavity 2250 in the branch 2204. An open, proximal end 2252 of the proximal extension 1910 of the pusher shaft 1900 can be fluidly coupled to and/or arranged within the internal cavity 2250 (as shown in FIGS. 24A, 35, and 36). As explained above, the proximal extension 1910 routes through the branch 2204, into the straight section 2202 of the hub assembly 2230, and connects to the main tube 1902 of the pusher shaft (FIG. 36). Thus, the pusher shaft lumen 3210 is formed by and within the main tube 1902 and the proximal extension 1910. As such, the flush fluid flow 3204 from the first flushing port 2210 enters the pusher shaft lumen 3210 at the proximal end 2252 of the proximal extension 1910 and continues into and through an entirety of the main tube 1902 of the pusher shaft, to the distal end 1914 (as shown in FIG. 38.

The second flushing port 2216 has an inner flow lumen that is fluidly connected to an elongate space or cavity 2254 (which may be annular along at least a portion of the cavity) surrounding an exterior of the proximal extension 1910 within the branch 2204 and extending into the straight section 2202, in a space between an inner surface of the cut portion 1508 of the proximal section 1504 of the sleeve shaft 1500 and the proximal extension 1910. Thus, the flush fluid flow 3202 from the second flushing port 2216 can enter the cavity 2254 and flow through the cavity 2254, around the proximal extension 1910, and into the annular cavity 1946 (FIG. 37). As explained above with reference to FIGS. 21A and 22A, the flush fluid flow 3203 can flow through the annular cavity 1946 and exit the distal end of the shell 1904, as shown by arrows 3202 in FIGS. 21A and 22A, to enter the delivery shaft lumen 3216.

In some embodiments, as shown in FIGS. 24B and 35, the delivery shaft lumen 3216 can be provided with additional flush fluid from a third flushing port 2218 (in addition to the fluid from the second flushing port 2216) fluidly coupled to the annular cavity 1946, downstream of (e.g., distal to) the plug 1906. In this way, in some embodiments, supplemental flush fluid 3218 can be combined with the flush fluid flow 3202 and supplied to the delivery shaft lumen 3216. In some embodiments, as shown in FIGS. 24B and 35, the third flushing port 2218 can be arranged on a portion of the handle 2222. In alternate embodiments, the third flushing port 2218 can be arranged at a more distal location on the handle than shown in FIGS. 24B and 35. In some embodiments, the third flushing port 2218 may not be used during an implantation procedure, but instead, may only be used for flushing the delivery shaft lumen 3216 prior to insertion of the delivery system into a patient. In some embodiments, the delivery system may not include the third flushing port 2218.

Figure 28A:
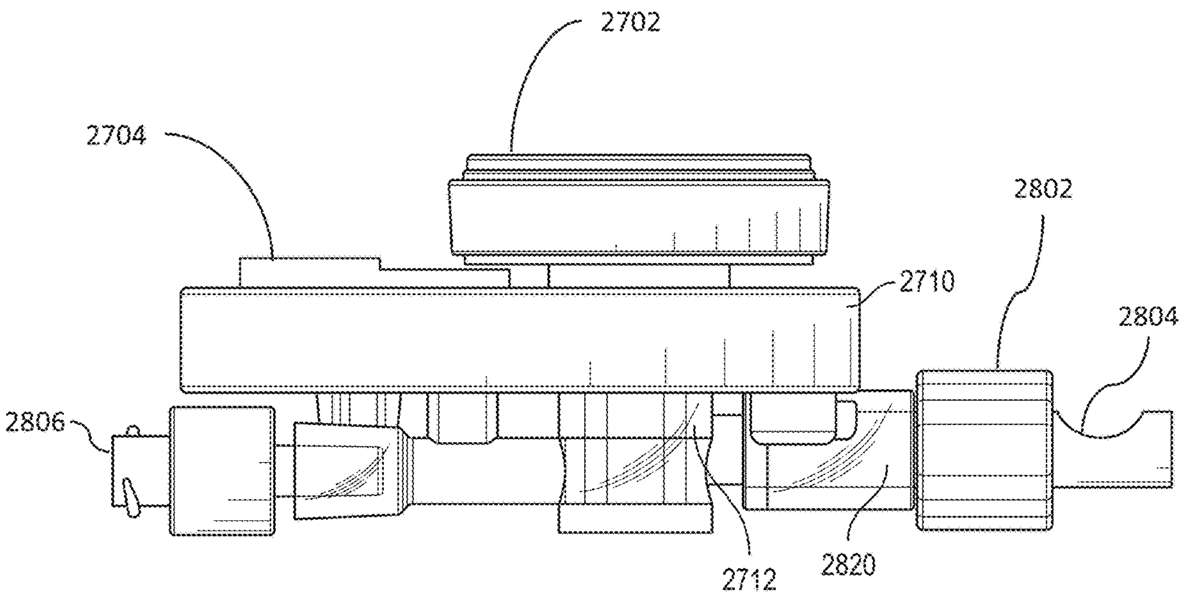
FIG. 28A illustrates a side view of an embodiment of the suture lock of FIGS. 27A-27C including a flushing port at a proximal end of the suture lock.

Various embodiments of the hub assembly 2230, including the first embodiment of the flushing port arrangement described above, can include a gasket 2211 located within branch 2204, between the two flushing ports on the branch 2204, to create separate and distinct fluid flow lumens fed by the two flushing ports on the branch 2204 (e.g., first flushing port 2210 and second flushing port 2216 shown in FIGS. 24A, 35, and 36 or the second flushing port 2216 and a flushing port 2806 shown FIG. 28A). For example, the gasket 2211 can be configured as a disc with a single (e.g., central in some embodiments) hole configured to tightly receive the proximal extension 1910 therein. The gasket 2211 may not included any additional holes and can be further configured to provide a seal between the internal cavity 2250 and the cavity 2254. As a result, all of the flush fluid flow 3204 entering the internal cavity 2250 from the first flushing port 2210 (or, alternatively, from the flushing port 2806, as described further below) can enter the pusher shaft lumen 3210, without entering the cavity 2254 and flowing to the delivery shaft lumen 3216. Likewise, all of the flush fluid flow 3202 entering the cavity 2254 from the second flushing port 2216 can enter the annular cavity 1946 and the delivery shaft lumen 3216.

In a second embodiment of a flushing port arrangement, the handle assembly 2200 can include two flushing ports arranged on the branch 2204 (which may be referred to as a suture lock branch) of the hub assembly 2230, one of which provides the flush fluid flow 3204 to the pusher shaft lumen 3210 and another of which provides the flush fluid flow 3202 to the delivery shaft lumen 3216. However, in the second embodiment, the flushing port providing the flush fluid flow 3204 to the pusher shaft lumen 3210 can be arranged on a proximal end of the branch 2204, at an end of a suture lock assembly (e.g., suture lock assembly 2206 of FIGS. 24A and 24B or suture lock assembly 2700 of FIGS. 27A-29D). For example, as shown in FIG. 28A, the flush fluid flow 3204 can be provided via a flushing port 2806 arranged at a proximal end of a suture lock assembly 2700). In this way, the flush fluid flow 3204 can be provided to the pusher shaft lumen 3210 via a flushing port (e.g., flushing port 2806) with a flow lumen arranged in parallel with the pusher shaft lumen 3210 (instead of perpendicular to the pusher shaft lumen 3210, as shown in FIGS. 24A, 24B, 35, and 36).

Flushing port arrangement embodiments possessing multiple flushing ports, such as the first and second embodiments described above, can be supplied with flush fluid independently (e.g., with two separate fluid supply sources) or together with a common fluid supply source. For example, in some embodiments, each flushing port (e.g., first flushing port 2210 and second flushing port 2216 or flushing port 2806 and second flushing port 2216) can be supplied with flush fluid from two separate infusion pumps (one fluidly coupled to each of the flushing ports) or another set of fluid sources. In alternate embodiments, a single infusion device (e.g., pump) 3220 can be connected to multiple flushing ports, such as through a Y-connector 3222 that connects a single fluid line to multiple flushing ports, as shown in FIG. 35. As shown in FIG. 35, the first flushing port 2210 and the second flushing port 2216 are supplied with fluid from the same source (e.g., the infusion pump 3220). In some embodiments, the infusion pump 3220 can supply fluid to the flushing port 2806 and the second flushing port 2216.

It may be desirable to have the flush fluid flow be balanced between the lumens, such that the flow of flush fluid is equal in each lumen. However, in some embodiments, flush fluid flow passing through the pusher shaft lumen 3210 can possess increased resistance, relative to the delivery shaft lumen 3216. In one example, this increased resistance may be due to a narrower flow lumen and/or friction between a covering (e.g., covering 100, FIGS. 12A-12D) and sleeve section of a sleeve shaft (e.g., sleeve 1502, FIG. 17). As one example, an additional flushing port can be added to supplement the flow to the pusher shaft lumen 3210, in order to make the flow equal between the lumens. As another example, two separate infusion devices can be used to provide desired flow rates of flush fluid to the pusher shaft lumen 3210 and the delivery shaft lumen 3216. As yet another example, when using the single infusion device to supply both flushing ports, the resistance in the delivery shaft lumen 3216 can be increased in order to equalize the relative resistance between the delivery shaft lumen 3216 and the pusher shaft lumen 3210. For example, certain embodiments can alter a flow rate of fluid received by the delivery shaft lumen 3216 and the pusher shaft lumen 3210 from the single infusion device 3220 by altering an inner diameter of one or both of the flushing port lumen (e.g., decrease a diameter of an inner lumen of the second flushing port 2216 relative to the first flushing port 2210), a diameter of the branch portions of the Y-connector 3222, or other another component to alter the relative flows to the cavity 2254 (feeding the delivery shaft lumen 3216) and the pusher shaft lumen 3210.

In this way, it may be desirable to balance the fluid flow resistance between the flow paths in and/or to the pusher shaft lumen 3210 and the delivery shaft lumen 3216, such that both of these lumens receives equal flow of flush fluid from a single source (e.g., single infusion device 3220). Various embodiments may include altering the resistance of one or more components in one of the two flow paths (e.g., pusher shaft lumen flow path or delivery shaft lumen flow path) and/or providing one or more devices that meter an even flow rate of flush fluid to each of the pusher shaft lumen 3210 and the delivery shaft lumen 3216. Thus, the flush fluid flow into these two lumens can be controlled by any way known in the art to ensure the flow rate in the lumens is equal, based on their relative resistances. Further, during an implantation procedure, differences in flow resistance may be experienced within each of and between the pusher shaft lumen 3210 and the delivery shaft lumen. Thus, it may be desirable to either delivery flush fluid flow to these lumens individually (e.g., via separately controlled flow sources) or via the single infusion device 3220 with a mechanism for balancing resistance between the lumens (and providing a target flow rate).

Some embodiments can include a mechanism (such as a sensor, alarm, or the like) for detecting when a flow rate of flush fluid drops below a preset, threshold flow rate within one or more of the lumens receiving the flush fluid (e.g., the pusher shaft lumen and the delivery shaft lumen). For example, infusion devices may possess alarms to alert a medical professional or user of a blockage in flow, which may occur due to an occlusion in the system from a thrombus. Thrombi can cause a stroke if they are dislodged during installation of a docking device. Additionally, thrombi can increase a force experienced during removal of the distal portion of the sleeve shaft 1502 from the docking device due to causing increased friction between the sleeve and the docking device. As one example, using two infusion devices allow for certain embodiments to identify when a thrombus forms in one or more of the lumens, including when cross-lumen flow is prevented using gaskets or other sealing mechanisms (e.g., gasket 1804, shown in FIG. 20 and sealing mechanism 1908 shown in FIG. 22C). Further embodiments utilize a single infusion device connected to multiple flushing ports and the use of flow sensors connected to the flow lines (and/or alarms) to notify a medical professional of changes in flow rate, which may indicate a blockage, such as a thrombus.

In a third embodiment of a flushing port arrangement, the handle assembly 2200 can include a single flushing port arranged on the branch 2204 of the hub assembly 2230, the single flushing port configured to provide both the flush fluid flow 3204 to the pusher shaft lumen 3210 and the flush fluid flow 3202 to the delivery shaft lumen 3216. For example, certain configurations are able to flush all of the lumens described above with only one flushing line, such as the first flushing port 2210 (or alternatively, the flushing port 2806 shown in FIG. 28A). In such embodiments, the single flushing port can provide fluid to the two separate lumens (pusher shaft lumen 3210 and delivery shaft lumen 3216), by incorporating a flushing plate 2300 (shown in FIG. 25) in the branch 2204, normal to the flow paths through the pusher shaft lumen 3210 and the cavity 2254. For example, in some embodiments, the flushing plate 2300 can be arranged where the gasket 2211 is shown in FIG. 36 (e.g., in place of the gasket 2211 and with no second flushing port 2216), or further downstream of where the gasket is shown.

Figure 25:
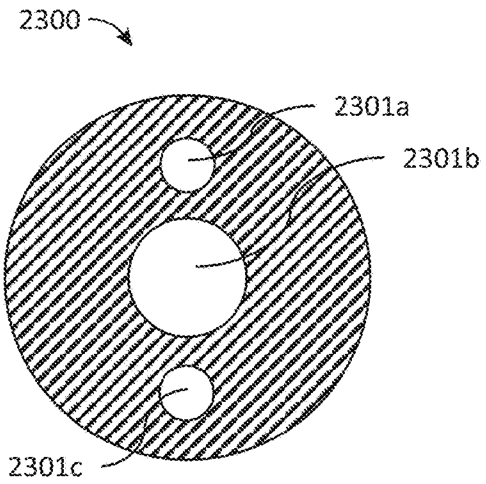
FIG. 25 illustrates an example embodiment of a flushing plate in accordance with various embodiments.

FIG. 25 illustrates the flushing plate 2300 which may be used in various embodiments. As shown in FIG. 25, the flushing plate 2300 can have openings or pores 2301*a*, 2301*b*, and 2301*c* cut into it to equalize resistance among the various lumens. The openings/pores 2301*a*, 2301*b*, and 2301*c* cut into the flushing plate 2300 are designed to equalize the flow of flush fluid into each lumen from the pores, thereby ensuring that adequate flow of the flushing fluid is provided to both the pusher shaft lumen 3210 and the delivery shaft lumen 3216.

Figure 26A:
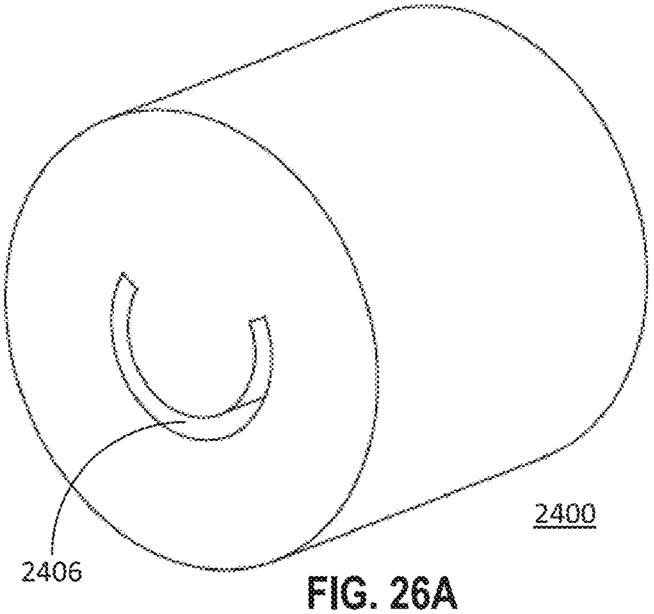
FIGS. 26A and 26B illustrate example embodiments of a hemostatic seal in accordance with various embodiments.
Figure 26B:
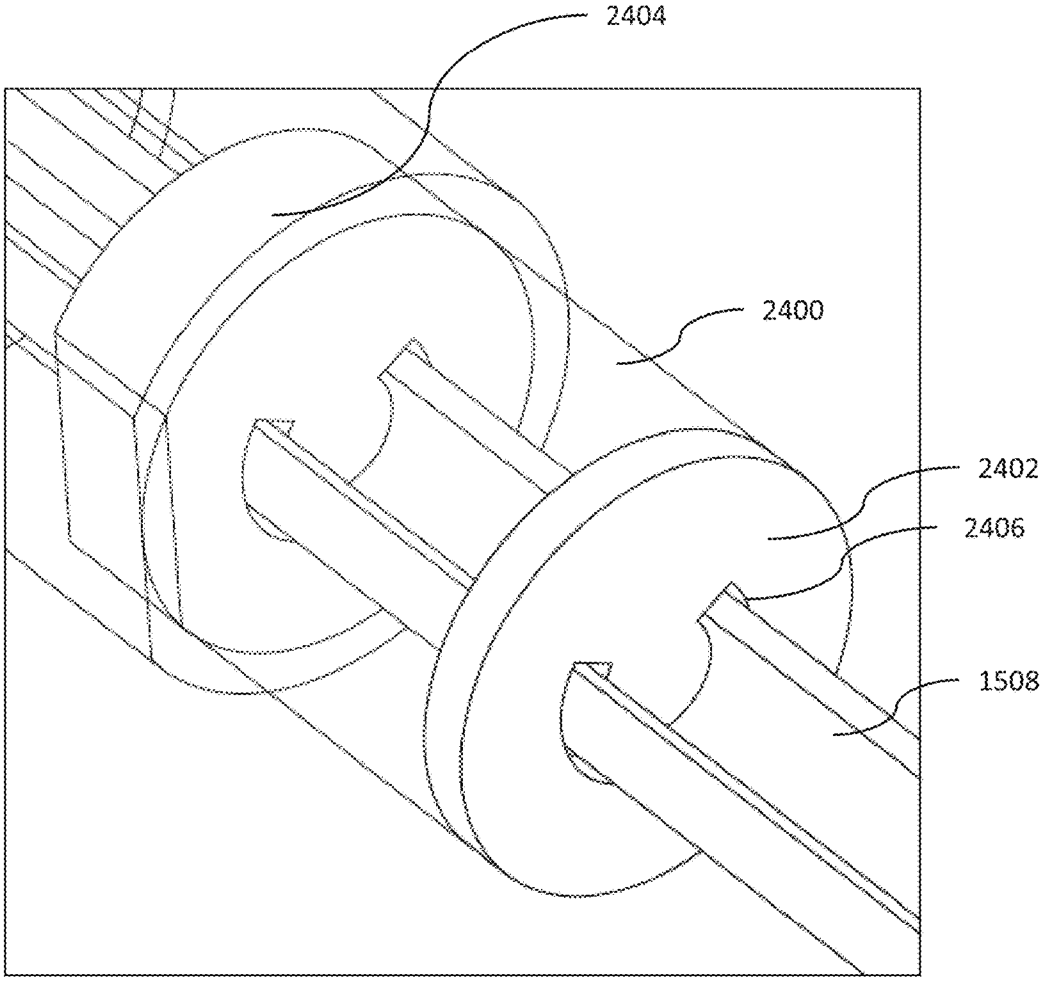

Returning to FIG. 24A, in some embodiments, a hemostatic seal (such as hemostatic seal 2400 illustrated in FIGS. 26A and 26B) is used to seal around the cut portion 1508 of the proximal section 1504 of the sleeve shaft 1500, proximate to the sleeve actuating handle 2208. FIG. 26A illustrates a hemostatic seal 2400 in accordance with various embodiments. As seen in FIG. 26A, the hemostatic seal 2400 can possess an opening 2406 in the shape of a cross-section of the cut section 1508 of the sleeve shaft 1500, such as a U-shape or incomplete (e.g., partial) annulus, configured to receive the cut portion 1508 therein and to seal on all sides of the sleeve shaft 1500. FIG. 26B illustrates the hemostatic seal 2400 in operation and arranged within the straight section 2202 of the hub assembly 2230, in accordance with many embodiments. In some embodiments, as shown in FIG. 26B, two rigid washers 2402 and 2404 can support each end of the hemostatic seal 2400. The rigid washers 2402, 2404 can possess the same profile as the hemostatic seal 2400 to maintain the integrity of the hemostatic seal 2400. In several embodiments, the rigid washers 2402, 2404 place inward pressure on the hemostatic seal 2400 to ensure a seal between the hemostatic seal 2400 and the cut portion 1508 of the sleeve shaft 1500. Turning back to FIG. 24A, this hemostatic seal 2400 can be located near the sleeve actuating handle 2208, such as at point 2212 in many embodiments. By placing the hemostatic seal 2400 near the sleeve actuating handle 2208, some embodiments will incorporate a locking cap assembly 2214 into the handle assembly 2200 to allow for the adjustment of inward pressure placed on the hemostatic seal, in order to lock and/or immobilize the sleeve shaft 1500 (e.g., from axial translation relative to a remainder of the hub assembly 2230 and the pusher shaft 1900) by placing additional pressure on the sleeve shaft.

Figure 27A:
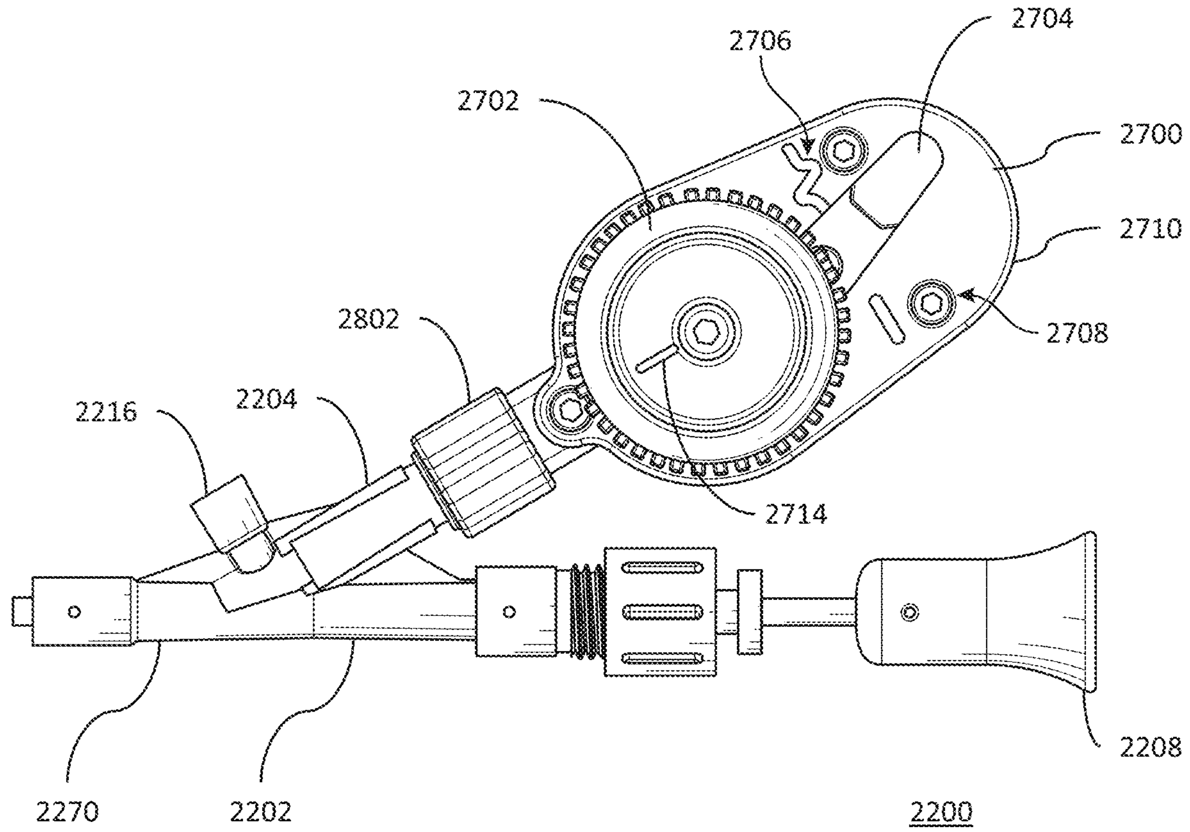
FIG. 27A illustrates an example embodiment of a portion of a handle assembly for a delivery system including a suture lock and sleeve handle in accordance with various embodiments.

As shown in FIGS. 24A and 24B and introduced above, the delivery system can include a suture lock assembly 2206 located on the branch 2204 of the hub assembly 2230 of the handle assembly 2200. FIGS. 27A-29D show embodiments of a ratcheting suture lock 2700 which may be used as the suture lock assembly 2206 of the delivery system 2220 of FIGS. 24A and 24B. The hub assembly 2230 can be adapted and configured to allow the proximal extension of a pusher shaft (e.g., proximal extension 1910) to extend to the suture lock 2700 at the end of branch 2204, while the sleeve shaft (e.g., sleeve shaft 1500) extends to a sleeve actuating handle 2208 at the end of the straight section 2202 (e.g., as shown in FIG. 27A).

Additional embodiments of the hub assembly including the suture lock 2700, as shown in FIG. 27A, include a flush line 2216 to allow flushing of one or more lumens within the delivery device (e.g., the delivery shaft lumen 3216) to maintain hemostasis within the delivery device and/or to sterilize a delivery device (as described above with reference to FIGS. 35-38). As with the system illustrated in FIGS. 24A and 24B, a medical professional operates the deployment of the docking device by manipulating the position of the handle assembly 2200 and only adds one additional step to retract the sleeve by pulling back on the sleeve actuating handle 2208. The sleeve assembly and pusher assembly can be configured to work together such that they can be moved simultaneously together when deploying and positioning the docking device at the native valve (e.g., by moving the entire hub assembly and/or Y-shaped connector forward and/or backward), but can also to move independently so the pusher/pusher shaft can hold the docking device in position while the sleeve is retracted off from the docking device (e.g., by holding the hub assembly and/or Y-shaped connector in place relative to the main shaft of the delivery system and/or other parts of the delivery system and/or docking device while pulling proximally on the sleeve actuating handle 2208 to withdraw the sleeve). The sleeve shaft and pusher shaft can be coaxial along some, all, or a majority of the delivery system to facilitate this working together, as explained above.

As shown in FIGS. 27A-28A and 29C, suture lock 2700 of many embodiments comprises a rotator 2702 (also may be referred to as a rotatable handle) to increase and decrease tension on a suture 2812 (shown in FIGS. 28B-28D) which can extend from the suture lock 2700, through branch 2204, and through the delivery system to connect to the docking device (e.g., similar to release suture 2236 shown in FIG. 24B and FIG. 34).

Figure 27B:
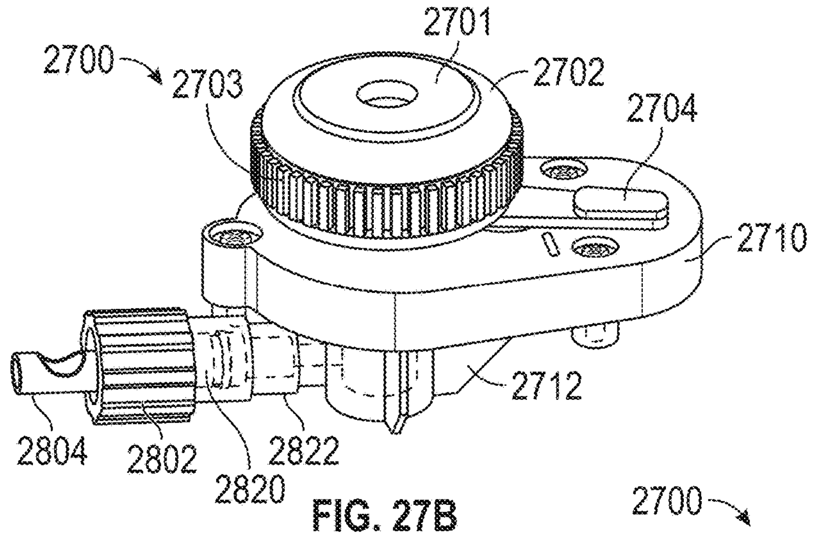
FIG. 27B illustrates a perspective view of the suture lock of FIG. 27A, disconnected from a branch of the handle assembly.
Figure 27C:
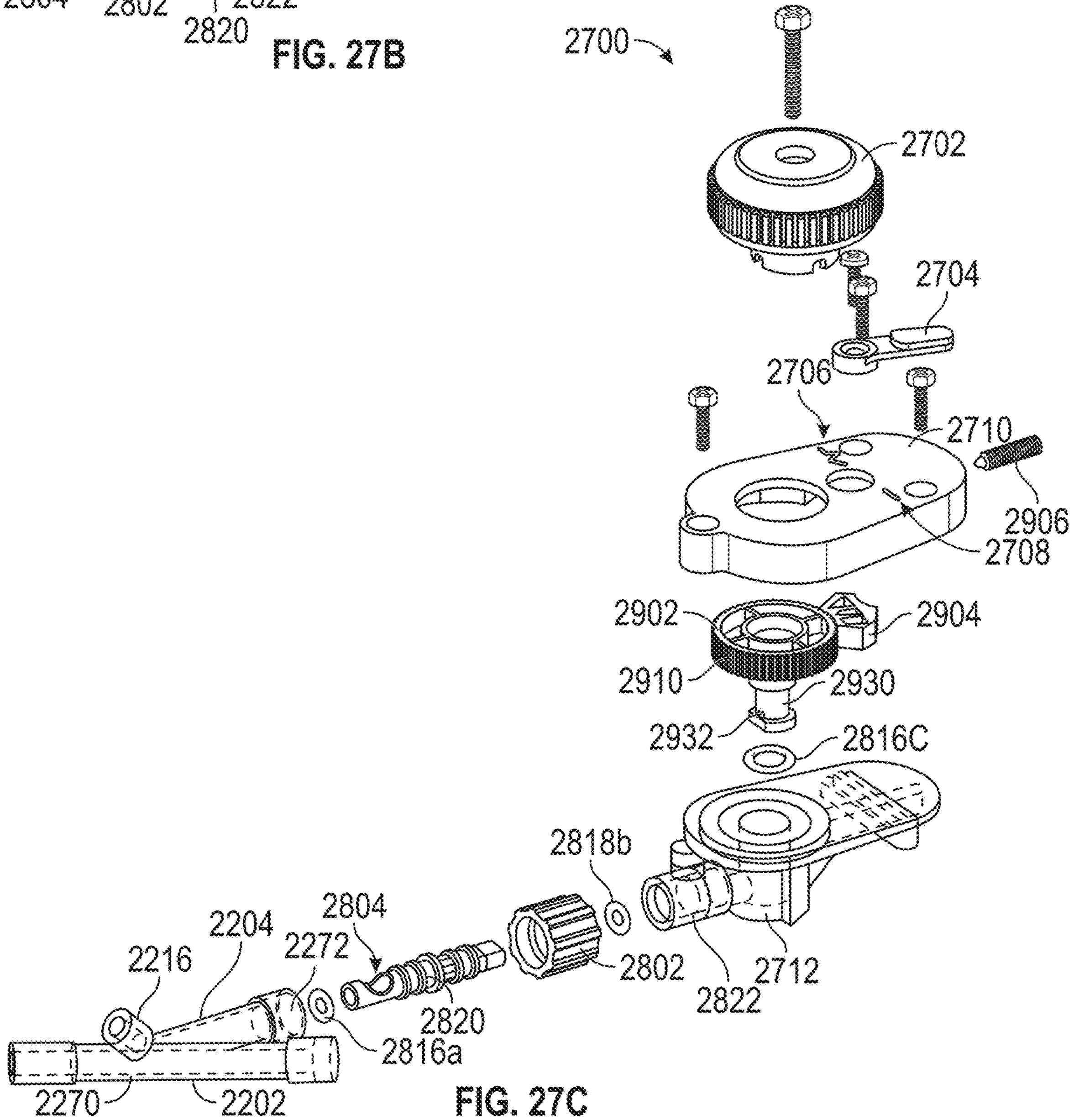
FIG. 27C illustrates an exploded view of the suture lock of FIG. 27A.
Figure 29A:
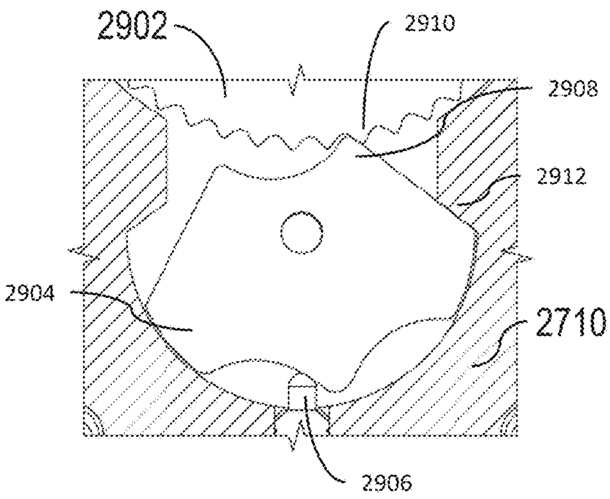
FIGS. 29A-29E illustrate example embodiments of directional mechanisms for a suture lock in accordance with various embodiments.
Figure 29B:
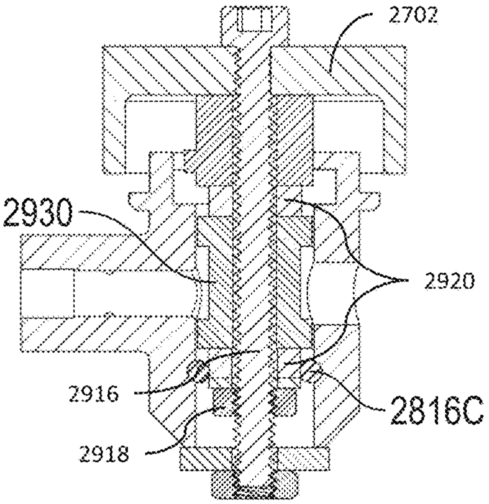
Figure 29C:
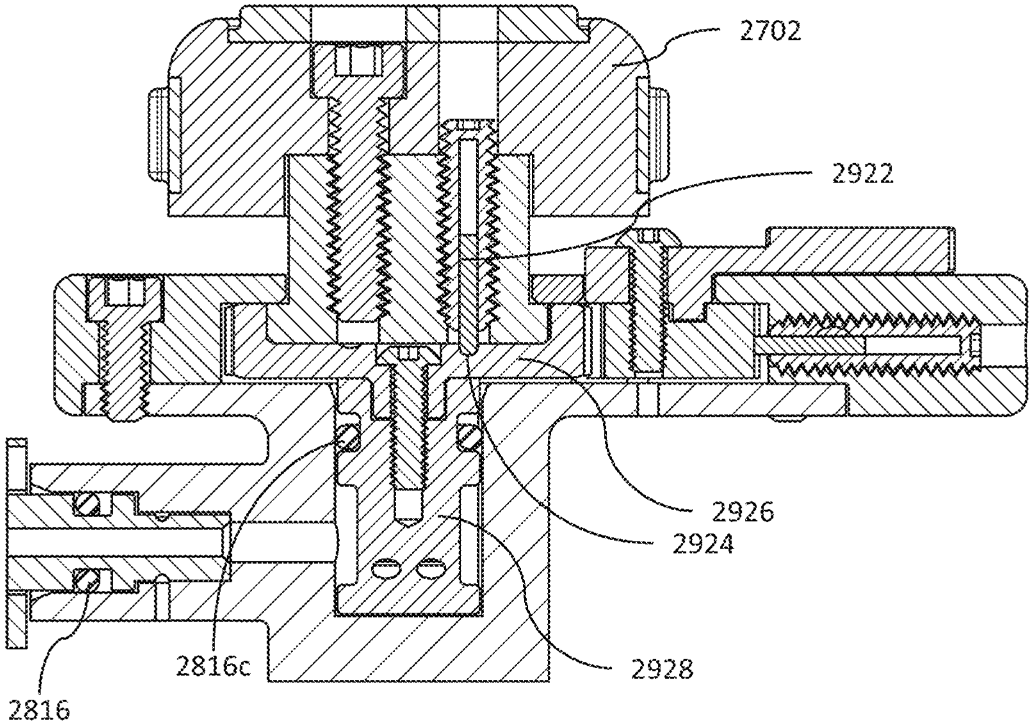
Figure 29D:
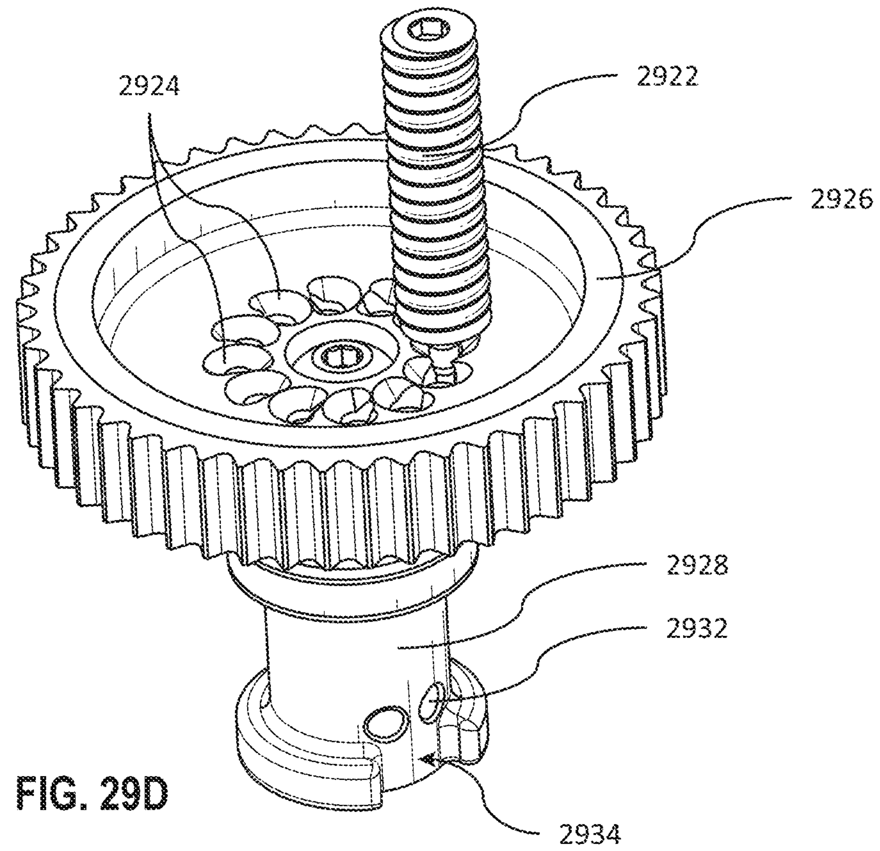

In many embodiments, the suture 2812 is wrapped around a spool 2930 of the suture lock 2700 (FIGS. 27C, 29C, and 29D). The rotator (e.g., handle) 2702 can be coupled to the spool 2930, such that rotating rotator 2702 in a given direction will adjust tension (e.g., increase or decrease) tension on the suture 2812 traversing the delivery device (e.g., delivery system 2220). Providing tension or slack to the suture 2812 via rotating the rotator 2702 (and thus the spool 2930) can bring the docking device closer to or further away from the delivery system, respectively.

As shown in FIG. 27B, in some embodiments, the rotator 2702 can include one or more gripping portions or grips that increase an ease of gripping the rotator 2702 (e.g., via a user's hand), without slipping. For example, the rotator 2702 can include a first gripping portion 2703 arranged around a circumference of the rotator and that is configured to be gripped by a user during turning of the rotator 2702. In some embodiments, the first gripping portion 2703 can include a plurality of ridges to increase traction and ease of gripping. The rotator 2702 can further include a second gripping portion 2701 arranged on a top surface of the rotator 2702. Further, in some embodiments, the first gripping portion 2703 and/or the second gripping portion 2701 can comprise a material having a lower durometer (e.g., reduced hardness).

In some embodiments, the suture lock 2700 can further include a directional control mechanism which may include a directional selector 2704 (e.g., in a form of a switch, as shown in FIGS. 27A-27C) that allows a medical practitioner or other user to select whether to increase or decrease slack in the suture 2812 traversing the delivery device. For example, the directional selector 2704 of various embodiments will allow a medical practitioner or other user to select a direction (e.g., increase or decrease tension), which will allow the rotator 2702 to turn in only one direction to prevent an incorrect direction by a medical practitioner or other user.

For example, as shown in FIGS. 27C and 29A, the spool 2930 can include a gear 2902 that can engage with a pawl 2904 that allows rotation of the gear 2902, and thus rotator 2702 and spool 2930, in only one direction. The direction the rotator 2702 can be rotated depends on the orientation of the pawl 2904, which is controlled by the directional selector 2704. In some embodiments, as shown in FIGS. 27A and 27C, a top housing 2710 can include a first icon 2706 indicating a slack position of the directional selector 2704 and a second icon 2708 indicating a tension position of the directional selector 2704.

As shown in FIG. 29A, in some embodiments, the directional control mechanism can be a ratcheting mechanism that limits directional movement from the rotator 2702 by a medical practitioner or other user. As shown in FIGS. 27B, 27C, and 29A, the gear 2902 is attached to the rotator 2702, while the pawl 2904 is attached to the directional selector 2704. The pawl 2904 can be designed to engage with teeth 2910 of the gear 2902 such that the gear 2902 can only rotate in one direction at a time. When pawl 2904 is actuated (e.g., pivoted) to a position (e.g., tension or slack), a spring plunger 2906 engages a back of the pawl 2904, thereby retaining the pawl 2904 in the selected direction/position (as shown in FIGS. 27C and 29A). When engaged in one direction, one or more teeth 2908 of pawl 2904 interact with the teeth 2910 on gear 2902. Additionally, a stop 2912 can be created to prevent the pawl 2904 from moving bidirectionally, thus allowing gear 2902 to only move in one direction. Stop 2912 can be constructed in a number of ways including by making it part of the top housing 2710 or by adding additional materials (e.g., pins, spacers, etc.) inside of housing 2710 to prevent bidirectional movement of pawl 2904.

Figure 29E:
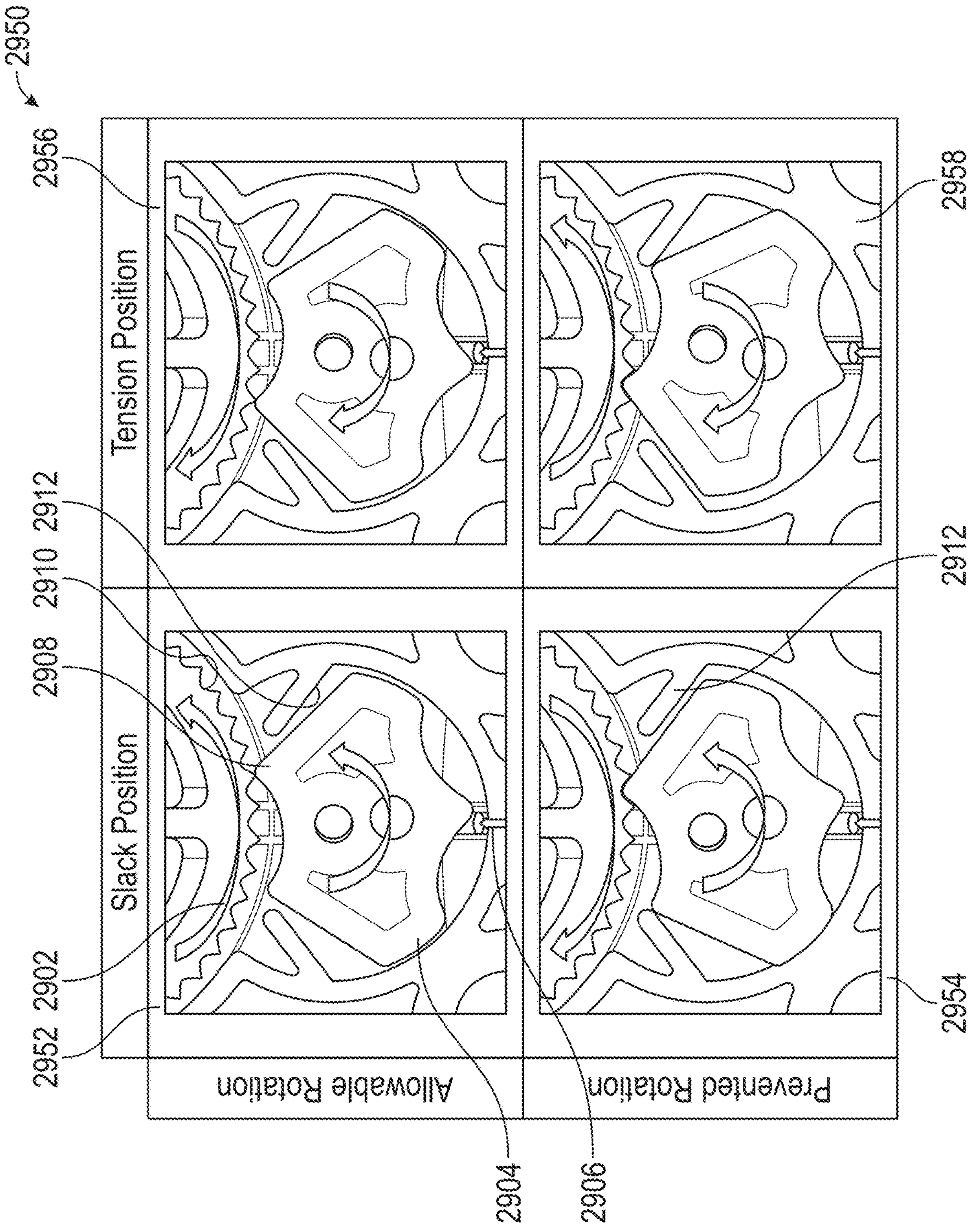

FIG. 29E is a pictorial chart 2950 illustrating exemplary operation of the directional control mechanism shown in FIG. 29A. As shown in FIG. 29E, when the directional selector 2704 in the slack position (e.g., pointing to first icon 2706, as shown in FIG. 27A), when the rotator 2702 is rotated counterclockwise, the pawl 2904 is pushed clockwise by the gear 2902 to allow rotation (as shown in box 2952 of chart 2950). When the teeth 2910 of the gear 2902 pass over the tooth 2908 of the pawl 2904, the spring plunger 2906 pushes the pawl 2904 counterclockwise to engage with the next gear tooth of the gear 2902. When the rotator 2702 is rotated clockwise (e.g., with the directional selector 2704 in the slack position), the gear 2902 rotates the pawl 2904 counterclockwise until it hits the hard stop 2912 on the top housing 2710 (e.g., as shown in FIG. 29A and box 2954 of chart 2950). As introduced above, this hard stop 2912 prevents further rotation of the spool 2930 and takes the load from resisting rotation rather than the tooth 2908 of the pawl 2904. When the directional selector 2704 is moved to the tension position, the spool 2930 can only be rotated clockwise due to the same mechanisms described above for the slack position (as shown in boxes 2956 and 2958 of chart 2950). In some embodiments, the hard stop 2912 is designed to engage while the spring plunger 2906 is still engaged with the pawl 2904, which can prevent a loose feeling in the directional selector 2704 while at rest.

FIGS. 29B-D show additional embodiments of a directional control mechanism for a suture lock, such as suture lock 2700, which include a clutch system. The clutch system can be configured to limit the amount of tension that may be applied to the suture (e.g., suture 2812) and avoid potential damage or degradation to the delivery system and/or docking device.

Turning to FIG. 29B, a directional control mechanism having a clutch that disengages the spool 2930 from the rotator 2702 and that uses friction pads to transfer the torque from the rotator 2702 to the spool 2930 is illustrated in accordance with some embodiments. In particular, FIG. 29B illustrates a side cross-sectional view of a portion of a suture lock (e.g., suture lock 2700) where rotator 2702 is connected to a central screw 2916 and a friction control nut 2918 is connected near the distal end of the central screw 2916. The central screw 2916 extends through a center of the spool 2930 and is coupled to the spool 2930. Friction pads 2920 are arranged around the central screw 2916, above and below a central portion of the spool 2930, such that rotating rotator 2702 too far in one direction will cause increased friction on central screw 2916, such that further rotation is prevented. For example, when the tension in the suture reaches a predetermined threshold, the increased friction from the friction pads 2920 may prevent the spool 2930 from being rotated when the rotator 2702 is turned. In alternate embodiments, as shown in FIGS. 29C-29D, a pin-based clutch system used in certain embodiments is illustrated. In such embodiments, a spring plunger 2922 transfers torque from rotator 2702 to the spool 2928 (which may be similar to spool 2930). Spring plunger 2922 rests in (e.g., mates with) detents 2924 in gear 2926 (which may be similar to and used similarly as gear 2902) to allow driving of the spool 2928 to increase or decrease tension in a suture. The detents 2924 may be arranged in an outer-facing surface of the gear 2926, where a line normal to the outer-facing surface is arranged perpendicular to a circumferential surface of the gear including the gear teeth. At a designed suture tension (e.g., tension above a predetermined threshold), the spring plunger 2922 can slip out of one of the detents and move to an adjacent (e.g., next) detent 2924. In this way, when rotator 2702 is rotated beyond a certain point, spring plunger 2922 retracts, thus preventing additional rotation of rotator 2702 and reducing degradation to the docking device and/or delivery system due to too much tension being applied in the suture. Degradation to the docking device and/or delivery system may only be a risk when applying tension to the suture. Thus, the detents 2924 can be designed to only slip in the tension configuration, and may not slip in the slack configuration.

Returning to FIGS. 27A-27C and 28A-28B, in some embodiments, the suture lock can include a connector or connecting portion to attach the suture lock 2700 to a handle assembly (e.g., handle assembly 2200 of FIG. 27A). For example, the suture lock 2700 can include a release bar 2820 which extends into and couples with a bottom housing 2712 of the suture lock 2702 (FIGS. 27B-28C). In some embodiments, the release bar 2820 is bonded to the bottom housing 2712 (e.g., via an adhesive, weld, or other non-removable fixing means). As shown in FIGS. 27B and 28A-28C, a release knob 2802 can be arranged around a portion of the release bar 2820, adjacent to a connecting portion 2822 of the bottom housing 2712. The release knob 2802 can be configured to connect the suture lock 2700 to an adaptor 2270 of the delivery system. In some embodiments, as shown in FIG. 27A, the adaptor 2270 can include branch 2204 and straight portion 2202, as discussed above. For example, the release knob 2802 can screw onto an end 2272 of the adaptor 2270 to secure the suture lock 2700 to the adaptor 2270. In some embodiments, a shape, size, and/or configuration of the adaptor 2270 may be different than shown in FIG. 27A and may change based on the delivery system to which the suture lock 2700 is configured to be attached to (and used with).

Figure 28B:
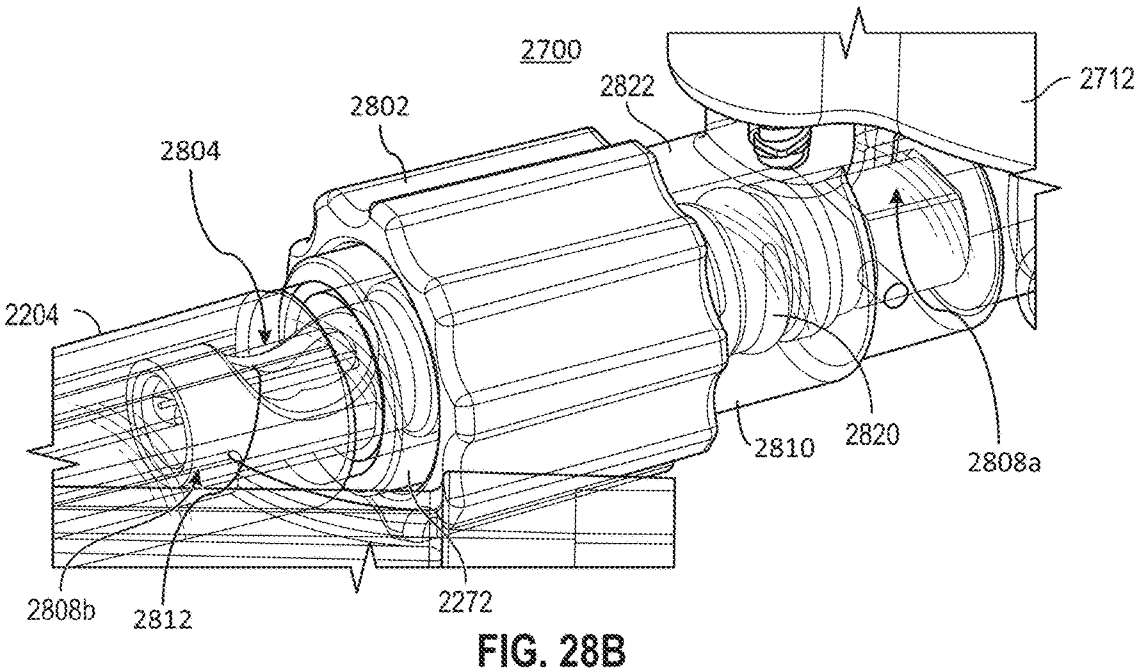
FIG. 28B illustrates a perspective view of a detail portion of the suture lock of FIGS. 27A-27C, showing a release knob and internal release bar.
Figure 28C:
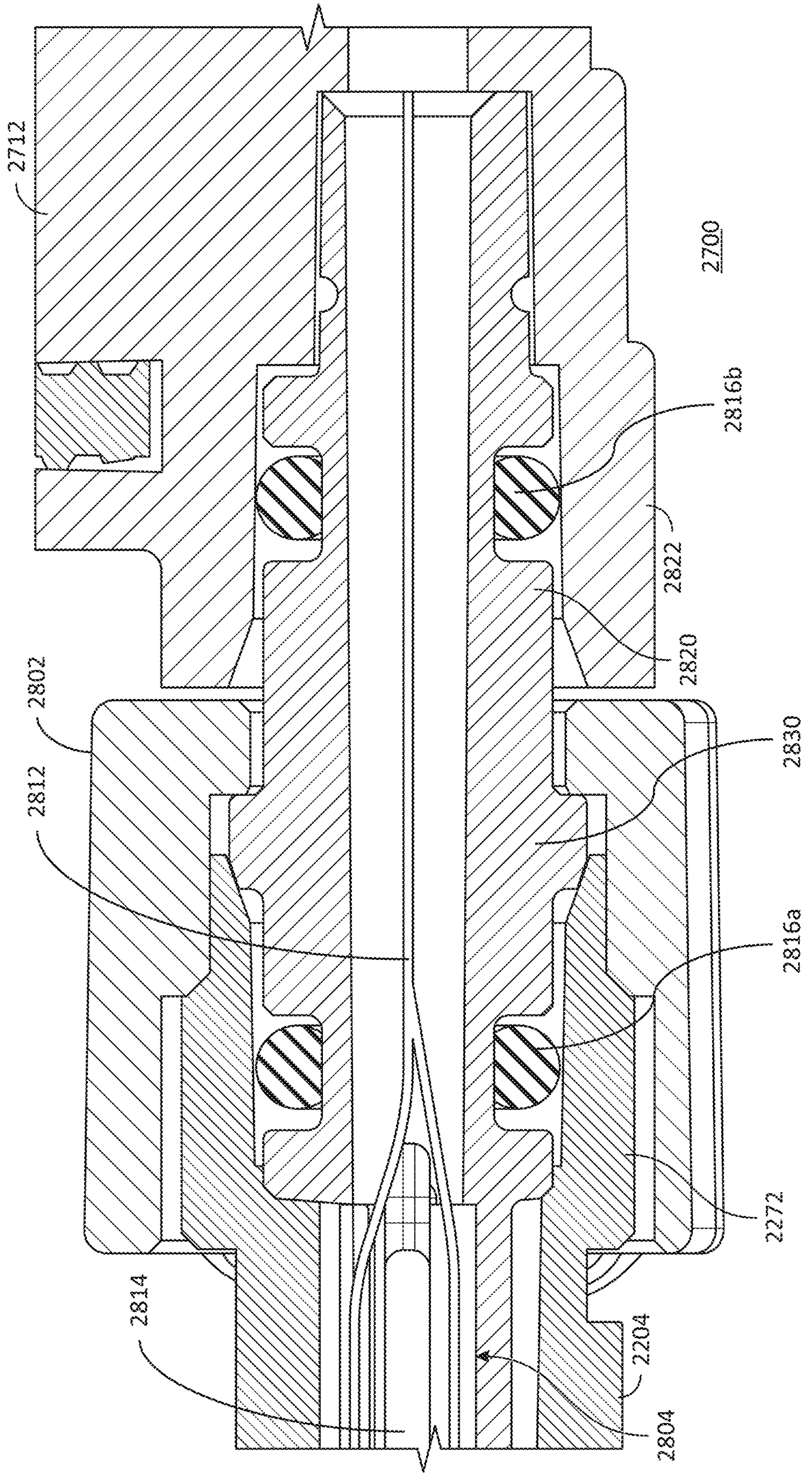
FIG. 28C illustrates a side cross-sectional view of the release bar of the suture lock of FIG. 28B.

For example, in some embodiments, when teeth of the release knob 2802 engage both the end 2272 of the adaptor 2270 (or another adaptor of a delivery system) and the release bar 2820, the suture lock 2700 is coupled to the delivery system and a suture cutting section 2804 is covered by the adaptor 2270 (as shown in FIGS. 27A, 28B, and 28C). In some embodiments, once the docking device (or other implant) is positioned in a desired position for release from the delivery system, the release knob 2802 can be unscrewed, toward the bottom housing 2712 and the suture lock 2700 can be pulled proximally away from the adaptor (e.g., delivery system adaptor) 2270 to expose a suture cutting section 2804. In alternate embodiments, rotation of the release knob 2802 toward the bottom housing 2712 can expose the suture cutting section 2804 without pulling the entire suture lock 2700 away from the adaptor 2270.

The suture cutting section 2804 allows for a user or medical practitioner to cut a suture 2812 that traverses the length of a delivery system (e.g., as shown as suture 2236 in FIGS. 24B and 34), to allow for the disconnection of a docking device from the delivery system upon its installation in a heart or heart analog.

In some embodiments, once the suture 2812 is wrapped around the docking device or implant (e.g., as shown in FIGS. 24B and 34) and routed through the delivery system, through the release bar 2820 (including across the suture cutting section 2804, as shown in FIG. 28B), and into the bottom housing 2712, the two suture ends of the suture 2812 can be threaded through the two apertures 2932 arranged in a bottom end of the spool 2930 (or 2928 of FIG. 29D) and then tied to complete the loop. As shown in FIG. 29D, the spool 2928 (or 2930) can include a gap 2934 in a flange at the bottom of the spool 2928 that can prevent the suture 2812 from getting crushed during assembly of the top housing 2710 and the bottom housing 2712.

In some embodiments, as shown in FIG. 27A, the rotator 2702 can include an indicator 2714 to track a number of turns applied and locate the spool gap 2934.

Figure 28D:
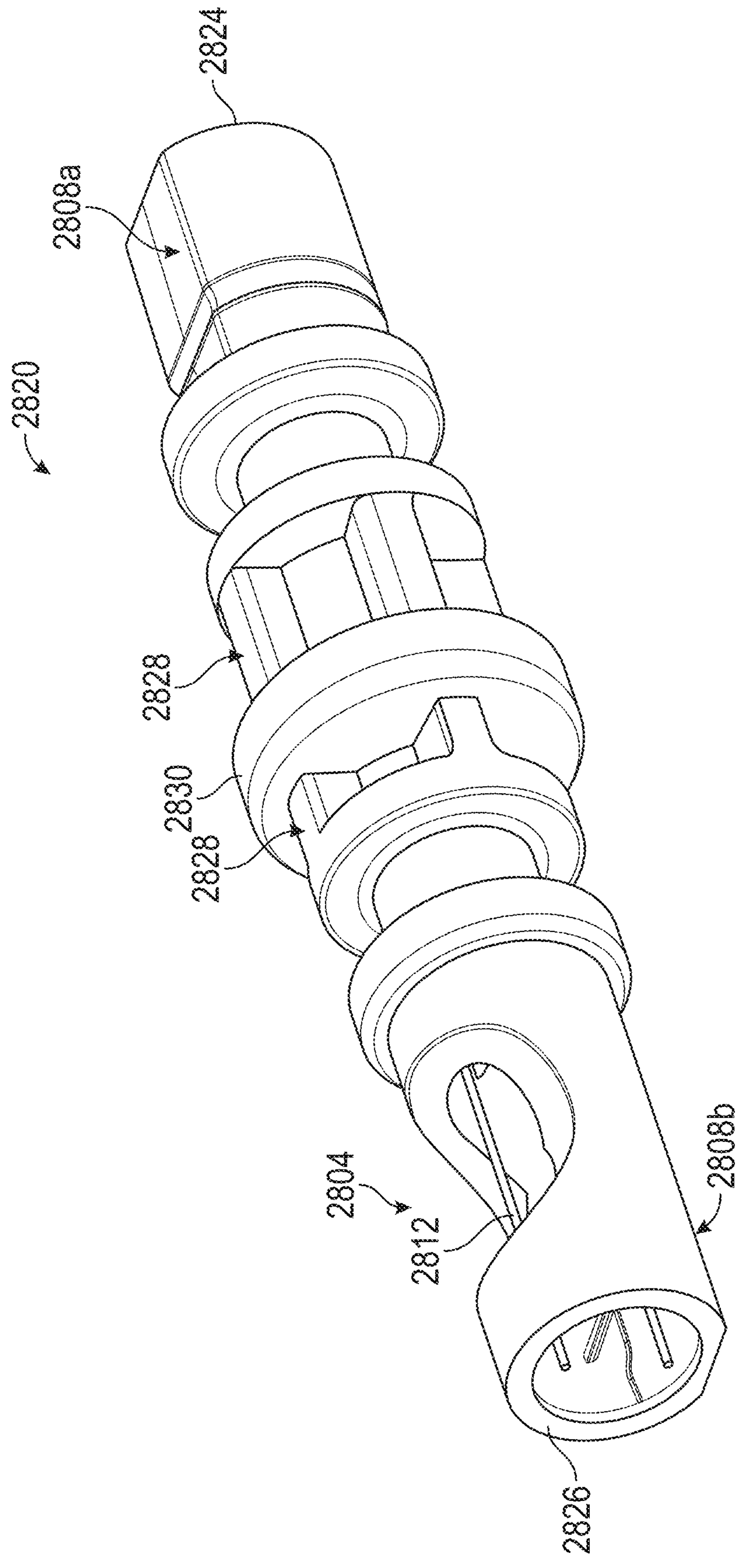
FIG. 28D illustrates a perspective view of the release bar of FIGS. 28B and 28C.
Figure 28E:
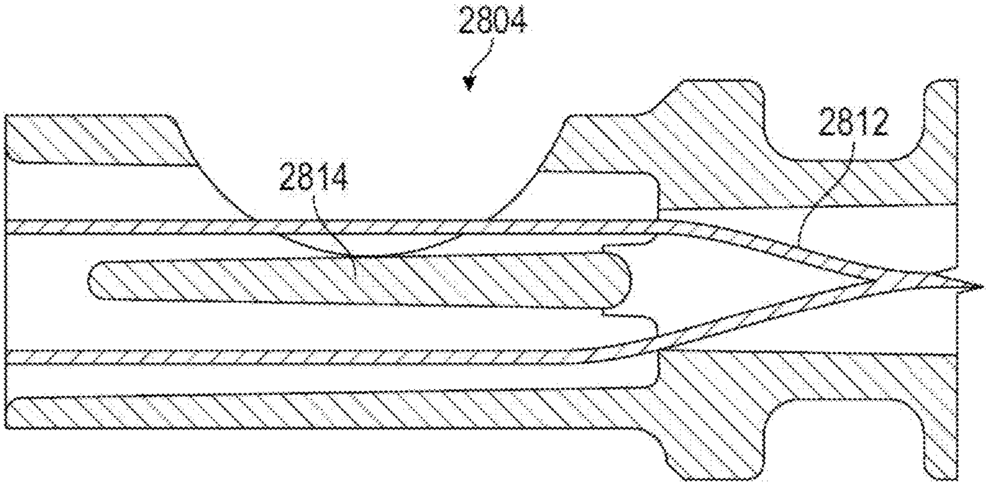
FIG. 28E illustrates a detail cross-sectional view of a suture cutting portion of the release bar of FIGS. 28B-28D.

In many embodiments, as shown in FIGS. 28C and 28D, suture 2812 runs longitudinally through the release bar 2820 of the suture lock 2700 and the two lines of the suture split to cross divider 2814 arranged in the suture cutting section 2804. Various embodiments use divider 2814 to separate the lines of suture 2812 such that only one line can be cut by a user or medical practitioner to release a docking device from the delivery device. For example, the exposed portion of the suture 2812, as shown in FIG. 28D, can then be cut by a cutting mechanism, such as the cutting mechanism of FIGS. 30A-30C. Once the suture is cut, it can be removed from the delivery system and the suture lock 2700 can be attached back onto the adaptor 2270 of the delivery system by screwing the release knob 2802 onto the adaptor 2270.

Additional embodiments maintain a seal within suture lock 2700 by using a plurality of annular sealing elements (e.g., O-rings) 2816*a-c* to prevent leakage of blood, saline, or other fluid through the system. For example, as shown in FIGS. 27C, 28C, 29B, and 29C, the suture lock 2700 can include a first, distal release bar O-ring 2816*a* (FIGS. 27C and 28C), a second, proximal release bar O-ring 2816*b* (FIGS. 27C and 28C), and a spool O-ring 2816*c* (FIGS. 27C, 29B, and 29C). These O-rings 2816*a-c* can be configured to seal the suture path when the suture lock 2700 is assembled, allowing for hemostasis when connected to a properly sealed delivery system. The spool O-ring 2816*c* can prevent leaks past the end of the suture routing. The proximal release bar O-ring 2816*b* can prevent leaks between the release bar 2820 and the bottom housing 2712. In some embodiments, this allows an adhesive or other bonding agent bonding the release bar 2820 to the bottom housing 2712 to act solely as a bond and does not require a sealing function. The distal release bar O-ring 2816*a* can prevent leaks between the release bar 2820 and the delivery system adapter 2270 while the release knob 2802 is engaged. The release knob 2802 can be designed such that the distal release bar O-Ring 2816*a* seals the suture lock mechanism when there is any thread engagement with the adaptor 2270 (e.g., there may be no variable sealing dependent on how tight the release knob is). In some embodiments, there may be a hole in the bottom housing 2712 to act as a leak path in the event of a seal degradation.

As introduced above with reference to FIG. 38, additional embodiments of suture lock 2700 comprise a flushing port 2806 to allow flushing of one or more lumens within the delivery device to reduce thrombus formation between components of the delivery system, maintain hemostasis within a delivery device, and/or to sterilize a delivery device. The flushing port 2806 allows for certain embodiments of a delivery device to flush lumens independently if a single flush line becomes clogged and/or is not maintaining hemostasis in a delivery device. In certain embodiments flushing port 2806 is an open port to allow constant flow through a delivery device, while certain embodiments possess a self-sealing flushing port 2806 such that fluids can be introduced into a delivery device as needed by a practitioner without requiring constant flow. A flushing port 2806 as illustrated in FIG. 28A allows for an additional flush line to be connected akin to multiple flushing ports, such as illustrated in FIG. 24B and discussed above.

Turning to FIGS. 28B and 28D, some embodiments of suture lock 2700 possess segments that are keyed to prevent rotation of a suture lock 2700 around a handle assembly, thus preventing twisting of suture lines and/or increasing ease of access for a practitioner. Keying of certain suture lock 2700 components can be accomplished various ways, including by creating a specific non-round shape in the components, use of pins, grooves, or any other methodology to maintain a non-rotating fit between suture lock 2700 and an outer housings or handle assembly. For example, in some embodiments, as shown in FIG. 28B, either end of the release bar can be shaped to form keyed connections 2808*a* and 2808*b* between the release bar 2820 and the bottom housing 2712 and the release bar 2820 and the adaptor 2270, respectively. For example, a proximal end 2824 of the release bar 2820 can be shaped to form the first keyed connection 2808*a* and a distal end 2826 of the release bar 2820 can be shaped to form the second keyed connection 2808*b*.

In some embodiments, as shown in FIGS. 28D, the release bar 2820 can include one or more supporting ribs 2828 arranged on a center portion of the release bar, the center portion arranged between the distal end 2826 and the proximal end 2824 of the release bar 2820. For example, in some embodiments, the supporting ribs 2828 can include a plurality of axially-extending ribs 2828 that are arranged around a circumference of the release bar 2820, on either side of a central ring element 2830 that extends around the circumference of the release bar 2820.

Figure 30A:
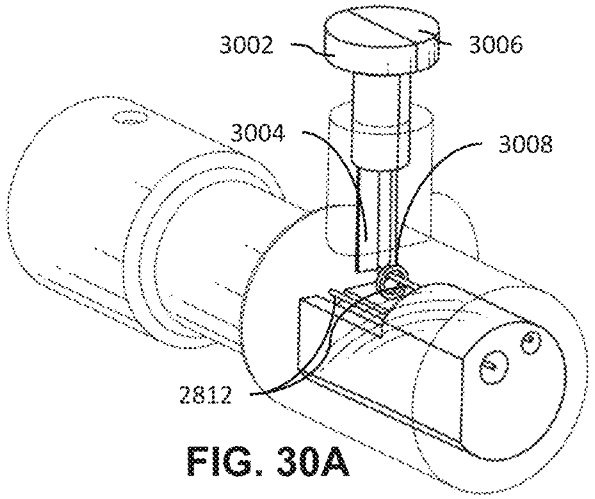
FIGS. 30A-30C illustrate an example embodiment of a suture cutting and removal mechanism in accordance with various embodiments.
Figure 30B:
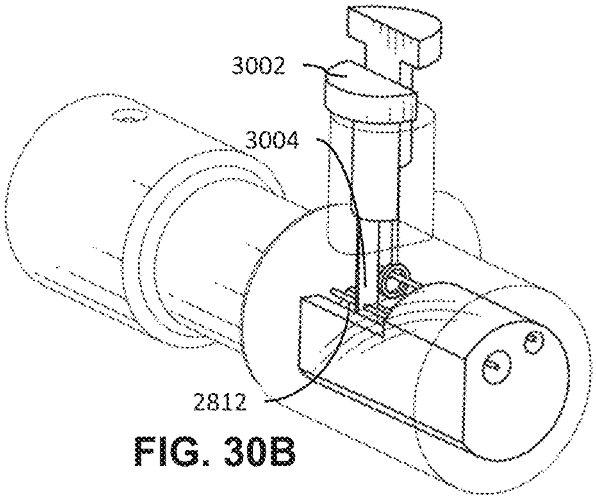
Figure 30C:
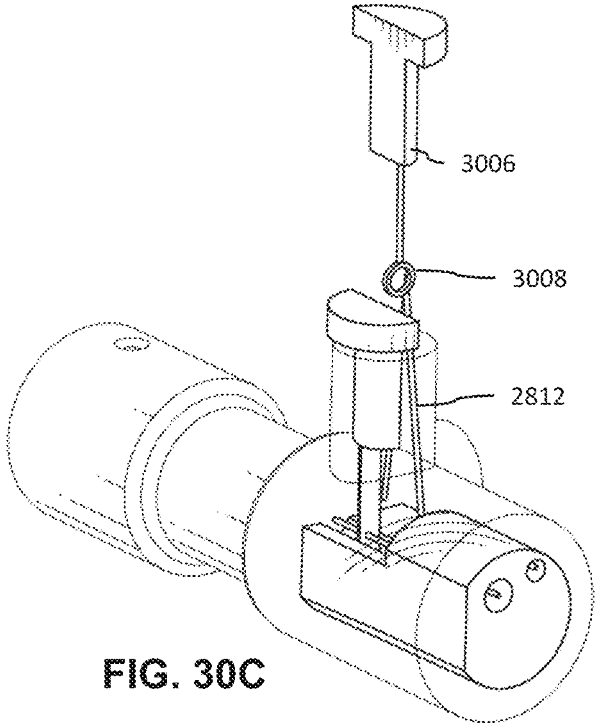

FIGS. 30A-30C illustrate a cutting and suture removal system used in various embodiments. Such embodiments allow for a user to cut and remove a suture, such as suture 2812 shown in FIGS. 28B-28E without breaking hemostasis of a system or relying on a scalpel or other cutting method to cut a suture. In particular, FIG. 30A illustrates a resting position with a cutting actuator 3002 attached to a blade 3004 and a suture removal actuator 3006 attached to a loop 3008 or hook attached to suture 2812. FIG. 30B illustrates cutting of suture 2812 by pressing down on cutting actuator 3002 to sever suture 2812. FIG. 30C illustrates removal of suture by removing suture removal actuator 3006, which brings along suture 2812 using loop 2008 from within a delivery device.

Packaging for Delivery System

As discussed above, many embodiments utilize a coating, lubricious coating, and/or hydrophilic coating, such as a hydrogel, on the lubricous sleeve covering the docking device. In some embodiments, the docking device itself may have a coating. After manufacture, docking devices and delivery systems will be transported for use. During transport or storage, the environment may change over time, such as with different weather patterns, and/or geographic locations. These environment changes can include changes in humidity. However, many hydrophilic coatings may absorb moisture in the environment. As delivery devices are transported or stored, the hydrophilic coatings may go through one or more wet-dry cycles. Due to wet-dry cycles, the hydrophilic coatings on adjacent coils may stick together. Other coatings may also be prone to sticking together on adjacent coils. Coils sticking together can be problematic when preparing or loading the docking device into the delivery system for use. As such, certain embodiments of the invention are directed to packaging for delivery systems and docking devices as discussed herein.

Figure 31A:
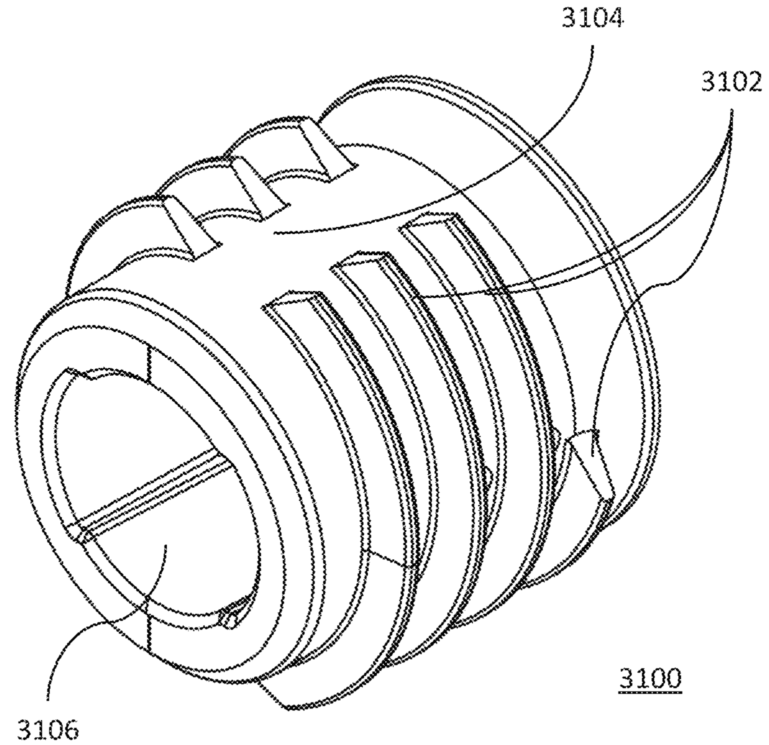
FIGS. 31A and 31B illustrate example embodiments of a coil holder in accordance with various embodiments.
Figure 31B:
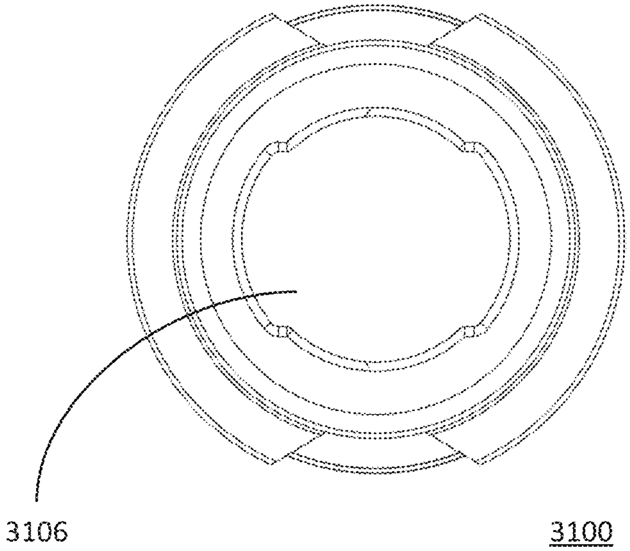

Turning to FIGS. 31A and 31B, a coil holder 3100 in accordance with various embodiments is illustrated. As seen in FIG. 31A, a series of fins 3102 protrude from a central pillar 3104. In many embodiments, the fins 3102 separate individual turns or coils of a docking device or of a sleeved docking device. By separating the individual coils or turns from each other, the coils will be unable to stick together, should they undergo wet-dry cycles during storage or transport or otherwise. Adjacent fins 3102 in various embodiments are separated by a distance sufficient to allow a single turn of a sleeved docking device to lay between them. Additionally, the coil holder 3100 of many embodiments includes a central opening 3106 formed in the central pillar 3104. In several embodiments, the central opening 3106 can be used to attach the coil holder 3100 to an outer packaging, which can have a complementary protrusion on which to mound the coil holder 3100 using the central opening 3106. In some embodiments, the coil holder 3100 comprises a central opening having an irregular shape, such as a winged circle, as illustrated in FIG. 31B, or another feature which will prevent the coil holder 3100 from rotating in the outer packaging. Additionally, the coil holder 3100 can be made of any material suitable for maintain separation of individual coils and preventing sticking or agglomerating of the coils, including plastics and polymer, such as an acetal homopolymer.

The coil holder 3100, when mounted in the outer packaging, can be placed in a low point or reservoir formed in the outer packaging. In some embodiments, the packaging and location and alignment of the coil holder 3100 is configured to allow the preparation and loading of the sleeved docking device (e.g., retracting the sleeve and docking device into an outer catheter or outer sheath of the delivery system) to occur without removing the delivery device from the outer packaging or while it is in its packaged position.

Methods

The present disclosure provides for methods of delivering implants to native valves of a heart. The methods can be used to deliver any of the implants described herein, including the docking devices having aspects thereof shown in the non-limiting FIGS. 7A to 16 and further described elsewhere herein. The methods can comprise positioning the selected docking device at the native valve of the heart, such that at least a portion of the leading turn of the docking device is positioned in a ventricle of the heart and around one or more valve leaflets of the native valve. In some implementations, the implantation of the docking device can act to reshape one or more tissues in the heart to repair the function of the native valve. In certain implementations, the methods can comprise delivering the docking device to a native mitral valve to repair the left ventricle and associated heart function. In further implementations, the methods can reduce the annulus diameter and place tension on the chordae. In yet further implementations, the methods can further include performing an edge to edge repair on the native leaflets of the native valve, such as by attaching a clip to attach a free edge of an anterior mitral valve leaflet to a free edge of a posterior mitral valve leaflet.

In some implementations, the methods can comprise delivering an implantable prosthetic heart valve within the docking device after the docking device is positioned at the native valve of the heart in the desired position. The methods can be used to deliver any of the implantable prosthetic heart valves described herein, including the valves having aspects thereof shown in the non-limiting FIGS. 3A to 6 and further described elsewhere herein. In some implementations, suitable implantable prosthetic heart valves that can be used in the methods can have an annular frame with an inflow end and an outflow end that is radially collapsible and expandable between a radially collapsed configuration and a radially expanded configuration, with the frame defining an axial direction extending from the inflow end to the outflow end; a leaflet structure positioned within the frame and secured thereto; and a flange attached to the inflow end of the annular frame and designed to extend outwardly therefrom. In certain implementations, the methods can further comprise positioning the implantable prosthetic heart valve in a radially collapsed configuration within the docking device and expanding the implantable prosthetic heart valve from the radially collapsed configuration to a radially expanded configuration, such that a radially outward pressure is applied by the frame of the implantable prosthetic heart valve on at least a portion of a central region of the docking device.

In some aspects, the present disclosure further provides for methods of delivering docking devices using the delivery systems described elsewhere herein, including the delivery systems having aspects thereof shown in non-limiting FIGS. 17-29E and 33-38. In certain implementations, the delivery systems suitable for use in the methods can include a delivery catheter, the docking device with an end portion at the end of the stabilization turn located opposite the central region, a pusher shaft disposed in the delivery catheter and coupled to the end portion of the docking device, and a sleeve shaft coaxially located with the pusher shaft and disposed between the delivery catheter and the pusher shaft. In some implementations, the delivery system can be configured such that the pusher shaft and sleeve shaft to operate in parallel. In certain implementations, the positioning step of the methods can comprise pushing the docking device out of the catheter with the pusher shaft. In some implementations, the positioning step of the methods can comprise using the pusher to hold the docking device in place while a sleeve and/or the catheter is retracted off the docking device.

Figure 39:
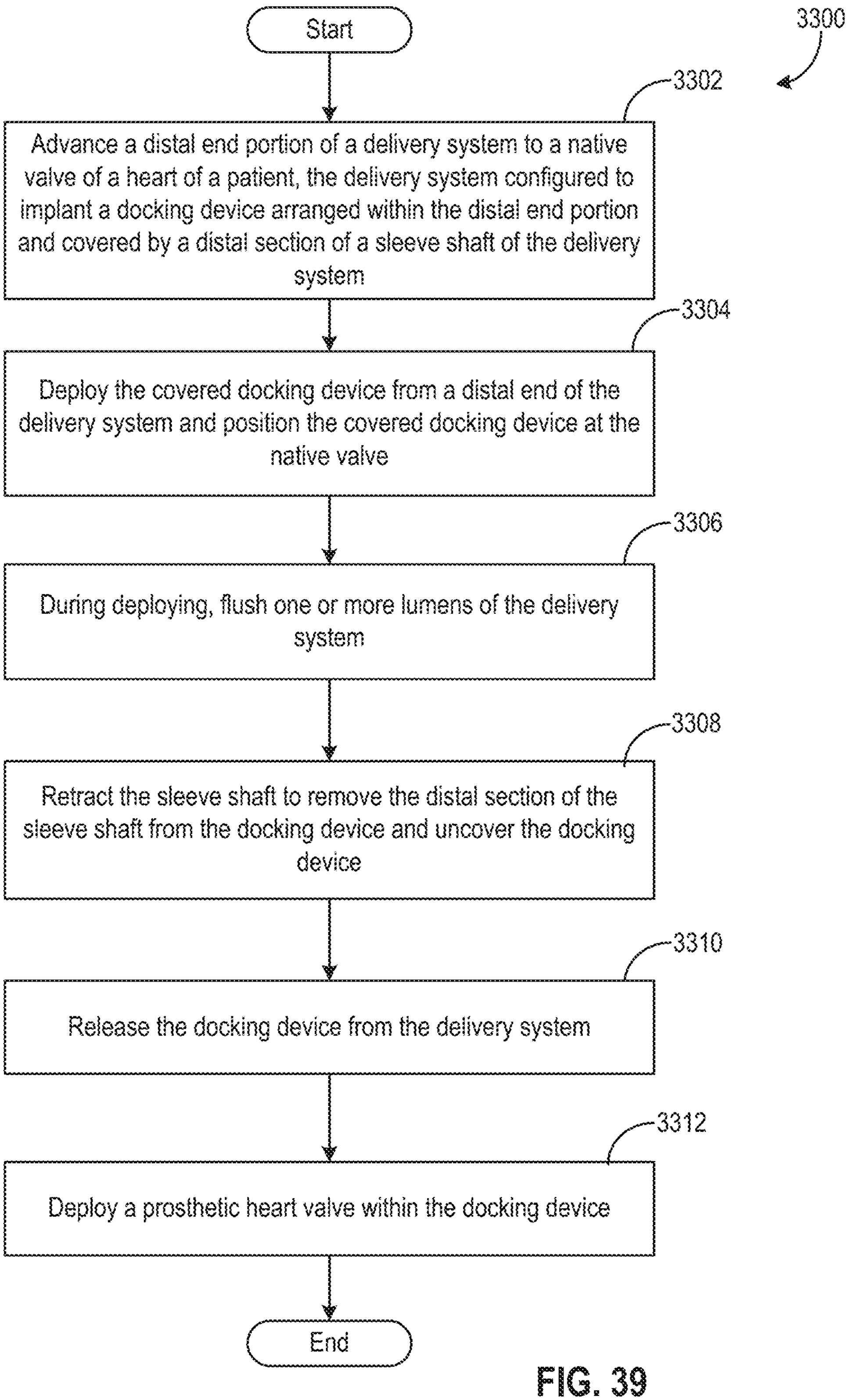
FIG. 39 is a flow chart of a method for delivering a docking device to a native valve of a heart and implanting the docking device and an associated prosthetic heart valve at the native valve.

FIG. 39 illustrates a flow chart of a method 3300 for delivering a docking device to a native valve of a heart and implanting the docking device and an associated prosthetic heart valve at the native valve. Method 3300 begins at 3302 and can include advancing a distal end portion of a delivery system to a native valve of a heart of a patient, the delivery system configured to delivery and implant a docking device arranged within the distal end portion and covered by a distal section of a sleeve shaft of the delivery system. The delivery system may be one of the delivery systems described herein, including the delivery system components described above with reference to FIGS. 17A-29E. The docking device can comprise a coil extending along a central axis and including a central region including a plurality of turns, a leading turn extending from a first end of the central region, and a stabilization turn extending from an opposite, second end of the central region, where a covering extends around and along a top turn of the central region, the top turn arranged at the second end of the central region. For example, in some embodiments, the docking device may be one of the docking devices described herein with reference to FIGS. 9A-12E. Further, in some embodiments, the covering extending around and along the top turn of the central region may be the covering 100 shown in FIG. 12E. In some embodiments, the native valve can be a mitral valve of the heart.

At 3304, method 3300 can include deploying the docking device from a distal end of the delivery system, the docking device covered by a distal section of a sleeve shaft of the delivery system. As described herein with reference to FIGS. 17A-29E and 33-37, deploying the docking device can include pushing the covered docking device outside of the outer shaft of the delivery system with the pusher shaft of the delivery system. For example, pushing the docking device outside of the outer shaft with the pusher shaft can include actuating the pusher shaft to extend distally (along the axial direction) out of the outer shaft of the delivery system, in response to a user moving the hub assembly and/or handle assembly in the distal direction. As a result, both the pusher shaft and the sleeve shaft can move axially together, in the distal direction, out of the outer shaft.

The method at 3304 can further include positioning the covered docking device at the native valve (e.g., mitral valve 10 shown in FIGS. 1 and 2), such that the covering of the top turn of the central region crosses and plugs a medial commis sure (e.g., the lower, right commis sure 24 shown in FIG. 2) of the native valve, at least a portion of the leading turn is positioned in a ventricle of the heart (e.g., left ventricle 14 shown in FIG. 1), and at least a portion of the stabilization turn is positioned in an atrium of the heart (e.g., left atrium 12 shown in FIG. 1).

During the advancing, deploying, and positioning of the covered docking device, as introduced above and shown in FIG. 33 and FIG. 17B, a distal tip of the distal section of the sleeve shaft can extend distal to (e.g., past) a distal end of the docking device, thereby providing the distal section of the sleeve shaft with a more atraumatic tip that can deform and bend as it navigates around the native anatomy.

The method at 3306 can include, during the deploying, flushing one or more lumens of the delivery system. The one or more lumens can include a first lumen arranged between the distal section of the sleeve shaft and the docking device and a second lumen arranged between an outer shaft of the delivery system and the sleeve shaft, as described above with reference to FIG. 38.

In some embodiments, flushing the first lumen can include providing flush fluid to a pusher shaft lumen extending through a pusher shaft from a proximal end of the pusher shaft arranged within a branch section of a hub assembly, where a suture lock is coupled to the branch section, to a distal end of the pusher shaft, the distal end arranged proximate to, but spaced away from, a proximal end of the docking device. Flushing the first lumen can further include flowing the flush fluid through the pusher shaft lumen and into and through the first lumen. In some embodiments, the flush fluid can be provided to the pusher shaft lumen via a flush port coupled to the branch section, distal to the suture lock. In alternate embodiments, the flush fluid can be provided to the pusher shaft lumen via a flush port that is part of the suture lock and arranged at a proximal end of the suture lock.

In some embodiments, flushing the second lumen can include providing flush fluid to a first cavity (e.g., cavity 2254 shown in FIG. 36) formed between an outer surface of the pusher shaft and an inner surface of a conduit of the branch section, flowing the flush fluid from the first cavity into a second cavity (e.g., cavity 1946 shown in FIG. 37) formed between a shell of the pusher shaft and the sleeve shaft, and flowing the flush fluid from the second cavity to the second lumen.

In some embodiments, flushing the lumens of the delivery device, as described above, can additional occur during preparing the delivery device for an implantation procedure, prior to inserting the delivery device into a patient.

At 3308, method 3300 can include, after positioning the covered docking device, retracting the sleeve shaft, in a proximal direction, to uncover the docking device. In some embodiments, retracting the sleeve shaft to uncover the docking device can include moving a sleeve actuating handle of the delivery system in the proximal direction. The method at 3308 can further include maintaining a position of the pusher shaft while retracting the sleeve shaft to uncover the docking device and, after uncovering the docking device, retracting the pusher shaft back into the outer shaft of the delivery system.

Method 3300 can continue to 3310 to release (e.g., disconnect) the docking device from the delivery system. As described herein, the delivery system can include a suture lock assembly (e.g., suture lock 2206 of FIG. 24A and/or suture lock 2700 of FIGS. 27A-29E) which includes a suture cutting location for cutting a suture (or other retrieval line) that extends from the suture lock, through the delivery system, and loops around an end of the docking device. In some embodiments, as described above with reference to FIGS. 27A-30C, the method at 3310 can include exposing the suture cutting location of the suture lock and using a cutting mechanism (such as the mechanism shown in FIGS. 30A-30C) to cut the suture and then pulling the suture out of and away from the docking device. As a result, the docking device may be disconnected from the delivery system.

At 3312, the method 3300 can include deploying a prosthetic heart valve (e.g., one of the valves shown in FIGS. 3A-8) within the implanted docking device, as described herein.

Figure 32A:
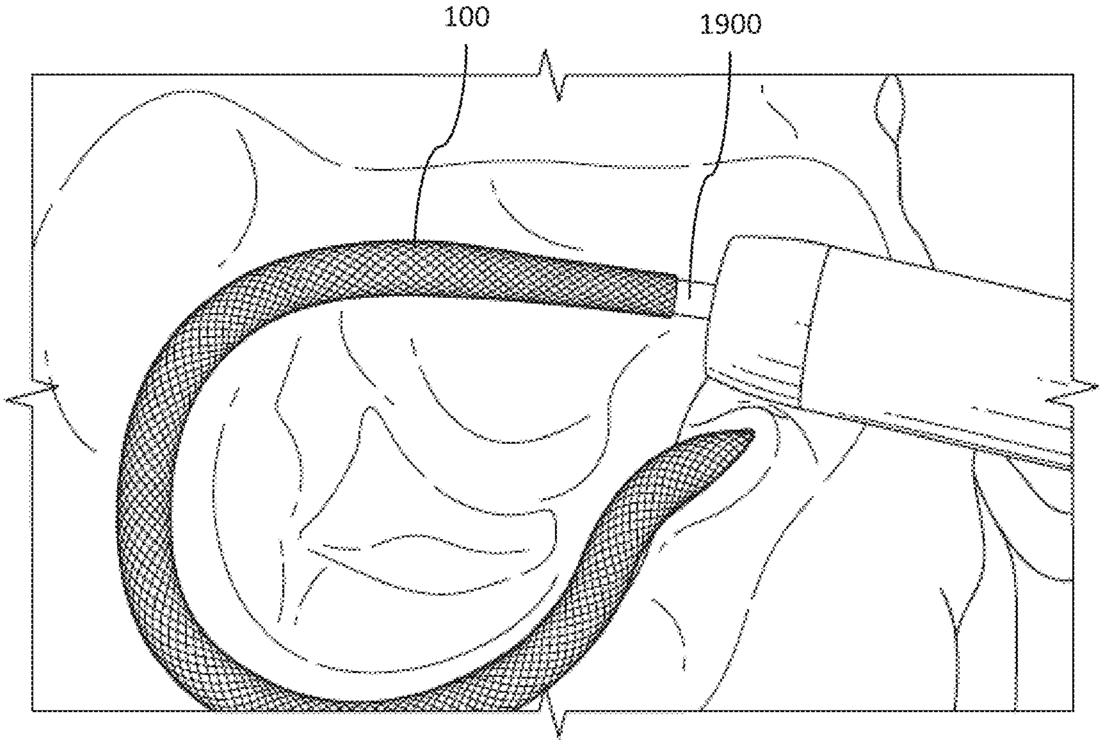
FIGS. 32A-32C illustrate a method to expand a covering over a docking device in accordance with various embodiments.
Figure 32B:
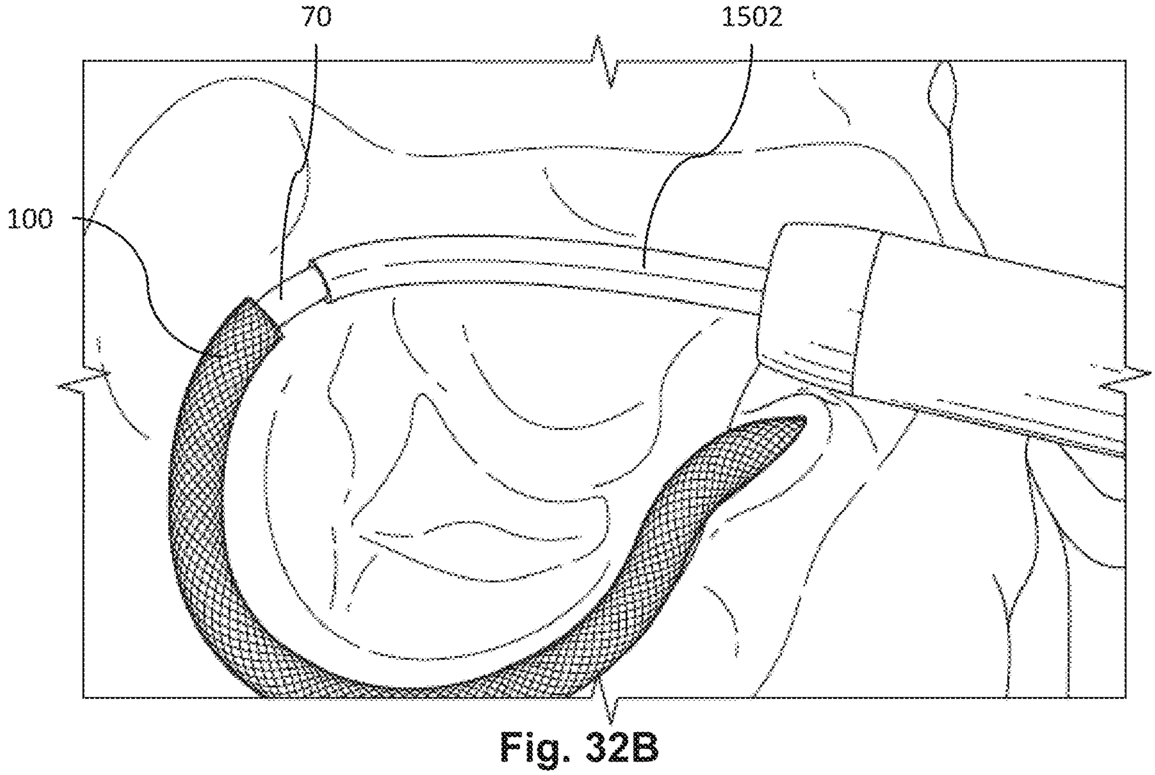
Figure 32C:
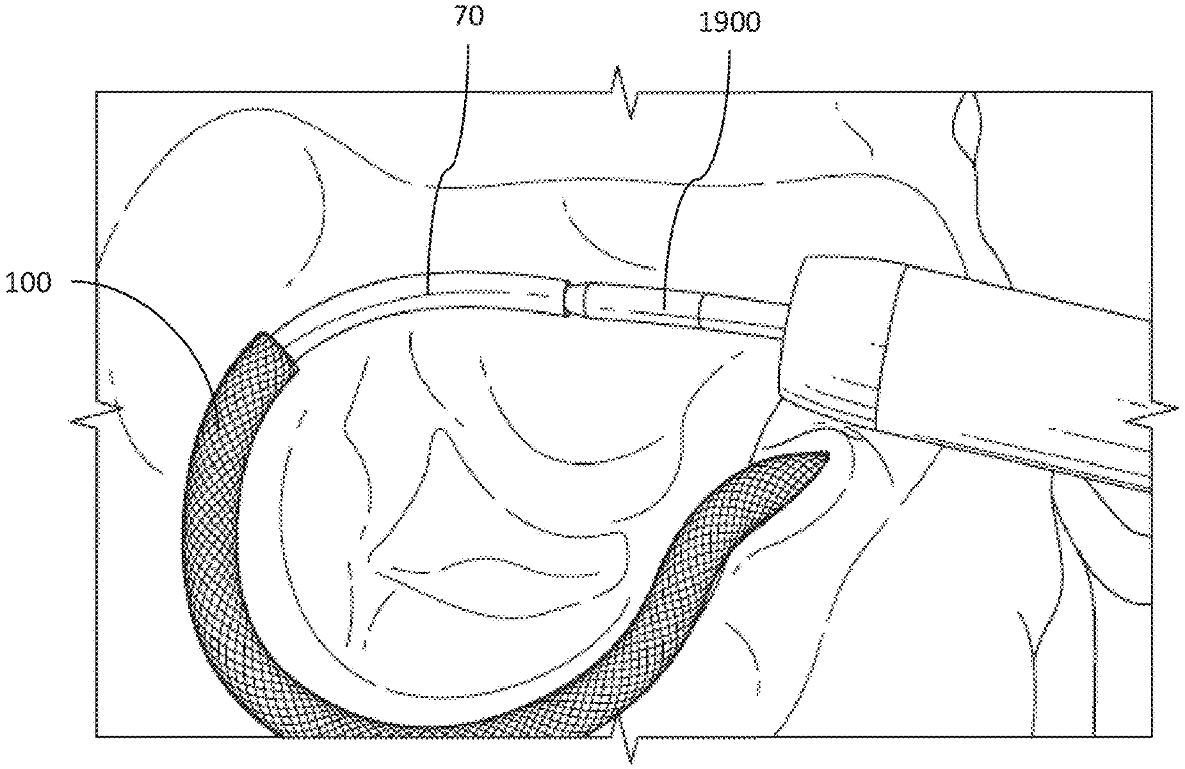

A method of delivering a docking device in accordance with certain embodiments is illustrated in FIGS. 32A-32C. FIG. 32A illustrates delivery of a docking device including a covering 100. In particular, FIG. 32A illustrates initial retraction of a sleeve or distal section into a delivery device. However, covering 100 is not fully expanded and extends over part of pusher shaft 1900. As such, FIG. 32B illustrates partial reinsertion of sleeve or distal section 1502 to push covering 100 into an expanded form, and FIG. 32C illustrates a full retraction of sleeve or distal section into a delivery device with covering 100 in an expanded form and no longer covering pusher shaft 1900.

Additional steps described anywhere herein can also be added and the systems and assemblies described herein can be used with these methods. Any and all of the methods, operations, steps, etc. described herein can be performed on a living animal or on a non-living cadaver, cadaver heart, simulator (e.g. with the body parts, tissue, etc. being simulated), anthropomorphic ghost, etc.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods.

These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein with reference to the delivery systems, docking devices, and prosthetic heart valves, the term "proximal" refers to a position, direction, or portion of a device that is closer to the user and/or a handle of the delivery system that is arranged outside the patient and further away from the implantation site. As used herein, the term "distal" refers to a position, direction, or portion of a device that is further away from the user and/or the handle of the delivery system and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined. Further, the term "radial" refers to a direction that is arranged perpendicular to the axis and points along a radius from a center of an object (where the axis is positioned at the center, such as the central longitudinal axis of the delivery system).

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. A delivery system for delivering a docking device to a native valve annulus of a patient's heart, comprising:

an outer shaft;

a sleeve shaft at least partially arranged within the outer shaft, the sleeve shaft comprising:

a distal section configured to cover the docking device; and a proximal section including a tubular portion and a cut portion, the cut portion having an open cross-section; and a pusher shaft at least partially arranged within the outer shaft, the pusher shaft comprising:

a main tube arranged interior to, in a radial direction that is relative to a central longitudinal axis of the delivery system, the sleeve shaft;

an annular shell surrounding a proximal end portion of the main tube and spaced away from, in the radial direction, an outer surface of the main tube; and a proximal extension connected to and extending proximally from a proximal end of the main tube, the proximal extension extending along a portion of an inner surface of the cut portion of the proximal section of the sleeve shaft.

2. The delivery system of claim 1, wherein the pusher shaft further comprises an annular plug arranged within the annular shell, at a proximal end of the shell, and surrounding the main tube, wherein the plug includes a crescent-shaped portion extending across and filling a first portion of an annular space arranged between the main tube and the shell.

3. The delivery system of claim 2, wherein the annular space includes a second portion that is open and not filled by the plug, wherein the proximal section of the sleeve shaft is configured to slide within the annular space, and wherein the cut portion of the proximal section is configured to slide through the second portion of the annular space.

4. The delivery system of claim 3, wherein the tubular portion of the proximal section has an end surface at an interface between the tubular portion and the cut portion, the end surface arranged normal to the central longitudinal axis, and wherein the plug is configured to interface with the end surface of the proximal section and stop the sleeve shaft from traveling further in a proximal, axial direction.

5. The delivery system of claim 1, wherein the distal section of the sleeve shaft comprises a flexible material, wherein the proximal section of the sleeve shaft comprises a rigid material, and wherein the sleeve shaft further includes a middle section arranged between the distal section and the proximal section of the sleeve shaft, the middle section forming a transition between the flexible material of the distal section and the rigid material of the proximal section, wherein the sleeve shaft further includes:

a flexible polymer jacket forming an outer surface of the distal section and the middle section, the flexible polymer jacket comprising the flexible material;

an inner liner forming an inner surface of each of the distal section and the middle section;

and a rigid tube including a first section forming an entirety of the proximal section and a second section forming a proximal portion of the middle section.

6. The delivery system of claim 5, wherein the rigid tube is a metal tube, wherein the second section includes a plurality of apertures arranged around a circumference of the rigid tube, along the second section, and wherein the rigid tube is coupled to the inner liner and the flexible polymer jacket via a bonding connection between the inner liner and the flexible polymer jacket, through the plurality of apertures.

7. The delivery system of claim 1, further comprising a handle assembly include a handle portion and a hub assembly extending proximally from a proximal end of the handle portion, wherein the outer shaft extends distally from a distal end of the handle portion, and wherein the hub assembly includes an adaptor with a straight section coupled to a suture lock assembly and a branch section coupled to a sleeve actuating handle, wherein the proximal extension of the pusher shaft extends into and through a portion of the branch section of the adaptor.

8. The delivery system of claim 7, further comprising a first flushing port coupled to the branch section of the adaptor and fluidly coupled with an inner lumen of the proximal extension of the pusher shaft and further comprising a second flushing port coupled to the branch section, distal to the first flushing port, and fluidly coupled with a lumen formed between an outer surface of the proximal extension and an inner surface of the branch section.

9. The delivery system of claim 7, further comprising a first flushing port coupled to a proximal end of the suture lock assembly and fluidly coupled with an inner lumen of the proximal extension of the pusher shaft and a second flushing port coupled to the branch section, distal to the first flushing port, and fluidly coupled with a lumen formed between an outer surface of the proximal extension and an inner surface of the branch section.

10. The delivery system of claim 7, wherein the cut portion of the sleeve shaft extends into the straight section of the adaptor and is coupled to the sleeve actuating handle.

11. The delivery system of claim 1, wherein the pusher shaft and the sleeve shaft are coaxial with one another, along the central longitudinal axis of the delivery system, and wherein each of the sleeve shaft and the pusher shaft are configured to slide axially along the central longitudinal axis, relative to the outer shaft.

12. A delivery system for delivering a docking device to a native valve annulus of a patient's heart, comprising:

a handle portion;

an outer shaft extending distally from a distal end of the handle portion;

a sleeve shaft extending through an interior of the outer shaft and configured to cover the docking device;

a pusher shaft including a main tube extending through an interior of the sleeve shaft; and a hub assembly extending proximally from a proximal end of the handle portion, the hub assembly comprising:

an adaptor coupled to the handle portion and including a first section and a second section that branches off from the first section, wherein a portion of the pusher shaft extends into the second section and a proximal section of the sleeve shaft extends through the first section;

a suture lock assembly coupled to a proximal end of the second section and configured to adjust tension in a suture extending from the suture lock assembly, through the pusher shaft, to the docking device;

a first flushing port coupled to the second section and fluidly coupled to a first fluid flow lumen arranged within an interior of the pusher shaft and to a second fluid flow lumen arranged between the sleeve shaft and the docking device; and a second flushing port coupled to the second section and fluidly coupled to a third fluid flow lumen arranged between the outer shaft and the sleeve shaft.

13. The delivery system of claim 12, further comprising a sleeve actuating handle arranged at a proximal end of the first section and coupled to an end of the proximal section of the sleeve shaft, the sleeve actuating handle configured to adjust an axial position of the sleeve shaft relative to the outer shaft.

14. The delivery system of claim 12, wherein the first fluid flow lumen extends through an interior of a proximal extension of the pusher shaft and an interior of the main tube of the pusher shaft, the main tube coupled to the proximal extension and extending through an interior of the outer shaft and the proximal extension extending through a portion of the outer shaft and into the second section, and wherein the first fluid flow lumen further extends to a distal end of the pusher shaft, the distal end arranged adjacent to but spaced away from a proximal end of the docking device when the docking device is arranged within the outer shaft.

15. The delivery system of claim 14, wherein the second flushing port is fluidly coupled to the third fluid flow lumen via an annular cavity arranged between a shell of the pusher shaft and the main tube of the pusher shaft, and a fourth fluid flow lumen formed between an outer surface of the proximal extension and an inner surface of the second section, the fourth fluid flow lumen fluidly coupled to the annular cavity.

16. The delivery system of claim 15, wherein the third fluid flow lumen is arranged between an inner surface of the outer shaft and a distal portion of the sleeve shaft, the distal portion configured to cover the docking device while the docking device is arranged inside the outer shaft and being implanted at the native valve annulus.

* * * * *